US007153828B2

(12) United States Patent
Sliwkowski et al.

(10) Patent No.: US 7,153,828 B2
(45) Date of Patent: Dec. 26, 2006

(54) USE OF HEREGULIN AS A GROWTH FACTOR

(75) Inventors: Mark X. Sliwkowski, San Carlos, CA (US); Jeffrey A. Kern, Iowa City, IA (US)

(73) Assignees: Genentech, Inc., South San Francisco, CA (US); University of Iowa Research Foundation, Iowa City, IA (US)

( * ) Notice: Subject to any disclaimer, the term of this patent is extended or adjusted under 35 U.S.C. 154(b) by 46 days.

(21) Appl. No.: 10/453,183

(22) Filed: Jun. 3, 2003

(65) Prior Publication Data

US 2003/0199429 A1 Oct. 23, 2003

Related U.S. Application Data

(63) Continuation of application No. 09/773,517, filed on Feb. 2, 2001, now abandoned, which is a continuation of application No. 09/243,198, filed on Feb. 2, 1999, now abandoned.

(60) Provisional application No. 60/073,866, filed on Feb. 4, 1998.

(51) Int. Cl.
C07K 14/475 (2006.01)
A61K 38/18 (2006.01)
(52) U.S. Cl. .......................... 514/12; 530/399; 435/377
(58) Field of Classification Search .................. 514/12, 514/2; 530/399, 350, 300; 435/377; 424/198.1, 424/172.1, 152.1
See application file for complete search history.

(56) References Cited

U.S. PATENT DOCUMENTS

| 4,935,341 | A | 6/1990 | Bargmann et al. |
| 4,968,603 | A | 11/1990 | Slamon et al. |
| 5,183,884 | A | 2/1993 | Kraus et al. |
| 5,288,477 | A | 2/1994 | Bacus et al. |
| 5,367,060 | A | 11/1994 | Vandlen et al. |
| 5,401,638 | A | 3/1995 | Carney et al. |
| 5,464,751 | A | 11/1995 | Greene et al. |
| 5,578,482 | A | 11/1996 | Lippman et al. |
| 5,686,415 | A | 11/1997 | Carnahan et al. |
| 5,720,954 | A | 2/1998 | Hudziak et al. |
| 5,772,997 | A | 6/1998 | Hudziak et al. |
| 5,840,525 | A | 11/1998 | Vandlen et al. |
| 6,015,567 | A | 1/2000 | Hudziak et al. |
| 6,033,660 | A | 3/2000 | Mather et al. |
| 6,096,873 | A | 8/2000 | Schaefer et al. |
| 6,165,464 | A | 12/2000 | Hudziak et al. |
| 6,500,941 | B1 | 12/2002 | Schaefer et al. |
| 2004/0258685 | A1* | 12/2004 | Brunetta et al. ......... 424/143.1 |

FOREIGN PATENT DOCUMENTS

| EP | 444961 | 9/1991 |
| EP | 505148 | 9/1992 |
| EP | 0 599 274 A1 | 6/1994 |
| WO | WO 87/07646 | 2/1988 |
| WO | WO 89/10412 | 11/1989 |
| WO | WO 91/15230 | 10/1991 |
| WO | WO 92/18627 | 10/1992 |
| WO | WO 92/20798 | 11/1992 |
| WO | WO 93/22424 | 11/1993 |
| WO | WO 94/00140 | 1/1994 |
| WO | WO 94/04560 | 3/1994 |
| WO | WO 94/08007 | 4/1994 |
| WO | WO 94/28133 | 8/1994 |
| WO | WO 94/26298 | 11/1994 |
| WO | WO 95/32724 | 12/1995 |
| WO | WO 96/15244 | 5/1996 |
| WO | WO 96/30403 | 10/1996 |
| WO | WO 98/02541 | 1/1998 |
| WO | WO 98/35036 | 8/1998 |

OTHER PUBLICATIONS

Patel et al., Am. J. Respiratory Cell and Molecular Biol. vol. 22, pp. 432-440, Apr. 2000.*
Crystal, RG., (JAMA, vol. 285(5): 612-618) Feb. 7, 2001.*
Carraway & Cantley, "A *Neu* Acquaintance for ErbB3 and ErbB4: A Role for Receptor Heterodimerization in Growth Signaling." *Cell* 78: 5-8 (Jul. 15, 1994).
Carter et al., "Humanization of an Anti-p185\supHER2\nor Antibody for Human Cancer Therapy." *Proc. Natl. Acad. Sci. USA* 89: 4285-4289 (May 1992).
Carter et al., "Towards an Immunotherapy for p185\supHER2\nor Overexpression Tumors." *Antigen and Antibody Molecular Engineering in Breast Cancer Diagnosis and Treatment*, R.L. Ceriani, ed., New York: Plenum Press pp. 83-94 (1994).
Cole et al., "The EBV-Hybridoma Technique and its Application to Human Lung Cancer." *Monoclonal Antibodies and Cancer Therapy*, New York: Alan R. Liss, Inc. pp. 77-96 (1985).
Dillman, R., "Antibodies as Cytotoxic Therapy." *J. Clin. Oncol.* 12(7): 1497-1515 (Jul. 1994).
Drebin et al., "Development of Monoclonal Antibodies Reactive with the Product of the neu Oncogene." *Symposium on Fundamental Cancer Research* 38: 277-289 (1986).
Sato et al., "Biological Effects in vitro of Monoclonal Antibodies to Human Epidermal Growth Factor Receptors." *Mol. Biol. Med.* 1: 511-529 (1983).
Taetle et al., "Effects of Anti-Epidermal Growth Factor (EGF) Receptor Antibodies and an Anti-EGF Receptor Recombinant-Ricin A Chain Immunoconjugate on Growth of Human Cells." *J. Natl. Cancer Inst.* 80(13): 1053-1059 (1988).
Patel, N.V. et al., "Heregulin (HRG) and human epideral receptor (HER) 2 and 3 are modulated during *in vitro* human lung growth and differentiation," *Jour. of Invest. Med.*, (XP-002113357), vol. 45, No. 3, pp. 284A (1997).
Brockes et al , "Glial growth factor-like activity in Schwann Cell tumors", *Annals of Neurology*, 20:317-322 (1986).
Brockes et al , "Purification and preliminary characterization of a glial growth factor from the bovine pituitary", *Journal of Biological Chemistry*, 255(18):8374-8377 (1980).

(Continued)

Primary Examiner—David S Romeo
Assistant Examiner—Daniel C Gamett
(74) Attorney, Agent, or Firm—Merchant & Gould P.C.

(57) ABSTRACT

Ligands which bind to the HER2, HER3 and/or HER4 receptors are useful as normal epithelial cell growth factors.

11 Claims, 28 Drawing Sheets

OTHER PUBLICATIONS

Brockes et al , "Assay and isolation of glial growth factor from the bovine pituitary", *Methods in Enzymology*, 147:217-223 (1987).

Carraway et al., "The erbB3 gene product is a receptor for heregulin", *Journal of Biological Chemistry*, 269(19):14303-14306 (1994).

Corfas & Fischback, "The number of Na+ channels in cultured chick muscle is increased by ARIA, an acetylcholine receptor-inducing activity", *J. Neuroscience*, 13(5):2118-2125 (1993).

Danilenko et al., "Neu differentiation factor (NDF) accelerates epidermal migration and differentiation in excisional wounds" *FASEB*, 8(4-5):abst. no. 3101, p. A535 (1994).

Danilenko et al, "Neu Differentiation Factor Upregulates Epidermal Migration and Integrin Expression in Excisional Wounds", *Journal of Clinical Investigation*, 95(2):842-851 (1995).

Falls et al., "ARIA, a protein that stimulates acetylcholine receptor synthesis, is a member of the Neu ligand family", *Cell*, 72:801-815 (1993).

Fendly et al., "Characterization of Murine Monoclonal Antibodies Reactive to Either the Human Epidermal Growth Factor Receptor or HER2/neu Gene Product", *Cancer Research*, 50:1550-1558 (Mar. 1, 1990).

Ho, W. et al., "Sensory and Motor Neuron-derived Factor" *Journal of Biological Chemistry*, 270(24):14523-14532 (Jun. 16, 1995).

Holmes et al., "Identification of Heregulin, a Specific Activator of $p185^{erbB2}$", *Science*, 256,1205-1210 (May 22, 1992).

Lee et al., "Assignment of heregulin (HGL) to human chromosome 8p22-p11 by PCR analysis of somatic cell hybrid DNA" *Genomics*, 16:790-791 (1993).

Lemke & Brockes, "Identification and purification of glial growth factor", *J. Neurosci.*, 4(1):75-83 (1984).

Levi et al., "The functional characteristics of Schwann Cells cultured from human peripheral nerve after transplantation into a gap within the rat sciatic nerve", *J. Neuroscience*, 14(3):1309-1319 (1994).

Marchionni et al., "Glial growth factors are alternatively spliced erbB2 ligands expressed in the nervous system", *Nature*, 362:312-318 (1993).

Marikovsky et al., "ErbB-3 mediates differential mitogenic effects of NDF heregulin isoforms on mouse keratinocytes", *Oncogene*, 10:1403-1411 (1995).

Meyer & Birchmeir, "Distinct isoforms of neuregulin are expressed in mesenchymal and neuronal cells during mouse development", *Proc. Natl. Acad. Sci.*, 91:1064-1068 (1994).

Meyer et al., "Isoform-specific expression and function of neuregulin", *Development*, 124:3575-3586 (1997).

Orr-Urteger et al., "Neural expression and chromosomal mapping of Neu differentiation factor to 8p12-p21", *Proc. Natl. Acad. Sci. USA*, 90:1867-1871 (1993).

Patel et al., "Heregulin (HRG) and human epideral receptor (HER) 2 and 3 are modulated duri", *Jour. of Invest. Med.*, (XP002123357) 45(3):284A (1997).

Patel et al., *Am. J. Resp. Cell and Mol.e Biol.*, 22(4):432-440 (2000).

Peles et al., "Isolation of the Neu/HER-2 Stimulatory Ligand: A 44 Kd Glycoprotein that Induces Differentiation of Mammary Tumor Cells", *Cell*, 69(1):205-216 (1992).

Pinkas-Kramarski et al.,, "Brain neurons and glial cells express Neu differentiation factor/heregulin: A survival factor for astrocytes", *Proc. Natl. Sci. USA*, 91:9387-9391 (1994).

Plowman et al., "Heregulin induces tyrosine phosphorylation of $HER4/p180^{erbB4}$", *Nature (Letters to Nature)*, 366:473-475 (Dec. 2, 1993).

Ram et al., "Mitogenic Activity of Neu Differentiation Factor/Heregulin Mimics that of Epidermal Growth Factor and Insulin-Like Growth Factor-1 in Human Mammary Epithlial Cells", *J. Cellular Physiology*, 163:589-596 (1995).

Shaefer et al., "γ-Heregulin: a novel heregulin isoforms that is an autocrine growth factor for the human breast cancer cell line, MDA-MB-175", *Onogene*, 15:1385-1394 (1997).

Sklar et al., "A novel growth factor for muscle-rhGGF2", *J. Cell Biochem.*, (abstract W462) p. 540 (1994).

Sliwkowski et al., "Coexpression of erbB2 and erbB3 Proteins Reconstitutes a High Affinity Receptor for Heregulin", *Journal of Biological Chemistry*, 269(20): 14661-14665 (May 20, 1994).

*Taber's Cyclopedic Medical Dictionary*, 12th edition, F.A. Davis Company, p. E-52 (1973).

Tzahar et al., *EMBO Journal*, 16(16):4938-4950 (1997).

Wada et al., " Intermolecular Association of the $p185^{neu}$ Protein and EGF Receptor Modulates EGF Receptor Function", *Cell*, 61:1339-1347 (Jun. 29, 1990).

Wen et al., "Neu differentiation factor: a transmembrane glycoprotein containing an EGF Domain and an Immunoglobulin Homology Unit", *Cell*, 69(3):559-572 (1992).

Wen et al., "Structural and functional aspects of the multiplicity of neu differentiation factors", *Molecular & Cellular Biology*, 14(3):1909-1919 (1994).

Friess, et al., "Enhanced erbB-3 Expression in Human Pancreatic Cancer Correlates with Tumor Progression", *Clinical Cancer Research*, vol. 1, pp. 1413-1420 (1995).

King et al., "Ligand-independent tyrosine phosphorylation of EGF receptor and the erbB-2/neu protooncogene product is induced by hypersmotic shock", *Oncogene*, 4:13-18 (1989).

Kokai et al., "Synergistic Interaction of p185c-*neu* and the EGF Receptor Leads to Transformation of Rodent Fibroblasts", *Cell*, 58:287-292 (1989).

Kraus et al., "Demonstration of ligand-dependent signaling by the *erb*B-3 tyrosine kinase and its constitutive activation in human breast tumor cells", *Proc. Natl. Acad. Sci. USA*, 90:2900-2904 (1993).

Kraus et al., "Isolation and characterization of *ERBB3*, a third member of the *ERBB* / epidermal growth receptor family: Evidence for overexpression in a subset of human mammary tumors", *Proc. Natl. Acad. Sci. USA*, 86:9193-9197 (1989).

Lemke et al., "Identification and Purification of Glial Growth Factor", *The Journal of Neuroscience*, 4(1): 75-83 (1984).

Lemoine et al., "The *erb*B-3 Gene in Human Pancreatic Cancer", *Journal of Pathology*, 168:269-273 (1992).

Lemoine et al., "Expression of the *ERBB3* gene product in breast cancer", *Cancer*, 66:1116-1121 (1992).

Li et al., "Identification of Gas6 as a Growth Factor for Human Schwann Cells", *The Journal of Neuroscience*, 16(6):2012-2019 (1996).

Peles et al., "Cell-type specific interaction of Neu differentiation factor (NDF/heregulin) with Neu/HER-2 suggests complex ligand-receptor relationships", *The EMBO Journal*, 12(3):961-971 (1993).

Plowman et al., "Ligand-specific activation of $HER4/p180^{erbB4}$, a fourth member of the epidermal growth factor receptor family", *Proc. Natl. Acad. Sci. USA*, 90:1746-1750 (1993).

Poller et al., "Production and Characterization of a Polyclonal Antibody to the c-*erb*B-3 Protein: Examination of c-*erb*B-3 Protein Expression in Adenocarcinomas", *Journal of Pathology*, 168:275-280 (1992).

Rajkumar et al., "Expression of the C-*erb*B-3 Protein in Gastrointestinal Tract Tumours Determined by Monoclonal Antibody RTJI", *Journal of Pathology*, 170:271-278 (1993).

Sadick et al., "Analysis of Heregulin-Induced ErbB2 Phosphorylation with a High-Throughput Kinase Receptor Activation Enzyme-Linked Immunosorbant Assay", *Analytical Biochemistry*, 235:207-214, Article No. 0114 (1996).

Sanidas et al., "Expression of the c-erbB3 Gene Product in Gastric Cancer", *J. Cancer*, 54:935-940 (1993).

Slamon et al., "Studies of the HER-2/*neu* Proto-oncogene in Human Breat and Ovarian Cancer", *Science*, 244:707-712 (1989).

Slamon et al., "Human Breast Cancer: Correlation of Relapse and Survival with Amplification of the HER-2/*neu* Oncogene", *Science*, 235:177-182 (1987).

Stern et al., "EGF-stimulated tyrosine phosphorylation of $p185^{new}$: a potential model for receptor interactions", *The EMBO Journal*, 7(4):995-1001 (1988).

Puchelle et al., "Human airway xenograpft models of epithelial cell regeneration", *Respiratory Research*, 1(3):125-128 (2000).

Randell et al., "Isolation and Culture of Airway Epithelial Cells from Chronically Infected Human Lungs", *In Vitro Cell. Dev. Biol.*, 37:480-489 (2001).

Shimizu et al., "Expression of "cell-type-specific" markers during rat tracheal epithelial regeneration", *Am. J. Respir. Cell. Mol. Biol.*, 7(1):30-41 (1992).

Yukawa et al., "The effects of activated cosinophils and neutrophils on guinea pig airway epithelium in vitro", *Am. J. Respir. Cell. Mol. Biol.*, 2(4):341-353 (1990)

Zahm et al., "Wound repair of human surface respiratory epithelium", *Am. J. Respir. Cell. Mol. Biol.*, 5(3):242-248 (1991).

* cited by examiner

```
 GG GCG CGA GCG CCT CAG CGC GGC CGC TCG CTC TCC CCC  38
    Ala Arg Ala Pro Gln Arg Gly Arg Ser Leu Ser Pro
     1               5                  10

TCG AGG GAC AAA CTT TTC CCA AAC CCG ATC CGA GCC CTT  77
Ser Arg Asp Lys Leu Phe Pro Asn Pro Ile Arg Ala Leu
         15              20                      25

GGA CCA AAC TCG CCT GCG CCG AGA GCC GTC CGC GTA GAG  116
Gly Pro Asn Ser Pro Ala Pro Arg Ala Val Arg Val Glu
             30                      35

CGC TCC GTC TCC GGC GAG ATG TCC GAG CGC AAA GAA GGC  155
Arg Ser Val Ser Gly Glu Met Ser Glu Arg Lys Glu Gly
         40              45                  50

AGA GGC AAA GGG AAG GGC AAG AAG AAG GAG CGA GGC TCC  194
Arg Gly Lys Gly Lys Gly Lys Lys Lys Glu Arg Gly Ser
             55                  60

GGC AAG AAG CCG GAG TCC GCG GCG GGC AGC CAG AGC CCA  233
Gly Lys Lys Pro Glu Ser Ala Ala Gly Ser Gln Ser Pro
 65              70                      75

GCC TTG CCT CCC CGA TTG AAA GAG ATG AAA AGC CAG GAA  272
Ala Leu Pro Pro Arg Leu Lys Glu Met Lys Ser Gln Glu
             80              85                  90

TCG GCT GCA GGT TCC AAA CTA GTC CTT CGG TGT GAA ACC  311
Ser Ala Ala Gly Ser Lys Leu Val Leu Arg Cys Glu Thr
                 95                      100

AGT TCT GAA TAC TCC TCT CTC AGA TTC AAG TGG TTC AAG  350
Ser Ser Glu Tyr Ser Ser Leu Arg Phe Lys Trp Phe Lys
         105             110                     115

AAT GGG AAT GAA TTG AAT CGA AAA AAC AAA CCA CAA AAT  389
Asn Gly Asn Glu Leu Asn Arg Lys Asn Lys Pro Gln Asn
                 120                 125

ATC AAG ATA CAA AAA AAG CCA GGG AAG TCA GAA CTT CGC  428
Ile Lys Ile Gln Lys Lys Pro Gly Lys Ser Glu Leu Arg
130             135                     140

ATT AAC AAA GCA TCA CTG GCT GAT TCT GGA GAG TAT ATG  467
Ile Asn Lys Ala Ser Leu Ala Asp Ser Gly Glu Tyr Met
        145                 150                 155

TGC AAA GTG ATC AGC AAA TTA GGA AAT GAC AGT GCC TCT  506
Cys Lys Val Ile Ser Lys Leu Gly Asn Asp Ser Ala Ser
                160                     165
```

FIGURE 1A

```
GCC AAT ATC ACC ATC GTG GAA TCA AAC GAG ATC ATC ACT 545
Ala Asn Ile Thr Ile Val Glu Ser Asn Glu Ile Ile Thr
    170             175             180

GGT ATG CCA GCC TCA ACT GAA GGA GCA TAT GTG TCT TCA 584
Gly Met Pro Ala Ser Thr Glu Gly Ala Tyr Val Ser Ser
            185             190

GAG TCT CCC ATT AGA ATA TCA GTA TCC ACA GAA GGA GCA 623
Glu Ser Pro Ile Arg Ile Ser Val Ser Thr Glu Gly Ala
195             200             205

AAT ACT TCT TCA TCT ACA TCT ACA TCC ACC ACT GGG ACA 662
Asn Thr Ser Ser Ser Thr Ser Thr Ser Thr Thr Gly Thr
        210             215             220

AGC CAT CTT GTA AAA TGT GCG GAG AAG GAG AAA ACT TTC 701
Ser His Leu Val Lys Cys Ala Glu Lys Glu Lys Thr Phe
                225             230

TGT GTG AAT GGA GGG GAG TGC TTC ATG GTG AAA GAC CTT 740
Cys Val Asn Gly Gly Glu Cys Phe Met Val Lys Asp Leu
            235             240             245

TCA AAC CCC TCG AGA TAC TTG TGC AAG TGC CAA CCT GGA 779
Ser Asn Pro Ser Arg Tyr Leu Cys Lys Cys Gln Pro Gly
                250             255

TTC ACT GGA GCA AGA TGT ACT GAG AAT GTG CCC ATG AAA 818
Phe Thr Gly Ala Arg Cys Thr Glu Asn Val Pro Met Lys
260             265             270

GTC CAA AAC CAA GAA AAG GCG GAG GAG CTG TAC CAG AAG 857
Val Gln Asn Gln Glu Lys Ala Glu Glu Leu Tyr Gln Lys
        275             280             285

AGA GTG CTG ACC ATA ACC GGC ATC TGC ATC GCC CTC CTT 896
Arg Val Leu Thr Ile Thr Gly Ile Cys Ile Ala Leu Leu
                290             295

GTG GTC GGC ATC ATG TGT GTG GTG GCC TAC TGC AAA ACC 935
Val Val Gly Ile Met Cys Val Val Ala Tyr Cys Lys Thr
        300             305             310

AAG AAA CAG CGG AAA AAG CTG CAT GAC CGT CTT CGG CAG 974
Lys Lys Gln Arg Lys Lys Leu His Asp Arg Leu Arg Gln
                315             320

AGC CTT CGG TCT GAA CGA AAC AAT ATG ATG AAC ATT GCC 1013
Ser Leu Arg Ser Glu Arg Asn Asn Met Met Asn Ile Ala
325             330             335
```

FIGURE 1B

```
AAT GGG CCT CAC CAT CCT AAC CCA CCC CCC GAG AAT GTC 1052
Asn Gly Pro His His Pro Asn Pro Pro Pro Glu Asn Val
        340             345                 350

CAG CTG GTG AAT CAA TAC GTA TCT AAA AAC GTC ATC TCC 1091
Gln Leu Val Asn Gln Tyr Val Ser Lys Asn Val Ile Ser
                355                 360

AGT GAG CAT ATT GTT GAG AGA GAA GCA GAG ACA TCC TTT 1130
Ser Glu His Ile Val Glu Arg Glu Ala Glu Thr Ser Phe
    365                 370                 375

TCC ACC AGT CAC TAT ACT TCC ACA GCC CAT CAC TCC ACT 1169
Ser Thr Ser His Tyr Thr Ser Thr Ala His His Ser Thr
            380                 385

ACT GTC ACC CAG ACT CCT AGC CAC AGC TGG AGC AAC GGA 1208
Thr Val Thr Gln Thr Pro Ser His Ser Trp Ser Asn Gly
390                 395                 400

CAC ACT GAA AGC ATC CTT TCC GAA AGC CAC TCT GTA ATC 1247
His Thr Glu Ser Ile Leu Ser Glu Ser His Ser Val Ile
        405                 410                 415

GTG ATG TCA TCC GTA GAA AAC AGT AGG CAC AGC AGC CCA 1286
Val Met Ser Ser Val Glu Asn Ser Arg His Ser Ser Pro
                420                 425

ACT GGG GGC CCA AGA GGA CGT CTT AAT GGC ACA GGA GGC 1325
Thr Gly Gly Pro Arg Gly Arg Leu Asn Gly Thr Gly Gly
    430                 435                 440

CCT CGT GAA TGT AAC AGC TTC CTC AGG CAT GCC AGA GAA 1364
Pro Arg Glu Cys Asn Ser Phe Leu Arg His Ala Arg Glu
            445                 450

ACC CCT GAT TCC TAC CGA GAC TCT CCT CAT AGT GAA AGG 1403
Thr Pro Asp Ser Tyr Arg Asp Ser Pro His Ser Glu Arg
455                 460                 465

TAT GTG TCA GCC ATG ACC ACC CCG GCT CGT ATG TCA CCT 1442
Tyr Val Ser Ala Met Thr Thr Pro Ala Arg Met Ser Pro
        470                 475                 480

GTA GAT TTC CAC ACG CCA AGC TCC CCC AAA TCG CCC CCT 1481
Val Asp Phe His Thr Pro Ser Ser Pro Lys Ser Pro Pro
                485                 490

TCG GAA ATG TCT CCA CCC GTG TCC AGC ATG ACG GTG TCC 1520
Ser Glu Met Ser Pro Pro Val Ser Ser Met Thr Val Ser
    495                 500                 505
```

FIGURE 1C

```
ATG CCT TCC ATG GCG GTC AGC CCC TTC ATG GAA GAA GAG 1559
Met Pro Ser Met Ala Val Ser Pro Phe Met Glu Glu Glu
            510             515

AGA CCT CTA CTT CTC GTG ACA CCA CCA AGG CTG CGG GAG 1598
Arg Pro Leu Leu Leu Val Thr Pro Pro Arg Leu Arg Glu
520             525             530

AAG AAG TTT GAC CAT CAC CCT CAG CAG TTC AGC TCC TTC 1637
Lys Lys Phe Asp His His Pro Gln Gln Phe Ser Ser Phe
        535             540             545

CAC CAC AAC CCC GCG CAT GAC AGT AAC AGC CTC CCT GCT 1676
His His Asn Pro Ala His Asp Ser Asn Ser Leu Pro Ala
            550             555

AGC CCC TTG AGG ATA GTG GAG GAT GAG GAG TAT GAA ACG 1715
Ser Pro Leu Arg Ile Val Glu Asp Glu Glu Tyr Glu Thr
    560             565             570

ACC CAA GAG TAC GAG CCA GCC CAA GAG CCT GTT AAG AAA 1754
Thr Gln Glu Tyr Glu Pro Ala Gln Glu Pro Val Lys Lys
            575             580

CTC GCC AAT AGC CGG CGG GCC AAA AGA ACC AAG CCC AAT 1793
Leu Ala Asn Ser Arg Arg Ala Lys Arg Thr Lys Pro Asn
585             590             595

GGC CAC ATT GCT AAC AGA TTG GAA GTG GAC AGC AAC ACA 1832
Gly His Ile Ala Asn Arg Leu Glu Val Asp Ser Asn Thr
        600             605             610

AGC TCC CAG AGC AGT AAC TCA GAG AGT GAA ACA GAA GAT 1871
Ser Ser Gln Ser Ser Asn Ser Glu Ser Glu Thr Glu Asp
            615                 620

GAA AGA GTA GGT GAA GAT ACG CCT TTC CTG GGC ATA CAG 1910
Glu Arg Val Gly Glu Asp Thr Pro Phe Leu Gly Ile Gln
    625             630             635

AAC CCC CTG GCA GCC AGT CTT GAG GCA ACA CCT GCC TTC 1949
Asn Pro Leu Ala Ala Ser Leu Glu Ala Thr Pro Ala Phe
            640             645

CGC CTG GCT GAC AGC AGG ACT AAC CCA GCA GGC CGC TTC 1988
Arg Leu Ala Asp Ser Arg Thr Asn Pro Ala Gly Arg Phe
650             655             660

TCG ACA CAG GAA GAA ATC CAG G 2010
Ser Thr Gln Glu Glu Ile Gln
        665             669
```

FIGURE 1D

```
GG  GAC AAA CTT TTC CCA AAC CCG ATC CGA GCC CTT GGA  38
    Asp Lys Leu Phe Pro Asn Pro Ile Arg Ala Leu Gly
    1               5                   10

CCA AAC TCG CCT GCG CCG AGA GCC GTC CGC GTA GAG CGC  77
Pro Asn Ser Pro Ala Pro Arg Ala Val Arg Val Glu Arg
        15              20                  25

TCC GTC TCC GGC GAG ATG TCC GAG CGC AAA GAA GGC AGA  116
Ser Val Ser Gly Glu Met Ser Glu Arg Lys Glu Gly Arg
                30                  35

GGC AAA GGG AAG GGC AAG AAG AAG GAG CGA GGC TCC GGC  155
Gly Lys Gly Lys Gly Lys Lys Lys Glu Arg Gly Ser Gly
    40                  45                  50

AAG AAG CCG GAG TCC GCG GCG GGC AGC CAG AGC CCA GCC  194
Lys Lys Pro Glu Ser Ala Ala Gly Ser Gln Ser Pro Ala
            55                  60

TTG CCT CCC CAA TTG AAA GAG ATG AAA AGC CAG GAA TCG  233
Leu Pro Pro Gln Leu Lys Glu Met Lys Ser Gln Glu Ser
65                  70                  75

GCT GCA GGT TCC AAA CTA GTC CTT CGG TGT GAA ACC AGT  272
Ala Ala Gly Ser Lys Leu Val Leu Arg Cys Glu Thr Ser
        80                  85                  90

TCT GAA TAC TCC TCT CTC AGA TTC AAG TGG TTC AAG AAT  311
Ser Glu Tyr Ser Ser Leu Arg Phe Lys Trp Phe Lys Asn
                95                  100

GGG AAT GAA TTG AAT CGA AAA AAC AAA CCA CAA AAT ATC  350
Gly Asn Glu Leu Asn Arg Lys Asn Lys Pro Gln Asn Ile
    105                 110                 115

AAG ATA CAA AAA AAG CCA GGG AAG TCA GAA CTT CGC ATT  389
Lys Ile Gln Lys Lys Pro Gly Lys Ser Glu Leu Arg Ile
            120                 125

AAC AAA GCA TCA CTG GCT GAT TCT GGA GAG TAT ATG TGC  428
Asn Lys Ala Ser Leu Ala Asp Ser Gly Glu Tyr Met Cys
130                 135                 140

AAA GTG ATC AGC AAA TTA GGA AAT GAC AGT GCC TCT GCC  467
Lys Val Ile Ser Lys Leu Gly Asn Asp Ser Ala Ser Ala
        145                 150                 155

AAT ATC ACC ATC GTG GAA TCA AAC GAG ATC ATC ACT GGT  506
Asn Ile Thr Ile Val Glu Ser Asn Glu Ile Ile Thr Gly
                160                 165
```

FIGURE 2A

```
ATG CCA GCC TCA ACT GAA GGA GCA TAT GTG TCT TCA GAG 545
Met Pro Ala Ser Thr Glu Gly Ala Tyr Val Ser Ser Glu
    170             175             180

TCT CCC ATT AGA ATA TCA GTA TCC ACA GAA GGA GCA AAT 584
Ser Pro Ile Arg Ile Ser Val Ser Thr Glu Gly Ala Asn
            185             190

ACT TCT TCA TCT ACA TCT ACA TCC ACC ACT GGG ACA AGC 623
Thr Ser Ser Ser Thr Ser Thr Ser Thr Thr Gly Thr Ser
195             200             205

CAT CTT GTA AAA TGT GCG GAG AAG GAG AAA ACT TTC TGT 662
His Leu Val Lys Cys Ala Glu Lys Glu Lys Thr Phe Cys
        210             215             220

GTG AAT GGA GGG GAG TGC TTC ATG GTG AAA GAC CTT TCA 701
Val Asn Gly Gly Glu Cys Phe Met Val Lys Asp Leu Ser
                225             230

AAC CCC TCG AGA TAC TTG TGC AAG TGC CCA AAT GAG TTT 740
Asn Pro Ser Arg Tyr Leu Cys Lys Cys Pro Asn Glu Phe
        235             240             245

ACT GGT GAT CGC TGC CAA AAC TAC GTA ATG GCC AGC TTC 779
Thr Gly Asp Arg Cys Gln Asn Tyr Val Met Ala Ser Phe
            250             255

TAC AAG CAT CTT GGG ATT GAA TTT ATG GAG GCG GAG GAG 818
Tyr Lys His Leu Gly Ile Glu Phe Met Glu Ala Glu Glu
260             265             270

CTG TAC CAG AAG AGA GTG CTG ACC ATA ACC GGC ATC TGC 857
Leu Tyr Gln Lys Arg Val Leu Thr Ile Thr Gly Ile Cys
        275             280             285

ATC GCC CTC CTT GTG GTC GGC ATC ATG TGT GTG GTG GCC 896
Ile Ala Leu Leu Val Val Gly Ile Met Cys Val Val Ala
                290             295

TAC TGC AAA ACC AAG AAA CAG CGG AAA AAG CTG CAT GAC 935
Tyr Cys Lys Thr Lys Lys Gln Arg Lys Lys Leu His Asp
        300             305             310

CGT CTT CGG CAG AGC CTT CGG TCT GAA CGA AAC AAT ATG 974
Arg Leu Arg Gln Ser Leu Arg Ser Glu Arg Asn Asn Met
            315             320

ATG AAC ATT GCC AAT GGG CCT CAC CAT CCT AAC CCA CCC 1013
Met Asn Ile Ala Asn Gly Pro His His Pro Asn Pro Pro
325             330             335
```

FIGURE 2B

```
CCC GAG AAT GTC CAG CTG GTG AAT CAA TAC GTA TCT AAA  1052
Pro Glu Asn Val Gln Leu Val Asn Gln Tyr Val Ser Lys
        340             345             350

AAC GTC ATC TCC AGT GAG CAT ATT GTT GAG AGA GAA GCA  1091
Asn Val Ile Ser Ser Glu His Ile Val Glu Arg Glu Ala
                355             360

GAG ACA TCC TTT TCC ACC AGT CAC TAT ACT TCC ACA GCC  1130
Glu Thr Ser Phe Ser Thr Ser His Tyr Thr Ser Thr Ala
        365             370             375

CAT CAC TCC ACT ACT GTC ACC CAG ACT CCT AGC CAC AGC  1169
His His Ser Thr Thr Val Thr Gln Thr Pro Ser His Ser
                380             385

TGG AGC AAC GGA CAC ACT GAA AGC ATC CTT TCC GAA AGC  1208
Trp Ser Asn Gly His Thr Glu Ser Ile Leu Ser Glu Ser
390             395             400

CAC TCT GTA ATC GTG ATG TCA TCC GTA GAA AAC AGT AGG  1247
His Ser Val Ile Val Met Ser Ser Val Glu Asn Ser Arg
        405             410             415

CAC AGC AGC CCA ACT GGG GGC CCA AGA GGA CGT CTT AAT  1286
His Ser Ser Pro Thr Gly Gly Pro Arg Gly Arg Leu Asn
                420             425

GGC ACA GGA GGC CCT CGT GAA TGT AAC AGC TTC CTC AGG  1325
Gly Thr Gly Gly Pro Arg Glu Cys Asn Ser Phe Leu Arg
        430             435             440

CAT GCC AGA GAA ACC CCT GAT TCC TAC CGA GAC TCT CCT  1364
His Ala Arg Glu Thr Pro Asp Ser Tyr Arg Asp Ser Pro
                445             450

CAT AGT GAA AGG TAT GTG TCA GCC ATG ACC ACC CCG GCT  1403
His Ser Glu Arg Tyr Val Ser Ala Met Thr Thr Pro Ala
455             460             465

CGT ATG TCA CCT GTA GAT TTC CAC ACG CCA AGC TCC CCC  1442
Arg Met Ser Pro Val Asp Phe His Thr Pro Ser Ser Pro
        470             475             480

AAA TCG CCC CCT TCG GAA ATG TCT CCA CCC GTG TCC AGC  1481
Lys Ser Pro Pro Ser Glu Met Ser Pro Pro Val Ser Ser
                485             490

ATG ACG GTG TCC ATG CCT TCC ATG GCG GTC AGC CCC TTC  1520
Met Thr Val Ser Met Pro Ser Met Ala Val Ser Pro Phe
        495             500             505
```

FIGURE 2C

```
ATG GAA GAA GAG AGA CCT CTA CTT CTC GTG ACA CCA CCA  1559
Met Glu Glu Glu Arg Pro Leu Leu Leu Val Thr Pro Pro
                    510                 515

AGG CTG CGG GAG AAG TTT GAC CAT CAC CCT CAG CAG       1598
Arg Leu Arg Glu Lys Phe Asp His His Pro Gln Gln
520                 525                 530

TTC AGC TCC TTC CAC CAC AAC CCC GCG CAT GAC AGT AAC   1637
Phe Ser Ser Phe His His Asn Pro Ala His Asp Ser Asn
        535                 540                 545

AGC CTC CCT GCT AGC CCC TTG AGG ATA GTG GAG GAT GAG   1676
Ser Leu Pro Ala Ser Pro Leu Arg Ile Val Glu Asp Glu
            550                 555

GAG TAT GAA ACG CAA ACC GAG TAC CCA CAA GCC CAA GAG   1715
Glu Tyr Glu Thr Gln Thr Glu Tyr Pro Gln Ala Gln Glu
        560                 565                 570

CCT GTT AAG AAA CTC GCC AAT AGC CGG CGG GCC AAA AGA   1754
Pro Val Lys Lys Leu Ala Asn Ser Arg Arg Ala Lys Arg
            575                 580

ACC AAG CCC AAT GGC CAC ATT GCT AAC AGA TTG GAA GTG   1793
Thr Lys Pro Asn Gly His Ile Ala Asn Arg Leu Glu Val
585                 590                 595

GAC AGC AAC ACA AGC TCC CAG AGC AGT AAC TCA GAG AGT   1832
Asp Ser Asn Thr Ser Ser Gln Ser Ser Asn Ser Glu Ser
        600                 605                 610
```

FIGURE 2D

```
GAA ACA GAA GAT GAA AGA GTA GGT GAA GAT ACG CCT TTC 1871
Glu Thr Glu Asp Glu Arg Val Gly Glu Asp Thr Pro Phe
            615                 620

CTG GGC ATA CAG AAC CCC CTG GCA GCC AGT CTT GAG GCA 1910
Leu Gly Ile Gln Asn Pro Leu Ala Ala Ser Leu Glu Ala
        625                 630                 635

ACA CCT GCC TTC CGC CTG GCT GAC AGC AGG ACT AAC CCA 1949
Thr Pro Ala Phe Arg Leu Ala Asp Ser Arg Thr Asn Pro
            640                 645

GCA GGC CGC TTC TCG ACA CAG GAA ATC CAG GCC AGG 1988
Ala Gly Arg Phe Ser Thr Gln Glu Ile Gln Ala Arg
        650                 655                 660

CTG TCT AGT GTA ATT GCT AAC CAA GAC CCT ATT GCT GTA TA 2029
Leu Ser Ser Val Ile Ala Asn Gln Asp Pro Ile Ala Val
            665                 670                 675

A AACCTAAATA AACACATAGA TTCACCTGTA AAACTTTATT                    2070

TTATATAATA AAGTATTCCA CCCTAAATTA AACAATTTAT TTTATTTTAG           2120

CAGTTCTGCA AATAGAAAAC AGGAAAAAAA CTTTTATAAA TTAAATATAT           2170

GTATGTAAAA ATGAAAAAAA AAAAAAAAA                                 2199
```

FIGURE 2E

```
GTGGCTGCGG GGCAATTGAA AAAGAGCCGG CGAGGAGTTC CCCGAAACTT 50

GTTGGAACTC CGGGCTCGCG CGGAGGCCAG GAGCTGAGCG GCGGCGGCTG 100

CCGGACGATG GGAGCGTGAG CAGGACGGTG ATAACCTCTC CCCGATCGGG 150

TTGCGAGGGC GCCGGGCAGA GGCCAGGACG CGAGCCGCCA GCGGCGGGAC 200

CCATCGACGA CTTCCCGGGG CGACAGGAGC AGCCCCGAGA GCCAGGGCGA 250

GCGCCCGTTC CAGGTGGCCG GACCGCCCGC CGCGTCCGCG CCGCGCTCCC 300

TGCAGGCAAC GGGAGACGCC CCCGCGCAGC GCGAGCGCCT CAGCGCGGCC 350

GCTCGCTCTC CCCATCGAGG GACAAACTTT TCCCAAACCC GATCCGAGCC 400

CTTGGACCAA ACTCGCCTGC GCCGAGAGCC GTCCGCGTAG AGCGCTCCGT 450
```

```
CTCCGGCGAG  ATG TCC GAG CGC AAA GAA GGC AGA GGC AAA 490
            Met Ser Glu Arg Lys Glu Gly Arg Gly Lys
             1               5                  10

GGG AAG GGC AAG AAG AAG GAG CGA GGC TCC GGC AAG AAG 529
Gly Lys Gly Lys Lys Lys Glu Arg Gly Ser Gly Lys Lys
             15                  20

CCG GAG TCC GCG GCG GGC AGC CAG AGC CCA GCC TTG CCT 568
Pro Glu Ser Ala Ala Gly Ser Gln Ser Pro Ala Leu Pro
 25                  30                  35

CCC CAA TTG AAA GAG ATG AAA AGC CAG GAA TCG GCT GCA 607
Pro Gln Leu Lys Glu Met Lys Ser Gln Glu Ser Ala Ala
             40                  45

GGT TCC AAA CTA GTC CTT CGG TGT GAA ACC AGT TCT GAA 646
Gly Ser Lys Leu Val Leu Arg Cys Glu Thr Ser Ser Glu
 50                  55                  60

TAC TCC TCT CTC AGA TTC AAG TGG TTC AAG AAT GGG AAT 685
Tyr Ser Ser Leu Arg Phe Lys Trp Phe Lys Asn Gly Asn
             65                  70                  75

GAA TTG AAT CGA AAA AAC AAA CCA CAA AAT ATC AAG ATA 724
Glu Leu Asn Arg Lys Asn Lys Pro Gln Asn Ile Lys Ile
             80                  85
```

FIGURE 3A

```
CAA AAA AAG CCA GGG AAG TCA GAA CTT CGC ATT AAC AAA  763
Gln Lys Lys Pro Gly Lys Ser Glu Leu Arg Ile Asn Lys
    90              95                  100

GCA TCA CTG GCT GAT TCT GGA GAG TAT ATG TGC AAA GTG  802
Ala Ser Leu Ala Asp Ser Gly Glu Tyr Met Cys Lys Val
            105                 110

ATC AGC AAA TTA GGA AAT GAC AGT GCC TCT GCC AAT ATC  841
Ile Ser Lys Leu Gly Asn Asp Ser Ala Ser Ala Asn Ile
115             120                 125

ACC ATC GTG GAA TCA AAC GAG ATC ATC ACT GGT ATG CCA  880
Thr Ile Val Glu Ser Asn Glu Ile Ile Thr Gly Met Pro
        130                 135                 140

GCC TCA ACT GAA GGA GCA TAT GTG TCT TCA GAG TCT CCC  919
Ala Ser Thr Glu Gly Ala Tyr Val Ser Ser Glu Ser Pro
                145                 150

ATT AGA ATA TCA GTA TCC ACA GAA GGA GCA AAT ACT TCT  958
Ile Arg Ile Ser Val Ser Thr Glu Gly Ala Asn Thr Ser
        155                 160                 165

TCA TCT ACA TCT ACA TCC ACC ACT GGG ACA AGC CAT CTT  997
Ser Ser Thr Ser Thr Ser Thr Thr Gly Thr Ser His Leu
                170                 175

GTA AAA TGT GCG GAG AAG GAG AAA ACT TTC TGT GTG AAT  1036
Val Lys Cys Ala Glu Lys Glu Lys Thr Phe Cys Val Asn
180                 185                 190

GGA GGG GAG TGC TTC ATG GTG AAA GAC CTT TCA AAC CCC  1075
Gly Gly Glu Cys Phe Met Val Lys Asp Leu Ser Asn Pro
        195                 200                 205

TCG AGA TAC TTG TGC AAG TGC CCA AAT GAG TTT ACT GGT  1114
Ser Arg Tyr Leu Cys Lys Cys Pro Asn Glu Phe Thr Gly
                210                 215

GAT CGC TGC CAA AAC TAC GTA ATG GCC AGC TTC TAC AAG  1153
Asp Arg Cys Gln Asn Tyr Val Met Ala Ser Phe Tyr Lys
        220                 225                 230

GCG GAG GAG CTG TAC CAG AAG AGA GTG CTG ACC ATA ACC  1192
Ala Glu Glu Leu Tyr Gln Lys Arg Val Leu Thr Ile Thr
                235                 240

GGC ATC TGC ATC GCC CTC CTT GTG GTC GGC ATC ATG TGT  1231
Gly Ile Cys Ile Ala Leu Leu Val Val Gly Ile Met Cys
245                 250                 255

GTG GTG GCC TAC TGC AAA ACC AAG AAA CAG CGG AAA AAG  1270
Val Val Ala Tyr Cys Lys Thr Lys Lys Gln Arg Lys Lys
        260                 265                 270
```

FIGURE 3B

```
CTG CAT GAC CGT CTT CGG CAG AGC CTT CGG TCT GAA CGA  1309
Leu His Asp Arg Leu Arg Gln Ser Leu Arg Ser Glu Arg
            275                 280

AAC AAT ATG ATG AAC ATT GCC AAT GGG CCT CAC CAT CCT  1348
Asn Asn Met Met Asn Ile Ala Asn Gly Pro His His Pro
        285                 290                 295

AAC CCA CCC CCC GAG AAT GTC CAG CTG GTG AAT CAA TAC  1387
Asn Pro Pro Pro Glu Asn Val Gln Leu Val Asn Gln Tyr
            300                 305

GTA TCT AAA AAC GTC ATC TCC AGT GAG CAT ATT GTT GAG  1426
Val Ser Lys Asn Val Ile Ser Ser Glu His Ile Val Glu
310                 315                 320

AGA GAA GCA GAG ACA TCC TTT TCC ACC AGT CAC TAT ACT  1465
Arg Glu Ala Glu Thr Ser Phe Ser Thr Ser His Tyr Thr
        325                 330                 335

TCC ACA GCC CAT CAC TCC ACT ACT GTC ACC CAG ACT CCT  1504
Ser Thr Ala His His Ser Thr Thr Val Thr Gln Thr Pro
            340                 345

AGC CAC AGC TGG AGC AAC GGA CAC ACT GAA AGC ATC CTT  1543
Ser His Ser Trp Ser Asn Gly His Thr Glu Ser Ile Leu
        350                 355                 360

TCC GAA AGC CAC TCT GTA ATC GTG ATG TCA TCC GTA GAA  1582
Ser Glu Ser His Ser Val Ile Val Met Ser Ser Val Glu
            365                 370

AAC AGT AGG CAC AGC AGC CCA ACT GGG GGC CCA AGA GGA  1621
Asn Ser Arg His Ser Ser Pro Thr Gly Gly Pro Arg Gly
375                 380                 385

CGT CTT AAT GGC ACA GGA GGC CCT CGT GAA TGT AAC AGC  1660
Arg Leu Asn Gly Thr Gly Gly Pro Arg Glu Cys Asn Ser
        390                 395                 400

TTC CTC AGG CAT GCC AGA GAA ACC CCT GAT TCC TAC CGA  1699
Phe Leu Arg His Ala Arg Glu Thr Pro Asp Ser Tyr Arg
            405                 410

GAC TCT CCT CAT AGT GAA AGG TAT GTG TCA GCC ATG ACC  1738
Asp Ser Pro His Ser Glu Arg Tyr Val Ser Ala Met Thr
        415                 420                 425

ACC CCG GCT CGT ATG TCA CCT GTA GAT TTC CAC ACG CCA  1777
Thr Pro Ala Arg Met Ser Pro Val Asp Phe His Thr Pro
            430                 435

AGC TCC CCC AAA TCG CCC CCT TCG GAA ATG TCT CCA CCC  1816
Ser Ser Pro Lys Ser Pro Pro Ser Glu Met Ser Pro Pro
440                 445                 450
```

FIGURE 3C

```
GTG TCC AGC ATG ACG GTG TCC AAG CCT TCC ATG GCG GTC 1855
Val Ser Ser Met Thr Val Ser Lys Pro Ser Met Ala Val
        455             460                 465

AGC CCC TTC ATG GAA GAA GAG AGA CCT CTA CTT CTC GTG 1894
Ser Pro Phe Met Glu Glu Glu Arg Pro Leu Leu Leu Val
        470                 475

ACA CCA CCA AGG CTG CGG GAG AAG AAG TTT GAC CAT CAC 1933
Thr Pro Pro Arg Leu Arg Glu Lys Lys Phe Asp His His
        480             485                 490

CCT CAG CAG TTC AGC TCC TTC CAC CAC AAC CCC GCG CAT 1972
Pro Gln Gln Phe Ser Ser Phe His His Asn Pro Ala His
        495             500

GAC AGT AAC AGC CTC CCT GCT AGC CCC TTG AGG ATA GTG 2011
Asp Ser Asn Ser Leu Pro Ala Ser Pro Leu Arg Ile Val
505             510             515

GAG GAT GAG GAG TAT GAA ACG ACC CAA GAG TAC GAG CCA 2050
Glu Asp Glu Glu Tyr Glu Thr Thr Gln Glu Tyr Glu Pro
        520             525             530

GCC CAA GAG CCT GTT AAG AAA CTC GCC AAT AGC CGG CGG 2089
Ala Gln Glu Pro Val Lys Lys Leu Ala Asn Ser Arg Arg
                535             540

GCC AAA AGA ACC AAG CCC AAT GGC CAC ATT GCT AAC AGA 2128
Ala Lys Arg Thr Lys Pro Asn Gly His Ile Ala Asn Arg
545             550             555

TTG GAA GTG GAC AGC AAC ACA AGC TCC CAG AGC AGT AAC 2167
Leu Glu Val Asp Ser Asn Thr Ser Ser Gln Ser Ser Asn
        560             565

TCA GAG AGT GAA ACA GAA GAT GAA AGA GTA GGT GAA GAT 2206
Ser Glu Ser Glu Thr Glu Asp Glu Arg Val Gly Glu Asp
570             575             580

ACG CCT TTC CTG GGC ATA CAG AAC CCC CTG GCA GCC AGT 2245
Thr Pro Phe Leu Gly Ile Gln Asn Pro Leu Ala Ala Ser
        585             590             595

CTT GAG GCA ACA CCT GCC TTC CGC CTG GCT GAC AGC AGG 2284
Leu Glu Ala Thr Pro Ala Phe Arg Leu Ala Asp Ser Arg
                600             605

ACT AAC CCA GCA GGC CGC TTC TCG ACA CAG GAA GAA ATC 2323
Thr Asn Pro Ala Gly Arg Phe Ser Thr Gln Glu Glu Ile
        610             615             620

CAG GCC AGG CTG TCT AGT GTA ATT GCT AAC CAA GAC CCT 2362
Gln Ala Arg Leu Ser Ser Val Ile Ala Asn Gln Asp Pro
            625             630
```

FIGURE 3D

```
ATT GCT GTA TAAAACCTA AATAAACACA TAGATTCACC TGTAAAACTT 2410
Ile Ala Val
635     637

TATTTTATAT AATAAAGTAT TCCACCTTAA ATTAAACAAT TTATTTTATT 2460

TTAGCAGTTC TGCAAATAAA AAAAAAAAAA 2490
```

FIGURE 3E

```
GCGCCTGCCT CCAACCTGCG GGCGGGAGGT GGGTGGCTGC GGGGCAATTG 50

AAAAAGAGCC GGCGAGGAGT TCCCCGAAAC TTGTTGGAAC TCCGGGCTCG 100

CGCGGAGGCC AGGAGCTGAG CGGCGGCGGC TGCCGGACGA TGGGAGCGTG 150

AGCAGGACGG TGATAACCTC TCCCCGATCG GGTTGCGAGG GCGCCGGGCA 200

GAGGCCAGGA CGCGAGCCGC CAGCGGCGGG ACCCATCGAC GACTTCCCGG 250

GGCGACAGGA GCAGCCCCGA GAGCCAGGGC GAGCGCCCGT TCCAGGTGGC 300

CGGACCGCCC GCCGCGTCCG CGCCGCGCTC CCTGCAGGCA ACGGGAGACG 350

CCCCCGCGCA GCGCGAGCGC CTCAGCGCGG CCGCTCGCTC TCCCCATCGA 400

GGGACAAACT TTTCCCAAAC CCGATCCGAG CCCTTGGACC AAACTCGCCT 450

GCGCCGAGAG CCGTCCGCGT AGAGCGCTCC GTCTCCGGCG AG    ATG   495
                                                  Met
                                                   1
```

| TCC | GAG | CGC | AAA | GAA | GGC | AGA | GGC | AAA | GGG | AAG | GGC | AAG | 534 |
|-----|-----|-----|-----|-----|-----|-----|-----|-----|-----|-----|-----|-----|-----|
| Ser | Glu | Arg | Lys | Glu | Gly | Arg | Gly | Lys | Gly | Lys | Gly | Lys |     |
|     |     |     |   5 |     |     |     |     |  10 |     |     |     |     |     |

| AAG | AAG | GAG | CGA | GGC | TCC | GGC | AAG | AAG | CCG | GAG | TCC | GCG | 573 |
| Lys | Lys | Glu | Arg | Gly | Ser | Gly | Lys | Lys | Pro | Glu | Ser | Ala |     |
|  15 |     |     |     |     |  20 |     |     |     |     |  25 |     |     |     |

| GCG | GGC | AGC | CAG | AGC | CCA | GCC | TTG | CCT | CCC | CAA | TTG | AAA | 612 |
| Ala | Gly | Ser | Gln | Ser | Pro | Ala | Leu | Pro | Pro | Gln | Leu | Lys |     |
|     |     |  30 |     |     |     |     |  35 |     |     |     |     |  40 |     |

| GAG | ATG | AAA | AGC | CAG | GAA | TCG | GCT | GCA | GGT | TCC | AAA | CTA | 651 |
| Glu | Met | Lys | Ser | Gln | Glu | Ser | Ala | Ala | Gly | Ser | Lys | Leu |     |
|     |     |     |     |  45 |     |     |     |     |  50 |     |     |     |     |

| GTC | CTT | CGG | TGT | GAA | ACC | AGT | TCT | GAA | TAC | TCC | TCT | CTC | 690 |
| Val | Leu | Arg | Cys | Glu | Thr | Ser | Ser | Glu | Tyr | Ser | Ser | Leu |     |
|     |  55 |     |     |     |     |  60 |     |     |     |     |  65 |     |     |

| AGA | TTC | AAG | TGG | TTC | AAG | AAT | GGG | AAT | GAA | TTG | AAT | CGA | 729 |
| Arg | Phe | Lys | Trp | Phe | Lys | Asn | Gly | Asn | Glu | Leu | Asn | Arg |     |
|     |     |  70 |     |     |     |     |  75 |     |     |     |     |     |     |

FIGURE 4A

```
AAA AAC AAA CCA CAA AAT ATC AAG ATA CAA AAA AAG CCA  768
Lys Asn Lys Pro Gln Asn Ile Lys Ile Gln Lys Lys Pro
 80              85              90

GGG AAG TCA GAA CTT CGC ATT AAC AAA GCA TCA CTG GCT  807
Gly Lys Ser Glu Leu Arg Ile Asn Lys Ala Ser Leu Ala
         95              100             105

GAT TCT GGA GAG TAT ATG TGC AAA GTG ATC AGC AAA TTA  846
Asp Ser Gly Glu Tyr Met Cys Lys Val Ile Ser Lys Leu
                 110             115

GGA AAT GAC AGT GCC TCT GCC AAT ATC ACC ATC GTG GAA  885
Gly Asn Asp Ser Ala Ser Ala Asn Ile Thr Ile Val Glu
     120             125             130

TCA AAC GAG ATC ATC ACT GGT ATG CCA GCC TCA ACT GAA  924
Ser Asn Glu Ile Ile Thr Gly Met Pro Ala Ser Thr Glu
             135             140

GGA GCA TAT GTG TCT TCA GAG TCT CCC ATT AGA ATA TCA  963
Gly Ala Tyr Val Ser Ser Glu Ser Pro Ile Arg Ile Ser
145             150             155

GTA TCC ACA GAA GGA GCA AAT ACT TCT TCA TCT ACA TCT 1002
Val Ser Thr Glu Gly Ala Asn Thr Ser Ser Ser Thr Ser
         160             165             170

ACA TCC ACC ACT GGG ACA AGC CAT CTT GTA AAA TGT GCG 1041
Thr Ser Thr Thr Gly Thr Ser His Leu Val Lys Cys Ala
                 175             180

GAG AAG GAG AAA ACT TTC TGT GTG AAT GGA GGG GAG TGC 1080
Glu Lys Glu Lys Thr Phe Cys Val Asn Gly Gly Glu Cys
     185             190             195

TTC ATG GTG AAA GAC CTT TCA AAC CCC TCG AGA TAC TTG 1119
Phe Met Val Lys Asp Leu Ser Asn Pro Ser Arg Tyr Leu
             200             205

TGC AAG TGC CCA AAT GAG TTT ACT GGT GAT CGC TGC CAA 1158
Cys Lys Cys Pro Asn Glu Phe Thr Gly Asp Arg Cys Gln
210             215             220

AAC TAC GTA ATG GCC AGC TTC TAC AGT ACG TCC ACT CCC 1197
Asn Tyr Val Met Ala Ser Phe Tyr Ser Thr Ser Thr Pro
         225             230             235

TTT CTG TCT CTG CCT GAA TAGGA GCATGCTCAG TTGGTGCTGC 1240
Phe Leu Ser Leu Pro Glu
                 240 241

TTTCTTGTTG CTGCATCTCC CCTCAGATTC CACCTAGAGC TAGATGTGTC 1290
```

FIGURE 4B

```
TTACCAGATC TAATATTGAC TGCCTCTGCC TGTCGCATGA GAACATTAAC 1340

AAAAGCAATT GTATTACTTC CTCTGTTCGC GACTAGTTGG CTCTGAGATA 1390

CTAATAGGTG TGTGAGGCTC CGGATGTTTC TGGAATTGAT ATTGAATGAT 1440

GTGATACAAA TTGATAGTCA ATATCAAGCA GTGAAATATG ATAATAAAGG 1490

CATTTCAAAG TCTCACTTTT ATTGATAAAA TAAAAATCAT TCTACTGAAC 1540

AGTCCATCTT CTTTATACAA TGACCACATC CTGAAAAGGG TGTTGCTAAG 1590

CTGTAACCGA TATGCACTTG AAATGATGGT AAGTTAATTT TGATTCAGAA 1640

TGTGTTATTT GTCACAAATA AACATAATAA AAGGAGTTCA GATGTTTTTC 1690

TTCATTAACC AAAAAAAAAA AAAAA 1715
```

FIGURE 4C

```
GAGGCGCCTG CCTCCAACCT GCGGGCGGGA GGTGGGTGGC TGCGGGGCAA  50

TTGAAAAAGA GCCGGCGAGG AGTTCCCCGA AACTTGTTGG AACTCCGGGC 100

TCGCGCGGAG GCCAGGAGCT GAGCGGCGGC GGCTGCCGGA CGATGGGAGC 150

GTGAGCAGGA CGGTGATAAC CTCTCCCCGA TCGGGTTGCG AGGGCGCCGG 200

GCAGAGGCCA GGACGCGAGC CGCCAGCGGC GGGACCCATC GACGACTTCC 250

CGGGGCGACA GGAGCAGCCC CGAGAGCCAG GGCGAGCGCC CGTTCCAGGT 300

GGCCGGACCG CCCGCCGCGT CCGCGCCGCG CTCCCTGCAG GCAACGGGAG 350

ACGCCCCCGC GCAGCGCGAG CGCCTCAGCG CGGCCGCTCG CTCTCCCCAT 400

CGAGGGACAA ACTTTTCCCA AACCCGATCC GAGCCCTTGG ACCAAACTCG 450

CCTGCGCCGA GAGCCGTCCG CGTAGAGCGC TCCGTCTCCG GCGAG    AT 497
                                                    Met
                                                     1
```

```
G TCC GAG CGC AAA GAA GGC AGA GGC AAA GGG AAG GGC AAG 537
  Ser Glu Arg Lys Glu Gly Arg Gly Lys Gly Lys Gly Lys
           5                   10

AAG AAG GAG CGA GGC TCC GGC AAG AAG CCG GAG TCC GCG 576
Lys Lys Glu Arg Gly Ser Gly Lys Lys Pro Glu Ser Ala
 15              20                  25

GCG GGC AGC CAG AGC CCA GCC TTG CCT CCC CAA TTG AAA 615
Ala Gly Ser Gln Ser Pro Ala Leu Pro Pro Gln Leu Lys
         30                  35                  40

GAG ATG AAA AGC CAG GAA TCG GCT GCA GGT TCC AAA CTA 654
Glu Met Lys Ser Gln Glu Ser Ala Ala Gly Ser Lys Leu
             45                  50

GTC CTT CGG TGT GAA ACC AGT TCT GAA TAC TCC TCT CTC 693
Val Leu Arg Cys Glu Thr Ser Ser Glu Tyr Ser Ser Leu
         55                  60                  65

AGA TTC AAG TGG TTC AAG AAT GGG AAT GAA TTG AAT CGA 732
Arg Phe Lys Trp Phe Lys Asn Gly Asn Glu Leu Asn Arg
             70                  75
```

FIGURE 5A

```
AAA AAC AAA CCA CAA AAT ATC AAG ATA CAA AAA AAG CCA  771
Lys Asn Lys Pro Gln Asn Ile Lys Ile Gln Lys Lys Pro
 80              85                  90

GGG AAG TCA GAA CTT CGC ATT AAC AAA GCA TCA CTG GCT  810
Gly Lys Ser Glu Leu Arg Ile Asn Lys Ala Ser Leu Ala
         95                 100             105

GAT TCT GGA GAG TAT ATG TGC AAA GTG ATC AGC AAA TTA  849
Asp Ser Gly Glu Tyr Met Cys Lys Val Ile Ser Lys Leu
                 110             115

GGA AAT GAC AGT GCC TCT GCC AAT ATC ACC ATC GTG GAA  888
Gly Asn Asp Ser Ala Ser Ala Asn Ile Thr Ile Val Glu
    120             125             130

TCA AAC GAG ATC ATC ACT GGT ATG CCA GCC TCA ACT GAA  927
Ser Asn Glu Ile Ile Thr Gly Met Pro Ala Ser Thr Glu
             135             140

GGA GCA TAT GTG TCT TCA GAG TCT CCC ATT AGA ATA TCA  966
Gly Ala Tyr Val Ser Ser Glu Ser Pro Ile Arg Ile Ser
145             150             155

GTA TCC ACA GAA GGA GCA AAT ACT TCT TCA TCT ACA TCT 1005
Val Ser Thr Glu Gly Ala Asn Thr Ser Ser Ser Thr Ser
         160             165             170

ACA TCC ACC ACT GGG ACA AGC CAT CTT GTA AAA TGT GCG 1044
Thr Ser Thr Thr Gly Thr Ser His Leu Val Lys Cys Ala
                 175             180

GAG AAG GAG AAA ACT TTC TGT GTG AAT GGA GGG GAG TGC 1083
Glu Lys Glu Lys Thr Phe Cys Val Asn Gly Gly Glu Cys
    185             190             195

TTC ATG GTG AAA GAC CTT TCA AAC CCC TCG AGA TAC TTG 1122
Phe Met Val Lys Asp Leu Ser Asn Pro Ser Arg Tyr Leu
             200             205

TGC AAG TGC CCA AAT GAG TTT ACT GGT GAT CGC TGC CAA 1161
Cys Lys Cys Pro Asn Glu Phe Thr Gly Asp Arg Cys Gln
210             215             220

AAC TAC GTA ATG GCC AGC TTC TAC AAG GCG GAG GAG CTG 1200
Asn Tyr Val Met Ala Ser Phe Tyr Lys Ala Glu Glu Leu
         225             230             235

TAC CAG AAG AGA GTG CTG ACC ATA ACC GGC ATC TGC ATC 1239
Tyr Gln Lys Arg Val Leu Thr Ile Thr Gly Ile Cys Ile
                 240             245

GCC CTC CTT GTG GTC GGC ATC ATG TGT GTG GCC TAC 1278
Ala Leu Leu Val Val Gly Ile Met Cys Val Val Ala Tyr
250             255             260
```

FIGURE 5B

```
TGC AAA ACC AAG AAA CAG CGG AAA AAG CTG CAT GAC CGT 1317
Cys Lys Thr Lys Lys Gln Arg Lys Lys Leu His Asp Arg
            265             270

CTT CGG CAG AGC CTT CGG TCT GAA CGA AAC AAT ATG ATG 1356
Leu Arg Gln Ser Leu Arg Ser Glu Arg Asn Asn Met Met
275             280             285

AAC ATT GCC AAT GGG CCT CAC CAT CCT AAC CCA CCC CCC 1395
Asn Ile Ala Asn Gly Pro His His Pro Asn Pro Pro Pro
        290             295             300

GAG AAT GTC CAG CTG GTG AAT CAA TAC GTA TCT AAA AAC 1434
Glu Asn Val Gln Leu Val Asn Gln Tyr Val Ser Lys Asn
                305             310

GTC ATC TCC AGT GAG CAT ATT GTT GAG AGA GAA GCA GAG 1473
Val Ile Ser Ser Glu His Ile Val Glu Arg Glu Ala Glu
    315             320             325

ACA TCC TTT TCC ACC AGT CAC TAT ACT TCC ACA GCC CAT 1512
Thr Ser Phe Ser Thr Ser His Tyr Thr Ser Thr Ala His
            330             335

CAC TCC ACT ACT GTC ACC CAG ACT CCT AGC CAC AGC TGG 1551
His Ser Thr Thr Val Thr Gln Thr Pro Ser His Ser Trp
340             345             350

AGC AAC GGA CAC ACT GAA AGC ATC CTT TCC GAA AGC CAC 1590
Ser Asn Gly His Thr Glu Ser Ile Leu Ser Glu Ser His
        355             360             365

TCT GTA ATC GTG ATG TCA TCC GTA GAA AAC AGT AGG CAC 1629
Ser Val Ile Val Met Ser Ser Val Glu Asn Ser Arg His
                370             375

AGC AGC CCA ACT GGG GGC CCA AGA GGA CGT CTT AAT GGC 1668
Ser Ser Pro Thr Gly Gly Pro Arg Gly Arg Leu Asn Gly
    380             385             390

ACA GGA GGC CCT CGT GAA TGT AAC AGC TTC CTC AGG CAT 1707
Thr Gly Gly Pro Arg Glu Cys Asn Ser Phe Leu Arg His
            395             400

GCC AGA GAA ACC CCT GAT TCC TAC CGA GAC TCT CCT CAT 1746
Ala Arg Glu Thr Pro Asp Ser Tyr Arg Asp Ser Pro His
405             410             415

AGT GAA AGG TAAAA CCGAAGGCAA AGCTACTGCA GAGGAGAAAC 1790
Ser Glu Arg
        420
```

FIGURE 5C

```
TCAGTCAGAG AATCCCTGTG AGCACCTGCG GTCTCACCTC AGGAAATCTA 1840

CTCTAATCAG AATAAGGGGC GGCAGTTACC TGTTCTAGGA GTGCTCCTAG 1890

TTGATGAAGT CATCTCTTTG TTTGACGGAA CTTATTTCTT CTGAGCTTCT 1940

CTCGTCGTCC CAGTGACTGA CAGGCAACAG ACTCTTAAAG AGCTGGGATG 1990

CTTTGATGCG GAAGGTGCAG CACATGGAGT TTCCAGCTCT GGCCATGGGC 2040

TCAGACCCAC TCGGGTCTC AGTGTCCTCA GTTGTAACAT TAGAGAGATG 2090

GCATCAATGC TTGATAAGGA CCCTTCTATA ATTCCAATTG CCAGTTATCC 2140

AAACTCTGAT TCGGTGGTCG AGCTGGCCTC GTGTTCTTAT CTGCTAACCC 2190

TGTCTTACCT TCCAGCCTCA GTTAAGTCAA ATCAAGGGCT ATGTCATTGC 2240

TGAATGTCAT GGGGGGCAAC TGCTTGCCCT CCACCCTATA GTATCTATTT 2290

TATGAAATTC CAAGAAGGGA TGAATAAATA AATCTCTTGG ATGCTGCGTC 2340

TGGCAGTCTT CACGGGTGGT TTTCAAAGCA GAAAAAAAAA AAAAAAAAAA 2390

AAAAAAAAAA AAAAAAAAAA AAAAAAAAAA AAAAAAAAAA A 2431
```

FIGURE 5D

```
  1  MSERKEGRGKQKGKKKERGSGKKPESAAGSQSPALPPRLKEMKSQESAAG   16
  1  MSERKEGRGKQKGKKKERGSGKKPESAAGSQSPALPPQLKEMKSQESAAG   71
  1  MSERKEGRGKQKGKKKERGSGKKPESAAGSQSPALPPQLKEMKSQESAAG   76
  1  MSERKEGRGKQKGKKKERGSGKKPESAAGSQSPALPPQLKEMKSQESAAG   84
  1  MSERKEGRGKQKGKKKERGSGKKPESAAGSQSPALPPQLKEMKSQESAAG   78

51  SKLVLRCETSSEYSSLRFKWFKNGNELNRKNKPQNIKIQKKPGKSELRIN   16
 51  SKLVLRCETSSEYSSLRFKWFKNGNELNRKNKPQNIKIQKKPGKSELRIN   71
 51  SKLVLRCETSSEYSSLRFKWFKNGNELNRKNKPQNIKIQKKPGKSELRIN   76
 51  SKLVLRCETSSEYSSLRFKWFKNGNELNRKNKPQNIKIQKKPGKSELRIN   84
 51  SKLVLRCETSSEYSSLRFKWFKNGNELNRKNKPQNIKIQKKPGKSELRIN   78

101  KASLADSGEYMCKVISKLGNDSASANITIVESNEIITGMPASTEGAYVSS   16
101  KASLADSGEYMCKVISKLGNDSASANITIVESNEIITGMPASTEGAYVSS   71
101  KASLADSGEYMCKVISKLGNDSASANITIVESNEIITGMPASTEGAYVSS   76
101  KASLADSGEYMCKVISKLGNDSASANITIVESNEIITGMPASTEGAYVSS   84
101  KASLADSGEYMCKVISKLGNDSASANITIVESNEIITGMPASTEGAYVSS   78

151  ESPIRISVSTEGANTSSSTSTSTTGTSHLVKCAEKEKTFCVNGGECFMVK   16
151  ESPIRISVSTEGANTSSSTSTSTTGTSHLVKCAEKEKTFCVNGGECFMVK   71
151  ESPIRISVSTEGANTSSSTSTSTTGTSHLVKCAEKEKTFCVNGGECFMVK   76
151  ESPIRISVSTEGANTSSSTSTSTTGTSHLVKCAEKEKTFCVNGGECFMVK   84
151  ESPIRISVSTEGANTSSSTSTSTTGTSHLVKCAEKEKTFCVNGGECFMVK   78
```

FIGURE 6A

```
 16  201  DLSNPSRYLCKCQPGFTGARCTENVPMKVQNQ.....EKAEELYQKRVLT
 11  201  DLSNPSRYLCKCPNEFTGDRCQNYVMASFYKHLGIEFMEAEELYQKRVLT
 76  201  DLSNPSRYLCKCPNEFTGDRCQNYVMASFYK......AEELYQKRVLT
 84  201  DLSNPSRYLCKCPNEFTGDRCQNYVMASFYK......AEELYQKRVLT
 78  201  DLSNPSRYLCKCPNEFTGDRCQNYVMASFYSTSTPFLSLPE 16  246  ITGICIALLVVGIMCVVAYCKTKKQRKKLHDRLRQSLRSERNNMMNIANG
 11  251  ITGICIALLVVGIMCVVAYCKTKKQRKKLHDRLRQSLRSERNNMMNIANG
 76  243  ITGICIALLVVGIMCVVAYCKTKKQRKKLHDRLRQSLRSERNNMMNIANG
 84  243  ITGICIALLVVGIMCVVAYCKTKKQRKKLHDRLRQSLRSERNNMMNIANG 16  296  PHHPNPPPENVQLVNQYVSKNVISSEHIVEREAETSFSTSHYTSTAHHST
 11  301  PHHPNPPPPENVQLVNQYVSKNVISSEHIVEREAETSFSTSHYTSTAHHST
 76  293  PHHPNPPPPENVQLVNQYVSKNVISSEHIVEREAETSFSTSHYTSTAHHST
 84  293  PHHPNPPPPENVQLVNQYVSKNVISSEHIVEREAETSFSTSHYTSTAHHST 16  346  TVTQTPSHSWSNGHTESILSESHSVIVMSSVENSRHSSPTGGPRGRLNGT
 11  351  TVTQTPSHSHSWSNGHTESILSESHSVIVMSSVENSRHSSPTGGPRGRLNGT
 76  343  TVTQTPSHSHSWSNGHTESILSESHSVIVMSSVENSRHSSPTGGPRGRLNGT
 84  343  TVTQTPSHSHSWSNGHTESILSESHSVIVMSSVENSRHSSPTGGPRGRLNGT
```

FIGURE 6B

```
16  396  GGPRECNSFLRHARETPDSYRDSPHSERYVSAMTTPARMSPVDFHTPSSP
11  401  GGPRECNSFLRHARETPDSYRDSPHSERYVSAMTTPARMSPVDFHTPSSP
76  393  GGPRECNSFLRHARETPDSYRDSPHSERYVSAMTTPARMSPVDFHTPSSP
84  393  GGPRECNSFLRHARETPDSYRDSPHSER......................

16  446  KSPPSEMSPPVSSMTVSMPSMAVSPFMEEERPLLLVTPPRLREKKFDHHP
11  451  KSPPSEMSPPVSSMTVSMPSMAVSPFMEEERPLLLVTPPRLREKKFDHHP
76  443  KSPPSEMSPPVSSMTVSKPSMAVSPFMEEERPLLLVTPPRLREKKFDHHP 16  496  QQFSSFHHNPAHDSNSLPASPLRIVEDEEYETTQEYEPAQEPVKKLANSR
11  501  QQFSSFHHNPAHDSNSLPASPLRIVEDEEYETTQEYEPAQEPVKKLANSR
76  493  QQFSSFHHNPAHDSNSLPASPLRIVEDEEYETTQEYEPAQEPVKKLANSR 16  546  RAKRTKPNGHIANRLEVDSNTSSQSSNSESETEDERVGEDTPFLGIQNPL
11  551  RAKRTKPNGHIANRLEVDSNTSSQSSNSESETEDERVGEDTPFLGIQNPL
76  543  RAKRTKPNGHIANRLEVDSNTSSQSSNSESETEDERVGEDTPFLGIQNPL 16  596  AASLEATPAFRLADSRT-NPAGRFSTQEEIQ...........
11  601  AASLEATPAFRLADSRTNPAGRFSTQEEIQARLSSVIANQDPIAV
76  593  AASLEATPAFRLADSRTNPAGRFSTQEEIQARLSSVIANQDPIAV
```

FIGURE 6C

```
  1 GGGTACCATGGGTCGGTGAGCGCGTTTCCCGCCTGAGCGCAACTAGCGGC
 51 GGGTCGTGGGCACCTCCAGAAAAGATCCGCACCATCCTCCAGGATCCAA
101 TGGCCTTGGAGAGAGGGCTGCAGGGCCCACGGACATTGCTGACTCTTCAG
151 AACGTGCTGACATGGAGCCAGGTAGACTGAAATTATCATGTGTCCAAATT
201 AAAATTGCATACTTCAAGGATTATTTGAAGGACTATTCTTAGACCCTTTT
251 AAGAAGATTTAAAGAAAAACCACTCGGCCCTGAGTGCGGCGAGGACCCTG

301 TTTGTGGATGTGGAGGAGCGCGGGCCGGAGGCCATGGACGTGAAGGAGAG
  1                                        M  D  V  K  E  R

351 GAAGCCTTACCGCTCGCTGACCCGGCGCCGCGACGCCGAGCGCCGCTACA
  7   K  P  Y  R  S  L  T  R  R  R  D  A  E  R  R  Y  T

401 CCAGCTCGTCCGCGGACAGCGAGGAGGGCAAAGCCCCGCAGAAATCGTAC
 24    S  S  S  A  D  S  E  E  G  K  A  P  Q  K  S  Y

451 AGCTCCAGCGAGACCCTGAAGGCCTACGACCAGGACGCCCGCCTAGCCTA
 40  S  S  S  E  T  L  K  A  Y  D  Q  D  A  R  L  A  Y

501 TGGCAGCCGCGTCAAGGACATTGTGCCGCAGGAGGCCGAGGAATTCTGCC
 57   G  S  R  V  K  D  I  V  P  Q  E  A  E  E  F  C  R

551 GCACAGGTGCCAACTTCACCCTGCGGGAGCTGGGGCTGGAAGAAGTAACG
 74    T  G  A  N  F  T  L  R  E  L  G  L  E  E  V  T

601 CCCCCTCACGGGACCCTGTACCGGACAGACATTGGCCTCCCCCACTGCGG
 90  P  P  H  G  T  L  Y  R  T  D  I  G  L  P  H  C  G

651 CTACTCCATGGGGGCTGGCTCTGATGCCGACATGGAGGCTGACACGGTGC
107  Y  S  M  G  A  G  S  D  A  D  M  E  A  D  T  V  L

701 TGTCCCCTGAGCACCCCGTGCGTCTGTGGGGCCGGAGCACACGGTCAGGG
124    S  P  E  H  P  V  R  L  W  G  R  S  T  R  S  G

751 CGCAGCTCCTGCCTGTCCAGCCGGGCCAATTCCAATCTCACACTCACCGA
140  R  S  S  C  L  S  S  R  A  N  S  N  L  T  L  T  D

801 CACCGAGCATGAAAACACTGAGACTGATCATCCGGGCGGCCTGCAGAACC
157   T  E  H  E  N  T  E  T  D  H  P  G  G  L  Q  N  H

851 ACGCGCGGCTCCGGACGCCGCCGCCGCCGCTCTCGCACGCCCACACCCCC
174     A  R  L  R  T  P  P  P  P  L  S  H  A  H  T  P

901 AACCAGCACCACGCGGCCTCCATTAACTCCCTGAACCGGGGCAACTTCAC
190  N  Q  H  H  A  A  S  I  N  S  L  N  R  G  N  F  T

951 GCCGAGGAGCAACCCCAGCCCGGCCCCACGGACCACTCGCTCTCCGGAG
207  P  R  S  N  P  S  P  A  P  T  D  H  S  L  S  G  E

1001 AGCCCCCTGCCGGCGGCGCCCAGGAGCCTGCCCACGCCCAGGAGAACTGG
 224    P  P  A  G  G  A  Q  E  P  A  H  A  Q  E  N  W

1051 CTGCTCAACAGCAACATCCCCCTGGAGACCAGAAACCTAGGCAAGCAGCC
 240  L  L  N  S  N  I  P  L  E  T  R  N  L  G  K  Q  P
```

FIG. 7A

```
1101 ATTCCTAGGGACATTGCAGGACAACCTCATTGAGATGGACATTCTCGGCG
 257   F  L  G  T  L  Q  D  N  L  I  E  M  D  I  L  G  A

1151 CCTCCCGCCATGATGGGGCTTACAGTGACGGGCACTTCCTCTTCAAGCCT
 274    S  R  H  D  G  A  Y  S  D  G  H  F  L  F  K  P

1201 GGAGGCACCTCCCCGCTCTTCTGCACCACATCACCAGGGTACCCACTGAC
 290  G  G  T  S  P  L  F  C  T  T  S  P  G  Y  P  L  T

1251 GTCCAGCACAGTGTACTCTCCTCCGCCCCGACCCCTGCCCCGCAGCACCT
 307    S  S  T  V  Y  S  P  P  P  R  P  L  P  R  S  T  F

1301 TCGCCCGGCCGGCCTTTAACCTCAAGAAGCCCTCCAAGTACTGTAACTGG
 324     A  R  P  A  F  N  L  K  K  P  S  K  Y  C  N  W

1351 AAGTGCGCAGCCCTGAGCGCCATCGTCATCTCAGCCACTCTGGTCATCCT
 340  K  C  A  A  L  S  A  I  V  I  S  A  T  L  V  I  L

1401 GCTGGCATACTTTGTGGCCATGCACCTGTTTGGCCTAAACTGGCACCTGC
 357  L  A  Y  F  V  A  M  H  L  F  G  L  N  W  H  L  Q

1451 AGCCGATGGAGGGGCAGATGTATGAGATCACGGAGGACACAGCCAGCAGT
 374     P  M  E  G  Q  M  Y  E  I  T  E  D  T  A  S  S

1501 TGGCCTGTGCCAACCGACGTCTCCCTATACCCCTCAGGGGGCACTGGCTT
 390  W  P  V  P  T  D  V  S  L  Y  P  S  G  G  T  G  L

1551 AGAGACCCCTGACAGGAAAGGCAAAGGAACCACAGAAGGAAAGCCCAGTA
 407  E  T  P  D  R  K  G  K  G  T  T  E  G  K  P  S  S

1601 GTTTCTTTCCAGAGGACAGTTTCATAGATTCTGGAGAAATTGATGTGGGA
 424    F  F  P  E  D  S  F  I  D  S  G  E  I  D  V  G

1651 AGGCGAGCTTCCCAGAAGATTCCTCCTGGCACTTTCTGGAGATCTCAAGT
 440  R  R  A  S  Q  K  I  P  P  G  T  F  W  R  S  Q  V

1701 GTTCATAGACCATCCTGTGCATCTGAAATTCAATGTGTCTCTGGGAAAGG
 457  F  I  D  H  P  V  H  L  K  F  N  V  S  L  G  K  A

1751 CAGCCCTGGTTGGCATTTATGGCAGAAAAGGCCTCCCTCCTTCACATACA
 474    A  L  V  G  I  Y  G  R  K  G  L  P  P  S  H  T

1801 CAGTTTGACTTTGTGGAGCTGCTGGATGGCAGGAGGCTCCTAACCCAGGA
 490  Q  F  D  F  V  E  L  L  D  G  R  R  L  L  T  Q  E

1851 GGCGCGGAGCCTAGAGGGGACCCCGCGCCAGTCTCGGGGAACTGTGCCCC
 507  A  R  S  L  E  G  T  P  R  Q  S  R  G  T  V  P  P

1901 CCTCCAGCCATGAGACAGGCTTCATCCAGTATTTGGATTCAGGAATCTGG
 524    S  S  H  E  T  G  F  I  Q  Y  L  D  S  G  I  W

1951 CACTTGGCTTTTTACAATGACGGAAAGGAGTCAGAAGTGGTTTCCTTTCT
 540  H  L  A  F  Y  N  D  G  K  E  S  E  V  V  S  F  L
```

FIG. 7B

```
2001 CACCACTGCCATTGCCTTGCCTCCCCGATTGAAAGAGATGAAAAGCCAGG
 557  T  T  A  I  A  L  P  P  R  L  K  E  M  K  S  Q  E

2051 AATCGGCTGCAGGTTCCAAACTAGTCCTTCGGTGTGAAACCAGTTCTGAA
 574   S  A  A  G  S  K  L  V  L  R  C  E  T  S  S  E

2101 TACTCCTCTCTCAGATTCAAGTGGTTCAAGAATGGGAATGAATTGAATCG
 590  Y  S  S  L  R  F  K  W  F  K  N  G  N  E  L  N  R

2151 AAAAAACAAACCACAAAATATCAAGATACAAAAAAAGCCAGGGAAGTCAG
 607  K  N  K  P  Q  N  I  K  I  Q  K  K  P  G  K  S  E

2201 AACTTCGCATTAACAAAGCATCACTGGCTGATTCTGGAGAGTATATGTGC
 624   L  R  I  N  K  A  S  L  A  D  S  G  E  Y  M  C

2251 AAAGTGATCAGCAAATTAGGAAATGACAGTGCCTCTGCCAATATCACCAT
 640  K  V  I  S  K  L  G  N  D  S  A  S  A  N  I  T  I

2301 CGTGGAATCAAACGAGATCATCACTGGTATGCCAGCCTCAACTGAAGGAG
 657  V  E  S  N  E  I  I  T  G  M  P  A  S  T  E  G  A

2351 CATATGTGTCTTCAGAGTCTCCCATTAGAATATCAGTATCCACAGAAGGA
 674   Y  V  S  S  E  S  P  I  R  I  S  V  S  T  E  G

2401 GCAAATACTTCTTCATCTACATCTACATCCACCACTGGGACAAGCCATCT
 690  A  N  T  S  S  S  T  S  T  S  T  T  G  T  S  H  L

2451 TGTAAAATGTGCGGAGAAGGAGAAAACTTTCTGTGTGAATGGAGGGGAGT
 707   V  K  C  A  E  K  E  K  T  F  C  V  N  G  G  E  C

2501 GCTTCATGGTGAAAGACCTTTCAAACCCCTCGAGATACTTGTGCAAGTGC
 724   F  M  V  K  D  L  S  N  P  S  R  Y  L  C  K  C

2551 CCAAATGAGTTTACTGGTGATCGCTGCCAAAACTACGTAATGGCCAGCTT
 740  P  N  E  F  T  G  D  R  C  Q  N  Y  V  M  A  S  F

2601 CTACAGTACGTCCACTCCCTTTCTGTCTCTGCCTGAATAGGAGCATGCTC
 757  Y  S  T  S  T  P  F  L  S  L  P  E

2651 AGTTGGTGCTGCTTTCTTGTTGCTGCATCTCCCCTCAGATTCCACCTAGA

2701 GCTAGATGTGTCTTACCAGATCTAATATTGACTGCCTCTGCCTGTCGCAT
2751 GAGAACATTAACAAAAGCAATTGTATTACTTCCTCTGTTCGCGACTAGTT
2801 GGCTCTGAGATACTAATAGGTGTGTGAGGCTCCGGATGTTTCTGGAATTG
2851 ATATTGAATGATGTGATACAAATTGATAGTCAATATCAAGCAGTGAAATA
2901 TGATAATAAAGGCATTTCAAAGTCTCACTTTTATTGATAAAATAAAAATC
2951 ATTCTACTGAACAGTCCATCTTCTTTATACAATGACCACATCCTGAAAAG
3001 GGTGTTGCTAAGCTGTAACCGATATGCACTTGAAATGATGGTAAGTTAAT
3051 TTTGATTCAGAATGTGTTATTTGTCACAAATAAACATAATAAAAGGAAAA
3101 AAAAAAAAAA
```

FIG. 7C

```
   1 GAATTCGGGACAGCCTCTCCTGCCGCCGCTGCTGCTGCCGCCGCCGCCACCGCCGGCTGGTCCTCCTTCTGCTTT

76 TACTTCTCCTGCATGACAGTTGTTTTCTTCATCTGAGCAGACACCAGCTTCAGATGCTCGAGGTGAGAAACATGC

151 CTTTCAGTTTGGGCTACTGGTTTACTTAATTAATCAGCCGGCAGCTCCGTCGATCTATTTTCGTCCCTGTCCTCT

226 TGACGAGCCCGGGATGGTTTGGAGTAGCATTTAAAAGAACTAGAAAAGTGGCCCAGAAACAGCAGCTTAAAGAAT

301 TATTACGATATACTTTGATTTTGTAGTTGCTAGGAGCTTTTCTTCCCCCCTTGCATCTTTCTGAACTCTTCTTGA

376 TTTTAATAATGGCCTTGGACTTGGACGATTTATCGATTTCCCCCTGTAAGATGCTGTATCATTTGGTTGGGGGGG

451 CCTCTGCGTGGTAATGGACCGTGAGAGCGGCCAGGCCTTCTTCTGGAGGTGAGCCGATGGAGATTTATTCCCCAG
   1                                                             M  E  I  Y  S  P  D

526 ACATGTCTGAGGTCGCCGCCGAGAGGTCCTCCAGCCCCTCCACTCAGCTGAGTGCAGACCCATCTCTTGATGGGC
   8  M  S  E  V  A  A  E  R  S  S  S  P  S  T  Q  L  S  A  D  P  S  L  D  G  L

601 TTCCGGCAGCAGAAGACATGCCAGAGCCCCAGACTGAAGATGGGAGAACCCCTGGACTCGTGGGCCTGGCCGTGC
  33  P  A  A  E  D  M  P  E  P  Q  T  E  D  G  R  T  P  G  L  V  G  L  A  V  P

676 CCTGCTGTGCGTGCCTAGAAGCTGAGCGCCTGAGAGGTTGCCTCAACTCAGAGAAAATCTGCATTGTCCCCATCC
  58     [C][C] A [C] L  E  A  E  R  L  R  G [C] L  N  S  E  K  I [C] I  V  P  I  L

751 TGGCTTGCCTGGTCAGCCTCTGCCTCTGCATCGCCGGCCTCAAGTGGGTATTTGTGGACAAGATCTTTGAATATG
  83  A [C] L  V  S  L [C] L [C] I  A  G  L  K  W  V  F  V  D  K  I  F  E  Y  D

826 ACTCTCCTACTCACCTTGACCCTGGGGGGTTAGGCCAGGACCCTATTATTTCTCTGGACGCAACTGCTGCCTCAG
 108  S  P  T  H  L  D  P  G  G  L  G  Q  D  P  I  I  S  L  D  A  T  A  A  S  A

901 CTGTGTGGGTGTCGTCTGAGGCATACACTTCACCTGTCTCTAGGGCTCAATCTGAAAGTGAGGTTCAAGTTACAG
 133  V  W  V  S  S  E  A  Y  T  S  P  V  S  R  A  Q  S  E  S  E  V  Q  V  T  V

976 TGCAAGGTGACAAGGCTGTTGTCTCCTTTGAACCATCAGCGGCACCGACACCGAAGAATCGTATTTTTGCCTTTT
 158  Q  G  D  K  A  V  V  S  F  E  P  S  A  A  P  T  P  K  N  R  I  F  A  F  S

1051 CTTTCTTGCCGTCCACTGCGCCATCCTTCCCTTCACCCACCCGGAACCCTGAGGTGAGAACGCCCAAGTCAGCAA
 183  F  L  P  S  T  A  P  S  F  P  S  P  T  R  N  P  E  V  R  T  P  K  S  A  T

1126 CTCAGCCACAAACAACAGAAACTAATCTCCAAACTGCTCCTAAACTTTCTACATCTACATCCACCACTGGGACAA
 208  Q  P  Q  T  T  E  T  N  L  Q  T  A  P  K  L  S  T  S  T  T  G  T  S

1201 GCCATCTTGTAAAATGTGCGGAGAAGGAGAAAACTTTCTGTGTGAATGGAGGGGAGTGCTTCATGGTGAAAGACC
 233  H  L  V  K [C] A  E  K  E  R  T  F [C] V  N  G  G  E [C] F  M  V  K  D  L

1276 TTTCAAACCCCTCGAGATACTTGTGCAAGTGCCCAAATGAGTTTACTGGTGATCGCTGCCAAAACTACGTAATGG
 258  S  N  P  S  R  Y  L [C] K [C] P  N  E  F  T  G  D  R [C] Q  N  Y  V  M  A

1351 CCAGCTTCTACAGTACGTCCACTCCCTTTCTGTCTCTGCCTGAATAGGAGCATGCTCAGTTGGTGCTGCTTTCTT
 283  S  F  Y  S  T  S  T  P  F  L  S  L  P  E  O

1426 GTTGCTGCATCTCCCCTCAGATTCCACCTAGAGCTAGATGTGTCTTACCAGATCTAATATTGACTGCCTCTGCCT

1501 GTCGCATGAGAACATTAACAAAAGCAATTGTATTACTTCCTCTGTTCGCGACTAGTTGGCTCTGAGATACTAATA

1576 GGTGTGTGAGGCTCCGGATGTTTCTGGAATTGATATTGAATGATGTGATACAAATTGATAGTCAATATCAAGCAG

1651 TGAAATATGATAATAAAGGCATTTCAAAGTCTCACTTTTATTGATAAAATAAAAATCATTCTACTGAACAGTCCA

1726 TCTTCTTTATACAATGACCACATCCTGAAAAGGGTGTTGCTAAGCTGTAACCGATATGCACTTGAAATGATGGTA

1801 AGTTAATTTTGATTCAGAATGTGTTATTTGTCACAAATAAACATAATAAAAGGAAAAAAAAAAACCCGAATTC
```

EGF-like (bracket covering residues 58–295)

FIG. 8

USE OF HEREGULIN AS A GROWTH FACTOR

This application is a continuation of Ser. No. 09/773,517 filed Feb. 2, 2001, now abandoned, which is a continuation of Ser. No. 09/243,198 filed Feb. 2, 1999, now abandoned, which claims priority to provisional application Ser. No. 60/073,866 filed Feb. 4, 1998, the entire disclosures of which are hereby incorporated by reference.

BACKGROUND OF THE INVENTION

1. Field of the Invention

This invention relates to the use of HER2, HER3 and/or HER4 ligands, in particular heregulin polypeptides, as epithelial cell growth factors.

2. Description of Background and Related Art

The HER (ErbB) family belongs to the subclass I receptor tyrosine kinase superfamily and consists of three distinct receptors, HER2, HER3, and HER4. A ligand for this ErbB family is the protein heregulin (HRG), a multidomain containing protein with at least 15 distinct isoforms.

Transduction of signals that regulate cell growth and differentiation is regulated in part by phosphorylation of various cellular proteins. Protein tyrosine kinases are enzymes that catalyze this process. Receptor protein tyrosine kinases are believed to direct cellular growth via ligand-stimulated tyrosine phosphorylation of intracellular substrates. Growth factor receptor protein tyrosine kinases of the class I subfamily include the 170 kDa epidermal growth factor receptor (EGFR) encoded by the erbB1 gene. erbB1 has been causally implicated in human malignancy. In particular, increased expression of this gene has been observed in more aggressive carcinomas of the breast, bladder, lung and stomach.

The second member of the class I subfamily, p185$^{neu}$, was originally identified as the product of the transforming gene from neuroblastomas of chemically treated rats. The neu gene (also called erbB2 and HER2) encodes a 185 kDa receptor protein tyrosine kinase. Amplification and/or overexpression of the human HER2 gene correlates with a poor prognosis in breast and ovarian cancers (Slamon et al., *Science* 235:177–182 (1987); and Slamon et al., *Science* 244:707–712 (1989)). Overexpression of HER2 has been correlated with other carcinomas including carcinomas of the stomach, endometrium, salivary gland, lung, kidney, colon and bladder. Accordingly, Slamon et al. in U.S. Pat. No. 4,968,603 describe and claim various diagnostic assays for determining HER2 gene amplification or expression in tumor cells. Slamon et al. discovered that the presence of multiple gene copies of HER2 oncogene in tumor cells indicates that the disease is more likely to spread beyond the primary tumor site, and that the disease may therefore require more aggressive treatment than might otherwise be indicated by other diagnostic factors. Slamon et al. conclude that the HER2 gene amplification test, together with the determination of lymph node status, provides greatly improved prognostic utility.

A further related gene, called erbB3 or HER3, has also been described. See U.S. Pat. No. 5,183,884; Kraus et al., *Proc. Natl. Acad. Sci. USA* 86:9193–9197 (1989); EP Pat Appln No 444,961A1; and Kraus et al., *Proc. Natl. Acad. Sci. USA* 90:2900–2904 (1993). Kraus et al. (1989) discovered that markedly elevated levels of erbB3 mRNA were present in certain human mammary tumor cell lines indicating that erbB3, like erbB1 and erbB2, may play a role in human malignancies. Also, Kraus et al. (1993) showed that EGF-dependent activation of the ErbB3 catalytic domain of a chimeric EGFR/ErbB3 receptor resulted in a proliferative response in transfected NIH-3T3 cells. This is now believed to be the result of endogenous ErbB1 or ErbB2 in NIH-3T3. Furthermore, these researchers demonstrated that some human mammary tumor cell lines display a significant elevation of steady-state ErbB3 tyrosine phosphorylation further indicating that this receptor may play a role in human malignancies. The role of erbB3 in cancer has been explored by others. It has been found to be overexpressed in breast (Lemoine et al., *Br. J. Cancer* 66:1116–1121 (1992)), gastrointestinal (Poller et al., *J. Pathol.* 168:275–280 (1992), Rajkumer et al., *J. Pathol.* 170:271–278 (1993), and Sanidas et al., *Int J. Cancer* 54:935–940 (1993)), and pancreatic cancers (Lemoine et al., *J. Pathol.* 168:269–273 (1992), and Friess et al., *Clinical Cancer Research* 1:1413–1420 (1995)).

The class I subfamily of growth factor receptor protein tyrosine kinases has been further extended to include the HER4/Erb4 receptor. See EP Pat Appln No 599,274; Plowman et al., *Proc. Natl. Acad. Sci. USA* 90:1746–1750 (1993); and Plowman et al., *Nature* 366:473–475 (1993). Plowman et al. found that increased HER4 expression closely correlated with certain carcinomas of epithelial origin, including breast adenocarcinomas. Diagnostic methods for detection of human neoplastic conditions (especially breast cancers) which evaluate HER4 expression are described in EP Pat Appln No. 599,274.

The quest for the activator of the HER2 oncogene has lead to the discovery of a family of heregulin polypeptides. These proteins appear to result from alternate splicing of a single gene which was mapped to the short arm of human chromosome 8 by Orr-Urtreger et al., *Proc. Natl. Acad. Sci. USA* 90:1867–1871(1993). See also Lee and Wood, *Genomics*, 16:790–791 (1993).

Holmes et al. isolated and cloned a family of polypeptide activators for the HER2 receptor which they called heregulin-α (HRG-α), heregulin-β1 (HRG-β1), heregulin-β2 (HRG-β2), heregulin-β2-like (HRG-β2-like), and heregulin-β3 (HRG-β3). See Holmes et al., *Science* 256:1205–1210 (1992); WO 92/20798; and U.S. Pat. No. 5,367,060. The 45 kDa polypeptide, HRG-α, was purified from the conditioned medium of the MDA-MB-231 human breast cancer cell line. These researchers demonstrated the ability of the purified heregulin polypeptides to activate tyrosine phosphorylation of the HER2 receptor in MCF7 breast tumor cells. Furthermore, the mitogenic activity of the heregulin polypeptides on SK-BR-3 cells (which express high levels of the HER2 receptor) was illustrated. Like other growth factors which belong to the EGF family, soluble HRG polypeptides appear to be derived from a membrane bound precursor (called pro-HRG) which is proteolytically processed to release the 45 kDa soluble form. These pro-HRGs lack a N-terminal signal peptide.

While heregulins are substantially identical in the first 213 amino acid residues, they are classified into two major types, α and β, based on two variant EGF-like domains which differ in their C-terminal portions. Nevertheless, these EGF-like domains are identical in the spacing of six cysteine residues contained therein. Based on an amino acid sequence comparison, Holmes et al. found that between the first and sixth cysteines in the EGF-like domain, HRGs were 45% similar to heparin-binding EGF-like growth factor (HB-EGF), 35% identical to amphiregulin (AR), 32% identical to TGF-α, and 27% identical to EGF.

The 44 kDa neu differentiation factor (NDF), which is the rat equivalent of human HRG, was first described by Peles et al., *Cell*, 69:205–216 (1992); and Wen et al., *Cell*, 69:559–572 (1992). Like the HRG polypeptides, NDF has an immunoglobulin (Ig) homology domain followed by an EGF-like domain and lacks a N-terminal signal peptide. Subsequently, Wen et al., *Mol. Cell. Biol.*, 14(3):1909–1919 (1994) carried out "exhaustive cloning" to extend the family of NDFs. This work revealed six distinct fibroblastic pro-NDFs. Adopting the nomenclature of Holmes et al., the NDFs are classified as either α or β polypeptides based on the sequences of the EGF-like domains. Isoforms 1 to 4.are characterized on the basis of the variable just a membrane stretch (between the EGF-like domain and transmembrane domain). Also, isoforms a, b and c are described which have variable length cytoplasmic domains. These researchers conclude that different NDF isoforms are generated by alternative splicing and perform distinct tissue-specific functions. See also EP 505 148; WO 93/22424; and WO 94/28133 concerning NDF.

Falls et al., *Cell*, 72:801–815 (1993) describe another member of the heregulin family which they call acetylcholine receptor inducing activity (ARIA) polypeptide. The chicken-derived ARIA polypeptide stimulates synthesis of muscle acetylcholine receptors. See also WO 94/08007. ARIA is a β-type heregulin and lacks the entire spacer region rich in glycosylation sites between the Ig-like domain and EGF-like domain of HRGα, and HRGβ1-β3.

Marchionni et al., *Nature*, 362:312–318 (1993) identified several bovine-derived proteins which they call glial growth factors (GGFs). These GGFs share the Ig-like domain and EGF-like domain with the other heregulin proteins described above, but also have an amino-terminal kringle domain. GGFs generally do not have the complete glycosylated spacer region between the Ig-like domain and EGF-like domain. Only one of the GGFs, GGFII, possessed a N-terminal signal peptide. See also WO 92/18627; WO 194/00140; WO 94104560; WO 94/26298; and WO 95/32724 which refer to GGFs and uses thereof.

Ho et al. in *J. Biol. Chem.* 270(4):14523–14532 (1995) describe another member of the heregulin family called sensory and motor neuron-derived factor (SMDF). This protein has an EGF-like domain characteristic of all other heregulin polypeptides but a distinct N-terminal domain. The major structural difference between SMDF and the other heregulin polypeptides is the lack in SMDF of the Ig-like domain and the "glyco" spacer characteristic of all the other heregulin polypeptides. Another feature of SMDF is the presence of two stretches of hydrophobic amino acids near the N-terminus.

While the heregulin polypeptides were first identified based on their ability to activate the HER2 receptor (see Holmes et al., supra), it was discovered that certain ovarian cells expressing neu and neu-transfected fibroblasts did not bind or crosslink to NDF, nor did they respond to NDF to undergo tyrosine phosphorylation (Peles et al., *EMBO J.* 12:961–971 (1993)). This indicated another cellular component was necessary for conferring full heregulin responsiveness. Carraway et al. subsequently demonstrated that $^{125}$I-rHRGβ1$_{177-244}$ bound to NIH-3T3 fibroblasts stably transfected with bovine erbB3 but not to non-transfected parental cells. Accordingly, they conclude that ErbB3 is a receptor for HRG and mediates phosphorylation of intrinsic tyrosine residues as well as phosphorylation of ErbB2 receptor in cells which express both receptors. Carraway et al., *J. Biol. Chem.* 269(19):14303–14306 (1994). Sliwkowski et al., *J. Biol. Chem.* 269(20):14661–14665 (1994) found that cells transfected with HER3 alone show low affinities for heregulin, whereas cells transfected with both HER2 and HER3 show higher affinities.

This observation correlates with the "receptor crosstalking" described previously by Kokai et al, *Cell* 58:287–292 (1989); Stern et al., *EMBO J.* 7:995–1001 (1988); and King et al., 4:13–18 (1989). These researchers found that binding of EGF to the EGFR resulted in activation of the EGFR kinase domain and cross-phosphorylation of p185$^{HER2}$. This is believed to be a result of ligand-induced receptor heterodimerization and the concomitant cross-phosphorylation of the receptors within the heterodimer (Wada et al., *Cell* 61:1339–1347 (1990)).

Plowman and his colleagues have similarly studied p185$^{HER4}$/p185$^{HER2}$ activation. They expressed p185$^{HER2}$ alone, p185$^{HER4}$ alone, or the two receptors together in human T lymphocytes and demonstrated that heregulin is capable of stimulating tyrosine phosphorylation of p185$^{HER4}$, but could only stimulate p185$^{HER2}$ phosphorylation in cells expressing both receptors. Plowman et al., *Nature* 336:473475 (1993).

The biological role of heregulin has been investigated by several groups. For example, Falls et al., (discussed above) found that ARIA plays a role in myotube differentiation, namely affecting the synthesis and concentration of neurotransmitter receptors in the postsynaptic muscle cells of motor neurons. Corfas and Fischbach demonstrated that ARIA also increases the number of sodium channels in chick muscle. Corfas and Fischbach, *J. Neuroscience*, 13(5): 2118–2125 (1993). It has also been shown that GGFII is mitogenic for subconfluent quiescent human myoblasts and that differentiation of clonal human myoblasts in the continuous presence of GGFII results in greater numbers of myotubes after six days of differentiation (Sklar et al., *J. Cell Biochem.*, Abst. W462, 18D, 540 (1994)). See also WO 94/26298 published Nov. 24, 1994.

Holmes et al., supra, found that HRG exerted a mitogenic effect on mammary cell lines (such as SK-BR-3 and MCF-7). The mitogenic activity of GGFs on Schwann cells has also been reported. See, e.g., Brockes et al., *J. Biol. Chem.* 255(18):8374–8377 (1980); Lemke and Brockes, *J. Neurosci.* 4:75–83 (1984 Lemke and Brockes, *J. Neurosci.* 4:75–83 (1984), Brockes et al., *Ann. Neurol.* 20(3):317–322 (1986); Brockes, J., *Methods in Enzym.*, 147: 217–225 (1987) and Marchionni et al., supra. Schwann cells constitute important glial cells which provide myelin sheathing around the axons of neurons, thereby forming individual nerve fibers. Thus, it is apparent that Schwann cells play an important role in the development, function and regeneration of peripheral nerves. The implications of this from a therapeutic standpoint have been addressed by Levi et al., *J. Neuroscience* 14(3):1309–1319 (1994). Levi et al. discuss the potential for construction of a cellular prosthesis comprising human Schwann cells which could be transplanted into areas of damaged spinal cord. Methods for culturing Schwann cells ex vivo have been described. See WO 94/00140 and Li et al., *J. Neuroscience* 16(6):2012–2019 (1996).

Pinkas-Kramarski et al. found that NDF seems to be expressed in neurons and glial cells in embryonic and adult rat brain and primary cultures of rat brain cells, and suggested that it may act as a survival and maturation factor for astrocytes (Pinkas-Kramarski et al., *PNAS, USA* 91:9387–9391 (1994)). Meyer and Birchmeier, *PNAS, USA* 91:1064–1068 (1994) analyzed expression of heregulin during mouse embryogenesis and in the perinatal animal using in situ hybridization and RNase protection experiments. See also Meyer et al., *Development* 124(18):3575–3586 (1997).

These authors conclude that, based on expression of this molecule, heregulin plays a role in vivo as a mesenchymal and neuronal factor. Similarly, Danilenko et al., Abstract 3101, *FASEB* 8(4–5):A535 (1994); Danilenko et al., *Journal of Clinical Investigation* 95(2): 842–851 (1995), found that the interaction of NDF and the HER2 receptor is important in directing epidermal migration and differentiation during wound repair.

Ram et al., *Journal of Cellular Physiology* 163:589–596 (1995) evaluated the mitogenic activity of NDF on the immortalized human mammary epithelial cell line MCF-10A. Danilenko et al, *J. Clin. Invest.* 95:842–851 (1995) investigated whether NDF would influence epidermal migration in an in vivo model of excisional deep partial-thickness wound repair. It is reported that there were no statistically significant differences in proliferating basal and superbasal keratinocytes in control wounds vs. wounds treated with rhNDF-$\alpha_2$. Marikovsky et al., *Oncogene* 10:1403–1411 (1995), studied the proliferative responses of an aneuploid BALB/MK continuous keratinocyte cell line and evaluated the effects of $\alpha$- and $\beta$-isoforms of NDF on epidermal keratinocytes.

The relationship between the structure and function of new proteins can be investigated using any of a variety of available mutational analysis techniques. Examples of such techniques include alanine scanning mutagenesis and phagemid display. Alanine scanning can be used to identify active residues (i.e., residues that have a significant effect on protein function) in a protein or protein domain. For example, Cunningham and Wells used alanine scanning to identify residues in human growth hormone that were important for binding its receptor. Cunningham and Wells, *Science* 244:1081–1085 (1989). In alanine scanning, a gene encoding the protein or domain to be scanned is inserted into an expression vector, and mutagenesis is carried out to generate a series of vectors that encode proteins or domains in which sequential residues are converted to alanine. The encoded proteins or domain are expressed from these vectors, and the activities of the alanine-substituted variants are then tested to identify those with altered activity. An alteration in activity indicates that the residue at the alanine-substituted position is an active residue.

Phagemid display was developed to allow the screening of a large number of variant polypeptides for a particular binding activity. Smith and Parmley demonstrated that foreign peptides can be "displayed" efficiently on the surface of filamentous phage by inserting short gene fragments into gene III of the fd phage. Smith, *Science* 228:1315–1317 (1985); Parmley and Smith, *Gene* 73:305–318 (1985). The gene III coat protein is present in about five copies at one end of the phage particle. The modified phage were termed "fusion phage" because they displayed the foreign peptides fused to the gene III coat protein. As each fusion phage particle displayed approximately five copies of the fusion protein, this mode of phage display was termed "polyvalent display."

Scott et al. and Cwirla et al. showed that fusion phage libraries could be screened by sequential affinity selections known as "panning." Scott et al., *Science* 249:386–390 (1990); Cwirla et al., *PNAS USA* 87:6378–6382 (1990). However, early efforts to select high affinity fusion phage failed, presumably due to the polyvalence of the phage particles. This problem was solved with the development of a "monovalent" phage display system in which the fusion protein is expressed at a low level from a phagemid and a helper phage provides a large excess of wild-type coat protein. Bass et al., *Proteins* 8:309–314 (1990); Lowman et al., *Biochem.* 30:10832–10838 (1991). Monovalent phage display can be used to generate and screen a large number of variant polypeptides to isolate those that bind with high affinity to a target of interest.

Approximately 50,000 infants are born in the United States every year with birth weights, less than 1.5 kg. About two thirds of these very low birth weight infants have evidence of pulmonary immaturity manifested as respiratory distress shortly after birth. The majority of these infants require mechanical ventilation. Respiratory distress syndrome, caused by insufficient pulmonary surfactant production, as well as structural immaturity of the lung, is responsible for respiratory difficulties observed in these prematurely born neonates. Well developed alveoli are necessary to provide efficient oxygen transfer from the air-liquid interface of the lung to the systemic circulation. Surfactant proteins are critical in reducing the alveolar surface tension at low lung volumes and preventing alveolar collapse.

A need continues to exist for a method of treatment for respiratory distress syndrome and other diseases associated with immature lung development and low lung surfactant production.

SUMMARY OF THE INVENTION

In general an object of the invention is to provide a method of inducing epithelial cell growth and development for the purpose of promoting repair and healing of tissue damage or injury.

Accordingly, one object of this invention is to provide a method of treating respiratory distress syndrome in patients, primarily human patients, in need of such treatment. A further object is to provide a method of inducing lung epithelial cell growth and development. A further object is to provide a method of increasing lung surfactant protein A production in the lung of persons with impaired oxygen transfer in the lung alveoli. This invention is useful in treating infants/neonates with respiratory distress as well as youth and adults with poor lung function due to lung injury or damage.

In one aspect of this invention, it has now been discovered that these objects and the broader objective of treating conditions associated with epithelial cell damage and injury are achieved by administering to a patient in need of such treatment an effective amount of a heregulin ligand, preferably a polypeptide or fragment thereof. These heregulin (HRG) polypeptides, include HRG-$\alpha$, HRG-$\beta$1, HRG-$\beta$2, HRG-$\beta$3 and other HRG polypeptides which cross-react with antibodies directed against these family members and/or which are substantially homologous as defined below and includes HRG variants such as N-terminal and C-terminal fragments thereof. A preferred HRG is the ligand disclosed in FIGS. 1A–1D and further designated HRG-$\alpha$. Other preferred HRGs are the ligands disclosed in FIGS. 2A–2E, and designated HRG-$\beta$1; disclosed in FIGS. 3A–3E designated HRG-$\beta$2; and disclosed in FIGS. 4A–4C designated HRG-$\beta$3.

In another aspect, the invention provides a method in which HRG agonist antibodies are administered to achieve the objects of the invention. In this embodiment, HER2/HER3 or fragments thereof (which also may be synthesized by in vitro methods) are fused (by recombinant expression or an in vitro peptidyl bond) to an immunogenic polypeptide and this fusion polypeptide, in turn, is used to raise antibodies against a HER2/HER3 epitope. Agonist antibodies are recovered from the serum of immunized animals. Alternatively, monoclonal-antibodies are prepared from in vitro cells or in vivo immunized animals in conventional fashion. If desired, the agonist antibodies may be obtained by phage display selection from a phage library of antibodies or antibody fragments. Preferred antibodies identified by routine screening will bind to the receptor, but will not substantially cross-react with any other known ligands such as EGF, and will activate the HER receptors HER2, HER3 and/or HER4. In addition, antibodies may be selected that are capable of binding specifically to individual family members of HRG family, e.g. HRG-α, HRG-β1, HRG-β2, HRG-β3, and which are agonists thereof.

In general, the invention is a method of regenerating and/or repairing epithelial cell injury by stimulating growth and proliferation of epithelial cells, in particular ductal and ciliated epithelial cells. The epithelial cells may be injured by many types of insults, for example, injury due to surgical incision or resection, chemical or smoke inhalation or aspiration, chemical or biochemical ulceration, cell damage due to viral or bacterial infection, etc. The epithelial cells which may be affected by the method of the invention include any epithelial cell which expresses HER2, HER3 and/or HER4; suitable cells are located, for example, in the lung, gastric mucosa, endometrium, oviducts, mammary glands, pancreas, salivary glands, etc. The method of the invention stimulates growth and proliferation of the epithelial cells, repairing and re-establishing the cellular barriers of organs and allowing the affected tissues to develop normal physiological functions more quickly. For example, lung epithelial cells are damaged by inhalation of smoke resulting in emphysema. Treatment of the lung cells by the method of the invention regenerates the barrier layer of lung epithelial cells, improves oxygenation and speeds the development of a barrier to infection. Similarly, cell damage due to aspiration of gastric acid can be treated by the method of the invention to facilitate regeneration of epithelial cells.

Accordingly, one embodiment of the invention is a method of inducing lung epithelial cell growth and development by contacting a lung epithelial cell which expresses HER2, HER3 and/or HER4 receptors with an effective amount of a HER2, HER3 and/or HER4 activating ligand.

Another embodiment is a method of increasing lung surfactant protein A in a patient by administering to a patient in need thereof an effective amount of a HER2, HER3 and/or HER4 activating ligand.

A further embodiment is a method of treating respiratory distress by administering to a patient in need thereof an effective amount of a HER2, HER3 and/or HER4 activating ligand.

A further embodiment is a method of treating emphysema by administering to a patient in need thereof an effective amount of a HER2, HER3 and/or HER4 activating ligand.

BRIEF DESCRIPTION OF THE DRAWINGS

FIGS. 1A–1D show the deduced amino acid sequence (SEQ ID NO:1) for the cDNA sequence (SEQ ID NO:2) contained in a clone obtained according to U.S. Pat. No. 5,367,060. The initiating methionine (Met) of HRG-α is at position 45.

FIGS. 2A–2E show the deduced amino acid sequence (SEQ ID NO:3) and cDNA sequence (SEQ ID NO:4) of a potential coding sequence of a clone obtained according to U.S. Pat. No. 5,367,060 for HRG-β1. The initiating Met is at M31.

FIGS. 3A–3E show the deduced amino acid sequence (SEQ ID NO:5) and cDNA sequence (SEQ ID NO:6) of a nucleotide sequence of a clone obtained according to U.S. Pat. No. 5,367,060 for HRG-β2.

FIGS. 4A–4C show the deduced amino acid sequence (SEQ ID NO:7) and cDNA sequence (SEQ ID NO:8) of a nucleotide sequence of a clone obtained according to U.S. Pat. No. 5,367,060 for HRG-β3.

FIGS. 5A–5D show the deduced amino acid sequence (SEQ ID NO:9) and cDNA sequence (SEQ ID NO:10) of a nucleotide sequence of a clone obtained according to U.S. Pat. No. 5,367,060 for HRG-β2-like protein.

FIG. 6A–6C show a comparison of the amino acid homologies of several known hereguligns a, β1, β2, β2-like, and β3 in descending order and illustrates the amino acid insertions, deletions, and substitutions that characterize these forms of HRG. The sequences are aligned starting from the initiating Met as shown in FIGS. 1–5. (SEQ ID NOS:1, 3, 5, 9 and 7; a 645 amino acid HRG β1 polypeptide starting from the initiating Met has the sequence of SEQ ID NO:15)

FIGS. 7A–7C show the deduced amino acid sequence (SEQ ID NO:11) and cDNA sequence (SEQ ID NO:12) of γ-HRG obtained as described in U.S. Ser. No. 08/891,845. The hydrophobic region is underlined. The EGF-like domain is shaded, cysteine residues in the EGF-like domain are circled. N-linked glycosylation sites are marked above the nucleic acid sequence with a (•).

FIG. 8 shows the cDNA sequence (SEQ ID NO:13) and amino acid sequence (SEQ ID NO:14) of SMDF obtained as described in U.S. Ser. No. 08/339,517. An EGF-like domain and the apolar and uncharged domains (i.e. "apolar I" consisting of residues from about 48–62 and "apolar II" consisting of residues from about 76–100) are underlined. Cysteines in the EGF-like domain and in the "cysteine knot" in the unique N-terminal domain ("NTD-cys knot") are boxed. The stop codon is denoted by the letter "O".

DETAILED DESCRIPTION OF THE PREFERRED EMBODIMENTS

HRG ligands, in particular polypeptides and agonist antibodies thereof, have affinity for and stimulate the HER2, HER3 and/or HER4 receptors or combinations thereof in autophosphorylation. Included within the definition of HRG ligands, in addition to HRG-α, HRG-β1, HRG-β2, HRG-β3 and HRG-β2-like, are other polypeptides binding to the HER2, HER3 and/or HER4 receptor, which bear substantial amino acid sequence homology to HRG-α or HRG-β1. Such additional polypeptides fall within the definition of HRG as a family of polypeptide ligands that bind to the HER2, HER3 and/or HER4 receptors.

Heregulin polypeptides bind with varying affinities to the HER2, HER3 and/or HER4 receptors. Generally, the HER3 and HER4 receptors are bound with high affinity. It is also known that heterodimerization of HER2 with HER3 and of HER2 with HER4 occurs with subsequent receptor cross-phosphorylation as described above. In the present invention, epithelial cell growth and/or proliferation is induced when a heregulin protein interacts and binds with an individual receptor molecule or a receptor dimer such that receptor phosphorylation is induced. Binding and activation of HER2, HER3, HER4 or combinations thereof, therefore, is meant to include activation of any form of the receptor necessary for receptor activation and biologic function including monomeric receptor and dimeric receptor forms. Dimeric receptor forms may be referred to below, for example, as HER2/HER3, HER2/HER4, and HER3/HER4.

I. Definitions

In general, the following words or phrases have the indicated definition when used in the description, examples, and claims.

"Heregulin" (HRG) ligand is defined herein to be any isolated ligand, preferably a polypeptide sequence which possesses a biological property of a naturally occurring HRG polypeptide. Ligands within the scope of this invention include the NDF, ARIA and GGF growth factor heregulin proteins identified above as well as the SMDF and HRG polypeptides discussed in detail herein. These isolated NDF, ARIA and GGF heregulin polypeptides are well known in the art. HRG includes the polypeptides shown in FIGS. 1A–1D, 2A–2E, 3A–3E, 4A–4C, 5A–5D, 6A–6C, 7A–7C and 8 and mammalian analogues thereof. Included are HRG variants such as the γ-HRG described in U.S. application Ser. No. 08/891,845 filed Jul. 10, 1997, the variants described in Ser. No. 08/799,054 filed Feb. 10, 1997 and the SMDF variants described in Ser. No. 08/339,517 filed Nov. 14, 1994 (WO 96/15244). These applications are incorporated herein in their entirety. These variants can be prepared by the methods described below, optionally together with alanine scanning and phage display techniques known in the art. Cunningham and Wells, Science 244:1081–85 (1989); Bass et al., Proteins 8:309–14 (1990); Lowman et al., Biochem. 30:10832–38 (1991).

The term a "normal" epithelial cell means an epithelial cell which is not transformed, i.e., is non-cancerous and/or non-immortalized. Further, the normal epithelial cell is preferably not aneuploid. Aneuploidy exists when the nucleus of a cell does not contain an exact multiple of the haploid number of chromosomes, one or more chromosomes being present in greater or lesser number than the rest. Typical properties of transformed cells which fall outside the scope of this invention include the ability to form tumors when implanted into immune-deprived mice (nude mice), the ability to grow in suspension or in semi-solid media such as agar, a loss of contact inhibition allowing piling up of cells into colonies or foci, a loss of dependence on growth factors or serum, cell death if cells are inhibited from growing, and disorganization of actin filaments. Specifically included within the invention are normal epithelial cells which will not form tumors in mice, grow attached to plastic or glass (are anchorage dependent), exhibit contact inhibition, require serum-containing hormones and growth factors, remain viable if growth is arrested by lack of serum, and contain well-organized actin filaments. Although the normal epithelial cells are preferably not cultured cells, also suitable for the invention are non-transformed, non-immortalized epithelial cells isolated from mammalian tissue. These isolated cells may be cultured for several generations (up to about 10 or even 50 generations) in the presence of a heregulin in order to induce growth and/or proliferation of the isolated epithelial cell sample, that is, to expand the sample. The expanded sample can then be reintroduced into the mammal for the purpose of repopulating the epithelial cell tissue (re-epithelialization). This is particularly useful for repairing tissue injury or damage.

An "epithelial" cell is a cell located in a cellular, avascular layer covering the free surface (cutaneous, mucous or serous) of an organ or lining a tube or cavity of an animal body. Lung epithelial cells include bronchial epithelial cells, Type II cells and Clara cells. The term "epithelial cell" as used herein is consistent with the art recognized definition of epithelial cells in epithelium. See, for example, the definition in Taber's Encyclopedic Medical Dictionary, Edition 12, (1973) F. A. Davis Company, publisher.

"Biological property" for the purposes herein means an in vivo biologic or antigenic function or activity that is directly or indirectly performed by an HRG sequence (whether in its native or denatured conformation), or by any subsequence thereof. Biologic functions include receptor binding, any enzyme activity or enzyme modulatory activity, any carrier binding activity, any hormonal activity, any activity in promoting or inhibiting adhesion of cells to extracellular matrix or cell surface molecules, or any structural role. However, biologic functions do not include antigenic functions, i.e. possession of an epitope or antigenic site that is capable of cross-reacting with antibodies raised against a naturally occurring HRG polypeptide.

"Biologically active" HRG is defined herein as a polypeptide sharing a biologic function of an HRG sequence which may (but need not) in addition possess an antigenic function. A principal known effect or function of HRG is as a ligand polypeptide having a qualitative biological activity of binding to HER2, HER3 and/or HER4 resulting in the activation of the receptor tyrosine kinase (an "activating ligand"). One test for activating ligands is the HRG tyrosine autophosphorylation assay described below. Included within the scope of HRG as that term is used herein are HRG having translated mature amino acid sequences of the complete human HRG as set forth herein; deglycosylated or unglycosylated derivatives of HRG, amino acid sequence variants of HRG sequence, and derivatives of HRG, which are capable of exhibiting a biological property in common with HRG. While native HRG is a membrane-bound polypeptide, soluble forms, such as those forms lacking a functional transmembrane domain, are also included within this definition. In particular, included are polypeptide fragments of HRG sequence which have an N-terminus at any residue from about S216 to about A227, and its C-terminus at any residue from about K268 to about R286, and the homologous sequences shown in FIGS. 6A–C, hereinafter referred to collectively for all HRGs as the growth factor domain (GFD).

"Antigenically active" HRG is defined as a polypeptide that possesses an antigenic function of an HRG and which may (but need not) in addition possess a biologic function.

In preferred embodiments, antigenically active HRG is a polypeptide that binds with an affinity of at least about $10^{-9}$ l/mole to an antibody raised against a naturally occurring HRG sequence. Ordinarily the polypeptide binds with an affinity of at least about $10^{-8}$ l/mole. Most preferably, the antigenically active HRG is a polypeptide that binds to an antibody raised against one of HRGs in its native conformation. HRG in its native conformation generally is HRG as found in nature which has not been denatured by chaotropic agents, heat or other treatment that substantially modifies the three dimensional structure of HRG as determined, for example, by migration on nonreducing, nondenaturing sizing gels. Antibody used in this determination may be rabbit polyclonal antibody raised by formulating native HRG from a non-rabbit species in Freund's complete adjuvant, subcutaneously injecting the formulation, and boosting the immune response by intraperitoneal injection of the formulation until the titer of anti-HRG antibody plateaus.

Ordinarily, biologically or antigenically active HRG will have an amino acid sequence having at least 75% amino acid sequence identity with a given HRG sequence, more preferably at least 80%, even more preferably at least 90%, and most preferably at least 95%. Identity or homology with respect to an HRG sequence is defined herein as the percentage of amino acid residues in the candidate sequence that are identical with HRG residues in the HRG of FIGS.

6A–6C, after aligning the sequences and introducing gaps, if necessary, to achieve the maximum percent homology, and not considering any conservative substitutions as part of the sequence identity. None of N-terminal, C-terminal or internal extensions, deletions, or insertions into HRG sequence shall be construed as affecting homology.

Thus, the biologically active and antigenically active HRG polypeptides that are the subject of this invention include each entire HRG sequence; fragments thereof having a consecutive sequence of at least 5, 10, 15, 20, 25, 30 or 40 amino acid residues from HRG sequence; amino acid sequence variants of HRG sequence wherein an amino acid residue has been inserted N- or C-terminal to, or within, HRG sequence or its fragment as defined above; amino acid sequence variants of HRG sequence or its fragment as defined above has been substituted by another residue. HRG polypeptides include those containing predetermined mutations by, e.g., site-directed or PCR mutagenesis, and other animal species of HRG polypeptides such as rabbit, rat, porcine, non-human primate, equine, murine, and ovine HRG and alleles or other naturally occurring variants of the foregoing and human sequences; derivatives of HRG or its fragments as defined above wherein HRG or its fragments have been covalently modified by substitution, chemical, enzymatic, or other appropriate means with a moiety other than a naturally occurring amino acid (for example a detectable moiety such as an enzyme or radioisotope); glycosylation variants of HRG (insertion of a glycosylation site or deletion of any glycosylation site by deletion, insertion or substitution of appropriate amino acid); and soluble forms of HRG, such as HRG-GFD or those that lack a functional transmembrane domain.

"Isolated" means a ligand, such as HRG, which has been identified and separated and/or recovered from a component of its natural environment. Contaminant components of its natural environment are materials which would interfere with diagnostic or therapeutic uses for HRG, and may include proteins, hormones, and other substances. In preferred embodiments, HRG will be purified (1) to greater than 95% by weight of protein as determined by the Lowry method or other validated protein determination method, and most preferably more than 99% by weight, (2) to a degree sufficient to obtain at least 15 residues of N-terminal or internal amino acid sequence by use of the best commercially available amino acid sequenator marketed on the filing date hereof, or (3) to homogeneity by SDS-PAGE using Coomassie blue or, preferably, silver stain. Isolated HRG includes HRG in situ within recombinant cells since at least one component of HRG natural environment will not be present. Isolated HRG includes HRG from one species in a recombinant cell culture of another species since HRG in such circumstances will be devoid of source polypeptides. Ordinarily, however, isolated HRG will be prepared by at least one purification step.

In accordance with this invention, HRG nucleic acid is RNA or DNA containing greater than ten bases that encodes a biologically or antigenically active HRG, is complementary to nucleic acid sequence encoding such HRG, or hybridizes to nucleic acid sequence encoding such HRG and remains stably bound to it under stringent conditions.

Preferably, HRG nucleic acid encodes a polypeptide sharing at least 75% sequence identity, more preferably at least 80%, still more preferably at least 85%, even more preferably at 90%, and most preferably 95%, with an HRG sequence. Preferably, the HRG nucleic acid that hybridizes contains at least 20, more preferably at least about 40, and most preferably at least about 90 bases.

Isolated HRG nucleic acid includes a nucleic acid that is identified and separated from at least one containment nucleic acid with which it is ordinarily associated in the natural source of HRG nucleic acid. Isolated HRG nucleic acid thus is present in other than in the form or setting in which it is found in nature. However, isolated HRG encoding nucleic acid includes HRG nucleic acid in ordinarily HRG-expressing cells where the nucleic acid is in a chromosomal location different from that of natural cells or is otherwise flanked by a different DNA sequence than that found in nature. Nucleic acid encoding HRG may be used in specific hybridization assays, particularly those portions of HRG encoding sequence that do not hybridize with other known DNA sequences. "Stringent conditions" are those that (1) employ low ionic strength and high temperature for washing, for example, 0.015 M NACl/0.0015 M sodium citrate/0/1% NaDodSO$_4$ at 50° C.; (2) employ during hybridization a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 μM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS, and 10% dextran sulfate at 42° C., with washes at 42° C. in 0.2×SSC and 0.1% SDS.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean nucleic acid sequence that is foreign to the cell, or homologous to the cell but in a position within the host cell nucleic acid in which the element is ordinarily not found.

As used herein, the expressions "cell", "cell line", and "cell culture" are used interchangeably, and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Plasmids" are designated by a lower case "p" preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Restriction enzyme digestion" of DNA refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained, and then a number designating the particular enzyme. In general, about 1 mg of plasmid or DNA fragment is used with about 1–2 units of enzyme in about 20 ml of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al., (*Molecular Cloning: A Laboratory Manual* New York: Cold Spring Harbor Laboratory Press, 1989)

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.* 9:6103–6114 (1981), and Goeddet et al., *Nucleic Acids Res.* 8:4057 1980).

"Northern analysis" is a method used to identify RNA sequences that hybridize to a known probe such as an oligonucleotide, DNA fragment, cDNA or fragment thereof, or RNA fragment. The probe is labeled with a radioisotope such as $^{32}P$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra "Ligation" refers to the process of forming phosphodiester bonds between two nucleic acid fragments. To ligate the DNA fragments together, the ends of the DNA fragments must be compatible with each other. In some cases, the ends will be directly compatible after endonuclease digestion. However, it may be necessary to first convert the staggered ends commonly produced after endonuclease digestion to blunt ends to make them compatible for ligation. To blunt the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 mg of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

"Preparation" of DNA from cells means isolating the plasmid DNA from a culture of the host cells. Commonly used methods for DNA preparation are the large and small-scale plasmid preparations described in sections 1.25–1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.* 14:5399–5407, 1986. They are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195, issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51: 263 (1987); Erlich, ed., *PCR Technology*, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer, and utilizes a nucleic acid polymerase to amplify or generate a specific piece of nucleic acid or to amplify or generate a specific piece of nucleic acid which is complementary to a particular nucleic acid.

The "HRG tyrosine autophosphorylation assay" to detect the presence or bioactivity of HRG ligands can be used to monitor the purification of a ligand for the HER2 and HER3 receptors. This assay is based on the assumption that a specific ligand for the receptor will stimulate autophosphorylation of the receptor, in analogy with EGF and its stimulation of EGF receptor autophosphorylation. See Sadich et al., *Anal. Biochem.* 235:207–214 (1996). MDA-MB453 cells or MCF7 cells which contain high levels of p185$^{HER2}$ receptors but negligible levels of human EGF receptors, were obtained from the American Type Culture Collection, Rockville, Md. (ATCC No HTB-131) and maintained in tissue culture with 10% fetal calf serum in DMEM/ Hams F12 (1:1) media. For assay, the cells were trypsinized and plated at 150,000 cells/well in 24 well dishes (Costar). After incubation with serum containing media overnight, the cells were placed in serum free media for 2–18 hours before assay. Test samples of 100 uL aliquots were added to each well. The cells were incubated for 5–30 minutes (typically 30 min) at 37° C. and the media removed. The cells in each well were treated with 100 uL SDS gel denaturing buffer (SEPROSOL, Enpotech, Inc.) and the plates heated at 100° C. for 5 minutes to dissolve the cells and denature the proteins. Aliquots from each well were electrophoresed on 5–20% gradient SDS gels (NOVEX, Encinitas, Calif.) according to the manufacturer's directions. After the dye front reached the bottom of the gel, the electrophoresis was terminated and a sheet of PVDF membrane (PROBLOTT, ABI) was placed on the gel and the proteins transferred from the gel to the membrane in a blotting chamber (BioRad) at 200 mAmps for 30–60 min. After blotting, the membranes were incubated with TRIS buffered saline containing 0.1% TWEEN 20 detergent buffer with 5% BSA for 2–18 hrs to block nonspecific binding, and then treated with a mouse anti-phosphotyrosine antibody (Upstate Biological Inc., N.Y.). Subsequently, the membrane blots were treated with goat anti-mouse antibody conjugated to alkaline phosphatase. The gels were developed using the PROTOBLOT System from Promega. After drying the membranes, the density of the bands corresponding to $p185^{HER2}$ in each sample lane was quantitated with a Hewlett Packard SCANJET Plus Scanner attached to a Macintosh computer. The number of receptors per cell in the MDA-MB453 cells is such that under these experimental conditions the $p185^{HER2}$ receptor protein is the major protein which is labeled.

"Protein microsequencing" was accomplished based upon the following procedures. Proteins from the final HPLC step were either sequenced directly by automated Edman degradation with a model 470A Applied Biosystems gas phase sequencer equipped with a 120A PTH amino acid analyzer or sequenced after digestion with various chemicals or enzymes. PTH amino acids were integrated using the CHROMPERFECT data system (Justice Innovations, Palo Alto, Calif.). Sequence interpretation was performed on a VAX 11/785 Digital Equipment Corporation computer as described (Henzel et al., *J. Chromatography* 404:41–52 (1987)). In some cases, aliquots of the HPLC fractions were electrophoresed on 5–20% SDS polyacrylamide gels, electrotransferred to a PVDF membrane (PROBLOTT, ABI, Foster City, Calif.) and stained with Coomassie Brilliant Blue (Matsudaira, P., *J. Biol. Chem.* 262:10035–10038, 1987). The specific protein was excised from the blot for N terminal sequencing. To determine internal protein sequences, HPLC fractions were dried under vacuum (SPEEDVAC), resuspended in appropriate buffers, and digested with cyanogen bromide, the lysine-specific enzyme Lys-C (Wako Chemicals, Richmond, Va.) or Asp-N (Boehringer Mannheim, Indianapolis, Ind.). After digestion, the resultant peptides were sequenced as a mixture or were resolved by HPLC on a C4 column developed with a propanol gradient in 0.1% TFA before sequencing as described above.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (K) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments" comprise a portion of a full length antibody, generally the antigen binding or variable domain thereof. Examples of antibody fragments include Fab, Fab', $F(ab')_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624–628 (1991) and Marks et al., *J. Mol. Biol.* 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851–6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522–525 (1986); Reichmann et al., *Nature* 332:323–329 (1988); and Presta, *Curr. Op. Struct. Biol.* 2:593–596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269–315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444–6448 (1993).

The expression "linear antibodies" when used throughout this application refers to the antibodies described in Zapata et al. *Protein Eng.* 8(10):1057–1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

II. Use and Preparation of HRG Sequences

H. Preparation of HRG Sequences, Including Variants

The system to be employed in preparing HRG sequence will depend upon the particular HRG sequence selected. If the sequence is sufficiently small HRG may be prepared by in vitro polypeptide synthetic methods. Most commonly, however, HRG will be prepared in recombinant cell culture using the host-vector systems described below. Suitable HRG includes any biologically active and antigenetically active HRG.

In general, mammalian host cells will be employed, and such hosts may or may not contain post-translational systems for processing HRG preprosequences in the normal fashion. If the host cells contain such systems then it will be possible to recover natural subdomain fragments such as HRG-GFD from the cultures. If not, then the proper processing can be accomplished by transforming the hosts with the required enzyme(s) or by supplying them in an in vitro method. However, it is not necessary to transform cells with the complete prepro or structural genes for a selected HRG when it is desired to only produce fragments of HRG sequences such as an HRG-GFD. For example, a start codon is ligated to the 5' end of DNA encoding an HRG-GFD, this DNA is used to transform host cells and the product expressed directly as the Met N-terminal form (if desired, the extraneous Met may be removed in vitro or by endogenous N-terminal demethionylases). Alternatively, HRG-GFD is expressed as a fusion with a signal sequence recognized by the host cell, which will process and secrete the mature HRG-GFD as is further described below. Amino acid sequence variants of native HRG-GFD sequences are produced in the same way.

HRG sequences located between the first N-terminal mature residue and the first IS N-terminal residue of HRG-GFD sequence, termed HRG-NTD, may function at least in part as an unconventional signal sequence or as a normally circulating carrier/precursor for HRG-GFD having unique biological activity. HRG-NTD is produced in the same fashion as the full length molecule but from expression of DNA in which a stop codon is located at the C-terminus of HRG-NTD. In addition, HRG variants are expressed from DNA encoding protein in which both the GFD and NTD domains are in their proper orientation but which contain an amino acid insertion, deletion or substitution at the GFD-NTD cleavage site (located within the sequence VKC) which inhibits or prevents proteolytic cleavage of the NTD-GFD joining site in vivo, and wherein a stop codon is positioned at the 3' end of the GFD-encoding sequence. In an example of this group of variants (termed HRG-NTDXGFD), (1) the lysine residue found in the NTD-GFD joining sequence VKC is deleted or (preferably) substituted by another residue other than arginyl such as histidyl, alanyl, threonyl or seryl and (2) a stop codon is introduced in the sequence RCT or RCQ in place of cysteinyl, or threonyl (for HRG-α) or glutaminyl (for HRG-β).

A preferred HRG-αligand with binding affinity to p185$^{HER2}$ comprises amino acids 226–265 of FIGS. 1A–D. This HRG-α ligand further may comprise up to an additional 1–20 amino acids preceding amino acid 226 and 1–20 amino acids following amino acid 265. A preferred HRG-β ligand with binding affinity to p185$^{HER2}$ comprises amino acids 226–265 of FIGS. 2A–E. This HRG-β ligand may comprise up to an additional 1–20 amino acids preceding amino acid 226 and 1–20 amino acids following amino acid 265.

As noted above, other HRG sequences to be prepared in accordance with this invention are those of the GFD. These are synthesized in vitro or are produced in recombinant cell culture. These are produced most inexpensively in yeast or E. coli by secretion under the control of a HRG-heterologous signal as described infra, although preparation in mammalian cells is also contemplated using a mammalian protein signal such as that of tPA, UK or a secreted viral protein. The GFD can be the sequence of a native HRG or may be a variant thereof as described below. GFD sequences include those in which one or more residues from a member of the EGF family are substituted into or onto the GFD sequence.

An additional HRG is one which contains the GFD and the sequence between the C-terminus of GFD and the N-terminus of the transmembrane domain (the later being termed the C-terminal cleavage domain or CTC). In this variant (HRG-GFD-CTC) the DNA start codon is present at the 5' end of HRG-heterologous signal sequence or adjacent the 5' end of the GFD-encoding region, and a stop codon is found in place of one of the first about 1 to 3 extra-cellular domain (ECD) residues or first about 1–2 transmembrane region residues. In addition, in some HRG-GFD-CTC variants the codons are modified in the GFD-CTC proteolysis site by substitution, insertion or deletion. The GFD-CTC proteolysis site is the domain that contains the GFD C-terminal residue and about 5 residues N- and 5 residues C-terminal from this residue. It is known that Met-227 terminal and Val-229 terminal HRG-α-GFD are biologically active. The C-terminus for HRG-α-GFD may be Met-227, Lys-228, Val-229, Gln-230, Asn-231 or Gln-232, and for HRG-β-GFD may be Met-226, Ala-227, Ser-228, Phe-229, Trp-230, or Lys231/Ser231. The native C-terminus is determined readily by C-terminal sequencing, although it is not critical that HRG-GFD have the native terminus so long as the GFD sequence possesses the desired activity. In some embodiments of HRG-GFD-CTC variants, the amino acid change(s) in the CTC are screened for their ability to resist proteolysis in vitro and inhibit the protease responsible for generation of HRG-GFD.

HRG-ECD variants are made by providing a stop codon at the same location as for HRG-GFD-CTC variants. HRG-ECD may comprise any one or more of the variants described above in connection with its subfragments, e.g. the GFD-CTC variants containing CTC-proteolysis site modifications.

If it is desired to prepare the longer HRG polypeptides and the 5' or 3' ends of the given HRG are not described herein, it may be necessary to prepare nucleic acids in which the missing domains are supplied by homologous regions from more complete HRG nucleic acids. Alternatively, the missing domains can be obtained by probing libraries using the DNAs disclosed in the Figures or fragments thereof.

A. Isolation of DNA Encoding Heregulin

The DNA encoding HRG may be obtained from any cDNA library prepared from tissue believed to possess HRG mRNA and to express it at a detectable level. HRG-α gene thus may be obtained from a genomic library. Similar procedures may be used for the isolation of other HRG, such as HRG-β1, HRG-β2, or HRG-β3 encoding genes.

Libraries are screened with probes designed to identify the gene of interest or the protein encoded by it. For cDNA expression libraries, suitable probes include monoclonal or polyclonal antibodies that recognize and specifically bind to HRG-α; oligonucleotides of about 20–80 bases in length that encode known or suspected portions of HRG-α cDNA from the same or different species; and/or complementary or homologous cDNAs or fragments thereof that encode the same or a similar gene. Appropriate probes for screening genomic DNA libraries include, but are not limited to, oligonucleotides; cDNAs or fragments thereof that encode the same or a similar gene; and/or homologous genomic DNAs or fragments thereof. Screening the cDNA or genomic library with the selected probe may be conducted using standard procedures as described in chapters 10–12 of Sambrook et al., supra.

An alternative means to isolate the gene encoding HRG-α is to use polymerase chain reaction (PCR) methodology as described in section 14 of Sambrook et al., supra. This method requires the use of oligonucleotide probes that will hybridize to HRG-α. Strategies for selection of oligonucleotides are described below.

Another alternative method for obtaining the gene of interest is to chemically synthesize it using one of the methods described in Engels et al. (*Agnew. Chem. Int. Ed. Engl.*, 28: 716–734,1989), specifically incorporated by reference. These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

A preferred method of practicing this invention is to use carefully selected oligonucleotide sequences to screen cDNA libraries from various tissues, preferably human breast, colon, salivary gland, placental, fetal, brain, and carcinoma cell lines. Other biological sources of DNA encoding an heregulin-like ligand include other mammals and birds. Among the preferred mammals are members of the following orders: bovine, ovine, equine, murine, and rodentia.

The oligonucleotide sequences selected as probes should be of sufficient length and sufficiently unambiguous that false positives are minimized. The actual nucleotide sequence(s) may, for example, be based on conserved or highly homologous nucleotide sequences or regions of HRG-α. The oligonucleotides may be degenerate at one or more positions. The use of degenerate oligonucleotides may be of particular importance where a library is screened from a species in which preferential codon usage in that species is not known. The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Of particular interest is HRG-α nucleic acid that encodes a full-length polypeptide. In some preferred embodiments, the nucleic acid sequence includes the native HRG-α signal sequence. Nucleic acid having all the protein coding sequence is obtained by screening selected cDNA or genomic libraries, and, if necessary, using conventional primer extension procedures as described in section 7.79 of Sambrook et al., supra, to detect precursors and processing intermediates of mRNA that may not have been reverse-transcribed into cDNA.

HRG-α encoding DNA of FIGS. 1A–1D may be used to isolate DNA encoding the analogous ligand from other animal species via hybridization employing the methods discussed above. The preferred animals are mammals, particularly bovine, ovine, equine, feline, canine and rodentia, and more specifically rats, mice and rabbits.

B. Amino Acid Sequence Variants of Heregulin

Amino acid sequence variants of HRG are prepared by introducing appropriate nucleotide changes into HRG DNA, or by in vitro synthesis of the desired HRG polypeptide. Such variants include, for example, deletions from, or insertions or substitutions of, residues within the amino acid sequence shown for human HRG sequences. Any combination of deletion, insertion, and substitution can be made to arrive at the final construct, provided that the final construct possesses the desired characteristics. Excluded from the scope of this invention are HRG variants or polypeptide sequences that are not novel and unobvious over the prior art. The amino acid changes also may alter post-translational processes of HRG-α, such as changing the number or position of glycosylation sites, altering the membrane anchoring characteristics, altering the intra-cellular location of HRG by inserting, deleting, or otherwise affecting the leader sequence of the native HRG, or modifying its susceptibility to proteolytic cleavage.

The HRG sequence may be proteolytically processed to create a number of HRG fragments. HRG-GFD sequences of HRG-a all contain the amino acid sequence between HRG-α cysteine 226 and cysteine 265. The amino terminus of HRG-α fragment may result from the cleavage of any peptide bond between alanine 1 and cysteine 226, preferably adjacent to an arginine, lysine, valine, or methionine, and most preferably between methionine 45 and serine 46. The carboxy terminus of HRG-α fragment may result from the cleavage of any peptide bond between cysteine 265, preferably adjacent to an arginine, lysine, valine, or methionine, and most preferably between lysine 272 and valine 273, between lysine 278 and alanine 279, or between lysine 285 and arginine 286. The resulting HRG-α ligands resulting from such proteolytic processing are the preferred ligands.

HRG-β-GFD's are analogous to those discussed above for HRG-α-GFD's. Each HRG-β-GFD contains the polypeptide segment from cysteine 212 to cysteine 251 of FIGS. 2A–E. The amino terminus of HRG-β1 fragment may result from the cleavage of any peptide bond between alanine 1 and cysteine 212, preferably adjacent to an arginine, lysine, valine, or methionine, and most preferably between methionine 31 and serine 32. The carboxy terminus of HRG-β1 fragment may result from the cleavage of any peptide bond between cysteine 251 of FIGS. 2A–2E, preferably adjacent to an arginine, lysine, valine, or methionine, and most preferably between valine 255 and methionine 256, between lysine 261 and histidine 262, between lysine 276 and alanine 277, or between lysine 301 and thrionine 302. The resulting HRG-β1 ligands resulting from such proteolytic processing are among the preferred ligands. Similarly, processing to produce preferred fragment ligands of HRG-β2 based upon the FIGS. 3A–3E and HRG-β3 based upon FIGS. 4A–4C may be accomplished by cleaving HRG sequences of FIGS. 3A–3E and 4A–4C preferably adjacent to an arginine, lysine, valine or methionine.

In designing amino acid sequence variants of HRG, the location of the mutation site and the nature of the mutation will depend on HRG characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of other receptor ligands adjacent to the located site.

A useful method for identification of certain residues or regions of HRG polypeptide that are preferred locations for mutagenesis is called "alanine scanning mutagenesis" as described by Cunningham and Wells (Science, 244: 1081–1085, 1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed HRG variants are screened for the optimal combination of desired activity.

There are two principal variables in the construction of amino acid sequence variants: the location of the mutation site and the nature of the mutation. These are variants from HRG sequence, and may represent naturally occurring alleles (which will not require manipulation of HRG DNA) or predetermined mutant forms made by mutating the DNA, either to arrive at an allele or a variant not found in nature. In general, the location and nature of the mutation chosen will depend upon HRG characteristic to be modified. Obviously, such variations that, for example, convert HRG into a known receptor ligand, are not included within the scope of this invention, nor are any other HRG variants or polypeptide sequences that are not novel and unobvious over the prior art.

Amino acid sequence deletions generally range from about 1 to 30 residues, more preferably about 1 to 10 residues, and typically about 1 to 5 are contiguous. Deletions may be introduced into regions of low homology with other EGF family precursors to modify the activity of HRG. Deletions from HRG in areas of substantial homology with other EGF family sequences will be more likely to modify the biological activity of HRG more significantly The number of consecutive deletions will be selected so as to preserve the tertiary structure of HRG in the affected domain, e.g., cysteine crosslinking, beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within HRG sequence) may range generally from about 1 to 10 residues, more preferably 1 to 5, and most preferably 1 to 3. Examples of terminal insertions include HRG with an N-terminal methionyl residue (an artifact of the direct expression of HRG in bacterial recombinant cell culture), and fusion of a heterologous N-terminal signal sequence to the N-terminus of HRG to facilitate the secretion of mature HRG from recombinant host cells. Such signal sequences generally will be obtained from, and thus be homologous to, the intended host cell species. Suitable sequences include STII, tPA or lpp for *E. coli*, alpha factor for yeast, and viral signals such as herpes gD for mammalian cells.

Other insertional variants of HRG include the fusion to the N- or C-terminus of HRG of an immunogenic polypeptide, e.g., bacterial polypeptides such as beta-lactamase or an enzyme encoded by the *E. coli* trp locus, or yeast protein, bovine serum albumin, and chemotactic polypeptides. C-terminal fusions of HRG-ECD with proteins having a long half-life such as immunoglobulin constant regions (or other immunoglobulin regions), albumin, or ferritin, as described in WO 89/02922, published 6 Apr. 1989 are contemplated.

Another group of variants are amino acid substitution variants. These variants have at least one amino acid residue in HRG molecule removed and a different residue inserted in its place. The sites of greatest interest for substitutional mutagenesis include sites identified as the active site(s) of HRG, and sites where the amino acids found in HRG ligands from various species are substantially different in terms of side-chain bulk, charge, and/or hydrophobicity. A likely sub-domain of HRG-GFD having biological activity as a growth factor is the C-terminal segment, in particular within the sequence about from glycine 218 to valine 226 (HRG-α), and glycine 218 to lysine 228/serine 228 (HRG-β) based upon analogy to the EGF sub-sequence found to have EGF activity.

Other sites of interest are those in which particular residues of HRG-like ligands obtained from various species are identical. These positions may be important for the biological activity of HRG. These sites, especially those falling within a sequence of at least three other identically conserved sites, are substituted in a relatively conservative manner. Such conservative substitutions are shown in Table 1 under the heading of "preferred substitutions". If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | tys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of HRG are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:
1) hydrophobic: norleucine, met, ala, val, leu, ile;
2) neutral hydrophilic: cys, ser, thr;
3) acidic: asp, glu;
4) basic: asn, gin, his, lys, arg;
5) residues that influence chain orientation: gly, pro; and
6) aromatic: trp, tyr, phe.

Non-conservative substitutions will entail exchanging a member of one of these classes for another. Such substituted residues may be introduced into regions of HRG that are homologous with other receptor ligands, or, more preferably, into the non-homologous regions of the molecule.

In one embodiment of the invention, it is desirable to inactivate one or more protease cleavage sites that are present in the molecule. These sites are identified by inspection of the encoded amino acid sequence. Where protease cleavage sites are identified, they are rendered inactive to proteolytic cleavage by substituting the targeted residue with another residue, preferably a basic residue such as glutamine or a hydrophylic residue such as serine; by deleting the residue; or by inserting a prolyl residue immediately after the residue.

In another embodiment, any methionyl residue other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of HRG also may be substituted, generally with serine, to improve the oxidative stability of the molecule and prevent aberrant crosslinking.

Sites particularly suited for substitutions, deletions or insertions, or use as fragments, include, numbered from the N-terminus of HRG-α of FIGS. 1A–1D:
1) potential glycosaminoglycan addition sites at the serine-glycine dipeptides at 42–43, 64–65, 151–152;
2) potential asparagine-linked glycosylation at positions 164, 170, 208 and 437, sites (NDS) 164–166, (NIT) 170–172, (NTS) 208–210, and NTS (609–611);
3) potential O-glycosylation in a cluster of serine and threonine at 209–218;
4) cysteines at 226, 234, 240, 254, 256 and 265;
5) transmembrane domain at 287–309;

6) loop 1 delineated by cysteines 226 and 240;
7) loop 2 delineated by cysteines 234 and 254;
8) loop 3 delineated by cysteines 256 and 265; and
9) potential protease processing sites at 2–3, 8–9, 23–24, 33–34, 36–37, 4546, 48–49, 62–63, 66–67, 86–87, 110–111, 123–124, 134–135, 142–143, 272–273, 278–279 and 285–286;

Analogous regions in HRG-β1 may be determined by reference to its' sequence. The analogous HRG-β1 amino acids may be mutated or modified as discussed above for HRG-α. Analogous regions in HRG-β2 may also be determined by reference to its' sequence. The analogous HRG-β2 amino acids may be mutated or modified as discussed above for HRG-α or HRG-β1. Analogous regions in HRG-β3 may be determined by reference to its' sequence. Further, the analogous HRG-β3 amino acids may be mutated or modified as discussed above for HRG-α, HRG-β1, or HRG-β2.

Another HRG variant is γ-HRG (or gamma-heregulin). γ-HRG is any polypeptide sequence that possesses at least one biological property of native sequence γ-HRG having SEQ ID NO:11. The biological property of this variant is the same as for HRG noted above. This variant encompasses not only the polypeptide isolated from a native γ-HRG source such as human MDA-MB-175 cells or from another source, such as another animal species, but also the polypeptide prepared by recombinant or synthetic methods. It also includes variant forms including functional derivatives, allelic variants, naturally occurring isoforms and analogues thereof. Sometimes the γ-HRG is "native γ-HRG" which refers to endogenous γ-HRG polypeptide which has been isolated from a mammal. The γ-HRG can also be "native sequence γ-HRG" insofar as it has the same amino acid sequence as a native γ-HRG (e.g. human γ-HRG shown in FIGS. 7A–7C). Amino acid sequence variants of the native sequence are prepared by introducing appropriate nucleotide changes into the native sequence DNA, or by in vitro synthesis of the desired polypeptide. Such variants include, for example, deletions from, or insertions or substitutions of, residues within the amino acid sequence shown for the human protein in FIGS. 7A–7C as generally described above for other HRG. Any combination of deletion, insertion, and substitution is made to arrive at the final construct, provided that the final construct possesses the desired characteristics. The amino acid changes also may alter post-translational processes of the native sequence, such as changing the number or position of O-linked glycosylation sites.

Another variant is the polypeptide referred to as sensory and motor neuron derived factor (SMDF) whose nucleic acid and amino acid sequences (SEQ ID NOS:13 and 14) are shown in FIG. 8 which can be prepared as described in WO 96/15244. The SMDF polypeptides of the invention exhibit the properties of binding to the HER2/HER3 receptors and stimulating epithelial cell growth and differentiation in a manner similar to HRG polypeptides discussed above. Amino acid sequence variants of native sequence SMDF are prepared by introducing appropriate nucleotide changes into the native sequence SMDF DNA, or by in vitro synthesis of the desired SMDF polypeptide as observed generally above for other HRG. Such variants include, for example, deletions from, or insertions or substitutions of, residues within the amino acid sequence shown for human SMDF in FIG. 8. Any combination of deletion, insertion, and substitution is made to arrive at the final construct, provided that the final construct possesses the desired characteristics. The amino acid changes also may alter post-translational processes of the native sequence SMDF, such as changing the number or position of O-linked glycosylation sites.

Additional variants include polypeptides in which the variant has an amino acid substitution at a selected residue corresponding to a residue of 645-amino acid native human heregulin-β1 selected from:
S177, H178, L179, V180, K181, E184, E186,
K187, T188, V191, N192, G193, G194, E195,
M198, V199, K200, D201, N204, P205, S206,
R207, Y208, L209, K211, P213, N214, E215,
T217, G218, D219, Q222, N223, Y224, S228, and F229.

In a variation of this embodiment, the amino acid substitution is not a replacement of the selected residue with an epidermal growth factor (EGF) residue corresponding to the selected residue.

Other heregulin-β1 variants include an amino acid substitution selected from:
S177W; H178S, E, R, or A; V180Q, I or E;
K181P or A; A183G; E184V, W, K, R, G, or N;
K185E, S, Q, or G; E186R; K187E or A; T188Q;
E195Q; F197Y; M198R or K; K200R; D201T or I;
P205T or Y; S206K, H, G, P, or R; R207Y;
Y208R or L; L209M or G; K211R; P213S, T, N, or K;
N214L, K, S, or E; F216M; N223H or W; and M226I.

In a variation of this embodiment, the heregulin variant includes sets of amino acid substitutions selected from this group. Some heregulin variants of the invention having sets of amino acid substitutions exhibit at least a 50-fold increase in HER3 receptor affinity, which is also accompanied by an increase in HER4 receptor affinity. Specific variants include:
A183G, E184W, K185D, E186R, K187E, T188G, M226I;
A183D, E184K, K185S, E186R, K187E, T188G, M226I;
F197Y, M198K, K200R, D2011, M226I;
P205Y, S206G, R207Y, Y208L, L209M;
P205Y, S206R, R207Y, Y208R, L209M, M226I;
P205T, S206H, R207Y, Y208R, L209M;
P205T, S206K, R207Y, Y208R, L209G;
N223W, M226I;
N223H, M226I;
S177W, H178E, K181P, A183G, E184W, K185D, E186R, K187E, T188G, M226I;
P205Y, S206G, R207Y, Y208L, L209M, M226I;
A183G, K185E, E186R, K187E, T188G, F197Y, M198R, D201T;
A183G, K185E, E186R, K187E, T188G, P205Y, S206G, R207Y, Y208L, L209M;
A183G, K185E, E186R, K187E, T188G, F197Y, M198R, D201T, P205Y, S206G, R207Y, Y208L, L209M;
A183G, K185E, E186R, K187E, T188G, M226I;
F197Y, M198R, D201T, P205Y, S206G, R207Y, Y208L, L209M;
F197Y, M198R, D201T, P205Y, S206G, R207Y, Y208L, L209M, M226I;
F197Y, M198R, D201T, M226I;
A183G, K185E, E186R, K187E, T188G, F197Y, M198R, D201T, M226I;
A183G, K185E, E186R, K187E, T188G, P205Y, S206G, R207Y, Y208L, L209M, M226I;
A183G, K185E, E186R, K187E, T188G, F197Y, M198R, D201T, P205Y, S206G, R207Y, Y208L, L209M, M226I;
F197Y, M198R, D201T, P205Y, S206G, R207Y, Y208L, L209M, N223H, M226I; and
A183G, K185E, E186R, K187E, T188G, F197Y, M198R, D201T, P205Y, S206G, R207Y, Y208L, L209M, N223H, M226I.

In addition to including one or more of the amino acid substitutions disclosed herein, the heregulin variant can have one or more other modifications, such as an amino acid substitution, an insertion of at least one amino acid, a deletion of at least one amino acid, or a chemical modification. For example, the invention provides a heregulin variant that is a fragment In a variation of this embodiment, the fragment includes residues corresponding to a portion of human heregulin-β1 extending from about residue 175 to about residue 230 (i.e., the EGF-like domain). For example, the fragment can extend from residue 177 to residue 244 and may be prepared by recombinant techniques (rHRGβ1-177–244).

DNA encoding amino acid sequence variants of HRG is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of HRG. These techniques may utilize HRG nucleic acid (DNA or RNA), or nucleic acid complementary to HRG nucleic acid.

Oligonucleotide-mediated mutagenesis is a preferred method for preparing substitution, deletion, and insertion variants of HRG DNA. This technique is well known in the art as described by Adelman et al., *DNA,* 2: 183 (1983). Briefly, HRG DNA is altered by hybridizing an oligonucleotide encoding the desired mutation to a DNA template, where the template is the single-stranded form of a plasmid or bacteriophage containing the unaltered or native DNA sequence of HRG. After hybridization, a DNA polymerase is used to synthesize an entire second complementary strand of the template that will thus incorporate the oligonucleotide primer, and will code for the selected alteration in HRG DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA,* 75: 5765,1978).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of HRG, and the other strand (the original template) encodes the native, unaltered sequence of HRG. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}$P-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: the single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding HRG mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of HRG. While the following discussion refers to DNA, it is understood that the technique also finds application with RNA. The PCR technique generally refers to the following procedure (see Erlich, supra, the chapter by R. Higuchi, p. 61–70). When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 mg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GENEAMP kits (obtained from Perkin-Elmer Cetus, Norwalk, Conn. and Emeryville, Calif.), and 25 pmole of each oligonucleotide primer, to a final volume of 50 ml. The reaction mixture is overlaid with 35 ml mineral oil. The reaction is denatured for 5 minutes at 100° C., placed briefly on ice, and then 1 ml *Thermus aquaticus* (Taq) DNA polymerase (5 units/ml, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C.,
30 sec. 72° C., then 19 cycles of the following:
30 sec. 94° C.,
30 sec. 55° C., and
30 sec. 72° C.

At the end of the program, the reaction vial is removed from the thermal cycler and the aqueous phase transferred to a new vial, extracted with phenol/chloroform (50:50:vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al. (*Gene,* 34: 315,1985). The starting material is the plasmid (or other vector) comprising HRG DNA to be mutated. The codon(s) in HRG DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in HRG DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated HRG DNA sequence.

C. Insertion of DNA into a Cloning Vehicle

The cDNA or genomic DNA encoding native or variant HRG is inserted into a replicable vector for further cloning (amplification of the DNA) or for expression. Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of HRG DNA that is inserted into the vector. The native HRG DNA is believed to encode a signal sequence at the amino terminus (5' end of the DNA encoding HRG) of the polypeptide that is cleaved during post-translational processing of the polypeptide to form the mature HRG polypeptide ligand that binds to the HER2/HER3 receptor, although a conventional signal structure is not apparent. Native HRG is, secreted from the cell but remains lodged in the membrane because it contains a transmembrane domain and a cytoplasmic region in the carboxyl terminal region of the polypeptide. Thus, in a secreted, soluble version of HRG the carboxyl terminal domain of the molecule, including the transmembrane domain, is ordinarily deleted. This truncated variant HRG polypeptide may be secreted from the cell, provided that the DNA encoding the truncated variant encodes a signal sequence recognized by the host.

HRG of this invention may be expressed not only directly, but also as a fusion with a heterologous polypeptide, preferably a signal sequence or other polypeptide having a specific cleavage site at the N-and/or C-terminus of the mature protein or polypeptide. In general, the signal sequence may be a component of the vector, or it may be a part of HRG DNA that is inserted into the vector. Included within the scope of this invention are HRG with the native signal sequence deleted and replaced with a heterologous signal sequence. The heterologous signal sequence selected should be one that is recognized and processed, i.e., cleaved by a signal peptidase, by the host cell. For prokaryotic host cells that do not recognize and process the native HRG signal sequence, the signal sequence is substituted by a prokaryotic signal sequence selected, for example, from the group of the alkaline phosphatase, penicillinase, lpp, or heat-stable enterotoxin II leaders. For yeast secretion the native HRG signal sequence may be substituted by the yeast invertase, alpha factor, or acid phosphatase leaders. In mammalian cell expression the native signal sequence is satisfactory, although other mammalian signal sequences may be suitable.

(ii) Origin of Replication Component

Both expression and cloning vectors generally contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2m plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of HRG DNA. However, the recovery of genomic DNA encoding HRG is more complex than that of an exogenously replicated vector because restriction enzyme digestion is required to excise HRG DNA. DNA can be amplified by PCR and directly transfected into the host cells without any replication component.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet* 1: 327, 1982), mycophenolic acid (Mulligan et al., *Science* 209: 1422,1980) or hygromycin (Sugden et al., *Mol. Cell. Biol.* 5: 410–413,1985). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up HRG nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes HRG. Amplification is the process by which genes in greater demand for the production of a protein critical for growth are reiterated in tandem within the chromosomes of successive generations of recombinant cells. Increased quantities of HRG are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Udaub and Chasin, *Proc. Natl. Acad. Sci. USA,* 77: 4216, 1980. The transformed cells are then exposed to increased levels of methotrexate. This leads to the synthesis of multiple copies of the DHFR gene, and, concomitantly, multiple copies of other DNA comprising the expression vectors, such as the DNA encoding HRG. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding HRG, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418 (see U.S. Pat. No. 4,965,199).

A suitable selection gene for use in yeast is the trp1 gene present in the yeast plasmid YRp7 (Stinchcomb et al., *Nature,* 282: 39, 1979; Kingsman et al., *Gene,* 7: 141, 1979 or Tschemper et al., *Gene,* 10: 157, 1980). The trp1 gene provides a selection marker for a mutant strain of yeast lacking the ability to grow in tryptophan, for example, ATCC No. 44076 or PEP4-1 (Jones, *Genetics,* 85: 12, 1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to HRG nucleic acid. Promoters are untranslated sequences located upstream (5') to the start codon of a structural gene (generally within about 100 to 1000 bp) that control the transcription and translation of a particular nucleic acid sequence, such as HRG to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to DNA encoding HRG by removing the promoter from the source DNA by restriction enzyme digestion and inserting the isolated promoter sequence into the vector. Both the native HRG promoter sequence and many (heterologous promoters may be used to direct amplification and/or expression of HRG DNA. However, heterologous promoters are preferred, as they generally permit greater transcription and higher yields of expressed HRG as compared to the native HRG promoter.

Promoters suitable for use with prokaryotic hosts include the b-lactamase and lactose promoter systems (Chang et al., Nature, 275: 615, 1978; and Goeddel et al., Nature 281: 544, 1979), alkaline phosphatase, a tryptophan (trp) promoter system (Goeddel, Nucleic Acids Res., 8: 4057, 1980 and EP 36,776), tPA (U.S. Pat. No. 5,641,655) and hybrid promoters such as the tac promoter (deBoer et al., Proc. Natl. Acad. Sci. USA 80: 21–25, 1983). However, other known bacterial promoters are suitable. Their nucleotide sequences have been published, thereby enabling a skilled worker operably to ligate them to DNA encoding HRG (Siebenlist et al., Cell 20: 269, 1980) using linkers or adaptors to supply any required restriction sites. Promoters for use in bacterial systems also generally will contain a Shine-Dalgarno (S.D.) sequence operably linked to the DNA encoding HRG.

Suitable promoting sequences for use with yeast hosts include the promoters for 3-phosphoglycerate kinase (Hitzeman et al., J. Biol. Chem., 255: 2073, 1980) or other glycolytic enzymes (Hess et al, J. Adv. Enzyme Reg 7: 149, 1968; and Holland, Biochemistry 17: 4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

HRG gene transcription from vectors in mammalian host cells may be controlled by promoters obtained from the genomes of viruses such as polyoma virus, fowlpox virus (UK 2,211,504, published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with HRG sequence, provided such promoters are compatible with the host cell systems.

The early and late promoters of the SV40 virus are conveniently obtained as an SV40 restriction fragment that also contains the SV40 viral origin of replication (Fiers et al., Nature, 273:113 (1978); Mulligan and Berg, Science, 209: 1422–1427 (1980); Pavlakis et al., Proc. Natl Acad. Sci. USA, 78: 7398–7402 (1981)). The immediate early promoter of the human cytomegalovirus is conveniently obtained as a HindIII E restriction fragment (Greenaway et al., Gene, 18: 355–360 (1982)). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., Nature, 295: 503–508 (1982) on expressing cDNA encoding immune interferon in monkey cells; Reyes et al., Nature, 297: 598–601 (1982) on expression of human b-interferon cDNA in mouse cells under the control of a thymidine kinase promoter from herpes simplex virus; Canaani and Berg, Proc. Natl. Acad. Sci. USA, 79: 5166–5170 (1982) on expression of the human interferon b1 gene in cultured mouse and rabbit cells; and Gorman et al., Proc. Natl. Acad. Sci. USA, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding HRG of this invention by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., Proc. Natl. Acad. Sci. USA, 78: 993, 1981) and 3' (Lusky et al., Mol. Cell Bio., 3: 1108, 1983) to the transcription unit, within an intron (Banerji et al., Cell, 33: 729, 1983) as well as within the coding sequence itself (Osborne et al., Mol. Cell Bio., 4: 1293, 1984). Many enhancer sequences are now known from mammalian genes (globin, elastase, albumin, a-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers (see also Yaniv, Nature, 297: 17–18 (1982)) on enhancing elements for activation of eukaryotic promoters. The enhancer may be spliced into the vector at a position 5' or 3' to HRG DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding HRG. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9: 309 (1981) or by the method of Maxam et al, *Methods in Enzymology* 65: 499 (1980).

Particularly useful in the practice of this invention are expression vectors that provide for the transient expression in mammalian cells of DNA encoding HRG. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of HRG that have HRG-like activity. Such a transient expression system is described in U.S. Pat. No. 5,024,939.

Other methods, vectors, and host cells suitable for adaptation to the synthesis of HRG in recombinant vertebrate cell culture are described in Gething et al., *Nature* 293: 620–625, 1981; Mantei et al., *Nature,* 281: 4046, 1979; Levinson et al., EP 117,060 and EP 117,058. A particularly useful expression plasmid for mammalian cell culture expression of HRG is pRK5 (EP pub. no. 307,247) or pSVI6B (U.S. Ser. No. 07/441,574. filed Nov. 22, 1989, the disclosure of which is incorporated herein by reference).

D. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli,* Bacilli such as *B. subtilis, Pseudomonas* species such as *P. aeruginosa, Salmonella typhimurium,* or *Serratia marcescans.* One preferred *E. coli* cloning host is *E. coli* 294 (ATCC 31,446), although other strains such as *E. coli* B, *E. coli* $_x$1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for HRG-encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharomyces pombe* (Beach and Nurse, *Nature,* 290: 140 (1981); EP 139,383, published May 2, 1985), Kluyveromyces hosts (U.S. Pat. No. 4,943,529) such as, e.g., *K. lactis* (Louvencourt et al., *J. Bacteriol.,* 737 (1983); *K. fragilis, K. bulgaricus, K. thermotolerans,* and *K. marxianus,* yarrowia (EP 402,226); *Pichia pastoris* (EP 183,070), Sreekrishna et al., *J. Basic Microbiol.,* 28: 265–278 (1988); Candida, *Trichoderma reesia* (EP 244,234); *Neurospora crassa* (Case et al., *Proc. Natl. Acad. Sci. USA,* 76: 5259–5263 (1979), and filamentous fungi such as, e.g, *Neurospora, Penicillium, Tolypocladium* (WO 91/00357, published Jan. 10, 1991), and *Aspergillus* hosts such as *A. nidulans* (Ballance et al., *Biochem. Biophys. Res. Commun.,* 112: 284–289 (1983); Tilburn et al., *Gene,* 26: 205–221 (1983); Yelton et al., *Proc. Natl. Acad. Sci. USA,* 81: 1470–1474 (1984) and *A. niger* (Kelly and Hynes, *EMBO J.,* 4: 475479 (1985)).

Suitable host cells for the expression of glycosylated HRG polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified (see, e.g., Luckow et al., *Bio/Technology,* 6: 47–55 (1988); Miller et al., in *Genetic Engineering,* Setlow, J. K. et al., eds., Vol. 8 (Plenum Publishing, 1986), pp. 277–279; and Maeda et al, *Nature,* 315: 592–594 (1985)). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain HRG DNA. During incubation of the plant cell culture with *A. tumefaciens,* the DNA encoding HRG is transferred to the plant cell host such that it is transfected, and will, under appropriate conditions, express HRG DNA. In addition, regulatory and signal sequences compatible with plant cells are available, such as the nopaline synthase promoter and polyadenylation signal sequences (Depicker et al., *J. Mol. Appl. Gen.,* 1: 561 (1982)). In addition, DNA segments isolated from the upstream region of the T-DNA 780 gene are capable of activating or increasing transcription levels of plant-expressible genes in recombinant DNA-containing plant tissue (see EP 321,196, published 21 Jun. 1989).

However, interest has been greatest in vertebrate cells, and propagation of vertebrate cells in culture (tissue culture) has become a routine procedure in recent years (*Tissue Culture,* Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36: 59, 1977); baby hamster kidney cells (BHK, ATCC CCL 10); Chinese hamster ovary cells/-DHFR (CHO, Urlaub and Chasin, *Proc. Natl. Acad. Sci. USA,* 77: 4216 (1980)); mouse sertoli cells (TM4, Mather, *Biol. Reprod.,* 23: 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383: 44–68 (1982)); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859, published Jun. 29, 1989. For mammalian cells without such cell walls, the calcium phosphate precipitation method described in sections 16.30–16.37 of Sambrook et al, supra, is preferred. General aspects of mammalian cell host system transformations have been described by Axel in U.S. Pat. No. 4,399,216, issued 16 Aug. 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing DNA into cells such as by nuclear injection, electroporation, or protoplast fusion may also be used.

E. Culturing the Host Cells

Prokaryotic cells used to produce HRG polypeptide of this invention are cultured in suitable media as described generally in Sambrook et al., supra.

The mammalian host cells used to produce HRG of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866; 4,927,762; or 4,560,655; WO 90/03430; WO 87/00195; U.S. Pat. No. Re. 30,985; U.S. Pat. No. 5,122,469 or U.S. Ser. No. 07/592,141, filed on 3 Oct. 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that HRG of this invention may be produced by homologous recombination, or with recombinant production methods utilizing control elements introduced into cells already containing DNA encoding HRG currently in use in the field. For example, a powerful promoter/enhancer element, a suppresser, or an exogenous transcription modulatory element is inserted in the genome of the intended host cell in proximity and orientation sufficient to influence the transcription of DNA encoding the desired HRG. The control element does not encode HRG of this invention, but the DNA is present in the host cell genome. One next screens for cells making HRG of this invention, or increased or decreased levels of expression, as desired.

F. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77: 5201–5205 (1980)), dot blotting (DNA analysis), or in situ hybridization, using an appropriately labeled probe based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled where the labels are usually visually detectable such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal, and may be prepared in any mammal. Conveniently, the antibodies may be prepared against a native HRG polypeptide or against a synthetic peptide based on the DNA sequences provided herein as described further below.

G. Purification of The Heregulin Polypeptides

HRG is recovered from a cellular membrane fraction. Alternatively, a proteolytically cleaved or a truncated expressed soluble HRG fragment or subdomain are recovered from the culture medium as a soluble polypeptide. A HRG is recovered from host cell lysates when directly expressed without a secretory signal.

When HRG is expressed in a recombinant cell other than one of human origin, HRG is completely free of proteins or polypeptides of human origin. However, it is desirable to purify HRG from recombinant cell proteins or polypeptides to obtain preparations that are substantially homogeneous as to HRG. As a first step, the culture medium or lysate is centrifuged to remove particulate cell debris. The membrane and soluble protein fractions are then separated. HRG is then be purified from both the soluble protein fraction (requiring the presence of a protease) and from the membrane fraction of the culture lysate, depending on whether HRG is membrane bound. The following procedures are exemplary of suitable purification procedures: fractionation on immunoaffinity or ion-exchange columns; ethanol precipitation; reverse phase HPLC; chromatography on silica, heparin SEPHAROSE or on a cation exchange resin such as DEAE; chromatofocusing; SDS-PAGE; ammonium sulfate precipitation; and gel filtration sing, for example, SEPHADEX G-75.

HRG variants in which residues have been deleted, inserted or substituted are recovered in the same fashion as the native HRG, taking account of any substantial changes in properties occasioned by the variation. For example, preparation of a HRG fusion with another protein or polypeptide, e.g., a bacterial or viral antigen, facilitates purification; an immunoaffinity column containing antibody to the antigen can be used to adsorb the fusion. Immunoaffinity columns such as a rabbit polyclonal anti-HRG column can be employed to absorb HRG variant by binding it to at least one remaining immune epitope. A protease inhibitor such as phenylmethylsulfonylfluoride (PMSF) also may be useful to inhibit proteolytic degradation during purification, and antibiotics may be included to prevent the growth of adventitious contaminants. One skilled in the art will appreciate that purification methods suitable for native HRG may require modification to account for changes in the character of HRG variants or upon expression in recombinant cell culture.

H. Covalent Modifications of HRG

Covalent modifications of HRG polypeptides are included within the scope of this invention. Both native HRG and amino acid sequence variants of HRG optionally are covalently modified. One type of covalent modification included within the scope of this invention is a HRG polypeptide fragment. HRG fragments, such as HRG-GDF, having up to about 40 amino acid residues are conveniently prepared by chemical synthesis, or by enzymatic or chemical cleavage of the full-length HRG polypeptide or HRG variant polypeptide. Other types of covalent modifications of HRG or fragments thereof are introduced into the molecule by reacting targeted amino acid residues of HRG or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisourea; 2,4-pentenedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking HRG to a water-insoluble support matrix or surface for use in a method for purifying anti-HRG antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-((p-azidophenyl)dithio)propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecular Properties,* W. H. Freeman & Co., San Francisco, pp. 79–86 (1983)), acetylation of the N-terminal amine, and amidation of any C-terminal carboxyl group.

HRG optionally is fused with a polypeptide heterologous to HRG. The heterologous polypeptide optionally is an anchor sequence such as that found in a phage coat protein such as M13 gene III or gene VIII proteins. These heterologous polypeptides can be covalently coupled to HRG polypeptide through side chains or through the terminal residues.

HRG may also be covalently modified by altering its native glycosylation pattern. One or more carbohydrate substituents in these embodiments, are modified by adding, removing or varying the monosaccharide components at a given site, or by modifying residues in HRG as that glycosylation sites are added or deleted.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Glycosylation sites are added to HRG by altering its amino acid sequence to contain one or more of the above-described tri-peptide sequences (for N-linked glycosylation sites). The alteration may also be made by the addition of, or substitution by, one or more serine or threonine residues to HRG (for O-linked glycosylation sites). For ease, HRG is preferably altered through changes at the DNA level, particularly by mutating the DNA encoding HRG at preselected bases such that codons are generated that will translate into the desired amino acids.

Chemical or enzymatic coupling of glycosides to HRG increases the number of carbohydrate substituents. These procedures are advantageous in that they do not require production of the polypeptide in a host cell that is capable of N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, published 11 Sep. 1987, and in Aplin and Wriston (CRC *Crit. Rev. Biochem.*, pp. 259–306 (1981)).

Carbohydrate moieties present on an HRG also are removed chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al. (*Arch. Biochem. Biophys.*, 259:52 (1987)) and by Edge et al. (*Anal. Biochem.*, 118:131 (1981)). Carbohydrate moieties are removed from HRG by a variety of endo- and exo-glycosidases as described by Thotakura et al. (*Meth. Enzymol.*, 138:350 (1987)).

Glycosylation also is suppressed by tunicamycin as described by Duskin et al. (*J. Biol. Chem.*, 257:3105 (1982)). Tunicamycin blocks the formation of protein-N-glycoside linkages.

HRG may also be modified by linking HRG to various nonproteinaceous polymers, e.g. polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

One preferred way to increase the in vivo circulating half life of non-membrane bound HRG is to conjugate it to a polymer that confers extended half-life, such as polyethylene glycol (PEG). (Maxfield, et al, *Polymer* 16,505–509 (1975); Bailey, F. E., et al, in Nonionic Surfactants (Schick, M. J., ed.) pp. 794–821, 1967); (Abuchowski, A. et al., *J. Biol. Chem.* 252, 3582–3586, 1977; Abuchowski, A. et al., *Cancer Biochem. Biophys.* 7, 175–186, 1984); (Katre, N. V. et al., *Proc. Natl. Acad. Sci.*, 84, 1487–1491, 1987; Goodson, R. et al. *Bio Technology*, 8, 343–346, 1990). Conjugation to PEG also has been reported to have reduced immunogenicity and toxicity (Abuchowski, A. et al., *J. Biol. Chem.*, 252, 3578–3581, 1977).

HRG may also be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Osol, A., Ed., (1980).

Those skilled in the art will be capable of screening variants in order to select the optimal variant for the purpose intended. For example, a change in the immunological character of HRG, such as a change in affinity for a given antigen or for the HER2 receptor, is measured by a competitive-type immunoassay using a standard or control such as a native HRG (in particular native HRG-GFD). Other potential modifications of protein or polypeptide properties such as redox or thermal stability, hydrophobicity, susceptibility to proteolytic degradation, stability in recombinant cell culture or in plasma, or the tendency to aggregate with carriers or into multimers are assayed by methods well known in the art.

I. Heregulin Antibody Preparation

The antibodies of this invention are obtained by routine screening and include polyclonal antibodies, monoclonal antibodies and fragments thereof.

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-SEPHAROSE, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

Hybridoma cell lines producing antibodies are identified by screening the culture supernatants for antibody which binds to HER2/HER3 receptors. This is routinely accomplished by conventional immunoassays using soluble receptor preparations or by FACS using cell-bound receptor and labeled candidate antibody. Agonist antibodies are preferably antibodies which stimulate autophosphorylation in the HRG tyrosine autophosphorylation assay described above.

The hybrid cell lines can be maintained in culture in vitro in cell culture media. The cell lines of this invention can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM as the case may be that heretofore have been used to purify these immunoglobulins from pooled plasma, e.g., ethanol or polyethylene glycol precipitation procedures.

Human antibodies may be used and are preferable. Such antibodies can be obtained by using human hybridomas (Cote et al., *Monoclonal Antibodies and Cancer Therapy*, Alan R. Liss, p. 77 (1985)). Chimeric antibodies, Cabilly et al., U.S. Pat. No. 4,816,567, (Morrison et al., *Proc. Natl. Acad. Sci.*, 81:6851 (1984); Neuberger et al., *Nature* 312: 604 (1984); Takeda et al., *Nature* 314:452 (1985)) containing a murine anti-HER2/HER3 variable region and a human constant region of appropriate biological activity (such as ability to activate human complement and mediate ADCC) are within the scope of this invention, as are humanized antibodies produced by conventional CDR-grafting methods (Riechmann et al., Nature 332:333–327(1988); EP 0328404 A1; EP 02394000 A2).

Techniques for creating recombinant DNA versions of the antigen-binding regions of antibody molecules (Fab or variable regions fragments) which bypass the generation of monoclonal antibodies are also encompassed within the practice of this invention. One extracts antibody-specific messenger RNA molecules from immune system cells taken from an immunized subject, transcribes these into complementary DNA (cDNA), and clones the cDNA into a bacterial expression system and selects for the desired binding characteristic. The Scripps/Stratagenemethod uses a bacteriophage lambda vector system containing a leader sequence that causes the expressed Fab protein to migrate to the periplasmic space (between the bacterial cell membrane and the cell wall) or to be secreted. One can rapidly generate and screen great numbers of functional Fab fragments to identify those which bind the receptors with the desired characteristics. Alternatively, the antibodies can be prepared by the phage display techniques described in Hoogenboom, *Tibtech* February 1997 (vol 15); Neri et al., *Cell Biophysics* 27:47–61 (1995); Winter et al., *Annu. Rev. Immunol* 12:433–55 (1994); and Soderlind et al., *Immunol. Rev.* 130:109–124 (1992) and the references described therein as well as the monovalent phage display technique described in Lowman et al., *Biochem.* 30:10832–10838 (1991).

2. Therapeutic Compositions, Administration and Use of Heregulins and Agonist Antibodies The HRG are used in the present invention to induce epithelial cell growth, for example lung epithelial cell growth, proliferation and differentiation, and to increase the production of surfactant protein A by lung cells. These effects allow treatment of disease states associated with tissue damage, for example, chronic obstructive pulmonary disease(COPD) including subtypes thereof such as chronic bronchitis, emphysema, asthma, etc., neonatal pulmonary diseases including neonatal respiratory distress syndrome, meconium aspiration syndrome, chronic lung disease of the neonate, congenital diaphragmatic hernia, etc., acute lung injuries including smoke or chemical inhalation, pneumonitis due to aspiration, radiation, etc., near drowning, cystic fibrosis and other epithelial cell trauma diseases, including injuries associated with surgical wounds and resections, ulcers, lesions, and tissue tears, with the method of the invention.

A preferred indication for treatment with the method of the invention is the treatment of COPD. COPD is a spectrum of chronic inflammatory respiratory diseases characterized by cough, sputum, dyspnea, airflow limitation and impaired gas exchange. COPD is common in older populations and presents a pattern of gradually declining lung function. Typically, a patient will exhibit a chronic cough with clear sputum which worsens to a cough with thick sputum and accompanying poor air exchange. These conditions frequently lead to heart disease and death. Many persons with COPD will have chronic bronchitis together with emphysema. The present invention is particularly important because it halts, slows and/or reverses the lung destruction process in COPD patients. In this action, the method of the invention is very different from typical treatments for COPD in which the symptoms are treated, but not the underlying destruction of lung cell tissue and function.

The method of the invention may, however, be combined with or administered together with other therapies for treatment of lung disease such as COPD. For example, the method of this invention can be used together with the administration of an anticholinergic bronchodilator such as ipratropium bromide (ATROVENT available from Boehringer Ingleheim) or tiotropium, a beta adrenergic receptor agonist such as albuterol (PROVENTIL available from Schering) or salmeterol, steroids such as prednisone, retinoic acid, phosphodiesterase inhibitors, endothelin antagonists, metalloproteinase inhibitors, elastase inhibitors, free radical inhibitors, serine proteinase inhibitors, neutrophil elastase inhibitors, pulmonary surfactant compositions such as beractant (SURVANTA available from Ross Labs.), PDGF, FGF, EGF, growth hormone or other protein growth factors, etc. or combinations thereof. The relative amount of the HRG and the additional compound(s) can be readily determined by a physician with regard to the individual symptoms of the patient. It is anticipated that these compositions and the relative amounts of the components therein will be varied as necessary to address the specific needs of a patient and will be monitored and adjusted using conventional physiochemical and medical tests for lung function.

Therapeutic formulations of HRG or agonist antibody are prepared for storage by mixing the HRG protein having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, PLURONICS or polyethylene glycol (PEG).

HRG or agonist antibody to be used for in vivo administration must be sterile. This is readily accomplished by filtration through sterile filtration membranes, prior to or following lyophilization and reconstitution. The HRG or antibody ordinarily will be stored in lyophilized form or in solution.

Therapeutic HRG or antibody compositions generally are placed into a container having a sterile access port, for example, an intravenous solution bag or vial having a stopper pierceable by a hypodermic injection needle.

The route of HRG or antibody administration is in accord with known methods, e.g., injection or infusion by intravenous, intraperitoneal, intracerebral, intramuscular, intraocular, intraarterial, powder or liquid aerosol administration to the nose or lung or intralesional routes, or by sustained release systems as noted below. The HRG ligand may be administered continuously by infusion or by bolus injection. An agonist antibody is preferably administered in the same fashion, or by administration into the blood stream or lymph.

The HRG, HRG variant or fragment and agonist antibodies may be spray dried r spray freeze dried using known techniques (Yeo et al, Biotech. and Bioeng., 41:341–346 (1993); Gombotz et al, PCT/US90/02421).

Suitable examples of sustained-release preparations include semipermeable matrices of solid hydrophobic polymers containing the protein, which matrices are in the form of shaped articles, e.g. films, or microcapsules. Examples of sustained-release matrices include polyesters, hydrogels (e.g., poly(2-hydroxyethyl-methacrylate) as described by Langer et al., *J. Biomed. Mater. Res.*, 15: 167–277 (1981) and Langer, *Chem. Tech.*, 12: 98–105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers,* 22: 547–556 (1983)), non-degradable ethylene-vinyl acetate (Langer et al, supra), degradable lactic acid-glycolic acid copolymers such as the LUPRON DEPOT (injectable microspheres composed of lactic acid-glycolic acid copolymer and leuprolide acetate), and poly-D-(–)-3-hydroxybutyric acid (EP 133,988). While polymers such as ethylene-vinyl acetate and lactic acid-glycolic acid enable release of molecules for over 100 days, certain hydrogens release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release HRG or antibody compositions also include liposomally entrapped HRG or antibody. Liposomes containing HRG or antibody are prepared by methods known per se: DE 3,218,121; Epstein et al., *Proc. Natl. Acad Sci. USA,* 82: 3688–3692 (1985); Hwang et al., *Proc. Natl. Acad. Sci. USA,* 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal HRG therapy. Liposomes with enhanced circulation time are disclosed in U.S. Pat. No. 5,013,556.

An effective amount of HRG or antibody to be employed therapeutically will depend, for example, upon the therapeutic objectives, the route of administration, and the condition of the patient. Also, the amount of HRG polypeptide will generally be less than the amount of an agonist antibody. Accordingly, it will be necessary for the therapist to titer the dosage and modify the route of administration as required to obtain the optimal therapeutic effect. A typical daily dosage might range from about 1 μg/kg to about 1 mg/kg and up to 100 mg/kg or more, depending on the factors mentioned above. Typically, the clinician will administer HRG or antibody until a dosage is reached that achieves the desired effect. The progress of this therapy is easily monitored by conventional assays, for example, surfactant protein A production.

In a further embodiment, epithelial cells may be obtained or isolated from a mammalian tissue to obtain a normal epithelial cell sample using techniques well known in the art (biopsy, etc.). This sample may then be treated with a heregulin protein in order to induce epithelial cell growth and/or proliferation in the sample thereby expanding the population of primary epithelial cells. Typically, heregulin will be added to the in vitro epithelial cell culture at a concentration of about 0.1 to about 100 nM preferably 1–50 nM. If desired, the primary epithelial cells may be cultured in vitro for several generations in order to sufficiently expand the epithelial cell population. The epithelial cells are cultured under conditions suitable for mammalian cell culture as discussed above. After expansion, the expanded sample is reintroduced into the mammal for the purpose of re-epithelializing the mammalian tissue. For example, lung epithelial cells isolated from a patient having emphysema or chronic obstructive pulmonary disease may be obtained, expanded and reintroduced into the lung in order to more quickly re-epithelialize the damaged lung tissue thereby reestablishing lung function. The expanded cells may be reintroduced into the lung by aspiration or intubation using methods well known in the art.

The methods and procedures described herein with respect to HRG-α or HRG in general may be applied similarly to other HRG such as HRG-β1, HRG-β2 and HRG-β3 and to variants thereof, as well as to the antibodies. All references cited in this specification are expressly incorporated by reference. The following examples are offered by way of illustration and not by way of limitation.

EXAMPLES

Example 1

Preparation of Heregulins (a) Heregulins HRG-α, HRG-β1, HRG-β2, HRG-β2-like, and HRG-β3 were isolated, cloned, expressed and isolated from the cell culture medium as described in U.S. Pat. No. 5,367,060.

(b) SMDF polypeptides are prepared as described in WO 96/15244.

(c) γ-HRG polypeptide was prepared and characterized as described below.

Reagents: The EGF-like domain of HRGβ1$_{(177-244)}$ was expressed in *E. coli,* purified and radioiodinated as described previously (Sliwkowski et al. *J. Biol. Chem.* 269:14661–14665 (1994)). The anti-HER2 monoclonal antibodies 2C4 and 4D5 have been described elsewhere (Fendly et al. *Cancer Research* 50:1550–1558 (1990)).

HER3 and HER4-immunoadhesins: A unique MI I site was engineered into a plasmid expressing human IgG heavy chain at the region encoding the hinge domain of the immunoglobulin. MI I sites were also engineered into a set of HER expression plasmids at the region encoding the ECD/TM junctions of these receptors. All mutageneses were done using the Kunkel method (Kunkel, T., *Proc. Natl. Acad. Sci. U.S.A.* 82:488 (1985)). The MI I sites were utilized to make the appropriate HER-IgG fusion constructs. The fusion junctions of the various HER-IgG chimeras were: for HER2, $E^{646}_{HER2}$-(TR)-DKTH$^{224}_{VH}$; for HER3, $L^{636}_{HER3}$-(TR)-DKTH$^{224}_{VH}$; for HER4, $G^{640}_{HER4}$-(TR)-DKTH$^{224}_{VH}$. The conserved TR sequence is derived from the MI I site. The final expression constructs were in a pRK-type plasmid backbone wherein eukaryotic expression is driven by a CMV promoter (Gorman et al., *DNA Prot. Eng. Tech.* 2:3–10 (1990)).

To obtain protein for in vitro experiments, adherent HEK-293 cells were transfected with the appropriate expression plasmids using standard calcium phosphate methods (Gorman et al, supra and Huang et al., *Nucleic Acids Res.* 18:937–947 (1990)). Serum-containing media was replaced with serum-free media 15 hours post-transfection and the transfected cells incubated for 5–7 days. The resulting conditioned media was harvested and passed through Protein A columns (1 mL Pharmacia HiTrap™). Purified IgG fusions were eluted with 0.1 M citric acid (pH 4.2) into tubes containing 1 M Tris pH 9.0. The eluted proteins were subsequently dialyzed against PBS and concentrated using Centri-prep-30 filters (Amicon). Glycerol was added to a final concentration of 25% and the material stored at –20° C. Concentrations of material were determined via a Fc-ELISA. Cell Culture: Human breast cancer cell lines MDA-MB-175, MDA-MB-231, SK-BR-3 and MCF7 were obtained from the American Type Culture Collection and maintained in a 50:50 mixture of F12 Ham's and Dulbecco's modified Eagle medium (DMEM), supplemented with 10% heat inactivated FBS, 2 mM glutamine and 10% penicillin-streptomycin.

Generation and Characterization of cDNA Library: Total RNA was purified from MDA-MB-175 cells using the guanidinium isothiocyanate-cesium chloride procedure (Sambrook et al., *Molecular Cloning: A Laboratory Manual* (New York: Cold Spring Harbor Laboratory Press, (1989)). Poly (A)$^+$ RNA was isolated using oligo (dT) Dynabeads (DYNAL) as recommended by the supplier. First and second strand syntheses were performed using a Gibco BRL cDNA synthesis kit. λgt10 cDNA recombinants were generated when a cDNA cloning system from Amersham was used. In vitro packaging was performed using Gigapack II packaging extract (Stratagene). PstI-XhoI HRGβ3 cDNA fragment (nt 144–618) was labeled by random priming and 1×10$^6$ plaques were screened. Positive clones were confirmed and purified by secondary and tertiary screening. Phage DNA was isolated as a BamHI fragment and subcloned into the corresponding site of pBluescript SK$^-$. Clone 5 was completely sequenced using the Sequenase version 2.0 DNA sequencing kit (United States Biochemicals, Inc.). Both strands were sequenced.

Bacterial Expression System: A cDNA fragment of clone 5 (nt 1690–2722) was subcloned into the pET-32 TRX fusion vector (Novagen). This BglII-BglII fragment was inserted into the BamHI site of the pET32a plasmid. The trxγ-HRG (amino acids 455–768) protein expression in *E. coli* was induced as recommended by the supplier.

Purification of Recombinant γ-HRG: *E. coli* cells expressing trxγ-HRG were collected and suspended at 9 ml/g in 50 mM Tris HCL pH 8. Lysozyme was added to a final concentration of 0.2 mg/ml and the solution was stirred on ice for 1 hr. Dnase I (10 μg/ml) and MgCl$_2$ (4 mM) were added. The solution was then sonicated for 30 min and cell pellets collected afterwards. The pellet fraction was dissolved at 250 ml/g in 6 M Gdn HCL, 0.1 M Tris HCL, pH 8.8. Solubilized proteins were sulfitolyzed by adding 1/10 volume of 1 M Na$_2$SO$_3$ and 1/10 volume of 0.2 M Na$_2$S$_4$O$_6$. The reaction was allowed to proceed for 1.5 hours at room temperature and protein was purified by gel filtration chromatography using a High Load Superdex™ 75 prep grade column (Pharmacia). Refolding was initiated by the addition of 1 mM cysteine, and 10 mM methionine was added as an antioxidant and incubated overnight at room temperature. Protein concentration was determined by quantitative amino acid analysis.

Northern and Southern Hybridization: Total RNA was isolated by the method of Chomczynski et al. *Anal Biochem.* 162:156–159 (1987). Poly (A)$^+$ was isolated using oligo d(T) cellulose columns (Qiagen) as recommended by the supplier. RNA was denatured and size fractioned in a 0.8% formaldehyde/1% agarose gel and transferred onto nylon membrane (Hybond, Amersham). RNA was UV crosslinked (UV Stratalinker, Stratagene). Prehybridization was carried out at 42° C. in 50% formamide/1% SDS/1 M NaCl, 10% dextransulfate and 100 μg/ml herring sperm DNA for at least 2 hours. cDNA probes using either a restriction fragment with complementary sequence to the EGF-like domain of HRGβ3 or a KpnI-AvaII cDNA fragment encoding the unique sequence of γ-HRG (nt 1238–1868) were radiolabeled by random priming (Prime-It II, Stratagene). Hybridization was done in equal solution at 42° C. containing the $^{32}$P labeled fragments for 16 hr. Blots were washed several times with 2×SSC/1% SDS at room temperature, washed with the same solution at 65° C. for 20 min and finally washed with 0.2×SSC/0.1% SDS at room temperature for 15 min. The blots were air dried and exposed to Du Pont Reflection™ film with intensifying screens at −80° C. for 7–40 hours. Human multiple tissue Northern blots (Clontech) containing 2 μg poly (A)$^+$ from spleen, thymus, prostate, testis, ovary, small intestine, colon, peripheral blood leukocytes, heart, brain, placenta, lung, liver, skeletal muscle, kidney and pancreas were hybridized with a radiolabeled γ-HRG cDNA probe (nt 841–1447) as recommended by the supplier.

MDA-MB-175 and MDA-MB-231 genomic DNA was isolated as described in Sambrook et al, supra. DNA was digested with different restriction enzymes, prior to transfer treated with 0.25 N HCl and transferred onto nylon membrane (Hybond, Amersham). BglII-NdeI cDNA fragment of γ-HRG (nt 1690–2351) was also radiolabeled by random priming and used as a hybridization probe. Prehybridization was carried out in 6×SSC/5× Denhardt's/0.75% SDS, 10% Dextransulfate and 100 μg/ml herring sperm DNA at 68° C. for 4 hours and hybridization with radiolabeled probe was done overnight. The same wash conditions as for Northern blots were used except a wash step with 0.2×SSC/0.1% SDS at 68° C. was added and detection was pursued as described above.

$^{125}$I-HRG Binding Assay. Binding assays were performed in Nunc breakapart strip wells. Plates were coated at 4° C. overnight with 100 μL of 5 μg/ml goat-anti-human antibody (Boehringer Mannheim) in 50 mM carbonate buffer (pH 9.6). Plates were rinsed twice with wash buffer (PBS/0.05% Tween-20) and blocked with 100 μl 1% BSA/PBS for 30 min. Buffer was removed and each well was incubated with 15 ng IgG fusion protein in 1% BSA/PBS under vigorous shaking for 1.5 hours. Plates were rinsed three times with wash buffer and competitive binding was carried out by adding various amounts of γ-HRG and $^{125}$I-HRGβ1 under vigorous shaking. After incubation for 1.5–2 hours, wells were rinsed three times with wash buffer, drained and individual wells were counted using a 100 Series Iso Data γ-counter.

Tyrosine Phosphorylation Assay: MCF7 cells were plated in 24 well plates at 1×10$^5$ cells/well in F12/DMEM containing 10% FBS. After 48 hours, cells were washed with serum free F12/DMEM and serum starved for 6 hours. Various concentrations of bacterial expressed truncated γ-HRG (i.e., 0 pM, 22 pM, 66 pM, 200 pM and 600 pM trxγ-HRG) or unpurified conditioned medium of MDA-MB-175 cells were prepared in binding buffer (0.1% BSA in F12/DMEM) and added to each well. After 8 min incubation at room temperature, media was carefully aspirated and reactions were stopped by adding 100 μl of sample buffer (5% SDS, 0.25% 2-mercaptoethanol, 25 mM Tris-HCL pH 6.8). 20 μl of each sample was size fractionated in a 4–12% gradient gel (Novex) and then electrophoretically transferred onto nitrocellulose membrane. Antiphosphotyrosine (4G10, from UBI, used at 1 μg/ml) immunoblots were developed and the predominant reactive band at $M_r$ ~180 kDa was quantified by reflectance densitometry.

Production and characterization of conditioned medium from MDA-MB-175 cells. Cells were seeded in T175 flasks and grown until reaching 70–80% confluency (~2.5×10$^7$ cells/flask). Subsequently, cells were washed with PBS and grown in serum free F12/DMEM medium for 3–4 days. Medium was then collected, filtered and concentrated using an ultrafiltration cell with YM10 Diaflo ultrafiltration membranes (Amicon). γ-HRG was visualized in conditioned medium of MDA-MB-175 cells by Western blot analysis under non reducing conditions. γ-HRG was partially purified by HPLC using a C4 reverse phase column. CHO expressed full length HRGβ1 (lane 1) and semi pure γ-HRG (lane 2) were electrophoresed, blot was probed with HER2/HER4 IgG heterodimers and Western blot was developed. A ~64 kDa band could be seen in the lane containing partial purified supernatant whereas CHO expressed full length HRGβ1 migrated as a 45 kDa protein.

Cell Proliferation Assay with Crystal Violet: Tumor cell lines were plated in 96 well plates at following densities: $2 \times 10^4$ cells/well for MDA-MB-175 and $1 \times 10^4$ cells/well for SK-BR-3. The media contained 1% FBS and cells were allowed to adhere for 2 hours. Monoclonal antibodies, immunoadhesions (10 μg/ml) or media alone were added and the cells were incubated for 2 hours at 37° C. rHRGβ1$_{177-244}$ was added at a final concentration of 1 nM, or 100 nM for neutralising the immunoadhesion, and the cells were incubated for 4 days. Monolayers were washed with PBS and stained/fixed with 0.5% crystal violet Plates were air dried, the dye was eluted with 0.1 M sodium citrate (pH 4.2) in ethanol (50:50) and the absorbance was measured at 540 nm.

Isolation and sequence analysis of γ-HRG: To characterize the hereguline transcript in MDA-MB-175 cells, a λgt 10 cDNA library was constructed with mRNA derived from this cell line. The library was screened with a cDNA probe corresponding to the EGF-like domain and part of the N-terminal sequence of HRGβ3. Various clones were identified. One of the clones which appeared to contain the full length cDNA sequence was isolated and sequenced. FIGS. 7A–7D shows the nucleotide sequence and the predicted amino acid sequence of γ-HRG. The single open reading frame of 2303 bp starts with an ATG codon at nt 334. This start codon lies in a nucleotide sequence context, which is known to be a potential translation initiation site (Kozak, *Nucleic Acid Research* 15:8125–8148 (1987)). Several termination codons were found upstream of the initiation codon. The stop codon TAG at nt 2637 is followed by the 3' noncoding sequence, which is identical to other HRG isoform sequences and includes a polyadenylation signal followed by an A-rich region. The open reading frame encodes a protein of 768 amino acid residues with a calculated molecular mass of 84.2 kDa.

(d) The selection of HRG-β1 variants containing residues corresponding to the minimal EGF-like domain (HRG-β1 177–228) was conducted using monovalent phage display. For these variants, residue numbers also are expressed, in parentheses, in terms of the position of the residue in the minimal EGF-like domain (i.e., HRG-β1 EGF 1–52).

Variants of HRG-β1 EGF were prepared and selected for binding to HER-3-Ig using monovalent phage display, according to the method of Bass et al., *Proteins* 8:309–314 (1990). As discussed in detail below, an HRG-β1 EGF phagemid vector was prepared, in which HRG-β1 EGF was fused to a C-terminal fragment of the M13 coat protein pIII. Kunkel mutagenesis was performed to introduce stop codons into this vector at sites selected for randomization. This step ensures that the starting vector is incapable of expressing the wild-type polypeptide. Stretches of four to six residues per library were randomized in a linear fashion, except for the six cysteines, Phe189 (HRG-β1 EGF Phe13) and the two most C-terminal residues. Phe189 was not altered because this residue is conserved as an aromatic residue in EGF and TGF-α and forms a stacking interaction with Tyr208 (HRG-β1 EGF Tyr32) Jacobsen et al., *Biochemistry* 35:3402–17 (1996). HRG-β1 EGF was thus covered in eight libraries, designated A–E, G, H and I.

Library E, covering HRG-β1 202–209 (HRG-β1 EGF 26–33), contained a three-residue deletion. The deleted region corresponds to a disordered turn between the second and third β-sheet of HRG-β1 EGF, and the equivalent amino acids are absent in EGF and TGF-α. An HRG-β1 EGF control variant in which HRG-β1 202–204 (HRG-β1 EGF 26–28) of HRG8 are deleted (HRG63) bound HER-3-Ig with an affinity similar to that of wild-type.

An additional library (F) was created to randomize a surface patch composed of side chains from the first and second β-sheets, which included HRG-β1 178, 180, 198, and 200 (HRG-β1 EGF 2, 4, 22, and 24).

The selected sites in the starting vectors were randomized by Kunkel mutagenesis to produce HRG-β1 EGF libraries. Phage displaying mutated HRG-β1 EGFs were produced from the libraries under conditions such that, statistically, each phage particle displayed no more than one copy of the mutated HRG-β1 EGF. See Bass et al., supra. These phage were then selected for binding to (sorted against) HER-3-Ig immobilized on an ELISA plate. Bound phage were eluted and used to reinfect host cells, which were used to produce new phage for another round of sorting. This process was repeated six to seven times for each library. Twelve clones from the phage selected from each library were then sequenced.

TABLE 2

Library A Variants

| | Position in HRG-β1 | | | | |
|---|---|---|---|---|---|
| Variant No. | 177 | 178 | 179 | 180 | 181 |
| Wild-type | S | H | L | V | K |
| 1 | W | R | — | — | P |
| 2 | W | S | — | Q | P |
| 3, 5, 10 | W | E | — | — | P |
| 4 | W | S | — | — | — |
| 6 | W | S | — | I | P |
| 7 | W | R | — | — | A |
| 8 | W | A | — | — | P |
| 9 | W | S | — | Q | — |
| 11 | W | E | — | — | A |
| 12 | W | S | — | E | P |

TABLE 3

Library B Variants

| | Position in HRG-β1 | | | | |
|---|---|---|---|---|---|
| Variant No. | 183 | 184 | 185 | 186 | 187 | 188 |
| Wild-type | A | E | K | E | K | T |
| 1* | G | V | G | R | D | G |
| 2* | G | G | E | R | E | G |
| 3 | G | — | E | R | E | G |
| 4*, 5* | G | W | D | R | E | G |
| 6* | G | V | Q | R | E | G |
| 7 | G | — | E | R | A | G |
| 8 | G | K | E | R | E | G |
| 9* | T | N | S | R | E | G |
| 10* | D | K | S | R | E | G |
| 11* | G | — | D | R | — | Q |
| 12 | G | R | E | R | E | G |

*Variant also contained Met226Ile—

TABLE 4

Library C Variants

| | Position in HRG-β1 | | | | |
|---|---|---|---|---|---|
| Variant No. | 191 | 192 | 193 | 194 | 195 |
| Wild-type | V | N | G | G | E |
| 1, 2, 4, 5, 7–12 | — | — | — | — | — |
| 3 | — | — | — | — | V |
| 6 | — | — | — | — | Q |

TABLE 5

Library D Variants

| | Position in HRG-β1 | | | | |
|---|---|---|---|---|---|
| Variant No. | 197 | 198 | 199 | 200 | 201 |
| Wild-type | F | M | V | K | D |
| 1*, 2*, 8*, 12* | Y | K | — | R | I |
| 3 | — | R | — | — | T |
| 4, 5, 7, 9 | Y | R | — | — | T |
| 6 | Y | — | I | — | Y |
| 10 | Y | — | — | — | T |
| 11 | M | R | — | R | T |

*Variant also contained Met226Ile—

TABLE 6

Library E Variants

| | Position in HRG-β1 | | | | |
|---|---|---|---|---|---|
| Variant No. | 205 | 206 | 207 | 208 | 209 |
| Wild-type | P | S | R | Y | L |
| 1 | T | P | Y | L | M |
| 2, 4 | Y | G | Y | L | M |
| 3* | Y | R | Y | R | M |
| 5, 12 | T | H | Y | R | G |
| 6 | T | H | Y | R | M |
| 7* | Y | K | Y | R | M |
| 8, 9 | T | K | Y | R | G |
| 10 | Y | K | Y | R | — |

*Variant also contained Met226Ile.

TABLE 7

Library G Variants

| | Position in HRG-β1 | | | | | |
|---|---|---|---|---|---|---|
| Variant No. | 211 | 212 | 213 | 214 | 215 | 216 |
| Wild-type | K | C | P | N | E | F |
| 1, 5, 6, 10, 12 | R | — | S | L | — | — |
| 2 | R | — | S | E | — | — |
| 3 | — | — | — | K | — | M |
| 4 | R | — | T | V | — | Y |
| 7, 8 | R | — | T | V | — | Y |
| 9 | — | — | N | S | — | — |
| 11 | R | — | K | K | — | — |

Example 2

HER2/HER3 Expression in Embryonic Rat Lung

Rat lungs were microdissected from rat embryos on embryologic day (E) 16, 18, 20, and post-natal (P) days 7, 14, and adult. Isolated lung tissue was homogenized in a standard protease inhibitor buffer, and equal protein amounts subjected to SDS-PAGE (4–20%), blotted to nitrocellulose and identified with specific antibodies (HER2, HER3, HER4-Santa Cruz Biological, San Jose, Calif. and HRG, 3G11, Genentech, Inc.) using chemiluminescent techniques.

Analysis of the blot indicates that HER2 is expressed at high levels throughout development in utero, appears to peak on E18 and declines after birth to lower adult levels. HER3 expression peaks at E18, and then declines after birth to lower adult levels. HER4 is not identified at any time during lung development. A proform of HRG may be present (75 kDa protein) on E16, peaking on E18 and then declining to low levels in the adult. These data suggest that the HER/HRG system is developmentally modulated during lung development and the active receptor may be a HER2/HER3 heterodimer. The time period during which the receptors peak in expression (E18) represents the pseudoglandular stage of rat lung development (days 13–18), bordering on the canalicular stage (days 19–20). During the pseudoglandular stage, pulmonary epithelial cell proliferation is higher than at any other time. During the canalicular stage, differentiation begins with the appearance of type I pneymocyte and type II (surfactant producing) pneymocytes. This indicates a role for HRG/HER interaction in either or both processes.

Example 3

HER2/HER3 Expression in Fetal Human Lung

Fetal human lung was obtained from mid trimester embryos (17–22 weeks). Lung tissue was cultured in serum free Weymouth's media at an air fluid interface at 37° C. in a humidified 5% $CO_2$ atmosphere. Tissue was harvested from the culture on days 0 (day tissue was received) and after 14 days (D) in culture (D1–D4), homogenized in a standard protease inhibitor buffer, equal protein amounts subjected to SDS-PAGE (4–20%), blotted to nitrocellulose and identified with specific antibodies.

HER2 is expressed on D0 and increases in expression level during in vitro culture. HER3 is present at low to undetectable levels at D0 and increases in expression level during in vitro culture. HER4 was not identified at any time during lung development. HRG was not identified on D0, however, it was identified as a 75,000 Da protein on D1–D2 and continued to rise in expression level throughout time in culture. This human explant model recapitulates part of the normal lung developmental program over the 5 days in culture. Development occurs rapidly with both epithelial cell proliferation, and differentiation occurring, along with air space formation. These data indicate that the HER/HRG system is also modulated during in vitro human lung development, and the active receptor may be a HER2/HER3 heterodimer. The third trimester represents late pseudoglandular (days 42–112) and canalicular stage (days 112–196) in human lung development. As in the rat, during the pseudoglandular stage epithelial cell proliferation and formation of the prospective airways occurs. During the canalicular stage differentiation of the epithelium occurs.

Example 4

Expression of HER2 and HER3 in Human Lung

HER2 and HER3 are expressed exclusively in the pulmonary epithelium during lung development. Mid-trimester human lung was cultured in vitro as outlined above. Tissue was harvested daily, snap frozen, and 5 micron sections cut. The sections were mounted on glass slides, and immunohistochemistry performed using standard ABC procedures. HER2, HER3, and HER4 were identified using specific antibodies as described above.

As a control, lung tissue was stained at D0 and D5 with an irrelevant antibody and no staining was detected. At D0, the lung is relatively unformed. The majority of the tissue is mesenchymal cells. Early air spaces are being developed. On D5, air spaces are clearly identifiable, with thinning of the mesenchymal tissue and proliferation of the lung epithelium required to cover the enlarging air spaces.

Using HER2 staining at D0 and D5, it was established that HER 2 is uniformly resent on D0 lung tissue throughout the lung epithelial tissue. No expression was resent in the mesenchymal tissue. By D5, HER2 remains uniform and restricted to the pulmonary epithelium.

Using HER3 staining control at D0 and D5, HER3 was identifiable in D0 lung tissue. The staining was relatively less than HER2, and was not homogenous, suggesting that there are specific epithelial areas expressing the HER3 receptor. By D5. expression had become more homogenous throughout the lung epithelium, but clearly not uniform. Expression remained epithelium specific.

Example 5

Preparation of rHRGβ1$_{177-244}$

The EGF-like domain fragment HRG-β1 177–244 was amplified from vector pHL89 (which is described in Holmes et al., Science 256:1205–1210 (1992)) by PCR with primers having NsiI/XbaI-containing overhangs. The fragment was inserted into phagemid display vector pam-g3 by restriction digest-ligation at the same sites to generate construct pHRG2-g3 (177–244). pam-g3 was a derivative of phGHam-g3, which was designed for phage display of human growth hormone (hGH) and was described in Lowman et al., Biochemistry 30:10832–10838 (1991). pam-g3 was produced by removing the hGH gene present in phGHam-g3 and replacing this gene with a stuffer fragment, which provides space for cleavage at the restriction sites used for cloning. The HRG-β1 fragment was attached to residue 247 of pIII.

The HRG-β1 EGF-like domain expressed from the above-described construct is designated by removing the "p" and the "-g3" that appear in the name of the construct. Thus, the HRG-β1 EGF-like domain expressed from the pHRG2-g3 construct is designated "HRG2."

The domain was displayed monovalently on phage as a pIII fusion protein, as described by Bass et al., Proteins 8:309–314 (1990).

Similarly, variants HRG-β1$_{147-227}$, HRG-β1$_{147-244}$, and HRG-β1$_{177-227}$ were prepared and expressed as described above.

Example 6 rHRGβ1$_{177-244}$ Causes Accelerated Lung Development

Exogenous rHRGβ1$_{177-244}$ caused accelerated lung development in vitro. To determine if the expressed HER2/HER3 receptors were functional and the role of HRG stimulation during lung development in vitro, rHRGβ1$_{177-244}$ was added to the in vitro culture at 10 nM. Tissue was harvested at D5, snap frozen, and 5 micron sections were cut for analysis.

The morphology, in comparison to the untreated control specimens was grossly different. There was marked proliferation of the epithelium. Air spaces which are typically lined with a single cell layer now had a 2–3 cell thickness. The changes were dose dependent with more epithelial cell response with higher concentrations. HER2 and HER3 were still identifiable in the epithelium only.

Example 7

Human Lung Differentiation

Differentiation of human lung epithelial cells occurs after HRG treatment. Differentiation was measured by Surfactant Protein A (SPA) production. All sections were stained for SPA. Human lung explant stained for SPA with stain localizing in epithelial cells of the prealveolar ducts. Human lung explant exposed to 10 nM HRG showed an effect on SPA production. As a differentiation control, a lung explant was exposed to 1 mM dibutyryl cAMP. A negative control was also run.

---

SEQUENCE LISTING

```
<160> NUMBER OF SEQ ID NOS: 14

<210> SEQ ID NO 1
<211> LENGTH: 669
<212> TYPE: PRT
<213> ORGANISM: Homo sapiens

<400> SEQUENCE: 1

Ala Arg Ala Pro Gln Arg Gly Arg Ser Leu Ser Pro Ser Arg Asp
 1               5                  10                  15

Lys Leu Phe Pro Asn Pro Ile Arg Ala Leu Gly Pro Asn Ser Pro
                20                  25                  30

Ala Pro Arg Ala Val Arg Val Glu Arg Ser Val Ser Gly Glu Met
                35                  40                  45
```

-continued

```
Ser Glu Arg Lys Glu Gly Arg Lys Gly Lys Gly Lys Lys
             50                  55                 60

Glu Arg Gly Ser Gly Lys Lys Pro Glu Ser Ala Ala Gly Ser Gln
             65                  70                 75

Ser Pro Ala Leu Pro Pro Arg Leu Lys Glu Met Lys Ser Gln Glu
             80                  85                 90

Ser Ala Ala Gly Ser Lys Leu Val Leu Arg Cys Glu Thr Ser Ser
             95                 100                105

Glu Tyr Ser Ser Leu Arg Phe Lys Trp Phe Lys Asn Gly Asn Glu
            110                 115                120

Leu Asn Arg Lys Asn Lys Pro Gln Asn Ile Lys Ile Gln Lys Lys
            125                 130                135

Pro Gly Lys Ser Glu Leu Arg Ile Asn Lys Ala Ser Leu Ala Asp
            140                 145                150

Ser Gly Glu Tyr Met Cys Lys Val Ile Ser Lys Leu Gly Asn Asp
            155                 160                165

Ser Ala Ser Ala Asn Ile Thr Ile Val Glu Ser Asn Glu Ile Ile
            170                 175                180

Thr Gly Met Pro Ala Ser Thr Glu Gly Ala Tyr Val Ser Ser Glu
            185                 190                195

Ser Pro Ile Arg Ile Ser Val Ser Thr Glu Gly Ala Asn Thr Ser
            200                 205                210

Ser Ser Thr Ser Thr Ser Thr Gly Thr Ser His Leu Val Lys
            215                 220                225

Cys Ala Glu Lys Glu Lys Thr Phe Cys Val Asn Gly Gly Glu Cys
            230                 235                240

Phe Met Val Lys Asp Leu Ser Asn Pro Ser Arg Tyr Leu Cys Lys
            245                 250                255

Cys Gln Pro Gly Phe Thr Gly Ala Arg Cys Thr Glu Asn Val Pro
            260                 265                270

Met Lys Val Gln Asn Gln Glu Lys Ala Glu Glu Leu Tyr Gln Lys
            275                 280                285

Arg Val Leu Thr Ile Thr Gly Ile Cys Ile Ala Leu Leu Val Val
            290                 295                300

Gly Ile Met Cys Val Val Ala Tyr Cys Lys Thr Lys Lys Gln Arg
            305                 310                315

Lys Lys Leu His Asp Arg Leu Arg Gln Ser Leu Arg Ser Glu Arg
            320                 325                330

Asn Asn Met Met Asn Ile Ala Asn Gly Pro His His Pro Asn Pro
            335                 340                345

Pro Pro Glu Asn Val Gln Leu Val Asn Gln Tyr Val Ser Lys Asn
            350                 355                360

Val Ile Ser Ser Glu His Ile Val Glu Arg Glu Ala Glu Thr Ser
            365                 370                375

Phe Ser Thr Ser His Tyr Thr Ser Thr Ala His His Ser Thr Thr
            380                 385                390

Val Thr Gln Thr Pro Ser His Ser Trp Ser Asn Gly His Thr Glu
            395                 400                405

Ser Ile Leu Ser Glu Ser His Ser Val Ile Val Met Ser Ser Val
            410                 415                420

Glu Asn Ser Arg His Ser Ser Pro Thr Gly Gly Pro Arg Gly Arg
            425                 430                435
```

```
Leu Asn Gly Thr Gly Gly Pro Arg Glu Cys Asn Ser Phe Leu Arg
            440                 445                 450

His Ala Arg Glu Thr Pro Asp Ser Tyr Arg Asp Ser Pro His Ser
            455                 460                 465

Glu Arg Tyr Val Ser Ala Met Thr Thr Pro Ala Arg Met Ser Pro
            470                 475                 480

Val Asp Phe His Thr Pro Ser Ser Pro Lys Ser Pro Pro Ser Glu
            485                 490                 495

Met Ser Pro Pro Val Ser Ser Met Thr Val Ser Met Pro Ser Met
            500                 505                 510

Ala Val Ser Pro Phe Met Glu Glu Glu Arg Pro Leu Leu Leu Val
            515                 520                 525

Thr Pro Pro Arg Leu Arg Glu Lys Lys Phe Asp His His Pro Gln
            530                 535                 540

Gln Phe Ser Ser Phe His His Asn Pro Ala His Asp Ser Asn Ser
            545                 550                 555

Leu Pro Ala Ser Pro Leu Arg Ile Val Glu Asp Glu Tyr Glu
            560                 565                 570

Thr Thr Gln Glu Tyr Glu Pro Ala Gln Glu Pro Val Lys Lys Leu
            575                 580                 585

Ala Asn Ser Arg Arg Ala Lys Arg Thr Lys Pro Asn Gly His Ile
            590                 595                 600

Ala Asn Arg Leu Glu Val Asp Ser Asn Thr Ser Ser Gln Ser Ser
            605                 610                 615

Asn Ser Glu Ser Glu Thr Glu Asp Glu Arg Val Gly Glu Asp Thr
            620                 625                 630

Pro Phe Leu Gly Ile Gln Asn Pro Leu Ala Ala Ser Leu Glu Ala
            635                 640                 645

Thr Pro Ala Phe Arg Leu Ala Asp Ser Arg Thr Asn Pro Ala Gly
            650                 655                 660

Arg Phe Ser Thr Gln Glu Glu Ile Gln
            665                 669

<210> SEQ ID NO 2
<211> LENGTH: 2226
<212> TYPE: DNA
<213> ORGANISM: Homo sapiens

<400> SEQUENCE: 2 gg gcg cga gcg cct cag cgc ggc cgc tcg ctc tcc ccc              38
   Ala Arg Ala Pro Gln Arg Gly Arg Ser Leu Ser Pro
   1               5                   10 tcg agg gac aaa ctt ttc cca aac ccg atc cga gcc ctt             77
Ser Arg Asp Lys Leu Phe Pro Asn Pro Ile Arg Ala Leu
         15                  20                  25 gga cca aac tcg cct gcg ccg aga gcc gtc cgc gta gag             116
Gly Pro Asn Ser Pro Ala Pro Arg Ala Val Arg Val Glu
                     30                  35 cgc tcc gtc tcc ggc gag atg tcc gag cgc aaa gaa ggc             155
Arg Ser Val Ser Gly Glu Met Ser Glu Arg Lys Glu Gly
         40                  45                  50 aga ggc aaa ggg aag ggc aag aag aag gag cga ggc tcc             194
Arg Gly Lys Gly Lys Gly Lys Lys Lys Glu Arg Gly Ser
         55                  60 ggc aag aag ccg gag tcc gcg gcg ggc agc cag agc cca             233
Gly Lys Lys Pro Glu Ser Ala Ala Gly Ser Gln Ser Pro
65                   70                  75
```

|     |     |
| --- | --- |
| gcc ttg cct ccc cga ttg aaa gag atg aaa agc cag gaa<br>Ala Leu Pro Pro Arg Leu Lys Glu Met Lys Ser Gln Glu<br>        80                  85                  90 | 272 |
| tcg gct gca ggt tcc aaa cta gtc ctt cgg tgt gaa acc<br>Ser Ala Ala Gly Ser Lys Leu Val Leu Arg Cys Glu Thr<br>                 95                  100 | 311 |
| agt tct gaa tac tcc tct ctc aga ttc aag tgg ttc aag<br>Ser Ser Glu Tyr Ser Ser Leu Arg Phe Lys Trp Phe Lys<br>105                   110                  115 | 350 |
| aat ggg aat gaa ttg aat cga aaa aac aaa cca caa aat<br>Asn Gly Asn Glu Leu Asn Arg Lys Asn Lys Pro Gln Asn<br>        120                  125 | 389 |
| atc aag ata caa aaa aag cca ggg aag tca gaa ctt cgc<br>Ile Lys Ile Gln Lys Lys Pro Gly Lys Ser Glu Leu Arg<br>130                   135                  140 | 428 |
| att aac aaa gca tca ctg gct gat tct gga gag tat atg<br>Ile Asn Lys Ala Ser Leu Ala Asp Ser Gly Glu Tyr Met<br>        145                  150                  155 | 467 |
| tgc aaa gtg atc agc aaa tta gga aat gac agt gcc tct<br>Cys Lys Val Ile Ser Lys Leu Gly Asn Asp Ser Ala Ser<br>                      160                  165 | 506 |
| gcc aat atc acc atc gtg gaa tca aac gag atc atc act<br>Ala Asn Ile Thr Ile Val Glu Ser Asn Glu Ile Ile Thr<br>170                   175                  180 | 545 |
| ggt atg cca gcc tca act gaa gga gca tat gtg tct tca<br>Gly Met Pro Ala Ser Thr Glu Gly Ala Tyr Val Ser Ser<br>                 185                  190 | 584 |
| gag tct ccc att aga ata tca gta tcc aca gaa gga gca<br>Glu Ser Pro Ile Arg Ile Ser Val Ser Thr Glu Gly Ala<br>195                   200                  205 | 623 |
| aat act tct tca tct aca tct aca tcc acc act ggg aca<br>Asn Thr Ser Ser Ser Thr Ser Thr Ser Thr Thr Gly Thr<br>        210                  215                  220 | 662 |
| agc cat ctt gta aaa tgt gcg gag aag gag aaa act ttc<br>Ser His Leu Val Lys Cys Ala Glu Lys Glu Lys Thr Phe<br>                      225                  230 | 701 |
| tgt gtg aat gga ggg gag tgc ttc atg gtg aaa gac ctt<br>Cys Val Asn Gly Gly Glu Cys Phe Met Val Lys Asp Leu<br>235                   240                  245 | 740 |
| tca aac ccc tcg aga tac ttg tgc aag tgc caa cct gga<br>Ser Asn Pro Ser Arg Tyr Leu Cys Lys Cys Gln Pro Gly<br>        250                  255 | 779 |
| ttc act gga gca aga tgt act gag aat gtg ccc atg aaa<br>Phe Thr Gly Ala Arg Cys Thr Glu Asn Val Pro Met Lys<br>260                   265                  270 | 818 |
| gtc caa aac caa gaa aag gcg gag gag ctg tac cag aag<br>Val Gln Asn Gln Glu Lys Ala Glu Glu Leu Tyr Gln Lys<br>                      275                  280                  285 | 857 |
| aga gtg ctg acc ata acc ggc atc tgc atc gcc ctc ctt<br>Arg Val Leu Thr Ile Thr Gly Ile Cys Ile Ala Leu Leu<br>                            290                  295 | 896 |
| gtg gtc ggc atc atg tgt gtg gtg gcc tac tgc aaa acc<br>Val Val Gly Ile Met Cys Val Val Ala Tyr Cys Lys Thr<br>300                   305                  310 | 935 |
| aag aaa cag cgg aaa aag ctg cat gac cgt ctt cgg cag<br>Lys Lys Gln Arg Lys Lys Leu His Asp Arg Leu Arg Gln<br>                  315                  320 | 974 |
| agc ctt cgg tct gaa cga aac aat atg atg aac att gcc<br>Ser Leu Arg Ser Glu Arg Asn Asn Met Met Asn Ile Ala<br>325                   330                  335 | 1013 |

-continued

| | | |
|---|---|---|
| aat ggg cct cac cat cct aac cca ccc ccc gag aat gtc<br>Asn Gly Pro His His Pro Asn Pro Pro Pro Glu Asn Val<br>340                   345                350 | | 1052 |
| cag ctg gtg aat caa tac gta tct aaa aac gtc atc tcc<br>Gln Leu Val Asn Gln Tyr Val Ser Lys Asn Val Ile Ser<br>                  355                     360 | | 1091 |
| agt gag cat att gtt gag aga gaa gca gag aca tcc ttt<br>Ser Glu His Ile Val Glu Arg Glu Ala Glu Thr Ser Phe<br>365                   370                375 | | 1130 |
| tcc acc agt cac tat act tcc aca gcc cat cac tcc act<br>Ser Thr Ser His Tyr Thr Ser Thr Ala His His Ser Thr<br>                  380                    385 | | 1169 |
| act gtc acc cag act cct agc cac agc tgg agc aac gga<br>Thr Val Thr Gln Thr Pro Ser His Ser Trp Ser Asn Gly<br>390                   395                400 | | 1208 |
| cac act gaa agc atc ctt tcc gaa agc cac tct gta atc<br>His Thr Glu Ser Ile Leu Ser Glu Ser His Ser Val Ile<br>                 405                 410                415 | | 1247 |
| gtg atg tca tcc gta gaa aac agt agg cac agc agc cca<br>Val Met Ser Ser Val Glu Asn Ser Arg His Ser Ser Pro<br>                  420                    425 | | 1286 |
| act ggg ggc cca aga gga cgt ctt aat ggc aca gga ggc<br>Thr Gly Gly Pro Arg Gly Arg Leu Asn Gly Thr Gly Gly<br>430                     435                440 | | 1325 |
| cct cgt gaa tgt aac agc ttc ctc agg cat gcc aga gaa<br>Pro Arg Glu Cys Asn Ser Phe Leu Arg His Ala Arg Glu<br>                 445                 450 | | 1364 |
| acc cct gat tcc tac cga gac tct cct cat agt gaa agg<br>Thr Pro Asp Ser Tyr Arg Asp Ser Pro His Ser Glu Arg<br>455                     460                465 | | 1403 |
| tat gtg tca gcc atg acc acc ccg gct cgt atg tca cct<br>Tyr Val Ser Ala Met Thr Thr Pro Ala Arg Met Ser Pro<br>                 470                 475                480 | | 1442 |
| gta gat ttc cac acg cca agc tcc ccc aaa tcg ccc cct<br>Val Asp Phe His Thr Pro Ser Ser Pro Lys Ser Pro Pro<br>                     485                 490 | | 1481 |
| tcg gaa atg tct cca ccc gtg tcc agc atg acg gtg tcc<br>Ser Glu Met Ser Pro Pro Val Ser Ser Met Thr Val Ser<br>495                     500                505 | | 1520 |
| atg cct tcc atg gcg gtc agc ccc ttc atg gaa gaa gag<br>Met Pro Ser Met Ala Val Ser Pro Phe Met Glu Glu Glu<br>                 510                 515 | | 1559 |
| aga cct cta ctt ctc gtg aca cca cca agg ctg cgg gag<br>Arg Pro Leu Leu Leu Val Thr Pro Pro Arg Leu Arg Glu<br>520                     525                530 | | 1598 |
| aag aag ttt gac cat cac cct cag cag ttc agc tcc ttc<br>Lys Lys Phe Asp His His Pro Gln Gln Phe Ser Ser Phe<br>                 535                 540                545 | | 1637 |
| cac cac aac ccc gcg cat gac agt aac agc ctc cct gct<br>His His Asn Pro Ala His Asp Ser Asn Ser Leu Pro Ala<br>                     550                 555 | | 1676 |
| agc ccc ttg agg ata gtg gag gat gag gag tat gaa acg<br>Ser Pro Leu Arg Ile Val Glu Asp Glu Glu Tyr Glu Thr<br>560                     565                570 | | 1715 |
| acc caa gag tac gag cca gcc caa gag cct gtt aag aaa<br>Thr Gln Glu Tyr Glu Pro Ala Gln Glu Pro Val Lys Lys<br>                 575                 580 | | 1754 |
| ctc gcc aat agc cgg cgg gcc aaa aga acc aag ccc aat<br>Leu Ala Asn Ser Arg Arg Ala Lys Arg Thr Lys Pro Asn<br>585                     590                595 | | 1793 |

-continued

| | | |
|---|---|---|
| ggc cac att gct aac aga ttg gaa gtg gac agc aac aca<br>Gly His Ile Ala Asn Arg Leu Glu Val Asp Ser Asn Thr<br>600               605               610 | | 1832 |
| agc tcc cag agc agt aac tca gag agt gaa aca gaa gat<br>Ser Ser Gln Ser Ser Asn Ser Glu Ser Glu Thr Glu Asp<br>               615               620 | | 1871 |
| gaa aga gta ggt gaa gat acg cct ttc ctg ggc ata cag<br>Glu Arg Val Gly Glu Asp Thr Pro Phe Leu Gly Ile Gln<br>625                 630               635 | | 1910 |
| aac ccc ctg gca gcc agt ctt gag gca aca cct gcc ttc<br>Asn Pro Leu Ala Ala Ser Leu Glu Ala Thr Pro Ala Phe<br>         640               645 | | 1949 |
| cgc ctg gct gac agc agg act aac cca gca ggc cgc ttc<br>Arg Leu Ala Asp Ser Arg Thr Asn Pro Ala Gly Arg Phe<br>650               655               660 | | 1988 |
| tcg aca cag gaa gaa atc cag g ccaggctgtc tagtgtaatt<br>Ser Thr Gln Glu Glu Ile Gln<br>         665               669 | | 2030 |
| gctaaccaag accctattgc tgtataaaac ctaaataaac acatagattc | | 2080 |
| acctgtaaaa ctttatttta tataataaag tattccacct taaattaaac | | 2130 |
| aatttatttt attttagcag ttctgcaaat agaaacagg aaaaaaactt | | 2180 |
| ttataaatta aatatatgta tgtaaaaatg aaaaaaaaaa aaaaaa | | 2226 |

<210> SEQ ID NO 3
<211> LENGTH: 675
<212> TYPE: PRT
<213> ORGANISM: Homo sapiens

<400> SEQUENCE: 3

Asp Lys Leu Phe Pro Asn Pro Ile Arg Ala Leu Gly Pro Asn Ser
1               5                   10                  15

Pro Ala Pro Arg Ala Val Arg Val Glu Arg Ser Val Ser Gly Glu
                20                  25                  30

Met Ser Glu Arg Lys Glu Gly Arg Gly Lys Gly Lys Gly Lys Lys
                35                  40                  45

Lys Glu Arg Gly Ser Gly Lys Lys Pro Glu Ser Ala Ala Gly Ser
                50                  55                  60

Gln Ser Pro Ala Leu Pro Pro Gln Leu Lys Glu Met Lys Ser Gln
                65                  70                  75

Glu Ser Ala Ala Gly Ser Lys Leu Val Leu Arg Cys Glu Thr Ser
                80                  85                  90

Ser Glu Tyr Ser Ser Leu Arg Phe Lys Trp Phe Lys Asn Gly Asn
                95                  100                 105

Glu Leu Asn Arg Lys Asn Lys Pro Gln Asn Ile Lys Ile Gln Lys
                110                 115                 120

Lys Pro Gly Lys Ser Glu Leu Arg Ile Asn Lys Ala Ser Leu Ala
                125                 130                 135

Asp Ser Gly Glu Tyr Met Cys Lys Val Ile Ser Lys Leu Gly Asn
                140                 145                 150

Asp Ser Ala Ser Ala Asn Ile Thr Ile Val Glu Ser Asn Glu Ile
                155                 160                 165

Ile Thr Gly Met Pro Ala Ser Thr Glu Gly Ala Tyr Val Ser Ser
                170                 175                 180

Glu Ser Pro Ile Arg Ile Ser Val Ser Thr Glu Gly Ala Asn Thr
                185                 190                 195

-continued

```
Ser Ser Ser Thr Ser Thr Ser Thr Thr Gly Thr Ser His Leu Val
            200                 205                 210

Lys Cys Ala Glu Lys Glu Lys Thr Phe Cys Val Asn Gly Gly Glu
            215                 220                 225

Cys Phe Met Val Lys Asp Leu Ser Asn Pro Ser Arg Tyr Leu Cys
            230                 235                 240

Lys Cys Pro Asn Glu Phe Thr Gly Asp Arg Cys Gln Asn Tyr Val
            245                 250                 255

Met Ala Ser Phe Tyr Lys His Leu Gly Ile Glu Phe Met Glu Ala
            260                 265                 270

Glu Glu Leu Tyr Gln Lys Arg Val Leu Thr Ile Thr Gly Ile Cys
            275                 280                 285

Ile Ala Leu Leu Val Val Gly Ile Met Cys Val Val Ala Tyr Cys
            290                 295                 300

Lys Thr Lys Lys Gln Arg Lys Lys Leu His Asp Arg Leu Arg Gln
            305                 310                 315

Ser Leu Arg Ser Glu Arg Asn Asn Met Met Asn Ile Ala Asn Gly
            320                 325                 330

Pro His His Pro Asn Pro Pro Glu Asn Val Gln Leu Val Asn
            335                 340                 345

Gln Tyr Val Ser Lys Asn Val Ile Ser Ser Glu His Ile Val Glu
            350                 355                 360

Arg Glu Ala Glu Thr Ser Phe Ser Thr Ser His Tyr Thr Ser Thr
            365                 370                 375

Ala His His Ser Thr Thr Val Thr Gln Thr Pro Ser His Ser Trp
            380                 385                 390

Ser Asn Gly His Thr Glu Ser Ile Leu Ser Glu Ser His Ser Val
            395                 400                 405

Ile Val Met Ser Ser Val Glu Asn Ser Arg His Ser Ser Pro Thr
            410                 415                 420

Gly Gly Pro Arg Gly Arg Leu Asn Gly Thr Gly Gly Pro Arg Glu
            425                 430                 435

Cys Asn Ser Phe Leu Arg His Ala Arg Glu Thr Pro Asp Ser Tyr
            440                 445                 450

Arg Asp Ser Pro His Ser Glu Arg Tyr Val Ser Ala Met Thr Thr
            455                 460                 465

Pro Ala Arg Met Ser Pro Val Asp Phe His Thr Pro Ser Ser Pro
            470                 475                 480

Lys Ser Pro Pro Ser Glu Met Ser Pro Val Ser Ser Met Thr
            485                 490                 495

Val Ser Met Pro Ser Met Ala Val Ser Pro Phe Met Glu Glu Glu
            500                 505                 510

Arg Pro Leu Leu Leu Val Thr Pro Pro Arg Leu Arg Glu Lys Lys
            515                 520                 525

Phe Asp His His Pro Gln Gln Phe Ser Ser Phe His His Asn Pro
            530                 535                 540

Ala His Asp Ser Asn Ser Leu Pro Ala Ser Pro Leu Arg Ile Val
            545                 550                 555

Glu Asp Glu Glu Tyr Glu Thr Thr Gln Glu Tyr Glu Pro Ala Gln
            560                 565                 570

Glu Pro Val Lys Lys Leu Ala Asn Ser Arg Arg Ala Lys Arg Thr
            575                 580                 585
```

```
Lys Pro Asn Gly His Ile Ala Asn Arg Leu Glu Val Asp Ser Asn
                590                 595                 600

Thr Ser Ser Gln Ser Ser Asn Ser Glu Ser Glu Thr Glu Asp Glu
                605                 610                 615

Arg Val Gly Glu Asp Thr Pro Phe Leu Gly Ile Gln Asn Pro Leu
                620                 625                 630

Ala Ala Ser Leu Glu Ala Thr Pro Ala Phe Arg Leu Ala Asp Ser
                635                 640                 645

Arg Thr Asn Pro Ala Gly Arg Phe Ser Thr Gln Glu Glu Ile Gln
                650                 655                 660

Ala Arg Leu Ser Ser Val Ile Ala Asn Gln Asp Pro Ile Ala Val
                665                 670                 675

<210> SEQ ID NO 4
<211> LENGTH: 2199
<212> TYPE: DNA
<213> ORGANISM: Homo sapiens

<400> SEQUENCE: 4 gg  gac aaa ctt ttc cca aac ccg atc cga gcc ctt gga           38
    Asp Lys Leu Phe Pro Asn Pro Ile Arg Ala Leu Gly
    1               5                   10 cca aac tcg cct gcg ccg aga gcc gtc cgc gta gag cgc           77
Pro Asn Ser Pro Ala Pro Arg Ala Val Arg Val Glu Arg
            15                  20                  25 tcc gtc tcc ggc gag atg tcc gag cgc aaa gaa ggc aga          116
Ser Val Ser Gly Glu Met Ser Glu Arg Lys Glu Gly Arg
                    30                  35 ggc aaa ggg aag ggc aag aag aag gag cga ggc tcc ggc          155
Gly Lys Gly Lys Gly Lys Lys Lys Glu Arg Gly Ser Gly
    40                  45                  50 aag aag ccg gag tcc gcg gcg ggc agc cag agc cca gcc          194
Lys Lys Pro Glu Ser Ala Ala Gly Ser Gln Ser Pro Ala
                55                  60 ttg cct ccc caa ttg aaa gag atg aaa agc cag gaa tcg          233
Leu Pro Pro Gln Leu Lys Glu Met Lys Ser Gln Glu Ser
65                  70                  75 gct gca ggt tcc aaa cta gtc ctt cgg tgt gaa acc agt          272
Ala Ala Gly Ser Lys Leu Val Leu Arg Cys Glu Thr Ser
            80                  85                  90 tct gaa tac tcc tct ctc aga ttc aag tgg ttc aag aat          311
Ser Glu Tyr Ser Ser Leu Arg Phe Lys Trp Phe Lys Asn
                    95                  100 ggg aat gaa ttg aat cga aaa aac aaa cca caa aat atc          350
Gly Asn Glu Leu Asn Arg Lys Asn Lys Pro Gln Asn Ile
    105                 110                 115 aag ata caa aaa aag cca ggg aag tca gaa ctt cgc att          389
Lys Ile Gln Lys Lys Pro Gly Lys Ser Glu Leu Arg Ile
                120                 125 aac aaa gca tca ctg gct gat tct gga gag tat atg tgc          428
Asn Lys Ala Ser Leu Ala Asp Ser Gly Glu Tyr Met Cys
130                 135                 140 aaa gtg atc agc aaa tta gga aat gac agt gcc tct gcc          467
Lys Val Ile Ser Lys Leu Gly Asn Asp Ser Ala Ser Ala
            145                 150                 155 aat atc acc atc gtg gaa tca aac gag atc atc act ggt          506
Asn Ile Thr Ile Val Glu Ser Asn Glu Ile Ile Thr Gly
                160                 165
```

-continued

| | |
|---|---|
| atg cca gcc tca act gaa gga gca tat gtg tct tca gag<br>Met Pro Ala Ser Thr Glu Gly Ala Tyr Val Ser Ser Glu<br>170                  175                  180 | 545 |
| tct ccc att aga ata tca gta tcc aca gaa gga gca aat<br>Ser Pro Ile Arg Ile Ser Val Ser Thr Glu Gly Ala Asn<br>              185                  190 | 584 |
| act tct tca tct aca tct aca tcc acc act ggg aca agc<br>Thr Ser Ser Ser Thr Ser Thr Ser Thr Thr Gly Thr Ser<br>195                  200                  205 | 623 |
| cat ctt gta aaa tgt gcg gag aag gag aaa act ttc tgt<br>His Leu Val Lys Cys Ala Glu Lys Glu Lys Thr Phe Cys<br>              210                  215                  220 | 662 |
| gtg aat gga ggg gag tgc ttc atg gtg aaa gac ctt tca<br>Val Asn Gly Gly Glu Cys Phe Met Val Lys Asp Leu Ser<br>                      225                  230 | 701 |
| aac ccc tcg aga tac ttg tgc aag tgc cca aat gag ttt<br>Asn Pro Ser Arg Tyr Leu Cys Lys Cys Pro Asn Glu Phe<br>              235                  240                  245 | 740 |
| act ggt gat cgc tgc caa aac tac gta atg gcc agc ttc<br>Thr Gly Asp Arg Cys Gln Asn Tyr Val Met Ala Ser Phe<br>                      250                  255 | 779 |
| tac aag cat ctt ggg att gaa ttt atg gag gcg gag gag<br>Tyr Lys His Leu Gly Ile Glu Phe Met Glu Ala Glu Glu<br>260                  265                  270 | 818 |
| ctg tac cag aag aga gtg ctg acc ata acc ggc atc tgc<br>Leu Tyr Gln Lys Arg Val Leu Thr Ile Thr Gly Ile Cys<br>              275                  280                  285 | 857 |
| atc gcc ctc ctt gtg gtc ggc atc atg tgt gtg gtg gcc<br>Ile Ala Leu Leu Val Val Gly Ile Met Cys Val Val Ala<br>                      290                  295 | 896 |
| tac tgc aaa acc aag aaa cag cgg aaa aag ctg cat gac<br>Tyr Cys Lys Thr Lys Lys Gln Arg Lys Lys Leu His Asp<br>300                  305                  310 | 935 |
| cgt ctt cgg cag agc ctt cgg tct gaa cga aac aat atg<br>Arg Leu Arg Gln Ser Leu Arg Ser Glu Arg Asn Asn Met<br>              315                  320 | 974 |
| atg aac att gcc aat ggg cct cac cat cct aac cca ccc<br>Met Asn Ile Ala Asn Gly Pro His His Pro Asn Pro Pro<br>325                  330                  335 | 1013 |
| ccc gag aat gtc cag ctg gtg aat caa tac gta tct aaa<br>Pro Glu Asn Val Gln Leu Val Asn Gln Tyr Val Ser Lys<br>              340                  345                  350 | 1052 |
| aac gtc atc tcc agt gag cat att gtt gag aga gaa gca<br>Asn Val Ile Ser Ser Glu His Ile Val Glu Arg Glu Ala<br>                      355                  360 | 1091 |
| gag aca tcc ttt tcc acc agt cac tat act tcc aca gcc<br>Glu Thr Ser Phe Ser Thr Ser His Tyr Thr Ser Thr Ala<br>365                  370                  375 | 1130 |
| cat cac tcc act act gtc acc cag act cct agc cac agc<br>His His Ser Thr Thr Val Thr Gln Thr Pro Ser His Ser<br>              380                  385 | 1169 |
| tgg agc aac gga cac act gaa agc atc ctt tcc gaa agc<br>Trp Ser Asn Gly His Thr Glu Ser Ile Leu Ser Glu Ser<br>390                  395                  400 | 1208 |
| cac tct gta atc gtg atg tca tcc gta gaa aac agt agg<br>His Ser Val Ile Val Met Ser Ser Val Glu Asn Ser Arg<br>              405                  410                  415 | 1247 |
| cac agc agc cca act ggg ggc cca aga gga cgt ctt aat<br>His Ser Ser Pro Thr Gly Gly Pro Arg Gly Arg Leu Asn<br>                      420                  425 | 1286 |

-continued

| | |
|---|---|
| ggc aca gga ggc cct cgt gaa tgt aac agc ttc ctc agg<br>Gly Thr Gly Gly Pro Arg Glu Cys Asn Ser Phe Leu Arg<br>430                          435                     440 | 1325 |
| cat gcc aga gaa acc cct gat tcc tac cga gac tct cct<br>His Ala Arg Glu Thr Pro Asp Ser Tyr Arg Asp Ser Pro<br>                     445                     450 | 1364 |
| cat agt gaa agg tat gtg tca gcc atg acc acc ccg gct<br>His Ser Glu Arg Tyr Val Ser Ala Met Thr Thr Pro Ala<br>455                          460                     465 | 1403 |
| cgt atg tca cct gta gat ttc cac acg cca agc tcc ccc<br>Arg Met Ser Pro Val Asp Phe His Thr Pro Ser Ser Pro<br>                     470                     475                     480 | 1442 |
| aaa tcg ccc cct tcg gaa atg tct cca ccc gtg tcc agc<br>Lys Ser Pro Pro Ser Glu Met Ser Pro Pro Val Ser Ser<br>                          485                     490 | 1481 |
| atg acg gtg tcc atg cct tcc atg gcg gtc agc ccc ttc<br>Met Thr Val Ser Met Pro Ser Met Ala Val Ser Pro Phe<br>                     495                     500                     505 | 1520 |
| atg gaa gaa gag aga cct cta ctt ctc gtg aca cca cca<br>Met Glu Glu Glu Arg Pro Leu Leu Leu Val Thr Pro Pro<br>                     510                          515 | 1559 |
| agg ctg cgg gag aag aag ttt gac cat cac cct cag cag<br>Arg Leu Arg Glu Lys Lys Phe Asp His His Pro Gln Gln<br>520                          525                     530 | 1598 |
| ttc agc tcc ttc cac cac aac ccc gcg cat gac agt aac<br>Phe Ser Ser Phe His His Asn Pro Ala His Asp Ser Asn<br>                     535                     540                     545 | 1637 |
| agc ctc cct gct agc ccc ttg agg ata gtg gag gat gag<br>Ser Leu Pro Ala Ser Pro Leu Arg Ile Val Glu Asp Glu<br>                          550                     555 | 1676 |
| gag tat gaa acg acc caa gag tac gag cca gcc caa gag<br>Glu Tyr Glu Thr Thr Gln Glu Tyr Glu Pro Ala Gln Glu<br>                     560                          565                     570 | 1715 |
| cct gtt aag aaa ctc gcc aat agc cgg cgg gcc aaa aga<br>Pro Val Lys Lys Leu Ala Asn Ser Arg Arg Ala Lys Arg<br>                     575                          580 | 1754 |
| acc aag ccc aat ggc cac att gct aac aga ttg gaa gtg<br>Thr Lys Pro Asn Gly His Ile Ala Asn Arg Leu Glu Val<br>585                          590                     595 | 1793 |
| gac agc aac aca agc tcc cag agc agt aac tca gag agt<br>Asp Ser Asn Thr Ser Ser Gln Ser Ser Asn Ser Glu Ser<br>                     600                     605                     610 | 1832 |
| gaa aca gaa gat gaa aga gta ggt gaa gat acg cct ttc<br>Glu Thr Glu Asp Glu Arg Val Gly Glu Asp Thr Pro Phe<br>                          615                     620 | 1871 |
| ctg ggc ata cag aac ccc ctg gca gcc agt ctt gag gca<br>Leu Gly Ile Gln Asn Pro Leu Ala Ala Ser Leu Glu Ala<br>625                          630                     635 | 1910 |
| aca cct gcc ttc cgc ctg gct gac agc agg act aac cca<br>Thr Pro Ala Phe Arg Leu Ala Asp Ser Arg Thr Asn Pro<br>                     640                     645 | 1949 |
| gca ggc cgc ttc tcg aca cag gaa gaa atc cag gcc agg<br>Ala Gly Arg Phe Ser Thr Gln Glu Glu Ile Gln Ala Arg<br>650                          655                     660 | 1988 |
| ctg tct agt gta att gct aac caa gac cct att gct gta ta<br>Leu Ser Ser Val Ile Ala Asn Gln Asp Pro Ile Ala Val<br>                     665                     670                     675 | 2029 |
| a aacctaaata aacacataga ttcacctgta aaactttatt | 2070 |
| ttatataata aagtattcca ccttaaatta aacaatttat tttatttag | 2120 |

```
cagttctgca aatagaaaac aggaaaaaaa cttttataaa ttaaatatat                    2170
gtatgtaaaa atgaaaaaaa aaaaaaaaa                                           2199
```

<210> SEQ ID NO 5
<211> LENGTH: 637
<212> TYPE: PRT
<213> ORGANISM: Homo sapiens

<400> SEQUENCE: 5

```
Met Ser Glu Arg Lys Glu Gly Arg Gly Lys Gly Lys Gly Lys Lys
 1               5                  10                  15

Lys Glu Arg Gly Ser Gly Lys Lys Pro Glu Ser Ala Ala Gly Ser
                20                  25                  30

Gln Ser Pro Ala Leu Pro Pro Gln Leu Lys Glu Met Lys Ser Gln
                35                  40                  45

Glu Ser Ala Ala Gly Ser Lys Leu Val Leu Arg Cys Glu Thr Ser
                50                  55                  60

Ser Glu Tyr Ser Ser Leu Arg Phe Lys Trp Phe Lys Asn Gly Asn
                65                  70                  75

Glu Leu Asn Arg Lys Asn Lys Pro Gln Asn Ile Lys Ile Gln Lys
                80                  85                  90

Lys Pro Gly Lys Ser Glu Leu Arg Ile Asn Lys Ala Ser Leu Ala
                95                 100                 105

Asp Ser Gly Glu Tyr Met Cys Lys Val Ile Ser Lys Leu Gly Asn
               110                 115                 120

Asp Ser Ala Ser Ala Asn Ile Thr Ile Val Glu Ser Asn Glu Ile
               125                 130                 135

Ile Thr Gly Met Pro Ala Ser Thr Glu Gly Ala Tyr Val Ser Ser
               140                 145                 150

Glu Ser Pro Ile Arg Ile Ser Val Ser Thr Glu Gly Ala Asn Thr
               155                 160                 165

Ser Ser Ser Thr Ser Thr Ser Thr Thr Gly Thr Ser His Leu Val
               170                 175                 180

Lys Cys Ala Glu Lys Glu Lys Thr Phe Cys Val Asn Gly Gly Glu
               185                 190                 195

Cys Phe Met Val Lys Asp Leu Ser Asn Pro Ser Arg Tyr Leu Cys
               200                 205                 210

Lys Cys Pro Asn Glu Phe Thr Gly Asp Arg Cys Gln Asn Tyr Val
               215                 220                 225

Met Ala Ser Phe Tyr Lys Ala Glu Glu Leu Tyr Gln Lys Arg Val
               230                 235                 240

Leu Thr Ile Thr Gly Ile Cys Ile Ala Leu Leu Val Val Gly Ile
               245                 250                 255

Met Cys Val Val Ala Tyr Cys Lys Thr Lys Lys Gln Arg Lys Lys
               260                 265                 270

Leu His Asp Arg Leu Arg Gln Ser Leu Arg Ser Glu Arg Asn Asn
               275                 280                 285

Met Met Asn Ile Ala Asn Gly Pro His His Pro Asn Pro Pro Pro
               290                 295                 300

Glu Asn Val Gln Leu Val Asn Gln Tyr Val Ser Lys Asn Val Ile
               305                 310                 315

Ser Ser Glu His Ile Val Glu Arg Glu Ala Glu Thr Ser Phe Ser
               320                 325                 330
```

-continued

```
Thr Ser His Tyr Thr Ser Thr Ala His His Ser Thr Thr Val Thr
            335                 340                 345

Gln Thr Pro Ser His Ser Trp Ser Asn Gly His Thr Glu Ser Ile
            350                 355                 360

Leu Ser Glu Ser His Ser Val Ile Val Met Ser Ser Val Glu Asn
            365                 370                 375

Ser Arg His Ser Ser Pro Thr Gly Gly Pro Arg Gly Arg Leu Asn
            380                 385                 390

Gly Thr Gly Gly Pro Arg Glu Cys Asn Ser Phe Leu Arg His Ala
            395                 400                 405

Arg Glu Thr Pro Asp Ser Tyr Arg Asp Ser Pro His Ser Glu Arg
            410                 415                 420

Tyr Val Ser Ala Met Thr Thr Pro Ala Arg Met Ser Pro Val Asp
            425                 430                 435

Phe His Thr Pro Ser Ser Pro Lys Ser Pro Pro Ser Glu Met Ser
            440                 445                 450

Pro Pro Val Ser Ser Met Thr Val Ser Lys Pro Ser Met Ala Val
            455                 460                 465

Ser Pro Phe Met Glu Glu Glu Arg Pro Leu Leu Leu Val Thr Pro
            470                 475                 480

Pro Arg Leu Arg Glu Lys Lys Phe Asp His His Pro Gln Gln Phe
            485                 490                 495

Ser Ser Phe His His Asn Pro Ala His Asp Ser Asn Ser Leu Pro
            500                 505                 510

Ala Ser Pro Leu Arg Ile Val Glu Asp Glu Glu Tyr Glu Thr Thr
            515                 520                 525

Gln Glu Tyr Glu Pro Ala Gln Glu Pro Val Lys Lys Leu Ala Asn
            530                 535                 540

Ser Arg Arg Ala Lys Arg Thr Lys Pro Asn Gly His Ile Ala Asn
            545                 550                 555

Arg Leu Glu Val Asp Ser Asn Thr Ser Ser Gln Ser Ser Asn Ser
            560                 565                 570

Glu Ser Glu Thr Glu Asp Glu Arg Val Gly Asp Thr Pro Phe
            575                 580                 585

Leu Gly Ile Gln Asn Pro Leu Ala Ala Ser Leu Glu Ala Thr Pro
            590                 595                 600

Ala Phe Arg Leu Ala Asp Ser Arg Thr Asn Pro Ala Gly Arg Phe
            605                 610                 615

Ser Thr Gln Glu Glu Ile Gln Ala Arg Leu Ser Ser Val Ile Ala
            620                 625                 630

Asn Gln Asp Pro Ile Ala Val
            635         637

<210> SEQ ID NO 6
<211> LENGTH: 2490
<212> TYPE: DNA
<213> ORGANISM: Homo sapiens

<400> SEQUENCE: 6
gtggctgcgg ggcaattgaa aaagagccgg cgaggagttc cccgaaactt          50
gttggaactc cgggctcgcg cggaggccag gagctgagcg gcggcggctg          100
ccggacgatg ggagcgtgag caggacggtg ataacctctc cccgatcggg          150
ttgcgagggc gccgggcaga ggccaggacg cgagccgcca gcggcgggac          200
```

-continued

| | |
|---|---|
| ccatcgacga cttcccgggg cgacaggagc agccccgaga gccagggcga | 250 |
| gcgcccgttc caggtggccg gaccgcccgc cgcgtccgcg ccgcgctccc | 300 |
| tgcaggcaac gggagacgcc cccgcgcagc gcgagcgcct cagcgcggcc | 350 |
| gctcgctctc cccatcgagg gacaaacttt tcccaaaccc gatccgagcc | 400 |
| cttggaccaa actcgcctgc gccgagagcc gtccgcgtag agcgctccgt | 450 |

```
ctccggcgag  atg tcc gag cgc aaa gaa ggc aga ggc aaa              490
            Met Ser Glu Arg Lys Glu Gly Arg Gly Lys
              1               5                  10 ggg aag ggc aag aag aag gag cga ggc tcc ggc aag aag              529
Gly Lys Gly Lys Lys Lys Glu Arg Gly Ser Gly Lys Lys
             15                  20 ccg gag tcc gcg gcg ggc agc cag agc cca gcc ttg cct              568
Pro Glu Ser Ala Ala Gly Ser Gln Ser Pro Ala Leu Pro
 25                  30                  35 ccc caa ttg aaa gag atg aaa agc cag gaa tcg gct gca              607
Pro Gln Leu Lys Glu Met Lys Ser Gln Glu Ser Ala Ala
         40                  45 ggt tcc aaa cta gtc ctt cgg tgt gaa acc agt tct gaa              646
Gly Ser Lys Leu Val Leu Arg Cys Glu Thr Ser Ser Glu
 50                  55                  60 tac tcc tct ctc aga ttc aag tgg ttc aag aat ggg aat              685
Tyr Ser Ser Leu Arg Phe Lys Trp Phe Lys Asn Gly Asn
             65                  70                  75 gaa ttg aat cga aaa aac aaa cca caa aat atc aag ata              724
Glu Leu Asn Arg Lys Asn Lys Pro Gln Asn Ile Lys Ile
                 80                  85 caa aaa aag cca ggg aag tca gaa ctt cgc att aac aaa              763
Gln Lys Lys Pro Gly Lys Ser Glu Leu Arg Ile Asn Lys
 90                  95                 100 gca tca ctg gct gat tct gga gag tat atg tgc aaa gtg              802
Ala Ser Leu Ala Asp Ser Gly Glu Tyr Met Cys Lys Val
             105                 110 atc agc aaa tta gga aat gac agt gcc tct gcc aat atc              841
Ile Ser Lys Leu Gly Asn Asp Ser Ala Ser Ala Asn Ile
115                 120                 125 acc atc gtg gaa tca aac gag atc atc act ggt atg cca              880
Thr Ile Val Glu Ser Asn Glu Ile Ile Thr Gly Met Pro
         130                 135                 140 gcc tca act gaa gga gca tat gtg tct tca gag tct ccc              919
Ala Ser Thr Glu Gly Ala Tyr Val Ser Ser Glu Ser Pro
                 145                 150 att aga ata tca gta tcc aca gaa gga gca aat act tct              958
Ile Arg Ile Ser Val Ser Thr Glu Gly Ala Asn Thr Ser
 155                 160                 165 tca tct aca tct aca tcc acc act ggg aca agc cat ctt              997
Ser Ser Thr Ser Thr Ser Thr Thr Gly Thr Ser His Leu
             170                 175 gta aaa tgt gcg gag aag gag aaa act ttc tgt gtg aat             1036
Val Lys Cys Ala Glu Lys Glu Lys Thr Phe Cys Val Asn
180                 185                 190 gga ggg gag tgc ttc atg gtg aaa gac ctt tca aac ccc             1075
Gly Gly Glu Cys Phe Met Val Lys Asp Leu Ser Asn Pro
         195                 200                 205 tcg aga tac ttg tgc aag tgc cca aat gag ttt act ggt             1114
Ser Arg Tyr Leu Cys Lys Cys Pro Asn Glu Phe Thr Gly
                 210                 215
```

-continued

| | |
|---|---|
| gat cgc tgc caa aac tac gta atg gcc agc ttc tac aag<br>Asp Arg Cys Gln Asn Tyr Val Met Ala Ser Phe Tyr Lys<br>220                        225                        230 | 1153 |
| gcg gag gag ctg tac cag aag aga gtg ctg acc ata acc<br>Ala Glu Glu Leu Tyr Gln Lys Arg Val Leu Thr Ile Thr<br>               235                        240 | 1192 |
| ggc atc tgc atc gcc ctc ctt gtg gtc ggc atc atg tgt<br>Gly Ile Cys Ile Ala Leu Leu Val Val Gly Ile Met Cys<br>245                        250                        255 | 1231 |
| gtg gtg gcc tac tgc aaa acc aag aaa cag cgg aaa aag<br>Val Val Ala Tyr Cys Lys Thr Lys Lys Gln Arg Lys Lys<br>               260                        265                        270 | 1270 |
| ctg cat gac cgt ctt cgg cag agc ctt cgg tct gaa cga<br>Leu His Asp Arg Leu Arg Gln Ser Leu Arg Ser Glu Arg<br>                        275                        280 | 1309 |
| aac aat atg atg aac att gcc aat ggg cct cac cat cct<br>Asn Asn Met Met Asn Ile Ala Asn Gly Pro His His Pro<br>285                        290                        295 | 1348 |
| aac cca ccc ccc gag aat gtc cag ctg gtg aat caa tac<br>Asn Pro Pro Pro Glu Asn Val Gln Leu Val Asn Gln Tyr<br>               300                        305 | 1387 |
| gta tct aaa aac gtc atc tcc agt gag cat att gtt gag<br>Val Ser Lys Asn Val Ile Ser Ser Glu His Ile Val Glu<br>310                        315                        320 | 1426 |
| aga gaa gca gag aca tcc ttt tcc acc agt cac tat act<br>Arg Glu Ala Glu Thr Ser Phe Ser Thr Ser His Tyr Thr<br>               325                        330                        335 | 1465 |
| tcc aca gcc cat cac tcc act act gtc acc cag act cct<br>Ser Thr Ala His His Ser Thr Thr Val Thr Gln Thr Pro<br>                        340                        345 | 1504 |
| agc cac agc tgg agc aac gga cac act gaa agc atc ctt<br>Ser His Ser Trp Ser Asn Gly His Thr Glu Ser Ile Leu<br>350                        355                        360 | 1543 |
| tcc gaa agc cac tct gta atc gtg atg tca tcc gta gaa<br>Ser Glu Ser His Ser Val Ile Val Met Ser Ser Val Glu<br>               365                        370 | 1582 |
| aac agt agg cac agc agc cca act ggg ggc cca aga gga<br>Asn Ser Arg His Ser Ser Pro Thr Gly Gly Pro Arg Gly<br>375                        380                        385 | 1621 |
| cgt ctt aat ggc aca gga ggc cct cgt gaa tgt aac agc<br>Arg Leu Asn Gly Thr Gly Gly Pro Arg Glu Cys Asn Ser<br>               390                        395                        400 | 1660 |
| ttc ctc agg cat gcc aga gaa acc cct gat tcc tac cga<br>Phe Leu Arg His Ala Arg Glu Thr Pro Asp Ser Tyr Arg<br>                        405                        410 | 1699 |
| gac tct cct cat agt gaa agg tat gtg tca gcc atg acc<br>Asp Ser Pro His Ser Glu Arg Tyr Val Ser Ala Met Thr<br>415                        420                        425 | 1738 |
| acc ccg gct cgt atg tca cct gta gat ttc cac acg cca<br>Thr Pro Ala Arg Met Ser Pro Val Asp Phe His Thr Pro<br>                        430                        435 | 1777 |
| agc tcc ccc aaa tcg ccc cct tcg gaa atg tct cca ccc<br>Ser Ser Pro Lys Ser Pro Pro Ser Glu Met Ser Pro Pro<br>440                        445                        450 | 1816 |
| gtg tcc agc atg acg gtg tcc aag cct tcc atg gcg gtc<br>Val Ser Ser Met Thr Val Ser Lys Pro Ser Met Ala Val<br>                        455                        460                        465 | 1855 |
| agc ccc ttc atg gaa gaa gag aga cct cta ctt ctc gtg<br>Ser Pro Phe Met Glu Glu Glu Arg Pro Leu Leu Leu Val<br>               470                        475 | 1894 |

-continued

| | | |
|---|---|---|
| aca cca cca agg ctg cgg gag aag aag ttt gac cat cac<br>Thr Pro Pro Arg Leu Arg Glu Lys Lys Phe Asp His His<br>480                        485                    490 | | 1933 |
| cct cag cag ttc agc tcc ttc cac cac aac ccc gcg cat<br>Pro Gln Gln Phe Ser Ser Phe His His Asn Pro Ala His<br>                  495                    500 | | 1972 |
| gac agt aac agc ctc cct gct agc ccc ttg agg ata gtg<br>Asp Ser Asn Ser Leu Pro Ala Ser Pro Leu Arg Ile Val<br>505                        510                    515 | | 2011 |
| gag gat gag gag tat gaa acg acc caa gag tac gag cca<br>Glu Asp Glu Glu Tyr Glu Thr Thr Gln Glu Tyr Glu Pro<br>        520                    525                    530 | | 2050 |
| gcc caa gag cct gtt aag aaa ctc gcc aat agc cgg cgg<br>Ala Gln Glu Pro Val Lys Lys Leu Ala Asn Ser Arg Arg<br>                  535                    540 | | 2089 |
| gcc aaa aga acc aag ccc aat ggc cac att gct aac aga<br>Ala Lys Arg Thr Lys Pro Asn Gly His Ile Ala Asn Arg<br>545                        550                    555 | | 2128 |
| ttg gaa gtg gac agc aac aca agc tcc cag agc agt aac<br>Leu Glu Val Asp Ser Asn Thr Ser Ser Gln Ser Ser Asn<br>        560                    565 | | 2167 |
| tca gag agt gaa aca gaa gat gaa aga gta ggt gaa gat<br>Ser Glu Ser Glu Thr Glu Asp Glu Arg Val Gly Glu Asp<br>570                        575                    580 | | 2206 |
| acg cct ttc ctg ggc ata cag aac ccc ctg gca gcc agt<br>Thr Pro Phe Leu Gly Ile Gln Asn Pro Leu Ala Ala Ser<br>        585                    590                    595 | | 2245 |
| ctt gag gca aca cct gcc ttc cgc ctg gct gac agc agg<br>Leu Glu Ala Thr Pro Ala Phe Arg Leu Ala Asp Ser Arg<br>                  600                    605 | | 2284 |
| act aac cca gca ggc cgc ttc tcg aca cag gaa gaa atc<br>Thr Asn Pro Ala Gly Arg Phe Ser Thr Gln Glu Glu Ile<br>610                        615                    620 | | 2323 |
| cag gcc agg ctg tct agt gta att gct aac caa gac cct<br>Gln Ala Arg Leu Ser Ser Val Ile Ala Asn Gln Asp Pro<br>        625                    630 | | 2362 |
| att gct gta taaaaccta ataaacaca tagattcacc tgtaaactt<br>Ile Ala Val<br>635       637 | | 2410 |
| tattttatat aataaagtat tccaccttaa attaaacaat ttattttatt | | 2460 |
| ttagcagttc tgcaaataaa aaaaaaaaa | | 2490 |

<210> SEQ ID NO 7
<211> LENGTH: 241
<212> TYPE: PRT
<213> ORGANISM: Homo sapiens

<400> SEQUENCE: 7

Met Ser Glu Arg Lys Glu Gly Arg Gly Lys Gly Lys Gly Lys Lys
1               5                    10                    15

Lys Glu Arg Gly Ser Gly Lys Lys Pro Glu Ser Ala Ala Gly Ser
              20                    25                    30

Gln Ser Pro Ala Leu Pro Pro Gln Leu Lys Glu Met Lys Ser Gln
              35                    40                    45

Glu Ser Ala Ala Gly Ser Lys Leu Val Leu Arg Cys Glu Thr Ser
              50                    55                    60

Ser Glu Tyr Ser Ser Leu Arg Phe Lys Trp Phe Lys Asn Gly Asn
              65                    70                    75

```
Glu Leu Asn Arg Lys Asn Lys Pro Gln Asn Ile Lys Ile Gln Lys
                80                  85                  90
Lys Pro Gly Lys Ser Glu Leu Arg Ile Asn Lys Ala Ser Leu Ala
                95                 100                 105
Asp Ser Gly Glu Tyr Met Cys Lys Val Ile Ser Lys Leu Gly Asn
               110                 115                 120
Asp Ser Ala Ser Ala Asn Ile Thr Ile Val Glu Ser Asn Glu Ile
               125                 130                 135
Ile Thr Gly Met Pro Ala Ser Thr Glu Gly Ala Tyr Val Ser Ser
               140                 145                 150
Glu Ser Pro Ile Arg Ile Ser Val Ser Thr Glu Gly Ala Asn Thr
               155                 160                 165
Ser Ser Ser Thr Ser Thr Ser Thr Thr Gly Thr Ser His Leu Val
               170                 175                 180
Lys Cys Ala Glu Lys Glu Lys Thr Phe Cys Val Asn Gly Gly Glu
               185                 190                 195
Cys Phe Met Val Lys Asp Leu Ser Asn Pro Ser Arg Tyr Leu Cys
               200                 205                 210
Lys Cys Pro Asn Glu Phe Thr Gly Asp Arg Cys Gln Asn Tyr Val
               215                 220                 225
Met Ala Ser Phe Tyr Ser Thr Ser Thr Pro Phe Leu Ser Leu Pro
               230                 235                 240
Glu
241

<210> SEQ ID NO 8
<211> LENGTH: 1715
<212> TYPE: DNA
<213> ORGANISM: Homo sapiens

<400> SEQUENCE: 8
gcgcctgcct ccaacctgcg ggcgggaggt gggtggctgc ggggcaattg       50
aaaaagagcc ggcgaggagt tccccgaaac ttgttggaac tccgggctcg      100
cgcggaggcc aggagctgag cggcggcggc tgccggacga tgggagcgtg      150
agcaggacgg tgataacctc tccccgatcg ggttgcgagg gcgccgggca      200
gaggccagga cgcgagccgc cagcggcggg acccatcgac gacttcccgg      250
ggcgacagga gcagccccga gagccagggc gagcgcccgt tccaggtggc      300
cggaccgccc gccgcgtccg cgccgcgctc cctgcaggca acgggagacg      350 ccccgcgca gcgcgagcgc ctcagcgcgg ccgctcgctc tccccatcga      400
gggacaaact tttcccaaac ccgatccgag cccttggacc aaactcgcct      450
gcgccgagag ccgtccgcgt agagcgctcc gtctccggcg ag  atg          495
                                                Met
                                                 1 tcc gag cgc aaa gaa ggc aga ggc aaa ggg aag ggc aag           534
Ser Glu Arg Lys Glu Gly Arg Gly Lys Gly Lys Gly Lys
                5                  10 aag aag gag cga ggc tcc ggc aag aag ccg gag tcc gcg           573
Lys Lys Glu Arg Gly Ser Gly Lys Lys Pro Glu Ser Ala
 15              20                  25 gcg ggc agc cag agc cca gcc ttg cct ccc caa ttg aaa           612
Ala Gly Ser Gln Ser Pro Ala Leu Pro Pro Gln Leu Lys
         30                  35                  40
```

|  |  |
|---|---|
| gag atg aaa agc cag gaa tcg gct gca ggt tcc aaa cta<br>Glu Met Lys Ser Gln Glu Ser Ala Ala Gly Ser Lys Leu<br>                  45                    50 | 651 |
| gtc ctt cgg tgt gaa acc agt tct gaa tac tcc tct ctc<br>Val Leu Arg Cys Glu Thr Ser Ser Glu Tyr Ser Ser Leu<br>55                    60                    65 | 690 |
| aga ttc aag tgg ttc aag aat ggg aat gaa ttg aat cga<br>Arg Phe Lys Trp Phe Lys Asn Gly Asn Glu Leu Asn Arg<br>                  70                    75 | 729 |
| aaa aac aaa cca caa aat atc aag ata caa aaa aag cca<br>Lys Asn Lys Pro Gln Asn Ile Lys Ile Gln Lys Lys Pro<br>80                    85                    90 | 768 |
| ggg aag tca gaa ctt cgc att aac aaa gca tca ctg gct<br>Gly Lys Ser Glu Leu Arg Ile Asn Lys Ala Ser Leu Ala<br>                  95                    100                    105 | 807 |
| gat tct gga gag tat atg tgc aaa gtg atc agc aaa tta<br>Asp Ser Gly Glu Tyr Met Cys Lys Val Ile Ser Lys Leu<br>                  110                    115 | 846 |
| gga aat gac agt gcc tct gcc aat atc acc atc gtg gaa<br>Gly Asn Asp Ser Ala Ser Ala Asn Ile Thr Ile Val Glu<br>120                    125                    130 | 885 |
| tca aac gag atc atc act ggt atg cca gcc tca act gaa<br>Ser Asn Glu Ile Ile Thr Gly Met Pro Ala Ser Thr Glu<br>                  135                    140 | 924 |
| gga gca tat gtg tct tca gag tct ccc att aga ata tca<br>Gly Ala Tyr Val Ser Ser Glu Ser Pro Ile Arg Ile Ser<br>145                    150                    155 | 963 |
| gta tcc aca gaa gga gca aat act tct tca tct aca tct<br>Val Ser Thr Glu Gly Ala Asn Thr Ser Ser Ser Thr Ser<br>                  160                    165                    170 | 1002 |
| aca tcc acc act ggg aca agc cat ctt gta aaa tgt gcg<br>Thr Ser Thr Thr Gly Thr Ser His Leu Val Lys Cys Ala<br>                  175                    180 | 1041 |
| gag aag gag aaa act ttc tgt gtg aat gga ggg gag tgc<br>Glu Lys Glu Lys Thr Phe Cys Val Asn Gly Gly Glu Cys<br>185                    190                    195 | 1080 |
| ttc atg gtg aaa gac ctt tca aac ccc tcg aga tac ttg<br>Phe Met Val Lys Asp Leu Ser Asn Pro Ser Arg Tyr Leu<br>                  200                    205 | 1119 |
| tgc aag tgc cca aat gag ttt act ggt gat cgc tgc caa<br>Cys Lys Cys Pro Asn Glu Phe Thr Gly Asp Arg Cys Gln<br>210                    215                    220 | 1158 |
| aac tac gta atg gcc agc ttc tac agt acg tcc act ccc<br>Asn Tyr Val Met Ala Ser Phe Tyr Ser Thr Ser Thr Pro<br>                  225                    230                    235 | 1197 |
| ttt ctg tct ctg cct gaa tagga gcatgctcag ttggtgctgc<br>Phe Leu Ser Leu Pro Glu<br>                  240 241 | 1240 |
| tttcttgttg ctgcatctcc cctcagattc cacctagagc tagatgtgtc | 1290 |
| ttaccagatc taatattgac tgcctctgcc tgtcgcatga aacattaac | 1340 |
| aaaagcaatt gtattacttc ctctgttcgc gactagttgg ctctgagata | 1390 |
| ctaataggtg tgtgaggctc cggatgtttc tggaattgat attgaatgat | 1440 |
| gtgatacaaa ttgatagtca atatcaagca gtgaaatatg ataataagg | 1490 |
| catttcaaag tctcactttt attgataaaa taaaaatcat tctactgaac | 1540 |
| agtccatctt ctttatacaa tgaccacatc ctgaaagggg tgttgctaag | 1590 |
| ctgtaaccga tatgcacttg aaatgatggt aagttaattt tgattcagaa | 1640 |

```
tgtgttattt gtcacaaata aacataataa aaggagttca gatgtttttc         1690
ttcattaacc aaaaaaaaaa aaaaa                                    1715

<210> SEQ ID NO 9
<211> LENGTH: 420
<212> TYPE: PRT
<213> ORGANISM: Homo sapiens

<400> SEQUENCE: 9

Met Ser Glu Arg Lys Glu Gly Arg Gly Lys Gly Lys Gly Lys Lys
  1               5                  10                  15

Lys Glu Arg Gly Ser Gly Lys Lys Pro Glu Ser Ala Ala Gly Ser
                 20                  25                  30

Gln Ser Pro Ala Leu Pro Pro Gln Leu Lys Glu Met Lys Ser Gln
                 35                  40                  45

Glu Ser Ala Ala Gly Ser Lys Leu Val Leu Arg Cys Glu Thr Ser
                 50                  55                  60

Ser Glu Tyr Ser Ser Leu Arg Phe Lys Trp Phe Lys Asn Gly Asn
                 65                  70                  75

Glu Leu Asn Arg Lys Asn Lys Pro Gln Asn Ile Lys Ile Gln Lys
                 80                  85                  90

Lys Pro Gly Lys Ser Glu Leu Arg Ile Asn Lys Ala Ser Leu Ala
                 95                 100                 105

Asp Ser Gly Glu Tyr Met Cys Lys Val Ile Ser Lys Leu Gly Asn
                110                 115                 120

Asp Ser Ala Ser Ala Asn Ile Thr Ile Val Glu Ser Asn Glu Ile
                125                 130                 135

Ile Thr Gly Met Pro Ala Ser Thr Glu Gly Ala Tyr Val Ser Ser
                140                 145                 150

Glu Ser Pro Ile Arg Ile Ser Val Ser Thr Glu Gly Ala Asn Thr
                155                 160                 165

Ser Ser Ser Thr Ser Thr Ser Thr Thr Gly Thr Ser His Leu Val
                170                 175                 180

Lys Cys Ala Glu Lys Glu Lys Thr Phe Cys Val Asn Gly Gly Glu
                185                 190                 195

Cys Phe Met Val Lys Asp Leu Ser Asn Pro Ser Arg Tyr Leu Cys
                200                 205                 210

Lys Cys Pro Asn Glu Phe Thr Gly Asp Arg Cys Gln Asn Tyr Val
                215                 220                 225

Met Ala Ser Phe Tyr Lys Ala Glu Glu Leu Tyr Gln Lys Arg Val
                230                 235                 240

Leu Thr Ile Thr Gly Ile Cys Ile Ala Leu Leu Val Val Gly Ile
                245                 250                 255

Met Cys Val Val Ala Tyr Cys Lys Thr Lys Lys Gln Arg Lys Lys
                260                 265                 270

Leu His Asp Arg Leu Arg Gln Ser Leu Arg Ser Glu Arg Asn Asn
                275                 280                 285

Met Met Asn Ile Ala Asn Gly Pro His His Pro Asn Pro Pro Pro
                290                 295                 300

Glu Asn Val Gln Leu Val Asn Gln Tyr Val Ser Lys Asn Val Ile
                305                 310                 315

Ser Ser Glu His Ile Val Glu Arg Glu Ala Glu Thr Ser Phe Ser
                320                 325                 330
```

```
Thr Ser His Tyr Thr Ser Thr Ala His His Ser Thr Thr Val Thr
            335                 340                 345

Gln Thr Pro Ser His Ser Trp Ser Asn Gly His Thr Glu Ser Ile
            350                 355                 360

Leu Ser Glu Ser His Ser Val Ile Val Met Ser Val Glu Asn
            365                 370                 375

Ser Arg His Ser Ser Pro Thr Gly Gly Pro Arg Gly Arg Leu Asn
            380                 385                 390

Gly Thr Gly Gly Pro Arg Glu Cys Asn Ser Phe Leu Arg His Ala
            395                 400                 405

Arg Glu Thr Pro Asp Ser Tyr Arg Asp Ser Pro His Ser Glu Arg
            410                 415                 420

<210> SEQ ID NO 10
<211> LENGTH: 2431
<212> TYPE: DNA
<213> ORGANISM: Homo sapiens

<400> SEQUENCE: 10
gaggcgcctg cctccaacct gcgggcggga ggtgggtggc tgcggggcaa         50
ttgaaaaaga gccggcgagg agttccccga aacttgttgg aactccgggc        100
tcgcgcggag gccaggagct gagcggcggc ggctgccgga cgatgggagc        150
gtgagcagga cggtgataac ctctccccga tcgggttgcg agggcgccgg        200
gcagaggcca ggacgcgagc cgccagcggc gggacccatc gacgacttcc        250
cggggcgaca ggagcagccc cgagagccag ggcgagcgcc cgttccaggt        300
ggccggaccg cccgccgcgt ccgcgccgcg ctccctgcag gcaacgggag        350
acgcccccgc gcagcgcgag cgcctcagcg cggccgctcg ctctccccat        400
cgagggacaa acttttccca aacccgatcc gagcccttgg accaaactcg        450
cctgcgccga gagccgtccg cgtagagcgc tccgtctccg gcgag  atg        498
                                                    Met
                                                     1 tcc gag cgc aaa gaa ggc aga ggc aaa ggg aag ggc aag             537
Ser Glu Arg Lys Glu Gly Arg Gly Lys Gly Lys Gly Lys
         5                  10 aag aag gag cga ggc tcc ggc aag aag ccg gag tcc gcg             576
Lys Lys Glu Arg Gly Ser Gly Lys Lys Pro Glu Ser Ala
 15                  20                  25 gcg ggc agc cag agc cca gcc ttg cct ccc caa ttg aaa             615
Ala Gly Ser Gln Ser Pro Ala Leu Pro Pro Gln Leu Lys
         30                  35                  40 gag atg aaa agc cag gaa tcg gct gca ggt tcc aaa cta             654
Glu Met Lys Ser Gln Glu Ser Ala Ala Gly Ser Lys Leu
                 45                  50 gtc ctt cgg tgt gaa acc agt tct gaa tac tcc tct ctc             693
Val Leu Arg Cys Glu Thr Ser Ser Glu Tyr Ser Ser Leu
 55                  60                  65 aga ttc aag tgg ttc aag aat ggg aat gaa ttg aat cga             732
Arg Phe Lys Trp Phe Lys Asn Gly Asn Glu Leu Asn Arg
         70                  75 aaa aac aaa cca caa aat atc aag ata caa aaa aag cca             771
Lys Asn Lys Pro Gln Asn Ile Lys Ile Gln Lys Lys Pro
 80                  85                  90 ggg aag tca gaa ctt cgc att aac aaa gca tca ctg gct             810
Gly Lys Ser Glu Leu Arg Ile Asn Lys Ala Ser Leu Ala
         95                 100                 105
```

-continued

| | |
|---|---|
| gat tct gga gag tat atg tgc aaa gtg atc agc aaa tta<br>Asp Ser Gly Glu Tyr Met Cys Lys Val Ile Ser Lys Leu<br>110                    115 | 849 |
| gga aat gac agt gcc tct gcc aat atc acc atc gtg gaa<br>Gly Asn Asp Ser Ala Ser Ala Asn Ile Thr Ile Val Glu<br>120              125              130 | 888 |
| tca aac gag atc atc act ggt atg cca gcc tca act gaa<br>Ser Asn Glu Ile Ile Thr Gly Met Pro Ala Ser Thr Glu<br>              135              140 | 927 |
| gga gca tat gtg tct tca gag tct ccc att aga ata tca<br>Gly Ala Tyr Val Ser Ser Glu Ser Pro Ile Arg Ile Ser<br>145                 150             155 | 966 |
| gta tcc aca gaa gga gca aat act tct tca tct aca tct<br>Val Ser Thr Glu Gly Ala Asn Thr Ser Ser Ser Thr Ser<br>          160              165              170 | 1005 |
| aca tcc acc act ggg aca agc cat ctt gta aaa tgt gcg<br>Thr Ser Thr Thr Gly Thr Ser His Leu Val Lys Cys Ala<br>              175              180 | 1044 |
| gag aag gag aaa act ttc tgt gtg aat gga ggg gag tgc<br>Glu Lys Glu Lys Thr Phe Cys Val Asn Gly Gly Glu Cys<br>185                 190             195 | 1083 |
| ttc atg gtg aaa gac ctt tca aac ccc tcg aga tac ttg<br>Phe Met Val Lys Asp Leu Ser Asn Pro Ser Arg Tyr Leu<br>          200              205 | 1122 |
| tgc aag tgt cca aat gag ttt act ggt gat cgc tgc caa<br>Cys Lys Cys Pro Asn Glu Phe Thr Gly Asp Arg Cys Gln<br>210                 215             220 | 1161 |
| aac tac gta atg gcc agc ttc tac aag gcg gag gag ctg<br>Asn Tyr Val Met Ala Ser Phe Tyr Lys Ala Glu Glu Leu<br>          225              230              235 | 1200 |
| tac cag aag aga gtg ctg acc ata acc ggc atc tgc atc<br>Tyr Gln Lys Arg Val Leu Thr Ile Thr Gly Ile Cys Ile<br>              240              245 | 1239 |
| gcc ctc ctt gtg gtc ggc atc atg tgt gtg gtg gcc tac<br>Ala Leu Leu Val Val Gly Ile Met Cys Val Val Ala Tyr<br>250                 255             260 | 1278 |
| tgc aaa acc aag aaa cag cgg aaa aag ctg cat gac cgt<br>Cys Lys Thr Lys Lys Gln Arg Lys Lys Leu His Asp Arg<br>          265              270 | 1317 |
| ctt cgg cag agc ctt cgg tct gaa cga aac aat atg atg<br>Leu Arg Gln Ser Leu Arg Ser Glu Arg Asn Asn Met Met<br>275                 280             285 | 1356 |
| aac att gcc aat ggg cct cac cat cct aac cca ccc ccc<br>Asn Ile Ala Asn Gly Pro His His Pro Asn Pro Pro Pro<br>          290              295              300 | 1395 |
| gag aat gtc cag ctg gtg aat caa tac gta tct aaa aac<br>Glu Asn Val Gln Leu Val Asn Gln Tyr Val Ser Lys Asn<br>              305              310 | 1434 |
| gtc atc tcc agt gag cat att gtt gag aga gaa gca gag<br>Val Ile Ser Ser Glu His Ile Val Glu Arg Glu Ala Glu<br>315                 320             325 | 1473 |
| aca tcc ttt tcc acc agt cac tat act tcc aca gcc cat<br>Thr Ser Phe Ser Thr Ser His Tyr Thr Ser Thr Ala His<br>          330              335 | 1512 |
| cac tcc act act gtc acc cag act cct agc cac agc tgg<br>His Ser Thr Thr Val Thr Gln Thr Pro Ser His Ser Trp<br>340                 345             350 | 1551 |
| agc aac gga cac act gaa agc atc ctt tcc gaa agc cac<br>Ser Asn Gly His Thr Glu Ser Ile Leu Ser Glu Ser His<br>          355              360              365 | 1590 |

-continued

| | | |
|---|---|---|
| tct gta atc gtg atg tca tcc gta gaa aac agt agg cac<br>Ser Val Ile Val Met Ser Ser Val Glu Asn Ser Arg His<br>                        370                      375 | | 1629 |
| agc agc cca act ggg ggc cca aga gga cgt ctt aat ggc<br>Ser Ser Pro Thr Gly Gly Pro Arg Gly Arg Leu Asn Gly<br>   380                        385                      390 | | 1668 |
| aca gga ggc cct cgt gaa tgt aac agc ttc ctc agg cat<br>Thr Gly Gly Pro Arg Glu Cys Asn Ser Phe Leu Arg His<br>                      395                      400 | | 1707 |
| gcc aga gaa acc cct gat tcc tac cga gac tct cct cat<br>Ala Arg Glu Thr Pro Asp Ser Tyr Arg Asp Ser Pro His<br>405                        410                      415 | | 1746 |
| agt gaa agg taaaa ccgaaggcaa agctactgca gaggagaaac<br>Ser Glu Arg<br>         420 | | 1790 |
| tcagtcagag aatccctgtg agcacctgcg gtctcacctc aggaaatcta | | 1840 |
| ctctaatcag aataaggggc ggcagttacc tgttctagga gtgctcctag | | 1890 |
| ttgatgaagt catctctttg tttgacggaa cttatttctt ctgagcttct | | 1940 |
| ctcgtcgtcc cagtgactga caggcaacag actcttaaag agctgggatg | | 1990 |
| ctttgatgcg gaaggtgcag cacatggagt ttccagctct ggccatgggc | | 2040 |
| tcagacccac tcgggtctc agtgtcctca gttgtaacat tagagagatg | | 2090 |
| gcatcaatgc ttgataagga cccttctata attccaattg ccagttatcc | | 2140 |
| aaactctgat tcggtggtcg agctggcctc gtgttcttat ctgctaaccc | | 2190 |
| tgtcttacct tccagcctca gttaagtcaa atcaagggct atgtcattgc | | 2240 |
| tgaatgtcat gggggcaac tgcttgccct ccaccctata gtatctattt | | 2290 |
| tatgaaattc caagaaggga tgaataaata aatctcttgg atgctgcgtc | | 2340 |
| tggcagtctt cacgggtggt tttcaaagca gaaaaaaaaa aaaaaaaaa | | 2390 |
| aaaaaaaaaa aaaaaaaaaa aaaaaaaaaa aaaaaaaaa a | | 2431 |

<210> SEQ ID NO 11
<211> LENGTH: 768
<212> TYPE: PRT
<213> ORGANISM: Homo sapiens

<400> SEQUENCE: 11

Met Asp Val Lys Glu Arg Lys Pro Tyr Arg Ser Leu Thr Arg Arg
  1               5                  10                  15

Arg Asp Ala Glu Arg Arg Tyr Thr Ser Ser Ala Asp Ser Glu
                 20                  25                  30

Glu Gly Lys Ala Pro Gln Lys Ser Tyr Ser Ser Glu Thr Leu
                 35                  40                  45

Lys Ala Tyr Asp Gln Asp Ala Arg Leu Ala Tyr Gly Ser Arg Val
                 50                  55                  60

Lys Asp Ile Val Pro Gln Glu Ala Glu Phe Cys Arg Thr Gly
                 65                  70                  75

Ala Asn Phe Thr Leu Arg Glu Leu Gly Leu Glu Glu Val Thr Pro
                 80                  85                  90

Pro His Gly Thr Leu Tyr Arg Thr Asp Ile Gly Leu Pro His Cys
                 95                 100                 105

Gly Tyr Ser Met Gly Ala Gly Ser Asp Ala Asp Met Glu Ala Asp
                110                 115                 120

-continued

```
Thr Val Leu Ser Pro Glu His Pro Val Arg Leu Trp Gly Arg Ser
            125                 130                 135

Thr Arg Ser Gly Arg Ser Ser Cys Leu Ser Ser Arg Ala Asn Ser
            140                 145                 150

Asn Leu Thr Leu Thr Asp Thr Glu His Glu Asn Thr Glu Thr Asp
            155                 160                 165

His Pro Gly Gly Leu Gln Asn His Ala Arg Leu Arg Thr Pro Pro
            170                 175                 180

Pro Pro Leu Ser His Ala His Thr Pro Asn Gln His His Ala Ala
            185                 190                 195

Ser Ile Asn Ser Leu Asn Arg Gly Asn Phe Thr Pro Arg Ser Asn
            200                 205                 210

Pro Ser Pro Ala Pro Thr Asp His Ser Leu Ser Gly Glu Pro Pro
            215                 220                 225

Ala Gly Gly Ala Gln Glu Pro Ala His Ala Gln Glu Asn Trp Leu
            230                 235                 240

Leu Asn Ser Asn Ile Pro Leu Glu Thr Arg Asn Leu Gly Lys Gln
            245                 250                 255

Pro Phe Leu Gly Thr Leu Gln Asp Asn Leu Ile Glu Met Asp Ile
            260                 265                 270

Leu Gly Ala Ser Arg His Asp Gly Ala Tyr Ser Asp Gly His Phe
            275                 280                 285

Leu Phe Lys Pro Gly Gly Thr Ser Pro Leu Phe Cys Thr Thr Ser
            290                 295                 300

Pro Gly Tyr Pro Leu Thr Ser Ser Thr Val Tyr Ser Pro Pro Pro
            305                 310                 315

Arg Pro Leu Pro Arg Ser Thr Phe Ala Arg Pro Ala Phe Asn Leu
            320                 325                 330

Lys Lys Pro Ser Lys Tyr Cys Asn Trp Lys Cys Ala Ala Leu Ser
            335                 340                 345

Ala Ile Val Ile Ser Ala Thr Leu Val Ile Leu Ala Tyr Phe
            350                 355                 360

Val Ala Met His Leu Phe Gly Leu Asn Trp His Leu Gln Pro Met
            365                 370                 375

Glu Gly Gln Met Tyr Glu Ile Thr Glu Asp Thr Ala Ser Ser Trp
            380                 385                 390

Pro Val Pro Thr Asp Val Ser Leu Tyr Pro Ser Gly Gly Thr Gly
            395                 400                 405

Leu Glu Thr Pro Asp Arg Lys Gly Lys Gly Thr Thr Glu Gly Lys
            410                 415                 420

Pro Ser Ser Phe Phe Pro Glu Asp Ser Phe Ile Asp Ser Gly Glu
            425                 430                 435

Ile Asp Val Gly Arg Arg Ala Ser Gln Lys Ile Pro Pro Gly Thr
            440                 445                 450

Phe Trp Arg Ser Gln Val Phe Ile Asp His Pro Val His Leu Lys
            455                 460                 465

Phe Asn Val Ser Leu Gly Lys Ala Ala Leu Val Gly Ile Tyr Gly
            470                 475                 480

Arg Lys Gly Leu Pro Pro Ser His Thr Gln Phe Asp Phe Val Glu
            485                 490                 495

Leu Leu Asp Gly Arg Arg Leu Leu Thr Gln Glu Ala Arg Ser Leu
            500                 505                 510
```

-continued

```
Glu Gly Thr Pro Arg Gln Ser Arg Gly Thr Val Pro Pro Ser Ser
            515                 520                 525

His Glu Thr Gly Phe Ile Gln Tyr Leu Asp Ser Gly Ile Trp His
            530                 535                 540

Leu Ala Phe Tyr Asn Asp Gly Lys Glu Ser Glu Val Val Ser Phe
            545                 550                 555

Leu Thr Thr Ala Ile Ala Leu Pro Pro Arg Leu Lys Glu Met Lys
            560                 565                 570

Ser Gln Glu Ser Ala Ala Gly Ser Lys Leu Val Leu Arg Cys Glu
            575                 580                 585

Thr Ser Ser Glu Tyr Ser Ser Leu Arg Phe Lys Trp Phe Lys Asn
            590                 595                 600

Gly Asn Glu Leu Asn Arg Lys Asn Lys Pro Gln Asn Ile Lys Ile
            605                 610                 615

Gln Lys Lys Pro Gly Lys Ser Glu Leu Arg Ile Asn Lys Ala Ser
            620                 625                 630

Leu Ala Asp Ser Gly Glu Tyr Met Cys Lys Val Ile Ser Lys Leu
            635                 640                 645

Gly Asn Asp Ser Ala Ser Ala Asn Ile Thr Ile Val Glu Ser Asn
            650                 655                 660

Glu Ile Ile Thr Gly Met Pro Ala Ser Thr Glu Gly Ala Tyr Val
            665                 670                 675

Ser Ser Glu Ser Pro Ile Arg Ile Ser Val Ser Thr Glu Gly Ala
            680                 685                 690

Asn Thr Ser Ser Ser Thr Ser Thr Ser Thr Thr Gly Thr Ser His
            695                 700                 705

Leu Val Lys Cys Ala Glu Lys Glu Lys Thr Phe Cys Val Asn Gly
            710                 715                 720

Gly Glu Cys Phe Met Val Lys Asp Leu Ser Asn Pro Ser Arg Tyr
            725                 730                 735

Leu Cys Lys Cys Pro Asn Glu Phe Thr Gly Asp Arg Cys Gln Asn
            740                 745                 750

Tyr Val Met Ala Ser Phe Tyr Ser Thr Ser Thr Pro Phe Leu Ser
            755                 760                 765

Leu Pro Glu
       768

<210> SEQ ID NO 12
<211> LENGTH: 3111
<212> TYPE: DNA
<213> ORGANISM: Homo sapiens

<400> SEQUENCE: 12
gggtaccatg ggtcggtgag cgcgtttccc gcctgagcgc aactagcggc              50
gggtcgtggg cacctccaga aaagatcccg caccatcctc caggatccaa             100
tggccttgga gagggctg cagggcccac ggacattgct gactcttcag               150
aacgtgctga catggagcca ggtagactga aattatcatg tgtccaaatt             200
aaaattgcat acttcaagga ttatttgaag gactattctt agacccttt              250 aagaagattt aaagaaaaac cactcggccc tgagtgcggc gaggacccctg            300 tttgtggatg tggaggagcg cgggccggag gcc    atg gac gtg              342
                                        Met Asp Val
                                          1
```

```
aag gag agg aag cct tac cgc tcg ctg acc cgg cgc cgc                          381
Lys Glu Arg Lys Pro Tyr Arg Ser Leu Thr Arg Arg Arg
  5              10                  15 gac gcc gag cgc cgc tac acc agc tcg tcc gcg gac agc                          420
Asp Ala Glu Arg Arg Tyr Thr Ser Ser Ser Ala Asp Ser
         20                  25 gag gag ggc aaa gcc ccg cag aaa tcg tac agc tcc agc                          459
Glu Glu Gly Lys Ala Pro Gln Lys Ser Tyr Ser Ser Ser
 30              35                  40 gag acc ctg aag gcc tac gac cag gac gcc cgc cta gcc                          498
Glu Thr Leu Lys Ala Tyr Asp Gln Asp Ala Arg Leu Ala
             45                  50                  55 tat ggc agc cgc gtc aag gac att gtg ccg cag gag gcc                          537
Tyr Gly Ser Arg Val Lys Asp Ile Val Pro Gln Glu Ala
                 60                  65 gag gaa ttc tgc cgc aca ggt gcc aac ttc acc ctg cgg                          576
Glu Glu Phe Cys Arg Thr Gly Ala Asn Phe Thr Leu Arg
 70                  75                  80 gag ctg ggg ctg gaa gaa gta acg ccc cct cac ggg acc                          615
Glu Leu Gly Leu Glu Glu Val Thr Pro Pro His Gly Thr
             85                  90 ctg tac cgg aca gac att ggc ctc ccc cac tgc ggc tac                          654
Leu Tyr Arg Thr Asp Ile Gly Leu Pro His Cys Gly Tyr
 95                 100                 105 tcc atg ggg gct ggc tct gat gcc gac atg gag gct gac                          693
Ser Met Gly Ala Gly Ser Asp Ala Asp Met Glu Ala Asp
             110                 115                 120 acg gtg ctg tcc cct gag cac ccc gtg cgt ctg tgg ggc                          732
Thr Val Leu Ser Pro Glu His Pro Val Arg Leu Trp Gly
                 125                 130 cgg agc aca cgg tca ggg cgc agc tcc tgc ctg tcc agc                          771
Arg Ser Thr Arg Ser Gly Arg Ser Ser Cys Leu Ser Ser
 135                 140                 145 cgg gcc aat tcc aat ctc aca ctc acc gac acc gag cat                          810
Arg Ala Asn Ser Asn Leu Thr Leu Thr Asp Thr Glu His
             150                 155 gaa aac act gag act gat cat ccg ggc ggc ctg cag aac                          849
Glu Asn Thr Glu Thr Asp His Pro Gly Gly Leu Gln Asn
160                 165                 170 cac gcg cgg ctc cgg acg ccg ccg ccg ctc tcg cac                              888
His Ala Arg Leu Arg Thr Pro Pro Pro Leu Ser His
         175                 180                 185 gcc cac acc ccc aac cag cac cac gcg gcc tcc att aac                          927
Ala His Thr Pro Asn Gln His His Ala Ala Ser Ile Asn
             190                 195 tcc ctg aac cgg ggc aac ttc acg ccg agg agc aac ccc                          966
Ser Leu Asn Arg Gly Asn Phe Thr Pro Arg Ser Asn Pro
200                 205                 210 agc ccg gcc ccc acg gac cac tcg ctc tcc gga gag ccc                         1005
Ser Pro Ala Pro Thr Asp His Ser Leu Ser Gly Glu Pro
             215                 220 cct gcc ggc ggc gcc cag gag cct gcc cac gcc cag gag                         1044
Pro Ala Gly Gly Ala Gln Glu Pro Ala His Ala Gln Glu
225                 230                 235 aac tgg ctg ctc aac agc aac atc ccc ctg gag acc aga                         1083
Asn Trp Leu Leu Asn Ser Asn Ile Pro Leu Glu Thr Arg
             240                 245                 250 aac cta ggc aag cag cca ttc cta ggg aca ttg cag gac                         1122
Asn Leu Gly Lys Gln Pro Phe Leu Gly Thr Leu Gln Asp
                 255                 260
```

-continued

| | | | | | | | | | | |
|---|---|---|---|---|---|---|---|---|---|---|
| aac | ctc | att | gag | atg | gac | att | ctc | ggc | gcc | tcc | cgc | cat | 1161 |
| Asn | Leu | Ile | Glu | Met | Asp | Ile | Leu | Gly | Ala | Ser | Arg | His | |
| 265 | | | | 270 | | | | | 275 | | | | |

```
aac ctc att gag atg gac att ctc ggc gcc tcc cgc cat      1161
Asn Leu Ile Glu Met Asp Ile Leu Gly Ala Ser Arg His
265             270                 275 gat ggg gct tac agt gac ggg cac ttc ctc ttc aag cct      1200
Asp Gly Ala Tyr Ser Asp Gly His Phe Leu Phe Lys Pro
        280                 285 gga ggc acc tcc ccg ctc ttc tgc acc aca tca cca ggg      1239
Gly Gly Thr Ser Pro Leu Phe Cys Thr Thr Ser Pro Gly
290             295                 300 tac cca ctg acg tcc agc aca gtg tac tct cct ccg ccc      1278
Tyr Pro Leu Thr Ser Ser Thr Val Tyr Ser Pro Pro Pro
        305                 310                 315 cga ccc ctg ccc cgc agc acc ttc gcc cgg ccg gcc ttt      1317
Arg Pro Leu Pro Arg Ser Thr Phe Ala Arg Pro Ala Phe
            320                 325 aac ctc aag aag ccc tcc aag tac tgt aac tgg aag tgc      1356
Asn Leu Lys Lys Pro Ser Lys Tyr Cys Asn Trp Lys Cys
330             335                 340 gca gcc ctg agc gcc atc gtc atc tca gcc act ctg gtc      1395
Ala Ala Leu Ser Ala Ile Val Ile Ser Ala Thr Leu Val
            345                 350 atc ctg ctg gca tac ttt gtg gcc atg cac ctg ttt ggc      1434
Ile Leu Leu Ala Tyr Phe Val Ala Met His Leu Phe Gly
355             360                 365 cta aac tgg cac ctg cag ccg atg gag ggg cag atg tat      1473
Leu Asn Trp His Leu Gln Pro Met Glu Gly Gln Met Tyr
        370                 375                 380 gag atc acg gag gac aca gcc agc agt tgg cct gtg cca      1512
Glu Ile Thr Glu Asp Thr Ala Ser Ser Trp Pro Val Pro
            385                 390 acc gac gtc tcc cta tac ccc tca ggg ggc act ggc tta      1551
Thr Asp Val Ser Leu Tyr Pro Ser Gly Gly Thr Gly Leu
395             400                 405 gag acc cct gac agg aaa ggc aaa gga acc aca gaa gga      1590
Glu Thr Pro Asp Arg Lys Gly Lys Gly Thr Thr Glu Gly
        410                 415 aag ccc agt agt ttc ttt cca gag gac agt ttc ata gat      1629
Lys Pro Ser Ser Phe Phe Pro Glu Asp Ser Phe Ile Asp
420             425                 430 tct gga gaa att gat gtg gga agg cga gct tcc cag aag      1668
Ser Gly Glu Ile Asp Val Gly Arg Arg Ala Ser Gln Lys
            435                 440                 445 att cct cct ggc act ttc tgg aga tct caa gtg ttc ata      1707
Ile Pro Pro Gly Thr Phe Trp Arg Ser Gln Val Phe Ile
                450                 455 gac cat cct gtg cat ctg aaa ttc aat gtg tct ctg gga      1746
Asp His Pro Val His Leu Lys Phe Asn Val Ser Leu Gly
460             465                 470 aag gca gcc ctg gtt ggc att tat ggc aga aaa ggc ctc      1785
Lys Ala Ala Leu Val Gly Ile Tyr Gly Arg Lys Gly Leu
        475                 480 cct cct tca cat aca cag ttt gac ttt gtg gag ctg ctg      1824
Pro Pro Ser His Thr Gln Phe Asp Phe Val Glu Leu Leu
485             490                 495 gat ggc agg agg ctc cta acc cag gag gcg cgg agc cta      1863
Asp Gly Arg Arg Leu Leu Thr Gln Glu Ala Arg Ser Leu
        500                 505                 510 gag ggg acc ccg cgc cag tct cgg gga act gtg ccc ccc      1902
Glu Gly Thr Pro Arg Gln Ser Arg Gly Thr Val Pro Pro
            515                 520
```

|     |     |
| --- | --- |
| tcc agc cat gag aca ggc ttc atc cag tat ttg gat tca<br>Ser Ser His Glu Thr Gly Phe Ile Gln Tyr Leu Asp Ser<br>525                        530                   535 | 1941 |
| gga atc tgg cac ttg gct ttt tac aat gac gga aag gag<br>Gly Ile Trp His Leu Ala Phe Tyr Asn Asp Gly Lys Glu<br>             540                   545 | 1980 |
| tca gaa gtg gtt tcc ttt ctc acc act gcc att gcc ttg<br>Ser Glu Val Val Ser Phe Leu Thr Thr Ala Ile Ala Leu<br>550                        555                   560 | 2019 |
| cct ccc cga ttg aaa gag atg aaa agc cag gaa tcg gct<br>Pro Pro Arg Leu Lys Glu Met Lys Ser Gln Glu Ser Ala<br>             565                   570                   575 | 2058 |
| gca ggt tcc aaa cta gtc ctt cgg tgt gaa acc agt tct<br>Ala Gly Ser Lys Leu Val Leu Arg Cys Glu Thr Ser Ser<br>                      580                   585 | 2097 |
| gaa tac tcc tct ctc aga ttc aag tgg ttc aag aat ggg<br>Glu Tyr Ser Ser Leu Arg Phe Lys Trp Phe Lys Asn Gly<br>590                        595                   600 | 2136 |
| aat gaa ttg aat cga aaa aac aaa cca caa aat atc aag<br>Asn Glu Leu Asn Arg Lys Asn Lys Pro Gln Asn Ile Lys<br>             605                   610 | 2175 |
| ata caa aaa aag cca ggg aag tca gaa ctt cgc att aac<br>Ile Gln Lys Lys Pro Gly Lys Ser Glu Leu Arg Ile Asn<br>615                        620                   625 | 2214 |
| aaa gca tca ctg gct gat tct gga gag tat atg tgc aaa<br>Lys Ala Ser Leu Ala Asp Ser Gly Glu Tyr Met Cys Lys<br>                      630                   635                   640 | 2253 |
| gtg atc agc aaa tta gga aat gac agt gcc tct gcc aat<br>Val Ile Ser Lys Leu Gly Asn Asp Ser Ala Ser Ala Asn<br>             645                   650 | 2292 |
| atc acc atc gtg gaa tca aac gag atc atc act ggt atg<br>Ile Thr Ile Val Glu Ser Asn Glu Ile Ile Thr Gly Met<br>655                        660                   665 | 2331 |
| cca gcc tca act gaa gga gca tat gtg tct tca gag tct<br>Pro Ala Ser Thr Glu Gly Ala Tyr Val Ser Ser Glu Ser<br>                      670                   675 | 2370 |
| ccc att aga ata tca gta tcc aca gaa gga gca aat act<br>Pro Ile Arg Ile Ser Val Ser Thr Glu Gly Ala Asn Thr<br>680                        685                   690 | 2409 |
| tct tca tct aca tct aca tcc acc act ggg aca agc cat<br>Ser Ser Ser Thr Ser Thr Ser Thr Thr Gly Thr Ser His<br>             695                   700                   705 | 2448 |
| ctt gta aaa tgt gcg gag aag gag aaa act ttc tgt gtg<br>Leu Val Lys Cys Ala Glu Lys Glu Lys Thr Phe Cys Val<br>                      710                   715 | 2487 |
| aat gga ggg gag tgc ttc atg gtg aaa gac ctt tca aac<br>Asn Gly Gly Glu Cys Phe Met Val Lys Asp Leu Ser Asn<br>720                        725                   730 | 2526 |
| ccc tcg aga tac ttg tgc aag tgc cca aat gag ttt act<br>Pro Ser Arg Tyr Leu Cys Lys Cys Pro Asn Glu Phe Thr<br>             735                   740 | 2565 |
| ggt gat cgc tgc caa aac tac gta atg gcc agc ttc tac<br>Gly Asp Arg Cys Gln Asn Tyr Val Met Ala Ser Phe Tyr<br>745                        750                   755 | 2604 |
| agt acg tcc act ccc ttt ctg tct ctg cct gaa tag<br>Ser Thr Ser Thr Pro Phe Leu Ser Leu Pro Glu<br>             760                   765           768 | 2640 |
| gagcatgctc agttggtgct gctttcttgt tgctgcatct cccctcagat | 2690 |
| tccacctaga gctagatgtg tcttaccaga tctaatattg actgcctctg | 2740 |

-continued

| | |
|---|---|
| cctgtcgcat gagaacatta acaaaagcaa ttgtattact tcctctgttc | 2790 |
| gcgactagtt ggctctgaga tactaatagg tgtgtgaggc tccggatgtt | 2840 |
| tctggaattg atattgaatg atgtgataca aattgatagt caatatcaag | 2890 |
| cagtgaaata tgataataaa ggcatttcaa agtctcactt ttattgataa | 2940 |
| aataaaaatc attctactga acagtccatc ttctttatac aatgaccaca | 2990 |
| tcctgaaaag ggtgttgcta agctgtaacc gatatgcact tgaaatgatg | 3040 |
| gtaagttaat tttgattcag aatgtgttat ttgtcacaaa taaacataat | 3090 |
| aaaaggaaaa aaaaaaaaaa a | 3111 |

<210> SEQ ID NO 13
<211> LENGTH: 1872
<212> TYPE: DNA
<213> ORGANISM: Homo sapiens

<400> SEQUENCE: 13

| | |
|---|---|
| gaattcggga cagcctctcc tgccgccgct gctgctgccg ccgccgccac | 50 |
| cgccggctgg tcctccttct gcttttactt ctcctgcatg acagttgttt | 100 |
| tcttcatctg agcagacacc agcttcagat gctcgaggtg agaaacatgc | 150 |
| ctttcagttt gggctactgg tttacttaat taatcagccg gcagctccgt | 200 |
| cgatctattt tcgtccctgt cctcttgacg agcccgggat ggtttggagt | 250 |
| agcatttaaa agaactagaa aagtggccca gaaacagcag cttaaagaat | 300 |
| tattacgata tactttgatt ttgtagttgc taggagcttt tcttcccccc | 350 |
| ttgcatcttt ctgaactctt cttgatttta ataatggcct tggacttgga | 400 |
| cgatttatcg atttcccct gtaagatgct gtatcatttg gttgggggg | 450 |
| cctctgcgtg gtaatggacc gtgagagcgg ccaggccttc ttctggaggt | 500 |

| | | |
|---|---|---|
| gagccg atg gag att tat tcc cca gac atg tct gag gtc<br>Met Glu Ile Tyr Ser Pro Asp Met Ser Glu Val<br>1 5 10 | | 539 |
| gcc gcc gag agg tcc tcc agc ccc tcc act cag ctg agt<br>Ala Ala Glu Arg Ser Ser Ser Pro Ser Thr Gln Leu Ser<br>15 20 | | 578 |
| gca gac cca tct ctt gat ggg ctt ccg gca gca gaa gac<br>Ala Asp Pro Ser Leu Asp Gly Leu Pro Ala Ala Glu Asp<br>25 30 35 | | 617 |
| atg cca gag ccc cag act gaa gat ggg aga acc cct gga<br>Met Pro Glu Pro Gln Thr Glu Asp Gly Arg Thr Pro Gly<br>40 45 50 | | 656 |
| ctc gtg ggc ctg gcc gtg ccc tgc tgt gcg tgc cta gaa<br>Leu Val Gly Leu Ala Val Pro Cys Cys Ala Cys Leu Glu<br>55 60 | | 695 |
| gct gag cgc ctg aga ggt tgc ctc aac tca gag aaa atc<br>Ala Glu Arg Leu Arg Gly Cys Leu Asn Ser Glu Lys Ile<br>65 70 75 | | 734 |
| tgc att gtc ccc atc ctg gct tgc ctg gtc agc ctc tgc<br>Cys Ile Val Pro Ile Leu Ala Cys Leu Val Ser Leu Cys<br>80 85 | | 773 |
| ctc tgc atc gcc ggc ctc aag tgg gta ttt gtg gac aag<br>Leu Cys Ile Ala Gly Leu Lys Trp Val Phe Val Asp Lys<br>90 95 100 | | 812 |
| atc ttt gaa tat gac tct cct act cac ctt gac cct ggg<br>Ile Phe Glu Tyr Asp Ser Pro Thr His Leu Asp Pro Gly<br>105 110 115 | | 851 |

| | |
|---|---|
| ggg tta ggc cag gac cct att att tct ctg gac gca act<br>Gly Leu Gly Gln Asp Pro Ile Ile Ser Leu Asp Ala Thr<br>120                        125 | 890 |
| gct gcc tca gct gtg tgg gtg tcg tct gag gca tac act<br>Ala Ala Ser Ala Val Trp Val Ser Ser Glu Ala Tyr Thr<br>130                        135                       140 | 929 |
| tca cct gtc tct agg gct caa tct gaa agt gag gtt caa<br>Ser Pro Val Ser Arg Ala Gln Ser Glu Ser Glu Val Gln<br>                145                       150 | 968 |
| gtt aca gtg caa ggt gac aag gct gtt gtc tcc ttt gaa<br>Val Thr Val Gln Gly Asp Lys Ala Val Val Ser Phe Glu<br>155                        160                       165 | 1007 |
| cca tca gcg gca ccg aca ccg aag aat cgt att ttt gcc<br>Pro Ser Ala Ala Pro Thr Pro Lys Asn Arg Ile Phe Ala<br>                170                       175                       180 | 1046 |
| ttt tct ttc ttg ccg tcc act gcg cca tcc ttc cct tca<br>Phe Ser Phe Leu Pro Ser Thr Ala Pro Ser Phe Pro Ser<br>                       185                       190 | 1085 |
| ccc acc cgg aac cct gag gtg aga acg ccc aag tca gca<br>Pro Thr Arg Asn Pro Glu Val Arg Thr Pro Lys Ser Ala<br>                195                       200                       205 | 1124 |
| act cag cca caa aca aca gaa act aat ctc caa act gct<br>Thr Gln Pro Gln Thr Thr Glu Thr Asn Leu Gln Thr Ala<br>                       210                       215 | 1163 |
| cct aaa ctt tct aca tct aca tcc acc act ggg aca agc<br>Pro Lys Leu Ser Thr Ser Thr Ser Thr Thr Gly Thr Ser<br>220                        225                       230 | 1202 |
| cat ctt gta aaa tgt gcg gag aag gag aaa act ttc tgt<br>His Leu Val Lys Cys Ala Glu Lys Glu Lys Thr Phe Cys<br>                235                       240                       245 | 1241 |
| gtg aat gga ggg gag tgc ttc atg gtg aaa gac ctt tca<br>Val Asn Gly Gly Glu Cys Phe Met Val Lys Asp Leu Ser<br>                       250                       255 | 1280 |
| aac ccc tcg aga tac ttg tgc aag tgc cca aat gag ttt<br>Asn Pro Ser Arg Tyr Leu Cys Lys Cys Pro Asn Glu Phe<br>260                        265                       270 | 1319 |
| act ggt gat cgc tgc caa aac tac gta atg gcc agc ttc<br>Thr Gly Asp Arg Cys Gln Asn Tyr Val Met Ala Ser Phe<br>                275                       280 | 1358 |
| tac agt acg tcc act ccc ttt ctg tct ctg cct gaa taggag<br>Tyr Ser Thr Ser Thr Pro Phe Leu Ser Leu Pro Glu<br>285                        290                       295 296 | 1400 |
| catgctcagt tggtgctgct ttcttgttgc tgcatctccc ctcagattcc | 1450 |
| acctagagct agatgtgtct taccagatct aatattgact gcctctgcct | 1500 |
| gtcgcatgag aacattaaca aaagcaattg tattacttcc tctgttcgcg | 1550 |
| actagttggc tctgagatac taataggtgt gtgaggctcc ggatgtttct | 1600 |
| ggaattgata ttgaatgatg tgatacaaat tgatagtcaa tatcaagcag | 1650 |
| tgaaatatga taataaaggc atttcaaagt ctcactttta ttgataaaat | 1700 |
| aaaaatcatt ctactgaaca gtccatcttc tttatacaat gaccacatcc | 1750 |
| tgaaagggt gttgctaagc tgtaaccgat atgcacttga aatgatggta | 1800 |
| agttaatttt gattcagaat gtgttatttg tcacaaataa acataataaa | 1850 |
| aggaaaaaaa aaacccgaat tc | 1872 |

```
<210> SEQ ID NO 14
<211> LENGTH: 296
<212> TYPE: PRT
<213> ORGANISM: Homo sapiens

<400> SEQUENCE: 14

Met Glu Ile Tyr Ser Pro Asp Met Ser Glu Val Ala Ala Glu Arg
 1               5                  10                  15

Ser Ser Ser Pro Ser Thr Gln Leu Ser Ala Asp Pro Ser Leu Asp
                20                  25                  30

Gly Leu Pro Ala Ala Glu Asp Met Pro Glu Pro Gln Thr Glu Asp
                35                  40                  45

Gly Arg Thr Pro Gly Leu Val Gly Leu Ala Val Pro Cys Cys Ala
                50                  55                  60

Cys Leu Glu Ala Glu Arg Leu Arg Gly Cys Leu Asn Ser Glu Lys
                65                  70                  75

Ile Cys Ile Val Pro Ile Leu Ala Cys Leu Val Ser Leu Cys Leu
                80                  85                  90

Cys Ile Ala Gly Leu Lys Trp Val Phe Val Asp Lys Ile Phe Glu
                95                 100                 105

Tyr Asp Ser Pro Thr His Leu Asp Pro Gly Gly Leu Gly Gln Asp
               110                 115                 120

Pro Ile Ile Ser Leu Asp Ala Thr Ala Ala Ser Ala Val Trp Val
               125                 130                 135

Ser Ser Glu Ala Tyr Thr Ser Pro Val Ser Arg Ala Gln Ser Glu
               140                 145                 150

Ser Glu Val Gln Val Thr Val Gln Gly Asp Lys Ala Val Val Ser
               155                 160                 165

Phe Glu Pro Ser Ala Ala Pro Thr Pro Lys Asn Arg Ile Phe Ala
               170                 175                 180

Phe Ser Phe Leu Pro Ser Thr Ala Pro Ser Phe Pro Ser Pro Thr
               185                 190                 195

Arg Asn Pro Glu Val Arg Thr Pro Lys Ser Ala Thr Gln Pro Gln
               200                 205                 210

Thr Thr Glu Thr Asn Leu Gln Thr Ala Pro Lys Leu Ser Thr Ser
               215                 220                 225

Thr Ser Thr Thr Gly Thr Ser His Leu Val Lys Cys Ala Glu Lys
               230                 235                 240

Glu Lys Thr Phe Cys Val Asn Gly Gly Glu Cys Phe Met Val Lys
               245                 250                 255

Asp Leu Ser Asn Pro Ser Arg Tyr Leu Cys Lys Cys Pro Asn Glu
               260                 265                 270

Phe Thr Gly Asp Arg Cys Gln Asn Tyr Val Met Ala Ser Phe Tyr
               275                 280                 285

Ser Thr Ser Thr Pro Phe Leu Ser Leu Pro Glu
               290                 295 296
```

We claim:

1. A method of regenerating a layer of lung epithelial cells, comprising administering to a subject an effective amount of an isolated HER2, HER3 and/or HER4 activating ligand selected from the group consisting of a HRG-β1 polypeptide comprising at least 95% sequence identity to the amino acid sequence of SEQ ID NO:15, a fragment of a heregulin polypeptide, wherein the fragment comprises at least 95% sequence identity to the amino acid sequence of residues 177 to 244 of SEQ ID NO:15, the amino acid sequence of residues 147 to 227 of SEQ ID NO:15, the amino acid sequence of residues 147 to 244 of SEQ ID NO:15, or the amino acid sequence of residues 177 to 227 of SEQ ID NO:15, or a HRG agonist antibody or fragment thereof, wherein upon binding to a HER2, HER3 and/or HER4 receptor said ligand regenerates a layer of lung epithelial cells by inducing proliferation of the cells in said subject.

2. The method of claim 1, wherein the heregulin polypeptide is a HRG-βI polypeptide comprising at least 95% sequence identity to the amino acid sequence of SEQ ID NO:15, and binds to HER2, HER3 and/or HER4.

3. The method of claim 2, wherein the HRG-βI polypeptide having at least 95% sequence identity to the amino acid sequence of SEQ ID NO:15 binds to HER3.

4. The method of claim 1, wherein the heregulin polypeptide comprises a fragment of a heregulin polypeptide with at least 95% sequence identity to the amino acid sequence of residues 177 to 244 of SEQ ID NO:15, the amino acid sequence of residues 147 to 227 of SEQ ID NO:15, the amino acid sequence of residues 147 to 244 of SEQ ID NO:15, or the amino acid sequence of residues 177 to 227 of SEQ ID NO:15.

5. The method of claim 4, wherein the fragment of HRG polypeptide comprises amino acids 177 to 244 of SEQ ID NO:15.

6. The method of claim 2, wherein the heregulin polypeptide comprises at least two amino acid substitutions at a residue corresponding to human heregulin βI having a sequence of SEQ ID NO:15 wherein one amino acid substitution comprises M226I, and the other substitutions are selected from the group consisting of:
 a) S177W;
 b) H178 is substituted with S, E, R, or A;
 c) H180 is substituted with Q, I, or E;
 d) K181 is substituted with P or A;
 e) A183G;
 f) E184 is substituted with V, W, K, R, G, or N;
 g) K185 is substituted with E, S, Q, or G;
 h) E186R;
 i) K187 is substituted with E or A;
 j) T188Q;
 k) E195Q;
 l) F197Y;
 m) M198 is substituted with R or K;
 n) K200R;
 o) D201 is substituted with T or I;
 p) P205 is substituted with T or Y;
 q) S206 is substituted with K, H, G, P, or
 r) R207Y;
 s) Y208 is substituted with R or L;
 t) L209 is substituted with M or G;
 u) K211R;
 v) P213 is substituted with S, T, N, or K;
 w) N214 is substituted with L, K, S, or E;
 x) F216M;
 y) N223 is substituted with H or W; and mixtures thereof.

7. The method of claim 2, wherein the heregulin polypeptide comprises a set of amino acid substitutions selected from the group consisting of:
 a) A183G, E184W, K185D, E186R, K187E, T188G, and M226I;
 b) A183D, E184K, K185S, E186R, K187E, T188G, and M226I;
 c) F197Y, M198K, K200R, D201I, and M226I;
 d) P205Y, S206G, R207Y, Y208L, and L209M;
 e) P205Y, S206R, R207Y, Y208R, L209M, and M226I;
 f) P205T, S206H, R207Y, Y208R, and L209M;
 g) P205T, S206K, R207Y, Y208R, and L209G;
 h) N223W and M226I;
 i) N223H and M226I;
 j) S177W, H178E, K181P, A183G, E184W, K185D, E186R, K187E, T188G, and M226I;
 k) P205Y, S206G, R207Y, Y208L, L209M, and M226I;
 l) A183G, K185E, E186R, K187E, T188G, F197Y, M198R, D201T;
 m) A183G, K185E, E186R, K187E, T188G, P205Y, S206G, R207Y, Y208L, and L209M;
 n) A183G, K185E, E186R, K187E, T188G, F197Y, M198R, D201T, P205Y, S206G, R207Y, Y208L, and L209M;
 o) A183G, K185E, E186R, K187E, T188G, and M226I;
 p) F197Y, M198R, D201T, P205Y, S206G, R207Y, Y208L, and L209M;
 q) F197Y, M198R, D201T, P205Y, S206G, R207Y, Y208L, L209M, and M226I;
 r) F197Y, M198R, D201T, and M226I;
 s) A183G, K185E, E186R, K187E, T188G, F197Y, M198R, D201T, and M226I;
 t) A183G, K185E, E186R, K187E, T188G, P205Y, S206G, R207Y, Y208L, L209M, and M226I;
 u) A183G, K185E, E186R, K187E, T188G, F197Y, M198R, D201T, P205Y, S206G, R207Y, Y208L, L209M, and M226I;
 v) F197Y, M198R, D201T, P205Y, S206G, R207Y, Y208L, L209M, N223H, and M226I; and
 w) A183G, K185E, E186R, K187E, T188G, F197Y, M198R, D201T, P205Y, S206G, R207Y, Y208L, L209M, N223H, and M226I.

8. The method of claim 4, wherein the heregulin polypeptide fragment comprises at least two amino acid substitutions at a residue corresponding to human heregulin β1 having a sequence of SEQ ID NO:15, wherein one amino acid substitution comprises M226I, and the other substitutions are selected from the group consisting of:
 a) S177W;
 b) H178 is substituted with S, E, R, or A;
 c) V180 is substituted with Q, I, or E;
 d) K181 is substituted with P or A;
 e) A183G;
 f) E184 is substituted with V, W, K, R, G, or N;
 g) K185 is substituted with E, S, Q, or G;
 h) E186R;
 i) K187 is substituted with E or A;
 j) T188Q;
 k) E195Q;
 l) F197Y;
 m) M198 is substituted with R or K;
 n) K200R;
 o) D201 is substituted with T or I;
 p) P205 is substituted with T or Y;
 q) S206 is substituted with K, H, G, P, or
 r) R207Y;
 s) Y208 is substituted with R or L;
 t) L209 is substituted with M or G;
 u) K211R;
 v) P213 is substituted with S, T, N, or K;
 w) N214 is substituted with L, K, S, or E;
 x) F216M;
 y) N223 is substituted with H or W; and mixtures thereof.

9. The method of claim 4, wherein the heregulin polypeptide comprises a set of amino acid substitutions selected from the group consisting of:
 x) A183G, E184W, K185D, E186R, K187E, T188G, and M226I;
 y) A183D, E184K, K185S, E186R, K187E, T188G, and M226I;
 z) F197Y, M198K, K200R, D201I, and M226I;
 aa) P205Y, S206G, R207Y, Y208L, and L209M;
 bb) P205Y, S206R, R207Y, Y208R, L209M, and M226I;

cc) P205T, S206H, R207Y, Y208R, and L209M;
dd) P205T, S206K, R207Y, Y208R, and L209G;
ee) N223W and M226I;
ff) N223H and M226I;
gg) S177W, H178E, K181P, A183G, E184W, K185D, E186R, K187E, T188G, and M226I;
hh) P205Y, S206G, R207Y, Y208L, L209M, and M226I;
ii) A183G, K185E, E186R, K187E, T188G, F197Y, M198R, D201T;
jj) A183G, K185E, E186R, K188E, T187G, P205Y, S206G, R207Y, Y208L, and L209M;
kk) A183G, K185E, E186R, K187E, T188G, F197Y, M198R, D201T, P205Y, S206G, R207Y, Y208L, and L209M;
ll) A183G, K185E, E186R, K187E, T188G, and M226I;
mm) F197Y, M198R, D201T, P205Y, S206G, R207Y, Y208L, and L209M;
nn) F197Y, M198R, D201T, P205Y, S206G, R207Y, Y208L, L209M, and M226I;
oo) F197Y, M198R, D201T, and M226I;
pp) A183G, K185E, E186R, K187E, T188G, F197Y, M198R, D201T, and M226I;
qq) A183G, K185E, E186R, K187E, T188G, P205Y, S206G, R207Y, Y208L, L209M, and M226I;
rr) A183G, K185E, E186R, K187E, T188G, F197Y, M198R, D201T, P205Y, S206G, R207Y, Y208L, L209M, and M226I;
ss) F197Y, M198R, D201T, P205Y, S206G, R207Y, Y208L, L209M, N223H, and M226I; and
tt) A183G, K185E, E186R, K187E, T188G, F197Y, M198R, D201T, P205Y, S206G, R207Y, Y208L, L209M, N223H, and M226I.

10. The method of claim 1, wherein the administration is for the treatment of a lung epithelial cell trauma disease comprising loss or destruction of lung epithelial cells.

11. The method of claim 10, wherein the epithelial cell trauma disease comprises an injury associated with a surgical wound, surgical resection, tissue tear, chemical or smoke inhalation or aspiration, or viral or bacterial infection.

* * * * *

UNITED STATES PATENT AND TRADEMARK OFFICE
CERTIFICATE OF CORRECTION

PATENT NO.       : 7,153,828 B2
APPLICATION NO.  : 10/453183
DATED            : December 26, 2006
INVENTOR(S)      : Sliwkowski et al.

It is certified that error appears in the above-identified patent and that said Letters Patent is hereby corrected as shown below:

Col. 21, line 41: "HRG-a all contain" should read --HRG-α all contain--

Col. 36, line 6: "4: 475479 (1985))." should read --4: 475-479 (1985)).--

Col. 39, line 63: "2-chloromercuri4-nitrophenol," should read --2-chloromercuri-4-nitrophenol,--

Col. 46, line 50: "dried r spray" should read --dried or spray--

Col. 55-112: Delete incorrect sequence listing and insert correct sequence listing as follows:

```
<160> 15

<210> 1
<211> 669
<212> PRT
<213> Homo sapiens

<400> 1
 Ala Arg Ala Pro Gln Arg Gly Arg Ser Leu Ser Pro Ser Arg Asp
  1               5                  10                  15

Lys Leu Phe Pro Asn Pro Ile Arg Ala Leu Gly Pro Asn Ser Pro
                 20                  25                  30

Ala Pro Arg Ala Val Arg Val Glu Arg Ser Val Ser Gly Glu Met
                 35                  40                  45

Ser Glu Arg Lys Glu Gly Arg Gly Lys Gly Lys Lys Lys
                 50                  55                  60

Glu Arg Gly Ser Gly Lys Lys Pro Glu Ser Ala Ala Gly Ser Gln
                 65                  70                  75
```

UNITED STATES PATENT AND TRADEMARK OFFICE
CERTIFICATE OF CORRECTION

PATENT NO.        : 7,153,828 B2
APPLICATION NO.   : 10/453183
DATED             : December 26, 2006
INVENTOR(S)       : Sliwkowski et al.

It is certified that error appears in the above-identified patent and that said Letters Patent is hereby corrected as shown below:

```
Ser Pro Ala Leu Pro Pro Arg Leu Lys Glu Met Lys Ser Gln Glu
            80              85                      90

Ser Ala Ala Gly Ser Lys Leu Val Leu Arg Cys Glu Thr Ser Ser
            95              100                     105

Glu Tyr Ser Ser Leu Arg Phe Lys Trp Phe Lys Asn Gly Asn Glu
            110             115                     120

Leu Asn Arg Lys Asn Lys Pro Gln Asn Ile Lys Ile Gln Lys Lys
            125             130                     135

Pro Gly Lys Ser Glu Leu Arg Ile Asn Lys Ala Ser Leu Ala Asp
            140             145                     150

Ser Gly Glu Tyr Met Cys Lys Val Ile Ser Lys Leu Gly Asn Asp
            155             160                     165

Ser Ala Ser Ala Asn Ile Thr Ile Val Glu Ser Asn Glu Ile Ile
            170             175                     180

Thr Gly Met Pro Ala Ser Thr Glu Gly Ala Tyr Val Ser Ser Glu
            185             190                     195

Ser Pro Ile Arg Ile Ser Val Ser Thr Glu Gly Ala Asn Thr Ser
            200             205                     210

Ser Ser Thr Ser Thr Ser Thr Thr Gly Thr Ser His Leu Val Lys
            215             220                     225

Cys Ala Glu Lys Glu Lys Thr Phe Cys Val Asn Gly Gly Glu Cys
            230             235                     240

Phe Met Val Lys Asp Leu Ser Asn Pro Ser Arg Tyr Leu Cys Lys
            245             250                     255
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Cys Gln Pro Gly Phe Thr Gly Ala Arg Cys Thr Glu Asn Val Pro
                260                 265                 270
Met Lys Val Gln Asn Gln Glu Lys Ala Glu Glu Leu Tyr Gln Lys
                275                 280                 285
Arg Val Leu Thr Ile Thr Gly Ile Cys Ile Ala Leu Leu Val Val
                290                 295                 300
Gly Ile Met Cys Val Val Ala Tyr Cys Lys Thr Lys Lys Gln Arg
                305                 310                 315
Lys Lys Leu His Asp Arg Leu Arg Gln Ser Leu Arg Ser Glu Arg
                320                 325                 330
Asn Asn Met Met Asn Ile Ala Asn Gly Pro His His Pro Asn Pro
                335                 340                 345
Pro Pro Glu Asn Val Gln Leu Val Asn Gln Tyr Val Ser Lys Asn
                350                 355                 360
Val Ile Ser Ser Glu His Ile Val Glu Arg Glu Ala Glu Thr Ser
                365                 370                 375
Phe Ser Thr Ser His Tyr Thr Ser Thr Ala His His Ser Thr Thr
                380                 385                 390
Val Thr Gln Thr Pro Ser His Ser Trp Ser Asn Gly His Thr Glu
                395                 400                 405
Ser Ile Leu Ser Glu Ser His Ser Val Ile Val Met Ser Ser Val
                410                 415                 420
Glu Asn Ser Arg His Ser Ser Pro Thr Gly Gly Pro Arg Gly Arg
                425                 430                 435
```

UNITED STATES PATENT AND TRADEMARK OFFICE
CERTIFICATE OF CORRECTION

PATENT NO.      : 7,153,828 B2
APPLICATION NO. : 10/453183
DATED           : December 26, 2006
INVENTOR(S)     : Sliwkowski et al.

It is certified that error appears in the above-identified patent and that said Letters Patent is hereby corrected as shown below:

```
Leu Asn Gly Thr Gly Gly Pro Arg Glu Cys Asn Ser Phe Leu Arg
            440         445                         450

His Ala Arg Glu Thr Pro Asp Ser Tyr Arg Asp Ser Pro His Ser
            455         460                         465

Glu Arg Tyr Val Ser Ala Met Thr Thr Pro Ala Arg Met Ser Pro
            470         475                         480

Val Asp Phe His Thr Pro Ser Ser Pro Lys Ser Pro Pro Ser Glu
            485         490                         495

Met Ser Pro Pro Val Ser Ser Met Thr Val Ser Met Pro Ser Met
            500         505                         510

Ala Val Ser Pro Phe Met Glu Glu Glu Arg Pro Leu Leu Leu Val
            515         520                         525

Thr Pro Pro Arg Leu Arg Glu Lys Lys Phe Asp His His Pro Gln
            530         535                         540

Gln Phe Ser Ser Phe His His Asn Pro Ala His Asp Ser Asn Ser
            545         550                         555

Leu Pro Ala Ser Pro Leu Arg Ile Val Glu Asp Glu Glu Tyr Glu
            560         565                         570

Thr Thr Gln Glu Tyr Glu Pro Ala Gln Glu Pro Val Lys Lys Leu
            575         580                         585

Ala Asn Ser Arg Arg Ala Lys Arg Thr Lys Pro Asn Gly His Ile
            590         595                         600

Ala Asn Arg Leu Glu Val Asp Ser Asn Thr Ser Ser Gln Ser Ser
            605         610                         615
```

Page 4 of 67

UNITED STATES PATENT AND TRADEMARK OFFICE
CERTIFICATE OF CORRECTION

| | | |
|---|---|---|
| PATENT NO. | : 7,153,828 B2 | |
| APPLICATION NO. | : 10/453183 | |
| DATED | : December 26, 2006 | |
| INVENTOR(S) | : Sliwkowski et al. | |

It is certified that error appears in the above-identified patent and that said Letters Patent is hereby corrected as shown below:

```
    Asn Ser Glu Ser Glu Thr Glu Asp Glu Arg Val Gly Glu Asp Thr
                    620                 625                 630

Pro Phe Leu Gly Ile Gln Asn Pro Leu Ala Ala Ser Leu Glu Ala
                    635                 640                 645

Thr Pro Ala Phe Arg Leu Ala Asp Ser Arg Thr Asn Pro Ala Gly
                    650                 655                 660

Arg Phe Ser Thr Gln Glu Glu Ile Gln
                    665

<210> 2
<211> 2226
<212> DNA
<213> Homo sapiens

<400> 2
  gg  gcg cga gcg cct cag cgc ggc cgc tcg ctc tcc ccc           38
      Ala Arg Ala Pro Gln Arg Gly Arg Ser Leu Ser Pro
      1                   5                   10 tcg agg gac aaa ctt ttc cca aac ccg atc cga gcc ctt           77
  Ser Arg Asp Lys Leu Phe Pro Asn Pro Ile Arg Ala Leu
          15                  20                  25 gga cca aac tcg cct gcg ccg aga gcc gtc cgc gta gag          116
  Gly Pro Asn Ser Pro Ala Pro Arg Ala Val Arg Val Glu
                  30                  35 cgc tcc gtc tcc ggc gag atg tcc gag cgc aaa gaa ggc          155
  Arg Ser Val Ser Gly Glu Met Ser Glu Arg Lys Glu Gly
          40                  45                  50
```

UNITED STATES PATENT AND TRADEMARK OFFICE
CERTIFICATE OF CORRECTION

PATENT NO.       : 7,153,828 B2
APPLICATION NO.  : 10/453183
DATED            : December 26, 2006
INVENTOR(S)      : Sliwkowski et al.

It is certified that error appears in the above-identified patent and that said Letters Patent is hereby corrected as shown below:

```
aga  ggc  aaa  ggg  aag  ggc  aag  aag  aag  gag  cga  ggc  tcc
Arg  Gly  Lys  Gly  Lys  Gly  Lys  Lys  Lys  Glu  Arg  Gly  Ser
               55                       60 ggc  aag  aag  ccg  gag  tcc  gcg  gcg  ggc  agc  cag  agc  cca
Gly  Lys  Lys  Pro  Glu  Ser  Ala  Ala  Gly  Ser  Gln  Ser  Pro
 65                      70                       75 gcc  ttg  cct  ccc  cga  ttg  aaa  gag  atg  aaa  agc  cag  gaa
Ala  Leu  Pro  Pro  Arg  Leu  Lys  Glu  Met  Lys  Ser  Gln  Glu
               80                       85                  90 tcg  gct  gca  ggt  tcc  aaa  cta  gtc  ctt  cgg  tgt  gaa  acc
Ser  Ala  Ala  Gly  Ser  Lys  Leu  Val  Leu  Arg  Cys  Glu  Thr
                    95                       100 agt  tct  gaa  tac  tcc  tct  ctc  aga  ttc  aag  tgg  ttc  aag
Ser  Ser  Glu  Tyr  Ser  Ser  Leu  Arg  Phe  Lys  Trp  Phe  Lys
     105                      110                      115 aat  ggg  aat  gaa  ttg  aat  cga  aaa  aac  aaa  cca  caa  aat
Asn  Gly  Asn  Glu  Leu  Asn  Arg  Lys  Asn  Lys  Pro  Gln  Asn
               120                      125 atc  aag  ata  caa  aaa  aag  cca  ggg  aag  tca  gaa  ctt  cgc
Ile  Lys  Ile  Gln  Lys  Lys  Pro  Gly  Lys  Ser  Glu  Leu  Arg
130                      135                      140 att  aac  aaa  gca  tca  ctg  gct  gat  tct  gga  gag  tat  atg
Ile  Asn  Lys  Ala  Ser  Leu  Ala  Asp  Ser  Gly  Glu  Tyr  Met
          145                      150                      155 tgc  aaa  gtg  atc  agc  aaa  tta  gga  aat  gac  agt  gcc  tct
Cys  Lys  Val  Ile  Ser  Lys  Leu  Gly  Asn  Asp  Ser  Ala  Ser
                    160                      165
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
gcc aat atc acc atc gtg gaa tca aac gag atc atc act
Ala Asn Ile Thr Ile Val Glu Ser Asn Glu Ile Ile Thr
    170             175             180 ggt atg cca gcc tca act gaa gga gca tat gtg tct tca
Gly Met Pro Ala Ser Thr Glu Gly Ala Tyr Val Ser Ser
            185             190 gag tct ccc att aga ata tca gta tcc aca gaa gga gca
Glu Ser Pro Ile Arg Ile Ser Val Ser Thr Glu Gly Ala
195             200             205 aat act tct tca tct aca tct aca tcc acc act ggg aca
Asn Thr Ser Ser Ser Thr Ser Thr Ser Thr Thr Gly Thr
        210             215             220 agc cat ctt gta aaa tgt gcg gag aag gag aaa act ttc
Ser His Leu Val Lys Cys Ala Glu Lys Glu Lys Thr Phe
                225             230 tgt gtg aat gga ggg gag tgc ttc atg gtg aaa gac ctt
Cys Val Asn Gly Gly Glu Cys Phe Met Val Lys Asp Leu
        235             240             245 tca aac ccc tcg aga tac ttg tgc aag tgc caa cct gga
Ser Asn Pro Ser Arg Tyr Leu Cys Lys Cys Gln Pro Gly
            250             255 ttc act gga gca aga tgt act gag aat gtg ccc atg aaa
Phe Thr Gly Ala Arg Cys Thr Glu Asn Val Pro Met Lys
260             265             270 gtc caa aac caa gaa aag gcg gag gag ctg tac cag aag
Val Gln Asn Gln Glu Lys Ala Glu Glu Leu Tyr Gln Lys
        275             280             285
```

UNITED STATES PATENT AND TRADEMARK OFFICE
CERTIFICATE OF CORRECTION

PATENT NO. : 7,153,828 B2  Page 8 of 67
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
aga gtg ctg acc ata acc ggc atc tgc atc gcc ctc ctt           896
Arg Val Leu Thr Ile Thr Gly Ile Cys Ile Ala Leu Leu
            290             295 gtg gtc ggc atc atg tgt gtg gtg gcc tac tgc aaa acc           935
Val Val Gly Ile Met Cys Val Val Ala Tyr Cys Lys Thr
            300             305             310 aag aaa cag cgg aaa aag ctg cat gac cgt ctt cgg cag           974
Lys Lys Gln Arg Lys Lys Leu His Asp Arg Leu Arg Gln
                315             320 agc ctt cgg tct gaa cga aac aat atg atg aac att gcc          1013
Ser Leu Arg Ser Glu Arg Asn Asn Met Met Asn Ile Ala
325                 330             335 aat ggg cct cac cat cct aac cca ccc ccc gag aat gtc          1052
Asn Gly Pro His His Pro Asn Pro Pro Pro Glu Asn Val
            340             345             350 cag ctg gtg aat caa tac gta tct aaa aac gtc atc tcc          1091
Gln Leu Val Asn Gln Tyr Val Ser Lys Asn Val Ile Ser
                355             360 agt gag cat att gtt gag aga gaa gca gag aca tcc ttt          1130
Ser Glu His Ile Val Glu Arg Glu Ala Glu Thr Ser Phe
    365                 370             375 tcc acc agt cac tat act tcc aca gcc cat cac tcc act          1169
Ser Thr Ser His Tyr Thr Ser Thr Ala His His Ser Thr
                380             385 act gtc acc cag act cct agc cac agc tgg agc aac gga          1208
Thr Val Thr Gln Thr Pro Ser His Ser Trp Ser Asn Gly
390             395             400
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
cac act gaa agc atc ctt tcc gaa agc cac tct gta atc           1247
His Thr Glu Ser Ile Leu Ser Glu Ser His Ser Val Ile
    405             410                 415 gtg atg tca tcc gta gaa aac agt agg cac agc agc cca           1286
Val Met Ser Ser Val Glu Asn Ser Arg His Ser Ser Pro
                420             425 act ggg ggc cca aga gga cgt ctt aat ggc aca gga ggc           1325
Thr Gly Gly Pro Arg Gly Arg Leu Asn Gly Thr Gly Gly
    430             435                 440 cct cgt gaa tgt aac agc ttc ctc agg cat gcc aga gaa           1364
Pro Arg Glu Cys Asn Ser Phe Leu Arg His Ala Arg Glu
                445             450 acc cct gat tcc tac cga gac tct cct cat agt gaa agg           1403
Thr Pro Asp Ser Tyr Arg Asp Ser Pro His Ser Glu Arg
455             460                 465 tat gtg tca gcc atg acc acc ccg gct cgt atg tca cct           1442
Tyr Val Ser Ala Met Thr Thr Pro Ala Arg Met Ser Pro
        470             475                 480 gta gat ttc cac acg cca agc tcc ccc aaa tcg ccc cct           1481
Val Asp Phe His Thr Pro Ser Ser Pro Lys Ser Pro Pro
            485             490 tcg gaa atg tct cca ccc gtg tcc agc atg acg gtg tcc           1520
Ser Glu Met Ser Pro Pro Val Ser Ser Met Thr Val Ser
    495             500                 505 atg cct tcc atg gcg gtc agc ccc ttc atg gaa gaa gag           1559
Met Pro Ser Met Ala Val Ser Pro Phe Met Glu Glu Glu
                510             515
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
aga cct cta ctt ctc gtg aca cca cca agg ctg cgg gag     1598
Arg Pro Leu Leu Leu Val Thr Pro Pro Arg Leu Arg Glu
520                 525                 530 aag aag ttt gac cat cac cct cag cag ttc agc tcc ttc     1637
Lys Lys Phe Asp His His Pro Gln Gln Phe Ser Ser Phe
        535                 540                 545 cac cac aac ccc gcg cat gac agt aac agc ctc cct gct     1676
His His Asn Pro Ala His Asp Ser Asn Ser Leu Pro Ala
                550                 555 agc ccc ttg agg ata gtg gag gat gag gag tat gaa acg     1715
Ser Pro Leu Arg Ile Val Glu Asp Glu Glu Tyr Glu Thr
        560                 565                 570 acc caa gag tac gag cca gcc caa gag cct gtt aag aaa     1754
Thr Gln Glu Tyr Glu Pro Ala Gln Glu Pro Val Lys Lys
                575                 580 ctc gcc aat agc cgg cgg gcc aaa aga acc aag ccc aat     1793
Leu Ala Asn Ser Arg Arg Ala Lys Arg Thr Lys Pro Asn
585                 590                 595 ggc cac att gct aac aga ttg gaa gtg gac agc aac aca     1832
Gly His Ile Ala Asn Arg Leu Glu Val Asp Ser Asn Thr
        600                 605                 610 agc tcc cag agc agt aac tca gag agt gaa aca gaa gat     1871
Ser Ser Gln Ser Ser Asn Ser Glu Ser Glu Thr Glu Asp
                615                 620 gaa aga gta ggt gaa gat acg cct ttc ctg ggc ata cag     1910
Glu Arg Val Gly Glu Asp Thr Pro Phe Leu Gly Ile Gln
        625                 630                 635
```

UNITED STATES PATENT AND TRADEMARK OFFICE
CERTIFICATE OF CORRECTION

PATENT NO. : 7,153,828 B2  
APPLICATION NO. : 10/453183  
DATED : December 26, 2006  
INVENTOR(S) : Sliwkowski et al.

It is certified that error appears in the above-identified patent and that said Letters Patent is hereby corrected as shown below:

```
aac ccc ctg gca gcc agt ctt gag gca aca cct gcc ttc          1949
Asn Pro Leu Ala Ala Ser Leu Glu Ala Thr Pro Ala Phe
            640             645 cgc ctg gct gac agc agg act aac cca gca ggc cgc ttc          1988
Arg Leu Ala Asp Ser Arg Thr Asn Pro Ala Gly Arg Phe
650             655             660 tcg aca cag gaa gaa atc cag g ccaggctgtc tagtgtaatt          2030
Ser Thr Gln Glu Glu Ile Gln
        665             669 gctaaccaag accctattgc tgtataaaac ctaaataaac acatagattc        2080
acctgtaaaa ctttatttta tataataaag tattccacct taaattaaac        2130
aatttatttt attttagcag ttctgcaaat agaaaacagg aaaaaaactt        2180
ttataaatta aatatatgta tgtaaaaatg aaaaaaaaaa aaaaaa           2226

<210> 3
<211> 675
<212> PRT
<213> Homo sapiens

<400> 3
 Asp Lys Leu Phe Pro Asn Pro Ile Arg Ala Leu Gly Pro Asn Ser
  1               5                  10                  15

Pro Ala Pro Arg Ala Val Arg Val Glu Arg Ser Val Ser Gly Glu
                 20                  25                  30

Met Ser Glu Arg Lys Glu Gly Arg Gly Lys Gly Lys Gly Lys Lys
                 35                  40                  45
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Lys Glu Arg Gly Ser Gly Lys Lys Pro Glu Ser Ala Ala Gly Ser
                50              55              60

Gln Ser Pro Ala Leu Pro Pro Gln Leu Lys Glu Met Lys Ser Gln
                65              70              75

Glu Ser Ala Ala Gly Ser Lys Leu Val Leu Arg Cys Glu Thr Ser
                80              85              90

Ser Glu Tyr Ser Ser Leu Arg Phe Lys Trp Phe Lys Asn Gly Asn
                95              100             105

Glu Leu Asn Arg Lys Asn Lys Pro Gln Asn Ile Lys Ile Gln Lys
                110             115             120

Lys Pro Gly Lys Ser Glu Leu Arg Ile Asn Lys Ala Ser Leu Ala
                125             130             135

Asp Ser Gly Glu Tyr Met Cys Lys Val Ile Ser Lys Leu Gly Asn
                140             145             150

Asp Ser Ala Ser Ala Asn Ile Thr Ile Val Glu Ser Asn Glu Ile
                155             160             165

Ile Thr Gly Met Pro Ala Ser Thr Glu Gly Ala Tyr Val Ser Ser
                170             175             180

Glu Ser Pro Ile Arg Ile Ser Val Ser Thr Glu Gly Ala Asn Thr
                185             190             195

Ser Ser Ser Thr Ser Thr Ser Thr Thr Gly Thr Ser His Leu Val
                200             205             210

Lys Cys Ala Glu Lys Glu Lys Thr Phe Cys Val Asn Gly Gly Glu
                215             220             225
```

UNITED STATES PATENT AND TRADEMARK OFFICE
CERTIFICATE OF CORRECTION

PATENT NO.        : 7,153,828 B2
APPLICATION NO.   : 10/453183
DATED             : December 26, 2006
INVENTOR(S)       : Sliwkowski et al.

It is certified that error appears in the above-identified patent and that said Letters Patent is hereby corrected as shown below:

```
Cys Phe Met Val Lys Asp Leu Ser Asn Pro Ser Arg Tyr Leu Cys
            230                 235                 240

Lys Cys Pro Asn Glu Phe Thr Gly Asp Arg Cys Gln Asn Tyr Val
            245                 250                 255

Met Ala Ser Phe Tyr Lys His Leu Gly Ile Glu Phe Met Glu Ala
            260                 265                 270

Glu Glu Leu Tyr Gln Lys Arg Val Leu Thr Ile Thr Gly Ile Cys
            275                 280                 285

Ile Ala Leu Leu Val Val Gly Ile Met Cys Val Val Ala Tyr Cys
            290                 295                 300

Lys Thr Lys Lys Gln Arg Lys Lys Leu His Asp Arg Leu Arg Gln
            305                 310                 315

Ser Leu Arg Ser Glu Arg Asn Asn Met Met Asn Ile Ala Asn Gly
            320                 325                 330

Pro His His Pro Asn Pro Pro Pro Glu Asn Val Gln Leu Val Asn
            335                 340                 345

Gln Tyr Val Ser Lys Asn Val Ile Ser Ser Glu His Ile Val Glu
            350                 355                 360

Arg Glu Ala Glu Thr Ser Phe Ser Thr Ser His Tyr Thr Ser Thr
            365                 370                 375

Ala His His Ser Thr Thr Val Thr Gln Thr Pro Ser His Ser Trp
            380                 385                 390

Ser Asn Gly His Thr Glu Ser Ile Leu Ser Glu Ser His Ser Val
            395                 400                 405
```

UNITED STATES PATENT AND TRADEMARK OFFICE
CERTIFICATE OF CORRECTION

| | |
|---|---|
| PATENT NO. | : 7,153,828 B2 |
| APPLICATION NO. | : 10/453183 |
| DATED | : December 26, 2006 |
| INVENTOR(S) | : Sliwkowski et al. |

It is certified that error appears in the above-identified patent and that said Letters Patent is hereby corrected as shown below:

```
Ile Val Met Ser Ser Val Glu Asn Ser Arg His Ser Ser Pro Thr
                410             415                 420

Gly Gly Pro Arg Gly Arg Leu Asn Gly Thr Gly Gly Pro Arg Glu
                425             430                 435

Cys Asn Ser Phe Leu Arg His Ala Arg Glu Thr Pro Asp Ser Tyr
                440             445                 450

Arg Asp Ser Pro His Ser Glu Arg Tyr Val Ser Ala Met Thr Thr
                455             460                 465

Pro Ala Arg Met Ser Pro Val Asp Phe His Thr Pro Ser Ser Pro
                470             475                 480

Lys Ser Pro Pro Ser Glu Met Ser Pro Val Ser Ser Met Thr
                485             490                 495

Val Ser Met Pro Ser Met Ala Val Ser Pro Phe Met Glu Glu Glu
                500             505                 510

Arg Pro Leu Leu Leu Val Thr Pro Pro Arg Leu Arg Glu Lys Lys
                515             520                 525

Phe Asp His His Pro Gln Gln Phe Ser Ser Phe His His Asn Pro
                530             535                 540

Ala His Asp Ser Asn Ser Leu Pro Ala Ser Pro Leu Arg Ile Val
                545             550                 555

Glu Asp Glu Glu Tyr Glu Thr Thr Gln Glu Tyr Glu Pro Ala Gln
                560             565                 570

Glu Pro Val Lys Lys Leu Ala Asn Ser Arg Arg Ala Lys Arg Thr
                575             580                 585
```

UNITED STATES PATENT AND TRADEMARK OFFICE
CERTIFICATE OF CORRECTION

PATENT NO.      : 7,153,828 B2                                  Page 15 of 67
APPLICATION NO. : 10/453183
DATED           : December 26, 2006
INVENTOR(S)     : Sliwkowski et al.

It is certified that error appears in the above-identified patent and that said Letters Patent is hereby corrected as shown below:

```
Lys Pro Asn Gly His Ile Ala Asn Arg Leu Glu Val Asp Ser Asn
                590             595                 600

Thr Ser Ser Gln Ser Ser Asn Ser Glu Ser Glu Thr Glu Asp Glu
                605             610                 615

Arg Val Gly Glu Asp Thr Pro Phe Leu Gly Ile Gln Asn Pro Leu
                620             625                 630

Ala Ala Ser Leu Glu Ala Thr Pro Ala Phe Arg Leu Ala Asp Ser
                635             640                 645

Arg Thr Asn Pro Ala Gly Arg Phe Ser Thr Gln Glu Glu Ile Gln
                650             655                 660

Ala Arg Leu Ser Ser Val Ile Ala Asn Gln Asp Pro Ile Ala Val
                665             670                 675

<210> 4
<211> 2199
<212> DNA
<213> Homo sapiens

<400> 4
 gg  gac aaa ctt ttc cca aac ccg atc cga gcc ctt gga          38
     Asp Lys Leu Phe Pro Asn Pro Ile Arg Ala Leu Gly
      1               5                   10 cca aac tcg cct gcg ccg aga gcc gtc cgc gta gag cgc          77
 Pro Asn Ser Pro Ala Pro Arg Ala Val Arg Val Glu Arg
             15              20              25
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
tcc gtc tcc ggc gag atg tcc gag cgc aaa gaa ggc aga       116
Ser Val Ser Gly Glu Met Ser Glu Arg Lys Glu Gly Arg
             30                  35 ggc aaa ggg aag ggc aag aag aag gag cga ggc tcc ggc       155
Gly Lys Gly Lys Gly Lys Lys Lys Glu Arg Gly Ser Gly
         40              45                  50 aag aag ccg gag tcc gcg gcg ggc agc cag agc cca gcc       194
Lys Lys Pro Glu Ser Ala Ala Gly Ser Gln Ser Pro Ala
                 55              60 ttg cct ccc caa ttg aaa gag atg aaa agc cag gaa tcg       233
Leu Pro Pro Gln Leu Lys Glu Met Lys Ser Gln Glu Ser
 65                  70                  75 gct gca ggt tcc aaa cta gtc ctt cgg tgt gaa acc agt       272
Ala Ala Gly Ser Lys Leu Val Leu Arg Cys Glu Thr Ser
             80                  85                  90 tct gaa tac tcc tct ctc aga ttc aag tgg ttc aag aat       311
Ser Glu Tyr Ser Ser Leu Arg Phe Lys Trp Phe Lys Asn
                 95                 100 ggg aat gaa ttg aat cga aaa aac aaa cca caa aat atc       350
Gly Asn Glu Leu Asn Arg Lys Asn Lys Pro Gln Asn Ile
        105                 110                 115 aag ata caa aaa aag cca ggg aag tca gaa ctt cgc att       389
Lys Ile Gln Lys Lys Pro Gly Lys Ser Glu Leu Arg Ile
                120                 125 aac aaa gca tca ctg gct gat tct gga gag tat atg tgc       428
Asn Lys Ala Ser Leu Ala Asp Ser Gly Glu Tyr Met Cys
130                 135                 140
```

UNITED STATES PATENT AND TRADEMARK OFFICE
CERTIFICATE OF CORRECTION

PATENT NO.      : 7,153,828 B2
APPLICATION NO. : 10/453183
DATED           : December 26, 2006
INVENTOR(S)     : Sliwkowski et al.

It is certified that error appears in the above-identified patent and that said Letters Patent is hereby corrected as shown below:

```
aaa gtg atc agc aaa tta gga aat gac agt gcc tct gcc        467
Lys Val Ile Ser Lys Leu Gly Asn Asp Ser Ala Ser Ala
        145             150                 155 aat atc acc atc gtg gaa tca aac gag atc atc act ggt        506
Asn Ile Thr Ile Val Glu Ser Asn Glu Ile Ile Thr Gly
                160                 165 atg cca gcc tca act gaa gga gca tat gtg tct tca gag        545
Met Pro Ala Ser Thr Glu Gly Ala Tyr Val Ser Ser Glu
        170             175                 180 tct ccc att aga ata tca gta tcc aca gaa gga gca aat        584
Ser Pro Ile Arg Ile Ser Val Ser Thr Glu Gly Ala Asn
            185                 190 act tct tca tct aca tct aca tcc acc act ggg aca agc        623
Thr Ser Ser Ser Thr Ser Thr Ser Thr Thr Gly Thr Ser
195                 200                 205 cat ctt gta aaa tgt gcg gag aag gag aaa act ttc tgt        662
His Leu Val Lys Cys Ala Glu Lys Glu Lys Thr Phe Cys
            210                 215                 220 gtg aat gga ggg gag tgc ttc atg gtg aaa gac ctt tca        701
Val Asn Gly Gly Glu Cys Phe Met Val Lys Asp Leu Ser
                225                 230 aac ccc tcg aga tac ttg tgc aag tgc cca aat gag ttt        740
Asn Pro Ser Arg Tyr Leu Cys Lys Cys Pro Asn Glu Phe
        235                 240                 245 act ggt gat cgc tgc caa aac tac gta atg gcc agc ttc        779
Thr Gly Asp Arg Cys Gln Asn Tyr Val Met Ala Ser Phe
            250                 255
```

UNITED STATES PATENT AND TRADEMARK OFFICE
CERTIFICATE OF CORRECTION

PATENT NO.      : 7,153,828 B2                                   Page 18 of 67
APPLICATION NO. : 10/453183
DATED           : December 26, 2006
INVENTOR(S)     : Sliwkowski et al.

It is certified that error appears in the above-identified patent and that said Letters Patent is hereby corrected as shown below:

```
tac aag cat ctt ggg att gaa ttt atg gag gcg gag gag           818
Tyr Lys His Leu Gly Ile Glu Phe Met Glu Ala Glu Glu
260             265             270 ctg tac cag aag aga gtg ctg acc ata acc ggc atc tgc           857
Leu Tyr Gln Lys Arg Val Leu Thr Ile Thr Gly Ile Cys
        275             280             285 atc gcc ctc ctt gtg gtc ggc atc atg tgt gtg gtg gcc           896
Ile Ala Leu Leu Val Val Gly Ile Met Cys Val Val Ala
            290             295 tac tgc aaa acc aag aaa cag cgg aaa aag ctg cat gac           935
Tyr Cys Lys Thr Lys Lys Gln Arg Lys Lys Leu His Asp
    300             305             310 cgt ctt cgg cag agc ctt cgg tct gaa cga aac aat atg           974
Arg Leu Arg Gln Ser Leu Arg Ser Glu Arg Asn Asn Met
            315             320 atg aac att gcc aat ggg cct cac cat cct aac cca ccc           1013
Met Asn Ile Ala Asn Gly Pro His His Pro Asn Pro Pro
325             330             335 ccc gag aat gtc cag ctg gtg aat caa tac gta tct aaa           1052
Pro Glu Asn Val Gln Leu Val Asn Gln Tyr Val Ser Lys
        340             345             350 aac gtc atc tcc agt gag cat att gtt gag aga gaa gca           1091
Asn Val Ile Ser Ser Glu His Ile Val Glu Arg Glu Ala
            355             360 gag aca tcc ttt tcc acc agt cac tat act tcc aca gcc           1130
Glu Thr Ser Phe Ser Thr Ser His Tyr Thr Ser Thr Ala
    365             370             375
```

UNITED STATES PATENT AND TRADEMARK OFFICE
CERTIFICATE OF CORRECTION

PATENT NO.       : 7,153,828 B2                                    Page 19 of 67
APPLICATION NO.  : 10/453183
DATED            : December 26, 2006
INVENTOR(S)      : Sliwkowski et al.

It is certified that error appears in the above-identified patent and that said Letters Patent is hereby corrected as shown below:

```
cat cac tcc act act gtc acc cag act cct agc cac agc        1169
His His Ser Thr Thr Val Thr Gln Thr Pro Ser His Ser
            380             385 tgg agc aac gga cac act gaa agc atc ctt tcc gaa agc        1208
Trp Ser Asn Gly His Thr Glu Ser Ile Leu Ser Glu Ser
390             395                 400 cac tct gta atc gtg atg tca tcc gta gaa aac agt agg        1247
His Ser Val Ile Val Met Ser Ser Val Glu Asn Ser Arg
        405             410                 415 cac agc agc cca act ggg ggc cca aga gga cgt ctt aat        1286
His Ser Ser Pro Thr Gly Gly Pro Arg Gly Arg Leu Asn
            420                 425 ggc aca gga ggc cct cgt gaa tgt aac agc ttc ctc agg        1325
Gly Thr Gly Gly Pro Arg Glu Cys Asn Ser Phe Leu Arg
    430             435                 440 cat gcc aga gaa acc cct gat tcc tac cga gac tct cct        1364
His Ala Arg Glu Thr Pro Asp Ser Tyr Arg Asp Ser Pro
            445             450 cat agt gaa agg tat gtg tca gcc atg acc acc ccg gct        1403
His Ser Glu Arg Tyr Val Ser Ala Met Thr Thr Pro Ala
455             460             465 cgt atg tca cct gta gat ttc cac acg cca agc tcc ccc        1442
Arg Met Ser Pro Val Asp Phe His Thr Pro Ser Ser Pro
        470             475                 480 aaa tcg ccc cct tcg gaa atg tct cca ccc gtg tcc agc        1481
Lys Ser Pro Pro Ser Glu Met Ser Pro Pro Val Ser Ser
            485             490
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

| | | | | | | | | | | | |
|---|---|---|---|---|---|---|---|---|---|---|---|
| atg | acg | gtg | tcc | atg | cct | tcc | atg | gcg | gtc | agc | ccc | ttc | 1520 |
| Met | Thr | Val | Ser | Met | Pro | Ser | Met | Ala | Val | Ser | Pro | Phe |
| | 495 | | | | 500 | | | | | 505 | | |
| atg | gaa | gaa | gag | aga | cct | cta | ctt | ctc | gtg | aca | cca | cca | 1559 |
| Met | Glu | Glu | Glu | Arg | Pro | Leu | Leu | Leu | Val | Thr | Pro | Pro |
| | | | 510 | | | | | 515 | | | | |
| agg | ctg | cgg | gag | aag | aag | ttt | gac | cat | cac | cct | cag | cag | 1598 |
| Arg | Leu | Arg | Glu | Lys | Lys | Phe | Asp | His | His | Pro | Gln | Gln |
| 520 | | | | | 525 | | | | | 530 | | |
| ttc | agc | tcc | ttc | cac | cac | aac | ccc | gcg | cat | gac | agt | aac | 1637 |
| Phe | Ser | Ser | Phe | His | His | Asn | Pro | Ala | His | Asp | Ser | Asn |
| | | 535 | | | | | 540 | | | | | 545 |
| agc | ctc | cct | gct | agc | ccc | ttg | agg | ata | gtg | gag | gat | gag | 1676 |
| Ser | Leu | Pro | Ala | Ser | Pro | Leu | Arg | Ile | Val | Glu | Asp | Glu |
| | | | | 550 | | | | | 555 | | | |
| gag | tat | gaa | acg | acc | caa | gag | tac | gag | cca | gcc | caa | gag | 1715 |
| Glu | Tyr | Glu | Thr | Thr | Gln | Glu | Tyr | Glu | Pro | Ala | Gln | Glu |
| | 560 | | | | | 565 | | | | | 570 | |
| cct | gtt | aag | aaa | ctc | gcc | aat | agc | cgg | cgg | gcc | aaa | aga | 1754 |
| Pro | Val | Lys | Lys | Leu | Ala | Asn | Ser | Arg | Arg | Ala | Lys | Arg |
| | | | 575 | | | | | 580 | | | | |
| acc | aag | ccc | aat | ggc | cac | att | gct | aac | aga | ttg | gaa | gtg | 1793 |
| Thr | Lys | Pro | Asn | Gly | His | Ile | Ala | Asn | Arg | Leu | Glu | Val |
| 585 | | | | | 590 | | | | | 595 | | |
| gac | agc | aac | aca | agc | tcc | cag | agc | agt | aac | tca | gag | agt | 1832 |
| Asp | Ser | Asn | Thr | Ser | Ser | Gln | Ser | Ser | Asn | Ser | Glu | Ser |
| | | | 600 | | | | | 605 | | | | 610 |

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
gaa aca gaa gat gaa aga gta ggt gaa gat acg cct ttc       1871
Glu Thr Glu Asp Glu Arg Val Gly Glu Asp Thr Pro Phe
            615                 620 ctg ggc ata cag aac ccc ctg gca gcc agt ctt gag gca       1910
Leu Gly Ile Gln Asn Pro Leu Ala Ala Ser Leu Glu Ala
    625                 630                 635 aca cct gcc ttc cgc ctg gct gac agc agg act aac cca       1949
Thr Pro Ala Phe Arg Leu Ala Asp Ser Arg Thr Asn Pro
            640                 645 gca ggc cgc ttc tcg aca cag gaa gaa atc cag gcc agg       1988
Ala Gly Arg Phe Ser Thr Gln Glu Glu Ile Gln Ala Arg
650                 655                 660 ctg tct agt gta att gct aac caa gac cct att gct gta ta    2029
Leu Ser Ser Val Ile Ala Asn Gln Asp Pro Ile Ala Val
            665                 670             675 a aacctaaata aacacataga ttcacctgta aaactttatt             2070
ttatataata aagtattcca ccttaaatta aacaatttat tttattttag    2120
cagttctgca aatagaaaac aggaaaaaaa cttttataaa ttaaatatat    2170
gtatgtaaaa atgaaaaaaa aaaaaaaa                            2199

<210> 5
<211> 637
<212> PRT
<213> Homo sapiens
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
<400> 5
  Met Ser Glu Arg Lys Glu Gly Arg Gly Lys Gly Lys Gly Lys Lys
   1               5                  10                  15

Lys Glu Arg Gly Ser Gly Lys Lys Pro Glu Ser Ala Ala Gly Ser
                  20                  25                  30

Gln Ser Pro Ala Leu Pro Pro Gln Leu Lys Glu Met Lys Ser Gln
                  35                  40                  45

Glu Ser Ala Ala Gly Ser Lys Leu Val Leu Arg Cys Glu Thr Ser
                  50                  55                  60

Ser Glu Tyr Ser Ser Leu Arg Phe Lys Trp Phe Lys Asn Gly Asn
                  65                  70                  75

Glu Leu Asn Arg Lys Asn Lys Pro Gln Asn Ile Lys Ile Gln Lys
                  80                  85                  90

Lys Pro Gly Lys Ser Glu Leu Arg Ile Asn Lys Ala Ser Leu Ala
                  95                 100                 105

Asp Ser Gly Glu Tyr Met Cys Lys Val Ile Ser Lys Leu Gly Asn
                 110                 115                 120

Asp Ser Ala Ser Ala Asn Ile Thr Ile Val Glu Ser Asn Glu Ile
                 125                 130                 135

Ile Thr Gly Met Pro Ala Ser Thr Glu Gly Ala Tyr Val Ser Ser
                 140                 145                 150

Glu Ser Pro Ile Arg Ile Ser Val Ser Thr Glu Gly Ala Asn Thr
                 155                 160                 165
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Ser Ser Ser Thr Ser Thr Ser Thr Thr Gly Thr Ser His Leu Val
                170             175                 180
Lys Cys Ala Glu Lys Glu Lys Thr Phe Cys Val Asn Gly Gly Glu
                185             190                 195
Cys Phe Met Val Lys Asp Leu Ser Asn Pro Ser Arg Tyr Leu Cys
                200             205                 210
Lys Cys Pro Asn Glu Phe Thr Gly Asp Arg Cys Gln Asn Tyr Val
                215             220                 225
Met Ala Ser Phe Tyr Lys Ala Glu Glu Leu Tyr Gln Lys Arg Val
                230             235                 240
Leu Thr Ile Thr Gly Ile Cys Ile Ala Leu Leu Val Val Gly Ile
                245             250                 255
Met Cys Val Val Ala Tyr Cys Lys Thr Lys Lys Gln Arg Lys Lys
                260             265                 270
Leu His Asp Arg Leu Arg Gln Ser Leu Arg Ser Glu Arg Asn Asn
                275             280                 285
Met Met Asn Ile Ala Asn Gly Pro His His Pro Asn Pro Pro Pro
                290             295                 300
Glu Asn Val Gln Leu Val Asn Gln Tyr Val Ser Lys Asn Val Ile
                305             310                 315
Ser Ser Glu His Ile Val Glu Arg Glu Ala Glu Thr Ser Phe Ser
                320             325                 330
Thr Ser His Tyr Thr Ser Thr Ala His His Ser Thr Thr Val Thr
                335             340                 345
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Gln Thr Pro Ser His Ser Trp Ser Asn Gly His Thr Glu Ser Ile
                350             355             360

Leu Ser Glu Ser His Ser Val Ile Val Met Ser Ser Val Glu Asn
                365             370             375

Ser Arg His Ser Ser Pro Thr Gly Gly Pro Arg Gly Arg Leu Asn
                380             385             390

Gly Thr Gly Gly Pro Arg Glu Cys Asn Ser Phe Leu Arg His Ala
                395             400             405

Arg Glu Thr Pro Asp Ser Tyr Arg Asp Ser Pro His Ser Glu Arg
                410             415             420

Tyr Val Ser Ala Met Thr Thr Pro Ala Arg Met Ser Pro Val Asp
                425             430             435

Phe His Thr Pro Ser Ser Pro Lys Ser Pro Pro Ser Glu Met Ser
                440             445             450

Pro Pro Val Ser Ser Met Thr Val Ser Lys Pro Ser Met Ala Val
                455             460             465

Ser Pro Phe Met Glu Glu Glu Arg Pro Leu Leu Leu Val Thr Pro
                470             475             480

Pro Arg Leu Arg Glu Lys Lys Phe Asp His His Pro Gln Gln Phe
                485             490             495

Ser Ser Phe His His Asn Pro Ala His Asp Ser Asn Ser Leu Pro
                500             505             510

Ala Ser Pro Leu Arg Ile Val Glu Asp Glu Glu Tyr Glu Thr Thr
                515             520             525
```

UNITED STATES PATENT AND TRADEMARK OFFICE
CERTIFICATE OF CORRECTION

PATENT NO.        : 7,153,828 B2
APPLICATION NO.   : 10/453183
DATED             : December 26, 2006
INVENTOR(S)       : Sliwkowski et al.

It is certified that error appears in the above-identified patent and that said Letters Patent is hereby corrected as shown below:

```
        Gln Glu Tyr Glu Pro Ala Gln Glu Pro Val Lys Lys Leu Ala Asn
                        530                 535                 540

Ser Arg Arg Ala Lys Arg Thr Lys Pro Asn Gly His Ile Ala Asn
                        545                 550                 555

Arg Leu Glu Val Asp Ser Asn Thr Ser Ser Gln Ser Ser Asn Ser
                        560                 565                 570

Glu Ser Glu Thr Glu Asp Glu Arg Val Gly Glu Asp Thr Pro Phe
                        575                 580                 585

Leu Gly Ile Gln Asn Pro Leu Ala Ala Ser Leu Glu Ala Thr Pro
                        590                 595                 600

Ala Phe Arg Leu Ala Asp Ser Arg Thr Asn Pro Ala Gly Arg Phe
                        605                 610                 615

Ser Thr Gln Glu Glu Ile Gln Ala Arg Leu Ser Ser Val Ile Ala
                        620                 625                 630

Asn Gln Asp Pro Ile Ala Val
                        635

<210> 6
<211> 2490
<212> DNA
<213> Homo sapiens

<400> 6
  gtggctgcgg ggcaattgaa aaagagccgg cgaggagttc cccgaaactt       50
gttggaactc cgggctcgcg cggaggccag gagctgagcg gcggcggctg      100
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
ccggacgatg ggagcgtgag caggacggtg ataacctctc cccgatcggg      150
ttgcgagggc gccgggcaga ggccaggacg cgagccgcca gcggcgggac      200
ccatcgacga cttcccgggg cgacaggagc agccccgaga gccagggcga      250
gcgcccgttc caggtggccg gaccgcccgc cgcgtccgcg ccgcgctccc      300
tgcaggcaac gggagacgcc cccgcgcagc gcgagcgcct cagcgcggcc      350
gctcgctctc cccatcgagg gacaaacttt tcccaaaccc gatccgagcc      400
cttggaccaa actcgcctgc gccgagagcc gtccgcgtag agcgctccgt      450
ctccggcgag  atg tcc gag cgc aaa gaa ggc aga ggc aaa         490
            Met Ser Glu Arg Lys Glu Gly Arg Gly Lys
             1               5                  10 ggg aag ggc aag aag aag gag cga ggc tcc ggc aag aag          529
Gly Lys Gly Lys Lys Lys Glu Arg Gly Ser Gly Lys Lys
                    15                  20 ccg gag tcc gcg gcg ggc agc cag agc cca gcc ttg cct          568
Pro Glu Ser Ala Ala Gly Ser Gln Ser Pro Ala Leu Pro
        25                  30                  35 ccc caa ttg aaa gag atg aaa agc cag gaa tcg gct gca          607
Pro Gln Leu Lys Glu Met Lys Ser Gln Glu Ser Ala Ala
                40                  45 ggt tcc aaa cta gtc ctt cgg tgt gaa acc agt tct gaa          646
Gly Ser Lys Leu Val Leu Arg Cys Glu Thr Ser Ser Glu
 50                  55                  60
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
tac tcc tct ctc aga ttc aag tgg ttc aag aat ggg aat         685
Tyr Ser Ser Leu Arg Phe Lys Trp Phe Lys Asn Gly Asn
        65                  70                  75 gaa ttg aat cga aaa aac aaa cca caa aat atc aag ata         724
Glu Leu Asn Arg Lys Asn Lys Pro Gln Asn Ile Lys Ile
                80                  85 caa aaa aag cca ggg aag tca gaa ctt cgc att aac aaa         763
Gln Lys Lys Pro Gly Lys Ser Glu Leu Arg Ile Asn Lys
    90                  95                  100 gca tca ctg gct gat tct gga gag tat atg tgc aaa gtg         802
Ala Ser Leu Ala Asp Ser Gly Glu Tyr Met Cys Lys Val
            105                 110 atc agc aaa tta gga aat gac agt gcc tct gcc aat atc         841
Ile Ser Lys Leu Gly Asn Asp Ser Ala Ser Ala Asn Ile
115                 120                 125 acc atc gtg gaa tca aac gag atc atc act ggt atg cca         880
Thr Ile Val Glu Ser Asn Glu Ile Ile Thr Gly Met Pro
        130                 135                 140 gcc tca act gaa gga gca tat gtg tct tca gag tct ccc         919
Ala Ser Thr Glu Gly Ala Tyr Val Ser Ser Glu Ser Pro
                145                 150 att aga ata tca gta tcc aca gaa gga gca aat act tct         958
Ile Arg Ile Ser Val Ser Thr Glu Gly Ala Asn Thr Ser
    155                 160                 165 tca tct aca tct aca tcc acc act ggg aca agc cat ctt         997
Ser Ser Thr Ser Thr Ser Thr Thr Gly Thr Ser His Leu
            170                 175
```

UNITED STATES PATENT AND TRADEMARK OFFICE
CERTIFICATE OF CORRECTION

PATENT NO. : 7,153,828 B2  Page 28 of 67
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
gta aaa tgt gcg gag aag gag aaa act ttc tgt gtg aat       1036
Val Lys Cys Ala Glu Lys Glu Lys Thr Phe Cys Val Asn
180             185             190 gga ggg gag tgc ttc atg gtg aaa gac ctt tca aac ccc       1075
Gly Gly Glu Cys Phe Met Val Lys Asp Leu Ser Asn Pro
        195             200             205 tcg aga tac ttg tgc aag tgc cca aat gag ttt act ggt       1114
Ser Arg Tyr Leu Cys Lys Cys Pro Asn Glu Phe Thr Gly
                210             215 gat cgc tgc caa aac tac gta atg gcc agc ttc tac aag       1153
Asp Arg Cys Gln Asn Tyr Val Met Ala Ser Phe Tyr Lys
        220             225             230 gcg gag gag ctg tac cag aag aga gtg ctg acc ata acc       1192
Ala Glu Glu Leu Tyr Gln Lys Arg Val Leu Thr Ile Thr
            235             240 ggc atc tgc atc gcc ctc ctt gtg gtc ggc atc atg tgt       1231
Gly Ile Cys Ile Ala Leu Leu Val Val Gly Ile Met Cys
245             250             255 gtg gtg gcc tac tgc aaa acc aag aaa cag cgg aaa aag       1270
Val Val Ala Tyr Cys Lys Thr Lys Lys Gln Arg Lys Lys
        260             265             270 ctg cat gac cgt ctt cgg cag agc ctt cgg tct gaa cga       1309
Leu His Asp Arg Leu Arg Gln Ser Leu Arg Ser Glu Arg
                275             280 aac aat atg atg aac att gcc aat ggg cct cac cat cct       1348
Asn Asn Met Met Asn Ile Ala Asn Gly Pro His His Pro
285             290             295
```

UNITED STATES PATENT AND TRADEMARK OFFICE
CERTIFICATE OF CORRECTION

PATENT NO.         : 7,153,828 B2
APPLICATION NO.    : 10/453183
DATED              : December 26, 2006
INVENTOR(S)        : Sliwkowski et al.

It is certified that error appears in the above-identified patent and that said Letters Patent is hereby corrected as shown below:

```
aac cca ccc ccc gag aat gtc cag ctg gtg aat caa tac           1387
Asn Pro Pro Pro Glu Asn Val Gln Leu Val Asn Gln Tyr
        300             305 gta tct aaa aac gtc atc tcc agt gag cat att gtt gag           1426
Val Ser Lys Asn Val Ile Ser Ser Glu His Ile Val Glu
310             315             320 aga gaa gca gag aca tcc ttt tcc acc agt cac tat act           1465
Arg Glu Ala Glu Thr Ser Phe Ser Thr Ser His Tyr Thr
        325             330             335 tcc aca gcc cat cac tcc act act gtc acc cag act cct           1504
Ser Thr Ala His His Ser Thr Thr Val Thr Gln Thr Pro
                340             345 agc cac agc tgg agc aac gga cac act gaa agc atc ctt           1543
Ser His Ser Trp Ser Asn Gly His Thr Glu Ser Ile Leu
        350             355             360 tcc gaa agc cac tct gta atc gtg atg tca tcc gta gaa           1582
Ser Glu Ser His Ser Val Ile Val Met Ser Ser Val Glu
                365             370 aac agt agg cac agc agc cca act ggg ggc cca aga gga           1621
Asn Ser Arg His Ser Ser Pro Thr Gly Gly Pro Arg Gly
375             380             385 cgt ctt aat ggc aca gga ggc cct cgt gaa tgt aac agc           1660
Arg Leu Asn Gly Thr Gly Gly Pro Arg Glu Cys Asn Ser
        390             395             400 ttc ctc agg cat gcc aga gaa acc cct gat tcc tac cga           1699
Phe Leu Arg His Ala Arg Glu Thr Pro Asp Ser Tyr Arg
                405             410
```

UNITED STATES PATENT AND TRADEMARK OFFICE
CERTIFICATE OF CORRECTION

PATENT NO.        : 7,153,828 B2
APPLICATION NO. : 10/453183
DATED              : December 26, 2006
INVENTOR(S)       : Sliwkowski et al.

It is certified that error appears in the above-identified patent and that said Letters Patent is hereby corrected as shown below:

```
gac tct cct cat agt gaa agg tat gtg tca gcc atg acc        1738
Asp Ser Pro His Ser Glu Arg Tyr Val Ser Ala Met Thr
    415             420             425 acc ccg gct cgt atg tca cct gta gat ttc cac acg cca        1777
Thr Pro Ala Arg Met Ser Pro Val Asp Phe His Thr Pro
            430             435 agc tcc ccc aaa tcg ccc cct tcg gaa atg tct cca ccc        1816
Ser Ser Pro Lys Ser Pro Pro Ser Glu Met Ser Pro Pro
440             445             450 gtg tcc agc atg acg gtg tcc aag cct tcc atg gcg gtc        1855
Val Ser Ser Met Thr Val Ser Lys Pro Ser Met Ala Val
        455             460             465 agc ccc ttc atg gaa gaa gag aga cct cta ctt ctc gtg        1894
Ser Pro Phe Met Glu Glu Glu Arg Pro Leu Leu Leu Val
                470             475 aca cca cca agg ctg cgg gag aag aag ttt gac cat cac        1933
Thr Pro Pro Arg Leu Arg Glu Lys Lys Phe Asp His His
        480             485             490 cct cag cag ttc agc tcc ttc cac cac aac ccc gcg cat        1972
Pro Gln Gln Phe Ser Ser Phe His His Asn Pro Ala His
            495             500 gac agt aac agc ctc cct gct agc ccc ttg agg ata gtg        2011
Asp Ser Asn Ser Leu Pro Ala Ser Pro Leu Arg Ile Val
505             510             515 gag gat gag gag tat gaa acg acc caa gag tac gag cca        2050
Glu Asp Glu Glu Tyr Glu Thr Thr Gln Glu Tyr Glu Pro
        520             525             530
```

Page 30 of 67

UNITED STATES PATENT AND TRADEMARK OFFICE
CERTIFICATE OF CORRECTION

PATENT NO. : 7,153,828 B2  Page 31 of 67
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
gcc caa gag cct gtt aag aaa ctc gcc aat agc cgg cgg             2089
Ala Gln Glu Pro Val Lys Lys Leu Ala Asn Ser Arg Arg
            535                 540 gcc aaa aga acc aag ccc aat ggc cac att gct aac aga             2128
Ala Lys Arg Thr Lys Pro Asn Gly His Ile Ala Asn Arg
    545                 550                 555 ttg gaa gtg gac agc aac aca agc tcc cag agc agt aac             2167
Leu Glu Val Asp Ser Asn Thr Ser Ser Gln Ser Ser Asn
            560                 565 tca gag agt gaa aca gaa gat gaa aga gta ggt gaa gat             2206
Ser Glu Ser Glu Thr Glu Asp Glu Arg Val Gly Glu Asp
570             575                 580 acg cct ttc ctg ggc ata cag aac ccc ctg gca gcc agt             2245
Thr Pro Phe Leu Gly Ile Gln Asn Pro Leu Ala Ala Ser
        585                 590                 595 ctt gag gca aca cct gcc ttc cgc ctg gct gac agc agg             2284
Leu Glu Ala Thr Pro Ala Phe Arg Leu Ala Asp Ser Arg
                600                 605 act aac cca gca ggc cgc ttc tcg aca cag gaa gaa atc             2323
Thr Asn Pro Ala Gly Arg Phe Ser Thr Gln Glu Glu Ile
        610                 615                 620 cag gcc agg ctg tct agt gta att gct aac caa gac cct             2362
Gln Ala Arg Leu Ser Ser Val Ile Ala Asn Gln Asp Pro
                625                 630 att gct gta taaaccta aataaacaca tagattcacc tgtaaaactt           2410
Ile Ala Val
635     637
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
tattttatat aataaagtat tccaccttaa attaaacaat ttatttatt      2460 ttagcagttc tgcaaataaa aaaaaaaaaa                          2490

<210> 7
<211> 241
<212> PRT
<213> Homo sapiens

<400> 7
  Met Ser Glu Arg Lys Glu Gly Arg Gly Lys Gly Lys Gly Lys Lys
    1               5                  10                  15

Lys Glu Arg Gly Ser Gly Lys Lys Pro Glu Ser Ala Ala Gly Ser
                     20                  25                  30

Gln Ser Pro Ala Leu Pro Pro Gln Leu Lys Glu Met Lys Ser Gln
                     35                  40                  45

Glu Ser Ala Ala Gly Ser Lys Leu Val Leu Arg Cys Glu Thr Ser
                     50                  55                  60

Ser Glu Tyr Ser Ser Leu Arg Phe Lys Trp Phe Lys Asn Gly Asn
                     65                  70                  75

Glu Leu Asn Arg Lys Asn Lys Pro Gln Asn Ile Lys Ile Gln Lys
                     80                  85                  90

Lys Pro Gly Lys Ser Glu Leu Arg Ile Asn Lys Ala Ser Leu Ala
                     95                 100                 105

Asp Ser Gly Glu Tyr Met Cys Lys Val Ile Ser Lys Leu Gly Asn
                    110                 115                 120
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Asp Ser Ala Ser Ala Asn Ile Thr Ile Val Glu Ser Asn Glu Ile
            125                 130                 135

Ile Thr Gly Met Pro Ala Ser Thr Glu Gly Ala Tyr Val Ser Ser
            140                 145                 150

Glu Ser Pro Ile Arg Ile Ser Val Ser Thr Glu Gly Ala Asn Thr
            155                 160                 165

Ser Ser Ser Thr Ser Thr Ser Thr Thr Gly Thr Ser His Leu Val
            170                 175                 180

Lys Cys Ala Glu Lys Glu Lys Thr Phe Cys Val Asn Gly Gly Glu
            185                 190                 195

Cys Phe Met Val Lys Asp Leu Ser Asn Pro Ser Arg Tyr Leu Cys
            200                 205                 210

Lys Cys Pro Asn Glu Phe Thr Gly Asp Arg Cys Gln Asn Tyr Val
            215                 220                 225

Met Ala Ser Phe Tyr Ser Thr Ser Thr Pro Phe Leu Ser Leu Pro
            230                 235                 240

Glu
```

<210> 8
<211> 1715
<212> DNA
<213> Homo sapiens

<400> 8
 gcgcctgcct ccaacctgcg ggcgggaggt gggtggctgc ggggcaattg      50

UNITED STATES PATENT AND TRADEMARK OFFICE
CERTIFICATE OF CORRECTION

PATENT NO.         : 7,153,828 B2
APPLICATION NO.    : 10/453183
DATED              : December 26, 2006
INVENTOR(S)        : Sliwkowski et al.

It is certified that error appears in the above-identified patent and that said Letters Patent is hereby corrected as shown below:

```
aaaaagagcc ggcgaggagt tccccgaaac ttgttggaac tccgggctcg      100
cgcggaggcc aggagctgag cggcggcggc tgccggacga tgggagcgtg      150
agcaggacgg tgataacctc tccccgatcg ggttgcgagg gcgccgggca      200
gaggccagga cgcgagccgc cagcggcggg accatcgac  gacttcccgg      250 ggcgacagga gcagcccga  gagccagggc gagcgcccgt tccaggtggc      300
cggaccgccc gccgcgtccg cgccgcgctc cctgcaggca acgggagacg      350
cccccgcgca gcgcgagcgc ctcagcgcgg ccgctcgctc tccccatcga      400
gggacaaact tttcccaaac ccgatccgag cccttggacc aaactcgcct      450
gcgccgagag ccgtccgcgt agagcgctcc gtctccggcg ag    atg       495
                                                  Met
                                                   1 tcc gag cgc aaa gaa ggc aga ggc aaa ggg aag ggc aag          534
Ser Glu Arg Lys Glu Gly Arg Gly Lys Gly Lys Gly Lys
             5                      10 aag aag gag cga ggc tcc ggc aag aag ccg gag tcc gcg          573
Lys Lys Glu Arg Gly Ser Gly Lys Lys Pro Glu Ser Ala
 15                  20                  25 gcg ggc agc cag agc cca gcc ttg cct ccc caa ttg aaa          612
Ala Gly Ser Gln Ser Pro Ala Leu Pro Pro Gln Leu Lys
             30                  35                  40 gag atg aaa agc cag gaa tcg gct gca ggt tcc aaa cta          651
Glu Met Lys Ser Gln Glu Ser Ala Ala Gly Ser Lys Leu
                 45                      50
```

UNITED STATES PATENT AND TRADEMARK OFFICE
CERTIFICATE OF CORRECTION

PATENT NO.        : 7,153,828 B2
APPLICATION NO.   : 10/453183
DATED             : December 26, 2006
INVENTOR(S)       : Sliwkowski et al.

It is certified that error appears in the above-identified patent and that said Letters Patent is hereby corrected as shown below:

```
gtc ctt cgg tgt gaa acc agt tct gaa tac tcc tct ctc       690
Val Leu Arg Cys Glu Thr Ser Ser Glu Tyr Ser Ser Leu
    55              60              65 aga ttc aag tgg ttc aag aat ggg aat gaa ttg aat cga       729
Arg Phe Lys Trp Phe Lys Asn Gly Asn Glu Leu Asn Arg
            70              75 aaa aac aaa cca caa aat atc aag ata caa aaa aag cca       768
Lys Asn Lys Pro Gln Asn Ile Lys Ile Gln Lys Lys Pro
80              85              90 ggg aag tca gaa ctt cgc att aac aaa gca tca ctg gct       807
Gly Lys Ser Glu Leu Arg Ile Asn Lys Ala Ser Leu Ala
        95              100             105 gat tct gga gag tat atg tgc aaa gtg atc agc aaa tta       846
Asp Ser Gly Glu Tyr Met Cys Lys Val Ile Ser Lys Leu
                110             115 gga aat gac agt gcc tct gcc aat atc acc atc gtg gaa       885
Gly Asn Asp Ser Ala Ser Ala Asn Ile Thr Ile Val Glu
    120             125             130 tca aac gag atc atc act ggt atg cca gcc tca act gaa       924
Ser Asn Glu Ile Ile Thr Gly Met Pro Ala Ser Thr Glu
        135             140 gga gca tat gtg tct tca gag tct ccc att aga ata tca       963
Gly Ala Tyr Val Ser Ser Glu Ser Pro Ile Arg Ile Ser
145             150             155 gta tcc aca gaa gga gca aat act tct tca tct aca tct      1002
Val Ser Thr Glu Gly Ala Asn Thr Ser Ser Ser Thr Ser
    160             165             170
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
aca tcc acc act ggg aca agc cat ctt gta aaa tgt gcg              1041
Thr Ser Thr Thr Gly Thr Ser His Leu Val Lys Cys Ala
            175                     180 gag aag gag aaa act ttc tgt gtg aat gga ggg gag tgc              1080
Glu Lys Glu Lys Thr Phe Cys Val Asn Gly Gly Glu Cys
        185                     190                 195 ttc atg gtg aaa gac ctt tca aac ccc tcg aga tac ttg              1119
Phe Met Val Lys Asp Leu Ser Asn Pro Ser Arg Tyr Leu
                200                     205 tgc aag tgc cca aat gag ttt act ggt gat cgc tgc caa              1158
Cys Lys Cys Pro Asn Glu Phe Thr Gly Asp Arg Cys Gln
210                     215                     220 aac tac gta atg gcc agc ttc tac agt acg tcc act ccc              1197
Asn Tyr Val Met Ala Ser Phe Tyr Ser Thr Ser Thr Pro
                225                     230                 235 ttt ctg tct ctg cct gaa tagga gcatgctcag ttggtgctgc              1240
Phe Leu Ser Leu Pro Glu
                240 241 tttcttgttg ctgcatctcc cctcagattc cacctagagc tagatgtgtc           1290
ttaccagatc taatattgac tgcctctgcc tgtcgcatga gaacattaac           1340
aaaagcaatt gtattacttc ctctgttcgc gactagttgg ctctgagata           1390
ctaataggtg tgtgaggctc cggatgtttc tggaattgat attgaatgat           1440
gtgatacaaa ttgatagtca atatcaagca gtgaaatatg ataataaagg           1490
catttcaaag tctcactttt attgataaaa taaaatcat tctactgaac           1540
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
agtccatctt ctttatacaa tgaccacatc ctgaaaaggg tgttgctaag    1590
ctgtaaccga tatgcacttg aaatgatggt aagttaattt tgattcagaa    1640
tgtgttattt gtcacaaata aacataataa aaggagttca gatgttttc     1690 ttcattaacc aaaaaaaaaa aaaaa                                1715

<210> 9
<211> 420
<212> PRT
<213> Homo sapiens

<400> 9
   Met Ser Glu Arg Lys Glu Gly Arg Gly Lys Gly Lys Lys
    1               5                  10              15

Lys Glu Arg Gly Ser Gly Lys Lys Pro Glu Ser Ala Ala Gly Ser
                    20                  25              30

Gln Ser Pro Ala Leu Pro Pro Gln Leu Lys Glu Met Lys Ser Gln
                    35                  40              45

Glu Ser Ala Ala Gly Ser Lys Leu Val Leu Arg Cys Glu Thr Ser
                    50                  55              60

Ser Glu Tyr Ser Ser Leu Arg Phe Lys Trp Phe Lys Asn Gly Asn
                    65                  70              75

Glu Leu Asn Arg Lys Asn Lys Pro Gln Asn Ile Lys Ile Gln Lys
                    80                  85              90

Lys Pro Gly Lys Ser Glu Leu Arg Ile Asn Lys Ala Ser Leu Ala
                    95                 100             105
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Asp Ser Gly Glu Tyr Met Cys Lys Val Ile Ser Lys Leu Gly Asn
                110                 115                 120

Asp Ser Ala Ser Ala Asn Ile Thr Ile Val Glu Ser Asn Glu Ile
                125                 130                 135

Ile Thr Gly Met Pro Ala Ser Thr Glu Gly Ala Tyr Val Ser Ser
                140                 145                 150

Glu Ser Pro Ile Arg Ile Ser Val Ser Thr Glu Gly Ala Asn Thr
                155                 160                 165

Ser Ser Ser Thr Ser Thr Ser Thr Thr Gly Thr Ser His Leu Val
                170                 175                 180

Lys Cys Ala Glu Lys Glu Lys Thr Phe Cys Val Asn Gly Gly Glu
                185                 190                 195

Cys Phe Met Val Lys Asp Leu Ser Asn Pro Ser Arg Tyr Leu Cys
                200                 205                 210

Lys Cys Pro Asn Glu Phe Thr Gly Asp Arg Cys Gln Asn Tyr Val
                215                 220                 225

Met Ala Ser Phe Tyr Lys Ala Glu Glu Leu Tyr Gln Lys Arg Val
                230                 235                 240

Leu Thr Ile Thr Gly Ile Cys Ile Ala Leu Leu Val Val Gly Ile
                245                 250                 255

Met Cys Val Val Ala Tyr Cys Lys Thr Lys Lys Gln Arg Lys Lys
                260                 265                 270

Leu His Asp Arg Leu Arg Gln Ser Leu Arg Ser Glu Arg Asn Asn
                275                 280                 285
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
       Met Met Asn Ile Ala Asn Gly Pro His His Pro Asn Pro Pro Pro
                       290             295             300

Glu Asn Val Gln Leu Val Asn Gln Tyr Val Ser Lys Asn Val Ile
                       305             310             315

Ser Ser Glu His Ile Val Glu Arg Glu Ala Glu Thr Ser Phe Ser
                       320             325             330

Thr Ser His Tyr Thr Ser Thr Ala His His Ser Thr Thr Val Thr
                       335             340             345

Gln Thr Pro Ser His Ser Trp Ser Asn Gly His Thr Glu Ser Ile
                       350             355             360

Leu Ser Glu Ser His Ser Val Ile Val Met Ser Ser Val Glu Asn
                       365             370             375

Ser Arg His Ser Ser Pro Thr Gly Gly Pro Arg Gly Arg Leu Asn
                       380             385             390

Gly Thr Gly Gly Pro Arg Glu Cys Asn Ser Phe Leu Arg His Ala
                       395             400             405

Arg Glu Thr Pro Asp Ser Tyr Arg Asp Ser Pro His Ser Glu Arg
                       410             415             420

<210> 10
   <211> 2431
   <212> DNA
   <213> Homo sapiens

<400> 10
     gaggcgcctg cctccaacct gcgggcggga ggtgggtggc tgcggggcaa        50
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
ttgaaaaaga gccggcgagg agttccccga aacttgttgg aactccgggc      100
tcgcgcggag gccaggagct gagcggcggc ggctgccgga cgatgggagc      150
gtgagcagga cggtgataac ctctccccga tcgggttgcg agggcgccgg      200
gcagaggcca ggacgcgagc cgccagcggc gggacccatc gacgacttcc      250
cggggcgaca ggagcagccc cgagagccag ggcgagcgcc cgttccaggt      300
ggccggaccg cccgccgcgt ccgcgccgcg ctccctgcag gcaacgggag      350 acgccccgc gcagcgcgag cgcctcagcg cggccgctcg ctctccccat       400
cgagggacaa acttttccca aacccgatcc gagcccttgg accaaactcg      450
cctgcgccga gagccgtccg cgtagagcgc tccgtctccg gcgag   atg     498
                                                      Met
                                                      1 tcc gag cgc aaa gaa ggc aga ggc aaa ggg aag ggc aag         537
Ser Glu Arg Lys Glu Gly Arg Gly Lys Gly Lys Gly Lys
                5                   10 aag aag gag cga ggc tcc ggc aag aag ccg gag tcc gcg         576
Lys Lys Glu Arg Gly Ser Gly Lys Lys Pro Glu Ser Ala
 15                      20                  25 gcg ggc agc cag agc cca gcc ttg cct ccc caa ttg aaa         615
Ala Gly Ser Gln Ser Pro Ala Leu Pro Pro Gln Leu Lys
             30                  35                  40 gag atg aaa agc cag gaa tcg gct gca ggt tcc aaa cta         654
Glu Met Lys Ser Gln Glu Ser Ala Ala Gly Ser Lys Leu
                 45                      50
```

Page 40 of 67

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
gtc ctt cgg tgt gaa acc agt tct gaa tac tcc tct ctc        693
Val Leu Arg Cys Glu Thr Ser Ser Glu Tyr Ser Ser Leu
    55                  60                  65 aga ttc aag tgg ttc aag aat ggg aat gaa ttg aat cga        732
Arg Phe Lys Trp Phe Lys Asn Gly Asn Glu Leu Asn Arg
            70                  75 aaa aac aaa cca caa aat atc aag ata caa aaa aag cca        771
Lys Asn Lys Pro Gln Asn Ile Lys Ile Gln Lys Lys Pro
 80                  85                  90 ggg aag tca gaa ctt cgc att aac aaa gca tca ctg gct        810
Gly Lys Ser Glu Leu Arg Ile Asn Lys Ala Ser Leu Ala
        95                  100                 105 gat tct gga gag tat atg tgc aaa gtg atc agc aaa tta        849
Asp Ser Gly Glu Tyr Met Cys Lys Val Ile Ser Lys Leu
                110                 115 gga aat gac agt gcc tct gcc aat atc acc atc gtg gaa        888
Gly Asn Asp Ser Ala Ser Ala Asn Ile Thr Ile Val Glu
        120                 125                 130 tca aac gag atc atc act ggt atg cca gcc tca act gaa        927
Ser Asn Glu Ile Ile Thr Gly Met Pro Ala Ser Thr Glu
            135                 140 gga gca tat gtg tct tca gag tct ccc att aga ata tca        966
Gly Ala Tyr Val Ser Ser Glu Ser Pro Ile Arg Ile Ser
145                 150                 155 gta tcc aca gaa gga gca aat act tct tca tct aca tct      1005
Val Ser Thr Glu Gly Ala Asn Thr Ser Ser Ser Thr Ser
        160                 165                 170
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

| | | | | | | | | | | | | |
|---|---|---|---|---|---|---|---|---|---|---|---|---|
| aca | tcc | acc | act | ggg | aca | agc | cat | ctt | gta | aaa | tgt | gcg | 1044 |
| Thr | Ser | Thr | Thr | Gly | Thr | Ser | His | Leu | Val | Lys | Cys | Ala | |
| | | | | 175 | | | | | 180 | | | | |
| gag | aag | gag | aaa | act | ttc | tgt | gtg | aat | gga | ggg | gag | tgc | 1083 |
| Glu | Lys | Glu | Lys | Thr | Phe | Cys | Val | Asn | Gly | Gly | Glu | Cys | |
| | 185 | | | | | 190 | | | | | 195 | | |
| ttc | atg | gtg | aaa | gac | ctt | tca | aac | ccc | tcg | aga | tac | ttg | 1122 |
| Phe | Met | Val | Lys | Asp | Leu | Ser | Asn | Pro | Ser | Arg | Tyr | Leu | |
| | | | 200 | | | | | 205 | | | | | |
| tgc | aag | tgt | cca | aat | gag | ttt | act | ggt | gat | cgc | tgc | caa | 1161 |
| Cys | Lys | Cys | Pro | Asn | Glu | Phe | Thr | Gly | Asp | Arg | Cys | Gln | |
| 210 | | | | | 215 | | | | | 220 | | | |
| aac | tac | gta | atg | gcc | agc | ttc | tac | aag | gcg | gag | gag | ctg | 1200 |
| Asn | Tyr | Val | Met | Ala | Ser | Phe | Tyr | Lys | Ala | Glu | Glu | Leu | |
| | | 225 | | | | | 230 | | | | | 235 | |
| tac | cag | aag | aga | gtg | ctg | acc | ata | acc | ggc | atc | tgc | atc | 1239 |
| Tyr | Gln | Lys | Arg | Val | Leu | Thr | Ile | Thr | Gly | Ile | Cys | Ile | |
| | | | | 240 | | | | | 245 | | | | |
| gcc | ctc | ctt | gtg | gtc | ggc | atc | atg | tgt | gtg | gtg | gcc | tac | 1278 |
| Ala | Leu | Leu | Val | Val | Gly | Ile | Met | Cys | Val | Val | Ala | Tyr | |
| | 250 | | | | | 255 | | | | | 260 | | |
| tgc | aaa | acc | aag | aaa | cag | cgg | aaa | aag | ctg | cat | gac | cgt | 1317 |
| Cys | Lys | Thr | Lys | Lys | Gln | Arg | Lys | Lys | Leu | His | Asp | Arg | |
| | | | 265 | | | | | 270 | | | | | |
| ctt | cgg | cag | agc | ctt | cgg | tct | gaa | cga | aac | aat | atg | atg | 1356 |
| Leu | Arg | Gln | Ser | Leu | Arg | Ser | Glu | Arg | Asn | Asn | Met | Met | |
| 275 | | | | | 280 | | | | | 285 | | | |

UNITED STATES PATENT AND TRADEMARK OFFICE
CERTIFICATE OF CORRECTION

| | |
|---|---|
| PATENT NO. | : 7,153,828 B2 |
| APPLICATION NO. | : 10/453183 |
| DATED | : December 26, 2006 |
| INVENTOR(S) | : Sliwkowski et al. |

Page 43 of 67

It is certified that error appears in the above-identified patent and that said Letters Patent is hereby corrected as shown below:

| | | | | | | | | | | | | |
|---|---|---|---|---|---|---|---|---|---|---|---|---|
| aac | att | gcc | aat | ggg | cct | cac | cat | cct | aac | cca | ccc | ccc | 1395 |
| Asn | Ile | Ala | Asn | Gly | Pro | His | His | Pro | Asn | Pro | Pro | Pro | |
| | | 290 | | | | | 295 | | | | | 300 | |

| | | | | | | | | | | | |
|---|---|---|---|---|---|---|---|---|---|---|---|
| gag | aat | gtc | cag | ctg | gtg | aat | caa | tac | gta | tct | aaa | aac | 1434 |
| Glu | Asn | Val | Gln | Leu | Val | Asn | Gln | Tyr | Val | Ser | Lys | Asn | |
| | | | | 305 | | | | | 310 | | | | |

| | | | | | | | | | | | |
|---|---|---|---|---|---|---|---|---|---|---|---|
| gtc | atc | tcc | agt | gag | cat | att | gtt | gag | aga | gaa | gca | gag | 1473 |
| Val | Ile | Ser | Ser | Glu | His | Ile | Val | Glu | Arg | Glu | Ala | Glu | |
| | 315 | | | | | 320 | | | | | 325 | | |

| | | | | | | | | | | | |
|---|---|---|---|---|---|---|---|---|---|---|---|
| aca | tcc | ttt | tcc | acc | agt | cac | tat | act | tcc | aca | gcc | cat | 1512 |
| Thr | Ser | Phe | Ser | Thr | Ser | His | Tyr | Thr | Ser | Thr | Ala | His | |
| | | | 330 | | | | | 335 | | | | | |

| | | | | | | | | | | | |
|---|---|---|---|---|---|---|---|---|---|---|---|
| cac | tcc | act | act | gtc | acc | cag | act | cct | agc | cac | agc | tgg | 1551 |
| His | Ser | Thr | Thr | Val | Thr | Gln | Thr | Pro | Ser | His | Ser | Trp | |
| 340 | | | | | 345 | | | | | 350 | | | |

| | | | | | | | | | | | |
|---|---|---|---|---|---|---|---|---|---|---|---|
| agc | aac | gga | cac | act | gaa | agc | atc | ctt | tcc | gaa | agc | cac | 1590 |
| Ser | Asn | Gly | His | Thr | Glu | Ser | Ile | Leu | Ser | Glu | Ser | His | |
| | | 355 | | | | | 360 | | | | | 365 | |

| | | | | | | | | | | | |
|---|---|---|---|---|---|---|---|---|---|---|---|
| tct | gta | atc | gtg | atg | tca | tcc | gta | gaa | aac | agt | agg | cac | 1629 |
| Ser | Val | Ile | Val | Met | Ser | Ser | Val | Glu | Asn | Ser | Arg | His | |
| | | | | 370 | | | | | 375 | | | | |

| | | | | | | | | | | | |
|---|---|---|---|---|---|---|---|---|---|---|---|
| agc | agc | cca | act | ggg | ggc | cca | aga | gga | cgt | ctt | aat | ggc | 1668 |
| Ser | Ser | Pro | Thr | Gly | Gly | Pro | Arg | Gly | Arg | Leu | Asn | Gly | |
| | | 380 | | | | | 385 | | | | | 390 | |

| | | | | | | | | | | | |
|---|---|---|---|---|---|---|---|---|---|---|---|
| aca | gga | ggc | cct | cgt | gaa | tgt | aac | agc | ttc | ctc | agg | cat | 1707 |
| Thr | Gly | Gly | Pro | Arg | Glu | Cys | Asn | Ser | Phe | Leu | Arg | His | |
| | | | 395 | | | | | 400 | | | | | |

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
gcc aga gaa acc cct gat tcc tac cga gac tct cct cat    1746
Ala Arg Glu Thr Pro Asp Ser Tyr Arg Asp Ser Pro His
405                 410             415 agt gaa agg taaaa ccgaaggcaa agctactgca gaggagaaac      1790
Ser Glu Arg
        420 tcagtcagag aatccctgtg agcacctgcg gtctcacctc aggaaatcta  1840 ctctaatcag aataagggc ggcagttacc tgttctagga gtgctcctag   1890 ttgatgaagt catctctttg tttgacggaa cttatttctt ctgagcttct  1940 ctcgtcgtcc cagtgactga caggcaacag actcttaaag agctgggatg  1990 ctttgatgcg gaaggtgcag cacatggagt ttccagctct ggccatgggc  2040 tcagacccac tcggggtctc agtgtcctca gttgtaacat tagagagatg  2090 gcatcaatgc ttgataagga cccttctata attccaattg ccagttatcc  2140 aaactctgat tcggtggtcg agctggcctc gtgttcttat ctgctaaccc  2190 tgtcttacct tccagcctca gttaagtcaa atcaagggct atgtcattgc  2240 tgaatgtcat gggggcaac tgcttgccct ccaccctata gtatctattt   2290 tatgaaattc caagaaggga tgaataaata aatctcttgg atgctgcgtc  2340 tggcagtctt cacgggtggt tttcaaagca gaaaaaaaaa aaaaaaaaa   2390 aaaaaaaaaa aaaaaaaaaa aaaaaaaaaa aaaaaaaaa a           2431
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
<210> 11
<211> 768
<212> PRT
<213> Homo sapiens

<400> 11
 Met Asp Val Lys Glu Arg Lys Pro Tyr Arg Ser Leu Thr Arg Arg
  1               5                  10                  15

Arg Asp Ala Glu Arg Arg Tyr Thr Ser Ser Ala Asp Ser Glu
                  20                  25                  30

Glu Gly Lys Ala Pro Gln Lys Ser Tyr Ser Ser Glu Thr Leu
                  35                  40                  45

Lys Ala Tyr Asp Gln Asp Ala Arg Leu Ala Tyr Gly Ser Arg Val
                      50                  55                  60

Lys Asp Ile Val Pro Gln Glu Ala Glu Phe Cys Arg Thr Gly
                  65                  70                  75

Ala Asn Phe Thr Leu Arg Glu Leu Gly Leu Glu Glu Val Thr Pro
                      80                  85                  90

Pro His Gly Thr Leu Tyr Arg Thr Asp Ile Gly Leu Pro His Cys
                      95                 100                 105

Gly Tyr Ser Met Gly Ala Gly Ser Asp Ala Asp Met Glu Ala Asp
                     110                 115                 120

Thr Val Leu Ser Pro Glu His Pro Val Arg Leu Trp Gly Arg Ser
                     125                 130                 135

Thr Arg Ser Gly Arg Ser Ser Cys Leu Ser Ser Arg Ala Asn Ser
                     140                 145                 150
```

UNITED STATES PATENT AND TRADEMARK OFFICE
CERTIFICATE OF CORRECTION

PATENT NO.       : 7,153,828 B2
APPLICATION NO.  : 10/453183
DATED            : December 26, 2006
INVENTOR(S)      : Sliwkowski et al.

It is certified that error appears in the above-identified patent and that said Letters Patent is hereby corrected as shown below:

```
Asn Leu Thr Leu Thr Asp Thr Glu His Glu Asn Thr Glu Thr Asp
                155             160             165

His Pro Gly Gly Leu Gln Asn His Ala Arg Leu Arg Thr Pro Pro
                170             175             180

Pro Pro Leu Ser His Ala His Thr Pro Asn Gln His His Ala Ala
                185             190             195

Ser Ile Asn Ser Leu Asn Arg Gly Asn Phe Thr Pro Arg Ser Asn
                200             205             210

Pro Ser Pro Ala Pro Thr Asp His Ser Leu Ser Gly Glu Pro Pro
                215             220             225

Ala Gly Gly Ala Gln Glu Pro Ala His Ala Gln Glu Asn Trp Leu
                230             235             240

Leu Asn Ser Asn Ile Pro Leu Glu Thr Arg Asn Leu Gly Lys Gln
                245             250             255

Pro Phe Leu Gly Thr Leu Gln Asp Asn Leu Ile Glu Met Asp Ile
                260             265             270

Leu Gly Ala Ser Arg His Asp Gly Ala Tyr Ser Asp Gly His Phe
                275             280             285

Leu Phe Lys Pro Gly Gly Thr Ser Pro Leu Phe Cys Thr Thr Ser
                290             295             300

Pro Gly Tyr Pro Leu Thr Ser Ser Thr Val Tyr Ser Pro Pro Pro
                305             310             315

Arg Pro Leu Pro Arg Ser Thr Phe Ala Arg Pro Ala Phe Asn Leu
                320             325             330
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Lys Lys Pro Ser Lys Tyr Cys Asn Trp Lys Cys Ala Ala Leu Ser
            335             340                 345
Ala Ile Val Ile Ser Ala Thr Leu Val Ile Leu Leu Ala Tyr Phe
            350             355                 360
Val Ala Met His Leu Phe Gly Leu Asn Trp His Leu Gln Pro Met
            365             370                 375
Glu Gly Gln Met Tyr Glu Ile Thr Glu Asp Thr Ala Ser Ser Trp
            380             385                 390
Pro Val Pro Thr Asp Val Ser Leu Tyr Pro Ser Gly Gly Thr Gly
            395             400                 405
Leu Glu Thr Pro Asp Arg Lys Gly Lys Gly Thr Thr Glu Gly Lys
            410             415                 420
Pro Ser Ser Phe Phe Pro Glu Asp Ser Phe Ile Asp Ser Gly Glu
            425             430                 435
Ile Asp Val Gly Arg Arg Ala Ser Gln Lys Ile Pro Pro Gly Thr
            440             445                 450
Phe Trp Arg Ser Gln Val Phe Ile Asp His Pro Val His Leu Lys
            455             460                 465
Phe Asn Val Ser Leu Gly Lys Ala Ala Leu Val Gly Ile Tyr Gly
            470             475                 480
Arg Lys Gly Leu Pro Pro Ser His Thr Gln Phe Asp Phe Val Glu
            485             490                 495
Leu Leu Asp Gly Arg Arg Leu Leu Thr Gln Glu Ala Arg Ser Leu
            500             505                 510
```

UNITED STATES PATENT AND TRADEMARK OFFICE
CERTIFICATE OF CORRECTION

PATENT NO.        : 7,153,828 B2
APPLICATION NO.   : 10/453183
DATED             : December 26, 2006
INVENTOR(S)       : Sliwkowski et al.

It is certified that error appears in the above-identified patent and that said Letters Patent is hereby corrected as shown below:

```
Glu Gly Thr Pro Arg Gln Ser Arg Gly Thr Val Pro Pro Ser Ser
                515                 520                 525

His Glu Thr Gly Phe Ile Gln Tyr Leu Asp Ser Gly Ile Trp His
                530                 535                 540

Leu Ala Phe Tyr Asn Asp Gly Lys Glu Ser Glu Val Val Ser Phe
                545                 550                 555

Leu Thr Thr Ala Ile Ala Leu Pro Pro Arg Leu Lys Glu Met Lys
                560                 565                 570

Ser Gln Glu Ser Ala Ala Gly Ser Lys Leu Val Leu Arg Cys Glu
                575                 580                 585

Thr Ser Ser Glu Tyr Ser Ser Leu Arg Phe Lys Trp Phe Lys Asn
                590                 595                 600

Gly Asn Glu Leu Asn Arg Lys Asn Lys Pro Gln Asn Ile Lys Ile
                605                 610                 615

Gln Lys Lys Pro Gly Lys Ser Glu Leu Arg Ile Asn Lys Ala Ser
                620                 625                 630

Leu Ala Asp Ser Gly Glu Tyr Met Cys Lys Val Ile Ser Lys Leu
                635                 640                 645

Gly Asn Asp Ser Ala Ser Ala Asn Ile Thr Ile Val Glu Ser Asn
                650                 655                 660

Glu Ile Ile Thr Gly Met Pro Ala Ser Thr Glu Gly Ala Tyr Val
                665                 670                 675

Ser Ser Glu Ser Pro Ile Arg Ile Ser Val Ser Thr Glu Gly Ala
                680                 685                 690
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Asn Thr Ser Ser Ser Thr Ser Thr Ser Thr Thr Gly Thr Ser His
            695             700                     705

Leu Val Lys Cys Ala Glu Lys Glu Lys Thr Phe Cys Val Asn Gly
            710             715                     720

Gly Glu Cys Phe Met Val Lys Asp Leu Ser Asn Pro Ser Arg Tyr
            725             730                     735

Leu Cys Lys Cys Pro Asn Glu Phe Thr Gly Asp Arg Cys Gln Asn
            740             745                     750

Tyr Val Met Ala Ser Phe Tyr Ser Thr Ser Thr Pro Phe Leu Ser
            755             760                     765

Leu Pro Glu

<210> 12
<211> 3111
<212> DNA
<213> Homo sapiens

<400> 12
  gggtaccatg ggtcggtgag cgcgtttccc gcctgagcgc aactagcggc    50
gggtcgtggg cacctccaga aaagatcccg caccatcctc caggatccaa   100
tggccttgga gagagggctg cagggcccac ggacattgct gactcttcag   150
aacgtgctga catggagcca ggtagactga aattatcatg tgtccaaatt   200
aaaattgcat acttcaagga ttatttgaag gactattctt agacccttt    250
```

UNITED STATES PATENT AND TRADEMARK OFFICE
CERTIFICATE OF CORRECTION

PATENT NO.       : 7,153,828 B2
APPLICATION NO.  : 10/453183
DATED            : December 26, 2006
INVENTOR(S)      : Sliwkowski et al.

It is certified that error appears in the above-identified patent and that said Letters Patent is hereby corrected as shown below:

```
aagaagattt aaagaaaaac cactcggccc tgagtgcggc gaggaccctg         300
tttgtggatg tggaggagcg cgggccggag gcc     atg gac gtg           342
                                         Met Asp Val
                                          1 aag gag agg aag cct tac cgc tcg ctg acc cgg cgc cgc            381
Lys Glu Arg Lys Pro Tyr Arg Ser Leu Thr Arg Arg Arg
     5               10               15 gac gcc gag cgc cgc tac acc agc tcg tcc gcg gac agc            420
Asp Ala Glu Arg Arg Tyr Thr Ser Ser Ser Ala Asp Ser
             20              25 gag gag ggc aaa gcc ccg cag aaa tcg tac agc tcc agc            459
Glu Glu Gly Lys Ala Pro Gln Lys Ser Tyr Ser Ser Ser
 30               35               40 gag acc ctg aag gcc tac gac cag gac gcc cgc cta gcc            498
Glu Thr Leu Lys Ala Tyr Asp Gln Asp Ala Arg Leu Ala
         45              50               55 tat ggc agc cgc gtc aag gac att gtg ccg cag gag gcc            537
Tyr Gly Ser Arg Val Lys Asp Ile Val Pro Gln Glu Ala
                 60               65 gag gaa ttc tgc cgc aca ggt gcc aac ttc acc ctg cgg            576
Glu Glu Phe Cys Arg Thr Gly Ala Asn Phe Thr Leu Arg
 70               75               80 gag ctg ggg ctg gaa gaa gta acg ccc cct cac ggg acc            615
Glu Leu Gly Leu Glu Glu Val Thr Pro Pro His Gly Thr
         85              90
```

UNITED STATES PATENT AND TRADEMARK OFFICE
CERTIFICATE OF CORRECTION

| | | |
|---|---|---|
| PATENT NO. | : 7,153,828 B2 | |
| APPLICATION NO. | : 10/453183 | |
| DATED | : December 26, 2006 | |
| INVENTOR(S) | : Sliwkowski et al. | |

It is certified that error appears in the above-identified patent and that said Letters Patent is hereby corrected as shown below:

```
ctg tac cgg aca gac att ggc ctc ccc cac tgc ggc tac          654
Leu Tyr Arg Thr Asp Ile Gly Leu Pro His Cys Gly Tyr
 95              100             105 tcc atg ggg gct ggc tct gat gcc gac atg gag gct gac          693
Ser Met Gly Ala Gly Ser Asp Ala Asp Met Glu Ala Asp
    110             115             120 acg gtg ctg tcc cct gag cac ccc gtg cgt ctg tgg ggc          732
Thr Val Leu Ser Pro Glu His Pro Val Arg Leu Trp Gly
                125             130 cgg agc aca cgg tca ggg cgc agc tcc tgc ctg tcc agc          771
Arg Ser Thr Arg Ser Gly Arg Ser Ser Cys Leu Ser Ser
135             140             145 cgg gcc aat tcc aat ctc aca ctc acc gac acc gag cat          810
Arg Ala Asn Ser Asn Leu Thr Leu Thr Asp Thr Glu His
        150             155 gaa aac act gag act gat cat ccg ggc ggc ctg cag aac          849
Glu Asn Thr Glu Thr Asp His Pro Gly Gly Leu Gln Asn
160             165             170 cac gcg cgg ctc cgg acg ccg ccg ccg ctc tcg cac              888
His Ala Arg Leu Arg Thr Pro Pro Pro Leu Ser His
        175             180             185 gcc cac acc ccc aac cag cac cac gcg gcc tcc att aac          927
Ala His Thr Pro Asn Gln His His Ala Ala Ser Ile Asn
                190             195 tcc ctg aac cgg ggc aac ttc acg ccg agg agc aac ccc          966
Ser Leu Asn Arg Gly Asn Phe Thr Pro Arg Ser Asn Pro
    200             205             210
```

UNITED STATES PATENT AND TRADEMARK OFFICE
CERTIFICATE OF CORRECTION

PATENT NO. : 7,153,828 B2  
APPLICATION NO. : 10/453183  
DATED : December 26, 2006  
INVENTOR(S) : Sliwkowski et al.

It is certified that error appears in the above-identified patent and that said Letters Patent is hereby corrected as shown below:

```
agc ccg gcc ccc acg gac cac tcg ctc tcc gga gag ccc           1005
Ser Pro Ala Pro Thr Asp His Ser Leu Ser Gly Glu Pro
            215                 220 cct gcc ggc ggc gcc cag gag cct gcc cac gcc cag gag           1044
Pro Ala Gly Gly Ala Gln Glu Pro Ala His Ala Gln Glu
225                 230                 235 aac tgg ctg ctc aac agc aac atc ccc ctg gag acc aga           1083
Asn Trp Leu Leu Asn Ser Asn Ile Pro Leu Glu Thr Arg
            240                 245                 250 aac cta ggc aag cag cca ttc cta ggg aca ttg cag gac           1122
Asn Leu Gly Lys Gln Pro Phe Leu Gly Thr Leu Gln Asp
                255                 260 aac ctc att gag atg gac att ctc ggc gcc tcc cgc cat           1161
Asn Leu Ile Glu Met Asp Ile Leu Gly Ala Ser Arg His
        265                 270                 275 gat ggg gct tac agt gac ggg cac ttc ctc ttc aag cct           1200
Asp Gly Ala Tyr Ser Asp Gly His Phe Leu Phe Lys Pro
                280                 285 gga ggc acc tcc ccg ctc ttc tgc acc aca tca cca ggg           1239
Gly Gly Thr Ser Pro Leu Phe Cys Thr Thr Ser Pro Gly
290                 295                 300 tac cca ctg acg tcc agc aca gtg tac tct cct ccg ccc           1278
Tyr Pro Leu Thr Ser Ser Thr Val Tyr Ser Pro Pro Pro
                305                 310                 315 cga ccc ctg ccc cgc agc acc ttc gcc cgg ccg gcc ttt           1317
Arg Pro Leu Pro Arg Ser Thr Phe Ala Arg Pro Ala Phe
                320                 325
```

UNITED STATES PATENT AND TRADEMARK OFFICE
CERTIFICATE OF CORRECTION

PATENT NO.         : 7,153,828 B2                          Page 53 of 67
APPLICATION NO.    : 10/453183
DATED              : December 26, 2006
INVENTOR(S)        : Sliwkowski et al.

It is certified that error appears in the above-identified patent and that said Letters Patent is hereby corrected as shown below:

```
aac ctc aag aag ccc tcc aag tac tgt aac tgg aag tgc          1356
Asn Leu Lys Lys Pro Ser Lys Tyr Cys Asn Trp Lys Cys
    330             335             340 gca gcc ctg agc gcc atc gtc atc tca gcc act ctg gtc          1395
Ala Ala Leu Ser Ala Ile Val Ile Ser Ala Thr Leu Val
            345             350 atc ctg ctg gca tac ttt gtg gcc atg cac ctg ttt ggc          1434
Ile Leu Leu Ala Tyr Phe Val Ala Met His Leu Phe Gly
355             360             365 cta aac tgg cac ctg cag ccg atg gag ggg cag atg tat          1473
Leu Asn Trp His Leu Gln Pro Met Glu Gly Gln Met Tyr
        370             375             380 gag atc acg gag gac aca gcc agc agt tgg cct gtg cca          1512
Glu Ile Thr Glu Asp Thr Ala Ser Ser Trp Pro Val Pro
                385             390 acc gac gtc tcc cta tac ccc tca ggg ggc act ggc tta          1551
Thr Asp Val Ser Leu Tyr Pro Ser Gly Gly Thr Gly Leu
    395             400             405 gag acc cct gac agg aaa ggc aaa gga acc aca gaa gga          1590
Glu Thr Pro Asp Arg Lys Gly Lys Gly Thr Thr Glu Gly
            410             415 aag ccc agt agt ttc ttt cca gag gac agt ttc ata gat          1629
Lys Pro Ser Ser Phe Phe Pro Glu Asp Ser Phe Ile Asp
420             425             430 tct gga gaa att gat gtg gga agg cga gct tcc cag aag          1668
Ser Gly Glu Ile Asp Val Gly Arg Arg Ala Ser Gln Lys
        435             440             445
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
att cct cct ggc act ttc tgg aga tct caa gtg ttc ata         1707
Ile Pro Pro Gly Thr Phe Trp Arg Ser Gln Val Phe Ile
            450                 455 gac cat cct gtg cat ctg aaa ttc aat gtg tct ctg gga         1746
Asp His Pro Val His Leu Lys Phe Asn Val Ser Leu Gly
        460             465             470 aag gca gcc ctg gtt ggc att tat ggc aga aaa ggc ctc         1785
Lys Ala Ala Leu Val Gly Ile Tyr Gly Arg Lys Gly Leu
                475             480 cct cct tca cat aca cag ttt gac ttt gtg gag ctg ctg         1824
Pro Pro Ser His Thr Gln Phe Asp Phe Val Glu Leu Leu
485             490             495 gat ggc agg agg ctc cta acc cag gag gcg cgg agc cta         1863
Asp Gly Arg Arg Leu Leu Thr Gln Glu Ala Arg Ser Leu
        500             505                 510 gag ggg acc ccg cgc cag tct cgg gga act gtg ccc ccc         1902
Glu Gly Thr Pro Arg Gln Ser Arg Gly Thr Val Pro Pro
                515             520 tcc agc cat gag aca ggc ttc atc cag tat ttg gat tca         1941
Ser Ser His Glu Thr Gly Phe Ile Gln Tyr Leu Asp Ser
        525             530             535 gga atc tgg cac ttg gct ttt tac aat gac gga aag gag         1980
Gly Ile Trp His Leu Ala Phe Tyr Asn Asp Gly Lys Glu
            540             545 tca gaa gtg gtt tcc ttt ctc acc act gcc att gcc ttg         2019
Ser Glu Val Val Ser Phe Leu Thr Thr Ala Ile Ala Leu
550             555             560
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
cct ccc cga ttg aaa gag atg aaa agc cag gaa tcg gct        2058
Pro Pro Arg Leu Lys Glu Met Lys Ser Gln Glu Ser Ala
        565                 570                 575 gca ggt tcc aaa cta gtc ctt cgg tgt gaa acc agt tct        2097
Ala Gly Ser Lys Leu Val Leu Arg Cys Glu Thr Ser Ser
                580                 585 gaa tac tcc tct ctc aga ttc aag tgg ttc aag aat ggg        2136
Glu Tyr Ser Ser Leu Arg Phe Lys Trp Phe Lys Asn Gly
    590                 595                 600 aat gaa ttg aat cga aaa aac aaa cca caa aat atc aag        2175
Asn Glu Leu Asn Arg Lys Asn Lys Pro Gln Asn Ile Lys
                605                 610 ata caa aaa aag cca ggg aag tca gaa ctt cgc att aac        2214
Ile Gln Lys Lys Pro Gly Lys Ser Glu Leu Arg Ile Asn
615                 620                 625 aaa gca tca ctg gct gat tct gga gag tat atg tgc aaa        2253
Lys Ala Ser Leu Ala Asp Ser Gly Glu Tyr Met Cys Lys
        630                 635                 640 gtg atc agc aaa tta gga aat gac agt gcc tct gcc aat        2292
Val Ile Ser Lys Leu Gly Asn Asp Ser Ala Ser Ala Asn
                645                 650 atc acc atc gtg gaa tca aac gag atc atc act ggt atg        2331
Ile Thr Ile Val Glu Ser Asn Glu Ile Ile Thr Gly Met
    655                 660                 665 cca gcc tca act gaa gga gca tat gtg tct tca gag tct        2370
Pro Ala Ser Thr Glu Gly Ala Tyr Val Ser Ser Glu Ser
                670                 675
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
ccc att aga ata tca gta tcc aca gaa gga gca aat act         2409
Pro Ile Arg Ile Ser Val Ser Thr Glu Gly Ala Asn Thr
680             685                     690 tct tca tct aca tct aca tcc acc act ggg aca agc cat         2448
Ser Ser Ser Thr Ser Thr Ser Thr Thr Gly Thr Ser His
        695             700                     705 ctt gta aaa tgt gcg gag aag gag aaa act ttc tgt gtg         2487
Leu Val Lys Cys Ala Glu Lys Glu Lys Thr Phe Cys Val
                710                     715 aat gga ggg gag tgc ttc atg gtg aaa gac ctt tca aac         2526
Asn Gly Gly Glu Cys Phe Met Val Lys Asp Leu Ser Asn
        720             725                     730 ccc tcg aga tac ttg tgc aag tgc cca aat gag ttt act         2565
Pro Ser Arg Tyr Leu Cys Lys Cys Pro Asn Glu Phe Thr
            735                     740 ggt gat cgc tgc caa aac tac gta atg gcc agc ttc tac         2604
Gly Asp Arg Cys Gln Asn Tyr Val Met Ala Ser Phe Tyr
745                     750                     755 agt acg tcc act ccc ttt ctg tct ctg cct gaa tag             2640
Ser Thr Ser Thr Pro Phe Leu Ser Leu Pro Glu
        760                     765         768 gagcatgctc agttggtgct gctttcttgt tgctgcatct cccctcagat       2690
tccacctaga gctagatgtg tcttaccaga tctaatattg actgcctctg       2740
cctgtcgcat gagaacatta acaaaagcaa ttgtattact tcctctgttc       2790
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
gcgactagtt ggctctgaga tactaatagg tgtgtgaggc tccggatgtt      2840
tctggaattg atattgaatg atgtgataca aattgatagt caatatcaag      2890
cagtgaaata tgataataaa ggcatttcaa agtctcactt ttattgataa      2940
aataaaaatc attctactga acagtccatc ttctttatac aatgaccaca      2990
tcctgaaaag ggtgttgcta agctgtaacc gatatgcact tgaaatgatg      3040
gtaagttaat tttgattcag aatgtgttat ttgtcacaaa taaacataat      3090
aaaaggaaaa aaaaaaaaa a                                      3111

<210> 13
<211> 1872
<212> DNA
<213> Homo sapiens

<400> 13
 gaattcggga cagcctctcc tgccgccgct gctgctgccg ccgccgccac      50
cgccggctgg tcctccttct gcttttactt ctcctgcatg acagttgttt      100
tcttcatctg agcagacacc agcttcagat gctcgaggtg agaaacatgc      150
ctttcagttt gggctactgg tttacttaat taatcagccg gcagctccgt      200 cgatctatt tcgtccctgt cctcttgacg agcccgggat ggtttggagt       250
agcatttaaa agaactagaa aagtggccca gaaacagcag cttaaagaat      300
tattacgata tactttgatt ttgtagttgc taggagcttt tcttcccccc      350
```

UNITED STATES PATENT AND TRADEMARK OFFICE
CERTIFICATE OF CORRECTION

PATENT NO. : 7,153,828 B2  
APPLICATION NO. : 10/453183  
DATED : December 26, 2006  
INVENTOR(S) : Sliwkowski et al.

It is certified that error appears in the above-identified patent and that said Letters Patent is hereby corrected as shown below:

```
ttgcatcttt ctgaactctt cttgatttta ataatggcct tggacttgga      400
cgatttatcg atttccccct gtaagatgct gtatcatttg gttggggggg      450
cctctgcgtg gtaatggacc gtgagagcgg ccaggccttc ttctggaggt      500 gagccg  atg gag att tat tcc cca gac atg tct gag gtc        539
        Met Glu Ile Tyr Ser Pro Asp Met Ser Glu Val
         1               5                  10 gcc gcc gag agg tcc tcc agc ccc tcc act cag ctg agt        578
Ala Ala Glu Arg Ser Ser Ser Pro Ser Thr Gln Leu Ser
             15                  20 gca gac cca tct ctt gat ggg ctt ccg gca gca gaa gac        617
Ala Asp Pro Ser Leu Asp Gly Leu Pro Ala Ala Glu Asp
 25              30                  35 atg cca gag ccc cag act gaa gat ggg aga acc cct gga        656
Met Pro Glu Pro Gln Thr Glu Asp Gly Arg Thr Pro Gly
             40                  45              50 ctc gtg ggc ctg gcc gtg ccc tgc tgt gcg tgc cta gaa        695
Leu Val Gly Leu Ala Val Pro Cys Cys Ala Cys Leu Glu
                 55                  60 gct gag cgc ctg aga ggt tgc ctc aac tca gag aaa atc        734
Ala Glu Arg Leu Arg Gly Cys Leu Asn Ser Glu Lys Ile
         65                  70                  75 tgc att gtc ccc atc ctg gct tgc ctg gtc agc ctc tgc        773
Cys Ile Val Pro Ile Leu Ala Cys Leu Val Ser Leu Cys
             80                  85
```

UNITED STATES PATENT AND TRADEMARK OFFICE
CERTIFICATE OF CORRECTION

| | |
|---|---|
| PATENT NO. | : 7,153,828 B2 |
| APPLICATION NO. | : 10/453183 |
| DATED | : December 26, 2006 |
| INVENTOR(S) | : Sliwkowski et al. |

It is certified that error appears in the above-identified patent and that said Letters Patent is hereby corrected as shown below:

```
ctc tgc atc gcc ggc ctc aag tgg gta ttt gtg gac aag         812
Leu Cys Ile Ala Gly Leu Lys Trp Val Phe Val Asp Lys
 90              95                  100 atc ttt gaa tat gac tct cct act cac ctt gac cct ggg         851
Ile Phe Glu Tyr Asp Ser Pro Thr His Leu Asp Pro Gly
        105                 110                 115 ggg tta ggc cag gac cct att att tct ctg gac gca act         890
Gly Leu Gly Gln Asp Pro Ile Ile Ser Leu Asp Ala Thr
                120             125 gct gcc tca gct gtg tgg gtg tcg tct gag gca tac act         929
Ala Ala Ser Ala Val Trp Val Ser Ser Glu Ala Tyr Thr
        130             135                 140 tca cct gtc tct agg gct caa tct gaa agt gag gtt caa         968
Ser Pro Val Ser Arg Ala Gln Ser Glu Ser Glu Val Gln
                145             150 gtt aca gtg caa ggt gac aag gct gtt gtc tcc ttt gaa        1007
Val Thr Val Gln Gly Asp Lys Ala Val Val Ser Phe Glu
155             160                 165 cca tca gcg gca ccg aca ccg aag aat cgt att ttt gcc        1046
Pro Ser Ala Ala Pro Thr Pro Lys Asn Arg Ile Phe Ala
        170             175                 180 ttt tct ttc ttg ccg tcc act gcg cca tcc ttc cct tca        1085
Phe Ser Phe Leu Pro Ser Thr Ala Pro Ser Phe Pro Ser
                185             190 ccc acc cgg aac cct gag gtg aga acg ccc aag tca gca        1124
Pro Thr Arg Asn Pro Glu Val Arg Thr Pro Lys Ser Ala
        195             200                 205
```

UNITED STATES PATENT AND TRADEMARK OFFICE
CERTIFICATE OF CORRECTION

| | |
|---|---|
| PATENT NO. | : 7,153,828 B2 |
| APPLICATION NO. | : 10/453183 |
| DATED | : December 26, 2006 |
| INVENTOR(S) | : Sliwkowski et al. |

Page 60 of 67

It is certified that error appears in the above-identified patent and that said Letters Patent is hereby corrected as shown below:

```
act cag cca caa aca aca gaa act aat ctc caa act gct         1163
Thr Gln Pro Gln Thr Thr Glu Thr Asn Leu Gln Thr Ala
        210                 215 cct aaa ctt tct aca tct aca tcc acc act ggg aca agc         1202
Pro Lys Leu Ser Thr Ser Thr Ser Thr Thr Gly Thr Ser
220             225                 230 cat ctt gta aaa tgt gcg gag aag gag aaa act ttc tgt         1241
His Leu Val Lys Cys Ala Glu Lys Glu Lys Thr Phe Cys
        235                 240                 245 gtg aat gga ggg gag tgc ttc atg gtg aaa gac ctt tca         1280
Val Asn Gly Gly Glu Cys Phe Met Val Lys Asp Leu Ser
                250                 255 aac ccc tcg aga tac ttg tgc aag tgc cca aat gag ttt         1319
Asn Pro Ser Arg Tyr Leu Cys Lys Cys Pro Asn Glu Phe
        260                 265                 270 act ggt gat cgc tgc caa aac tac gta atg gcc agc ttc         1358
Thr Gly Asp Arg Cys Gln Asn Tyr Val Met Ala Ser Phe
                275                 280 tac agt acg tcc act ccc ttt ctg tct ctg cct gaa taggag     1400
Tyr Ser Thr Ser Thr Pro Phe Leu Ser Leu Pro Glu
285                 290                 295 296 catgctcagt tggtgctgct ttcttgttgc tgcatctccc ctcagattcc      1450
acctagagct agatgtgtct taccagatct aatattgact gcctctgcct      1500
gtcgcatgag aacattaaca aaagcaattg tattacttcc tctgttcgcg      1550
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
actagttggc tctgagatac taataggtgt gtgaggctcc ggatgtttct      1600
ggaattgata ttgaatgatg tgatacaaat tgatagtcaa tatcaagcag      1650
tgaaatatga taataaaggc atttcaaagt ctcacttta ttgataaaat       1700 aaaaatcatt ctactgaaca gtccatcttc tttatacaat gaccacatcc      1750 tgaaagggt gttgctaagc tgtaaccgat atgcacttga aatgatggta       1800
agttaatttt gattcagaat gtgttatttg tcacaaataa acataataaa      1850
aggaaaaaaa aaacccgaat tc                                    1872
```

<210> 14
<211> 296
<212> PRT
<213> Homo sapiens

<400> 14
```
Met Glu Ile Tyr Ser Pro Asp Met Ser Glu Val Ala Ala Glu Arg
 1               5                  10                  15

Ser Ser Ser Pro Ser Thr Gln Leu Ser Ala Asp Pro Ser Leu Asp
                20                  25                  30

Gly Leu Pro Ala Ala Glu Asp Met Pro Glu Pro Gln Thr Glu Asp
                35                  40                  45

Gly Arg Thr Pro Gly Leu Val Gly Leu Ala Val Pro Cys Cys Ala
                50                  55                  60
```

UNITED STATES PATENT AND TRADEMARK OFFICE
CERTIFICATE OF CORRECTION

PATENT NO.     : 7,153,828 B2
APPLICATION NO. : 10/453183
DATED          : December 26, 2006
INVENTOR(S)    : Sliwkowski et al.

It is certified that error appears in the above-identified patent and that said Letters Patent is hereby corrected as shown below:

```
Cys Leu Glu Ala Glu Arg Leu Arg Gly Cys Leu Asn Ser Glu Lys
                65                  70                  75

Ile Cys Ile Val Pro Ile Leu Ala Cys Leu Val Ser Leu Cys Leu
                80                  85                  90

Cys Ile Ala Gly Leu Lys Trp Val Phe Val Asp Lys Ile Phe Glu
                95                 100                 105

Tyr Asp Ser Pro Thr His Leu Asp Pro Gly Gly Leu Gly Gln Asp
               110                 115                 120

Pro Ile Ile Ser Leu Asp Ala Thr Ala Ala Ser Ala Val Trp Val
               125                 130                 135

Ser Ser Glu Ala Tyr Thr Ser Pro Val Ser Arg Ala Gln Ser Glu
               140                 145                 150

Ser Glu Val Gln Val Thr Val Gln Gly Asp Lys Ala Val Val Ser
               155                 160                 165

Phe Glu Pro Ser Ala Ala Pro Thr Pro Lys Asn Arg Ile Phe Ala
               170                 175                 180

Phe Ser Phe Leu Pro Ser Thr Ala Pro Ser Phe Pro Ser Pro Thr
               185                 190                 195

Arg Asn Pro Glu Val Arg Thr Pro Lys Ser Ala Thr Gln Pro Gln
               200                 205                 210

Thr Thr Glu Thr Asn Leu Gln Thr Ala Pro Lys Leu Ser Thr Ser
               215                 220                 225.

Thr Ser Thr Thr Gly Thr Ser His Leu Val Lys Cys Ala Glu Lys
               230                 235                 240
```

UNITED STATES PATENT AND TRADEMARK OFFICE
CERTIFICATE OF CORRECTION

PATENT NO.       : 7,153,828 B2
APPLICATION NO.  : 10/453183
DATED            : December 26, 2006
INVENTOR(S)      : Sliwkowski et al.

It is certified that error appears in the above-identified patent and that said Letters Patent is hereby corrected as shown below:

```
Glu Lys Thr Phe Cys Val Asn Gly Gly Glu Cys Phe Met Val Lys
                245                 250                 255

Asp Leu Ser Asn Pro Ser Arg Tyr Leu Cys Lys Cys Pro Asn Glu
                260                 265                 270

Phe Thr Gly Asp Arg Cys Gln Asn Tyr Val Met Ala Ser Phe Tyr
                275                 280                 285

Ser Thr Ser Thr Pro Phe Leu Ser Leu Pro Glu
                290                 295

<210> 15
<211> 645
<212> PRT
<213> Homo sapiens

<400> 15
Met Ser Glu Arg Lys Glu Gly Arg Gly Lys Gly Lys Gly Lys Lys
                5                   10                  15

Lys Glu Arg Gly Ser Gly Lys Lys Pro Glu Ser Ala Ala Gly Ser
                20                  25                  30

Gln Ser Pro Ala Leu Pro Pro Gln Leu Lys Glu Met Lys Ser Gln
                35                  40                  45

Glu Ser Ala Ala Gly Ser Lys Leu Val Leu Arg Cys Glu Thr Ser
                50                  55                  60

Ser Glu Tyr Ser Ser Leu Arg Phe Lys Trp Phe Lys Asn Gly Asn
                65                  70                  75
```

UNITED STATES PATENT AND TRADEMARK OFFICE
CERTIFICATE OF CORRECTION

PATENT NO. : 7,153,828 B2
APPLICATION NO. : 10/453183
DATED : December 26, 2006
INVENTOR(S) : Sliwkowski et al.

It is certified that error appears in the above-identified patent and that said Letters Patent is hereby corrected as shown below:

```
Glu Leu Asn Arg Lys Asn Lys Pro Gln Asn Ile Lys Ile Gln Lys
                80              85                      90

Lys Pro Gly Lys Ser Glu Leu Arg Ile Asn Lys Ala Ser Leu Ala
                95             100                     105

Asp Ser Gly Glu Tyr Met Cys Lys Val Ile Ser Lys Leu Gly Asn
               110             115                     120

Asp Ser Ala Ser Ala Asn Ile Thr Ile Val Glu Ser Asn Glu Ile
               125             130                     135

Ile Thr Gly Met Pro Ala Ser Thr Glu Gly Ala Tyr Val Ser Ser
               140             145                     150

Glu Ser Pro Ile Arg Ile Ser Val Ser Thr Glu Gly Ala Asn Thr
               155             160                     165

Ser Ser Ser Thr Ser Thr Ser Thr Thr Gly Thr Ser His Leu Val
               170             175                     180

Lys Cys Ala Glu Lys Glu Lys Thr Phe Cys Val Asn Gly Gly Glu
               185             190                     195

Cys Phe Met Val Lys Asp Leu Ser Asn Pro Ser Arg Tyr Leu Cys
               200             205                     210

Lys Cys Pro Asn Glu Phe Thr Gly Asp Arg Cys Gln Asn Tyr Val
               215             220                     225

Met Ala Ser Phe Tyr Lys His Leu Gly Ile Glu Phe Met Glu Ala
               230             235                     240
```

UNITED STATES PATENT AND TRADEMARK OFFICE
CERTIFICATE OF CORRECTION

PATENT NO.         : 7,153,828 B2
APPLICATION NO.    : 10/453183
DATED              : December 26, 2006
INVENTOR(S)        : Sliwkowski et al.

It is certified that error appears in the above-identified patent and that said Letters Patent is hereby corrected as shown below:

```
Glu Glu Leu Tyr Gln Lys Arg Val Leu Thr Ile Thr Gly Ile Cys
                245             250             255

Ile Ala Leu Leu Val Val Gly Ile Met Cys Val Val Ala Tyr Cys
                260             265             270

Lys Thr Lys Lys Gln Arg Lys Lys Leu His Asp Arg Leu Arg Gln
                275             280             285

Ser Leu Arg Ser Glu Arg Asn Asn Met Met Asn Ile Ala Asn Gly
                290             295             300

Pro His His Pro Asn Pro Pro Pro Glu Asn Val Gln Leu Val Asn
                305             310             315

Gln Tyr Val Ser Lys Asn Val Ile Ser Ser Glu His Ile Val Glu
                320             325             330

Arg Glu Ala Glu Thr Ser Phe Ser Thr Ser His Tyr Thr Ser Thr
                335             340             345

Ala His His Ser Thr Thr Val Thr Gln Thr Pro Ser His Ser Trp
                350             355             360

Ser Asn Gly His Thr Glu Ser Ile Leu Ser Glu Ser His Ser Val
                365             370             375

Ile Val Met Ser Ser Val Glu Asn Ser Arg His Ser Ser Pro Thr
                380             385             390

Gly Gly Pro Arg Gly Arg Leu Asn Gly Thr Gly Gly Pro Arg Glu
                395             400             405

Cys Asn Ser Phe Leu Arg His Ala Arg Glu Thr Pro Asp Ser Tyr
                410             415             420
```

UNITED STATES PATENT AND TRADEMARK OFFICE
CERTIFICATE OF CORRECTION

PATENT NO.        : 7,153,828 B2
APPLICATION NO.   : 10/453183
DATED             : December 26, 2006
INVENTOR(S)       : Sliwkowski et al.

It is certified that error appears in the above-identified patent and that said Letters Patent is hereby corrected as shown below:

```
Arg Asp Ser Pro His Ser Glu Arg Tyr Val Ser Ala Met Thr Thr
                425                 430                 435

Pro Ala Arg Met Ser Pro Val Asp Phe His Thr Pro Ser Ser Pro
                440                 445                 450

Lys Ser Pro Pro Ser Glu Met Ser Pro Pro Val Ser Ser Met Thr
                455                 460                 465

Val Ser Met Pro Ser Met Ala Val Ser Pro Phe Met Glu Glu Glu
                470                 475                 480

Arg Pro Leu Leu Leu Val Thr Pro Pro Arg Leu Arg Glu Lys Lys
                485                 490                 495

Phe Asp His His Pro Gln Gln Phe Ser Ser Phe His His Asn Pro
                500                 505                 510

Ala His Asp Ser Asn Ser Leu Pro Ala Ser Pro Leu Arg Ile Val
                515                 520                 525

Glu Asp Glu Glu Tyr Glu Thr Thr Gln Glu Tyr Glu Pro Ala Gln
                530                 535                 540

Glu Pro Val Lys Lys Leu Ala Asn Ser Arg Arg Ala Lys Arg Thr
                545                 550                 555

Lys Pro Asn Gly His Ile Ala Asn Arg Leu Glu Val Asp Ser Asn
                560                 565                 570

Thr Ser Ser Gln Ser Ser Asn Ser Glu Ser Glu Thr Glu Asp Glu
                575                 580                 585

Arg Val Gly Glu Asp Thr Pro Phe Leu Gly Ile Gln Asn Pro Leu
                590                 595                 600
```

UNITED STATES PATENT AND TRADEMARK OFFICE
CERTIFICATE OF CORRECTION

PATENT NO.        : 7,153,828 B2
APPLICATION NO.   : 10/453183
DATED             : December 26, 2006
INVENTOR(S)       : Sliwkowski et al.

It is certified that error appears in the above-identified patent and that said Letters Patent is hereby corrected as shown below:

```
Ala Ala Ser Leu Glu Ala Thr Pro Ala Phe Arg Leu Ala Asp Ser
                605             610              615

Arg Thr Asn Pro Ala Gly Arg Phe Ser Thr Gln Glu Glu Ile Gln
                620             625              630

Ala Arg Leu Ser Ser Val Ile Ala Asn Gln Asp Pro Ile Ala Val
                635             640              645
```

Col. 113, line 29, claim 6: "c) H180 is substituted" should read --c) V180 is substituted--

Col. 113, line 43, claim 6: "K, H, G, P, or" should read --K, H, G, P, or R;--

Col. 114, line 49, claim 8: "K, H, G, P, or" should read --H, K, G, P, or R;--

Signed and Sealed this

Fourth Day of September, 2007

JON W. DUDAS
*Director of the United States Patent and Trademark Office*